(12) United States Patent
Charifson et al.

(10) Patent No.: US 7,495,014 B2
(45) Date of Patent: *Feb. 24, 2009

(54) GYRASE INHIBITORS AND USES THEREOF

(75) Inventors: Paul S. Charifson, Framingham, MA (US); David D. Deininger, Arlington, MA (US); Anne-Laure Grillot, Cambridge, MA (US); Yusheng Liao, Lexington, MA (US); Steven M. Ronkin, Watertown, MA (US); Dean Stamos, Framingham, MA (US); Emanuele Perola, Cambridge, MA (US); Tiensheng Wang, Concord, MA (US); Arnaud LeTiran, Ashland, MA (US); Joseph Drumm, Westborough, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 405 days.

This patent is subject to a terminal disclaimer.

(21) Appl. No.: 10/767,638

(22) Filed: Jan. 29, 2004

(65) Prior Publication Data

US 2004/0235886 A1    Nov. 25, 2004

Related U.S. Application Data

(60) Provisional application No. 60/443,917, filed on Jan. 31, 2003.

(51) Int. Cl.
*A61K 31/44* (2006.01)
*C07D 401/04* (2006.01)
*C07D 401/14* (2006.01)

(52) U.S. Cl. .................... 514/338; 514/221; 514/227.8; 514/234.5; 514/255; 514/256; 514/269; 514/318; 514/394; 540/291; 544/81; 544/124; 544/132; 544/280; 544/281; 544/282; 544/319; 544/370; 544/380; 546/193; 546/273.4; 548/302.7; 548/304.4

(58) Field of Classification Search ................ 544/242, 544/81, 124, 132, 280, 281, 282, 319, 370; 544/380; 546/273.4, 193; 548/269.4, 304.4, 548/306.1, 302.7; 514/221, 227.8, 234.5, 514/255, 256, 269, 318, 338, 394; 540/291
See application file for complete search history.

(56) References Cited

U.S. PATENT DOCUMENTS 3,856,957 A * 12/1974 Seng et al. ............... 514/228.2

6,632,809 B2   10/2003  Grillot et al.
2004/0043989 A1  3/2004  Grillot et al.
2005/0038247 A1  2/2005  Charifson et al.
2005/0256136 A1  11/2005 Charifson et al.
2006/0025424 A1  2/2006  Charifson et al.

FOREIGN PATENT DOCUMENTS

WO   WO 02/060879    8/2002
WO   WO 03/105846   12/2003

OTHER PUBLICATIONS

Eckert et al. "The antifungal activity of . . . " CA 93:39290 (1980).*
MayoClinic "Antibiotic associated diarrhea" Mayoclinic.com. (2007).*
Wassenaar "Bacteria;more than pathogens" Am. Ins. biol. Sci. internet p. 1-7 (2002).*
Webster's Dictionary (1984) p. 933.*
Kus et al., "Synthesis and Antimicrobial Activities of 5-fluoro-1,2,6-trisubstituted Benzimidazole Carboxamide and Acetamide Derivatives" Arch. Pharm. Pharm. Med. Chem., vol. 334, No. 11, pp. 361-365, 2001.
Sun et al., "Synthesis and Evaluation of Terbenzimidazoles as Topoisomerase I Inhibitors" J. Med. Chem., vol. 38, No. 18, pp. 3638-3644, 1995.
Hubschwerlen et al., "Pyrimido[1,6-a]benzimidazoles: A New Class of DNA Gyrase Inhibitors" J. Med. Chem, vol. 35, No. 8, pp. 1385-1392, 1992.
Office Action mailed Aug. 26, 2005 for U.S. Appl. No. 10/833,995.
Office Action mailed Mar. 17, 2006 for U.S. Appl. No. 10/833,995.
Office Action mailed Mar. 15, 2007 for U.S. Appl. No. 10/833,995.
Office Action mailed Sep. 14, 2006 for U.S. Appl. No. 10/833,995.
Office Action mailed Mar. 25, 2005 for U.S. Appl. No. 10/833,995.
Office Action mailed Jun. 16, 2006 for U.S. Appl. No. 10/444,588.
Office Action mailed Mar. 21, 2007 for U.S. Appl. No. 10/444,588.
Office Action mailed Aug. 10, 2006 for U.S. Appl. No. 10/459,420.
Office Action mailed May 3, 2007 for U.S. Appl. No. 10/459,420.
Office Action mailed Dec. 28, 2007 for U.S. Appl. No. 10/459,420.
Office Action mailed Nov. 5, 2007 for U.S. Appl. No. 10/901,928.
Office Action mailed Dec. 21, 2007 for U.S. Appl. No. 10/971,573.
Office Action mailed Dec. 3, 2007 for U.S. Appl. No. 10/986,569.

* cited by examiner

*Primary Examiner*—Celia Chang
(74) *Attorney, Agent, or Firm*—Michael C. Badia

(57) ABSTRACT

The present invention relates to compounds which inhibit bacterial gyrase and/or Topo IV and pharmaceutically acceptable compositions comprising said compounds. These compounds, and compositions thereof, are useful in treating bacterial infection. Accordingly, the present invention also relates to methods for treating bacterial infections in mammals.

24 Claims, No Drawings

GYRASE INHIBITORS AND USES THEREOF

CROSS REFERENCE TO RELATED APPLICATIONS

This application claims priority to U.S. Provisional Patent Application 60/443,917 filed Jan. 31, 2003, the contents of which are incorporated herein by reference.

FIELD OF THE INVENTION

This invention is in the field of medicinal chemistry and relates to compounds, and pharmaceutical compositions thereof, that inhibit bacterial gyrase and Topo IV. The compounds are useful as inhibitors of bacterial gyrase and Topo IV activity. The present invention also relates to methods for treating bacterial infections in mammals and to methods for decreasing bacterial quantity in a biological sample.

BACKGROUND OF THE INVENTION

Bacterial resistance to antibiotics has long been recognized, and it is today considered to be a serious worldwide health problem. As a result of resistance, some bacterial infections are either difficult to treat with antibiotics or even untreatable. This problem has become especially serious with the recent development of multiple drug resistance in certain strains of bacteria, such as *Streptococcus pneumoniae* (SP), *Mycobacterium tuberculosis*, and *Enterococcus*. The appearance of vancomycin resistant enterococcus was particularly alarming because vancomycin was formerly the only effective antibiotic for treating this infection, and had been considered for many infections to be the drug of "last resort". While many other drug-resistant bacteria do not cause life-threatening disease, such as enterococci, there is the fear that the genes which induce resistance might spread to more deadly organisms such as *Staphylococcus aureus*, where methicillin resistance is already prevalent (De Clerq, et al., *Current Opinion in Anti-infective Investigational Drugs*, 1999, 1, 1; Levy, "The Challenge of Antibiotic Resistance", *Scientific American*, March, 1998).

Another concern is how quickly antibiotic resistance can spread. For example, until the 1960's SP was universally sensitive to penicillin, and in 1987 only 0.02% of the SP strains in the U.S. were resistant. However, by 1995 it was reported that SP resistance to penicillin was about seven percent and as high as 30% in some parts of the U.S. (Lewis, FDA Consumer magazine (September, 1995); Gershman in *The Medical Reporter*, 1997).

Hospitals, in particular, serve as centers for the formation and transmission of drug-resistant organisms. Infections occurring in hospitals, known as nosocomial infections, are becoming an increasingly serious problem. Of the two million Americans infected in hospitals each year, more than half of these infections resist at least one antibiotic. The Center for Disease Control reported that in 1992, over 13,000 hospital patients died of bacterial infections that were resistant to antibiotic treatment (Lewis, "The Rise of Antibiotic-Resistant Infections", *FDA Consumer* magazine, September, 1995).

As a result of the need to combat drug-resistant bacteria and the increasing failure of the available drugs, there has been a resurgent interest in discovering new antibiotics. One attractive strategy for developing new antibiotics is to inhibit DNA gyrase, a bacterial enzyme necessary for DNA replication, and therefore, necessary for bacterial cell growth and division. Gyrase activity is also associated with events in DNA transcription, repair and recombination.

Gyrase is one of the topoisomerases, a group of enzymes which catalyze the interconversion of topological isomers of DNA (see generally, Kornberg and Baker, *DNA Replication*, 2d Ed., Chapter 12, 1992, W. H. Freeman and Co.; Drlica, *Molecular Microbiology*, 1992, 6, 425; Drlica and Zhao, *Microbiology and Molecular Biology Reviews*, 1997, 61, 377). Gyrase itself controls DNA supercoiling and relieves topological stress that occurs when the DNA strands of a parental duplex are untwisted during the replication process. Gyrase also catalyzes the conversion of relaxed, closed circular duplex DNA to a negatively superhelical form which is more favorable for recombination. The mechanism of the supercoiling reaction involves the wrapping of gyrase around a region of the DNA, double strand breaking in that region, passing a second region of the DNA through the break, and rejoining the broken strands. Such a cleavage mechanism is characteristic of a type II topoisomerase. The supercoiling reaction is driven by the binding of ATP to gyrase. The ATP is then hydrolyzed during the reaction. This ATP binding and subsequent hydrolysis cause conformational changes in the DNA-bound gyrase that are necessary for its activity. It has also been found that the level of DNA supercoiling (or relaxation) is dependent on the ATP/ADP ratio. In the absence of ATP, gyrase is only capable of relaxing supercoiled DNA.

Bacterial DNA gyrase is a 400 kilodalton protein tetramer consisting of two A (GyrA) and two B subunits (GyrB). Binding and cleavage of the DNA is associated with GyrA, whereas ATP is bound and hydrolyzed by the GyrB protein. GyrB consists of an amino-terminal domain which has the ATPase activity, and a carboxy-terminal domain which interacts with GyrA and DNA. By contrast, eukaryotic type II topoisomerases are homodimers that can relax negative and positive supercoils, but cannot introduce negative supercoils. Ideally, an antibiotic based on the inhibition of bacterial DNA gyrase would be selective for this enzyme and be relatively inactive against the eukaryotic type II topoisomerases.

The widely used quinolone antibiotics inhibit bacterial DNA gyrase. Examples of the quinolones include the early compounds such as nalidixic acid and oxolinic acid, as well as the later, more potent fluoroquinolones such as norfloxacin, ciprofloxacin, and trovafloxacin. These compounds bind to GyrA and stabilize the cleaved complex, thus inhibiting overall gyrase function, leading to cell death. However, drug resistance has also been recognized as a problem for this class of compounds (WHO Report, "Use of Quinolones in Food Animals and Potential Impact on Human Health", 1998). With the quinolones, as with other classes of antibiotics, bacteria exposed to earlier compounds often quickly develop cross-resistance to more potent compounds in the same class.

There are fewer known inhibitors that bind to GyrB. Examples include the coumarins, novobiocin and coumermycin A1, cyclothialidine, cinodine, and clerocidin. The coumarins have been shown to bind to GyrB very tightly. For example, novobiocin makes a network of hydrogen bonds with the protein and several hydrophobic contacts. While novobiocin and ATP do appear to bind within the ATP binding site, there is minimal overlap in the bound orientation of the two compounds. The overlapping portions are the sugar unit of novobiocin and the ATP adenine (Maxwell, *Trends in Microbiology*, 1997, 5, 102).

For coumarin-resistant bacteria, the most prevalent point mutation is at a surface arginine residue that binds to the carbonyl of the coumarin ring (Arg136 in *E. coli* GyrB). While enzymes with this mutation show lower supercoiling and ATPase activity, they are also less sensitive to inhibition by coumarin drugs (Maxwell, *Mol. Microbiol.*, 1993, 9, 681).

Despite being potent inhibitors of gyrase supercoiling, the coumarins have not been widely used as antibiotics. They are generally not suitable due to their low permeability in bacteria, eukaryotic toxicity, and poor water solubility (Maxwell, *Trends in Microbiology*, 1997, 5, 102). It would be desirable to have a new, effective GyrB inhibitor that overcomes these drawbacks. Such an inhibitor would be an attractive antibiotic candidate, without a history of resistance problems that plague other classes of antibiotics.

Replication fork movement along circular DNA can generate topological changes both ahead of the replication complex as well as behind in the already replicated regions (Champoux, J. J., *Annu. Rev. Biochem.*, 2001, 70, 369-413). While DNA gyrase can introduce negative supercoils to compensate for the topological stresses ahead of the replication fork, some overwinding can diffuse back into the already replicated region of DNA resulting in precatenanes. If not removed, the presence of the precatenanes can result in interlinked (catenated) daughter molecules at the end of replication. TopoIV is responsible for separating the catenated daughter plasmids as well as removal of precatenanes formed during replication ultimately allowing for segragation of the daughter molecules into daughter cells. Topo IV is composed of two ParC and 2 parE subunits as a C2E2 tetramer (where the C and E monomers are homologuous to the A and B monomers of gyrase, respectively) that requires ATP hydrolysis (at the N-terminus of the E subunit) to reset the enzyme to re-enter the catalytic cycle. Topo IV is highly conserved among bacteria and is essential for bacterial replication (Drlica and Zhao, *Microbiol. Mol. Biol. Rev.*, 1997, 61, 377).

While little attention has been paid to inhibitors that target ParE of TopoIV, the action of the newer quinolones on the ParC region has been widely studied (Hooper, D. C., *Clin. Infect. Dis.*, 2000, 31(Suppl 2): S24-28). It has been demonstrated that moxifloxacin and gatifloxacin have more balanced activities against Gyrase and TopoIV resulting in expanded Gram positive coverage as well as lower levels of resistance caused primary-target mutation. In those cases, susceptibility is limited by the sensitivity of the second target to the antibacterial agent. Thus, agents that can effectively inhibit multiple essential targets can result in an expanded spectrum of potencies, improved antibacterial potencies, improved potency against single target mutants, and/or lower spontaneous rates of resistance.

As bacterial resistance to antibiotics has become an important public health problem, there is a continuing need to develop newer and more potent antibiotics. More particularly, there is a need for antibiotics that represent a new class of compounds not previously used to treat bacterial infection. Such compounds would be particularly useful in treating nosocomial infections in hospitals where the formation and transmission of resistant bacteria are becoming increasingly prevalent.

SUMMARY OF THE INVENTION

It has now been found that compounds of this invention, and pharmaceutically acceptable compositions thereof, are effective as inhibitors of gyrase and/or Topo IV. These compounds have the general formula I:

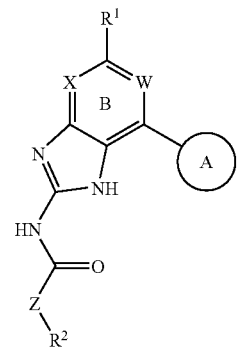

or a pharmaceutically acceptable salt thereof, wherein $R^1$, $R^2$, W, X, Z, and Ring A are as defined below.

These compounds, and pharmaceutically acceptable compositions thereof, are useful for treating or lessening the severity of bacterial infections. In particular, the compounds of the present invention are useful in treating or lessening the severity of urinary tract infections, pneumonia, prostatitis, skin and soft tissue infections, intra-abdominal infections, blood stream infections, or infections of febrile neutropenic patients

DESCRIPTION OF THE INVENTION

The present invention relates to a compound of formula I:

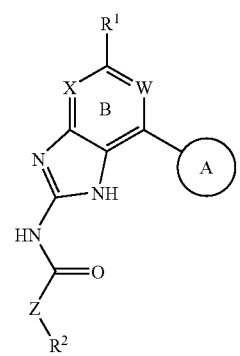

or a pharmaceutically acceptable salt thereof, wherein:
W is selected from nitrogen, CH, or CF;
X is selected from CH or CF;
Z is O or NH;
$R^1$ is phenyl or a 5-6 membered heteroaryl ring having 1-3 heteroatoms independently selected from oxygen, nitrogen, or sulfur, wherein:
  $R^1$ is substituted with 0-3 groups independently selected from -(T)$_y$-Ar, R', oxo, C(O)R', CO$_2$R', OR', N(R')$_2$, SR', NO$_2$, halogen, CN, C(O)N(R')$_2$, NR'C(O)R', SO$_2$R', SO$_2$N(R')$_2$, or NR'SO$_2$R';
y is 0 or 1;
T is a straight or branched $C_{1-4}$ alkylidene chain, wherein one methylene unit of T is optionally replaced by —O—, —NH—, or —S—;
each R' is independently selected from hydrogen, $C_{1-4}$ aliphatic, or a 5-6 membered saturated, unsaturated, or aryl ring having 0-3 heteroatoms independently selected from nitrogen, oxygen, or sulfur, wherein:

R' is substituted with 0-3 groups independently selected from halogen, oxo, R°, N(R°)$_2$, OR°, CO$_2$R°, NR°C(O) R°, C(O)N(R°)$_2$, SO$_2$R°, SO$_2$N(R°)$_2$, or NR°SO$_2$R°, wherein:

each R° is independently selected from hydrogen, C$_{1-4}$ aliphatic, or a 5-6 membered saturated, unsaturated, or aryl ring having 0-3 heteroatoms independently selected from nitrogen, oxygen, or sulfur, and wherein:

two substituents on adjacent positions of R$^1$ may be taken together to form a 5-7 membered saturated, partially unsaturated, or aryl ring having 0-3 heteroatoms independently selected from nitrogen, oxygen, or sulfur;

Ar is a 3-8 membered saturated, unsaturated, or aryl ring, a 3-7 membered heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur, wherein:

Ar is substituted with 0-3 groups independently selected from R', oxo, CO$_2$R', OR', N(R')$_2$, SR', NO$_2$, halogen, CN, C(O)N(R')$_2$, NR'C(O)R', SO$_2$R', C(O)R', SO$_2$N(R')$_2$, or NR'SO$_2$R';

R$^2$ is selected from hydrogen or a C$_{1-3}$ aliphatic group; and

Ring A is a 5-6 membered heteroaryl ring having 1-4 heteroatoms independently selected from nitrogen, oxygen, or sulfur, provided that said ring has a hydrogen-bond acceptor in the position adjacent to the point of attachment to Ring B, wherein:

Ring A is substituted with 0-3 groups independently selected from R', oxo, CO$_2$R', OR', N(R')$_2$, SR', NO$_2$, halogen, CN, C(O)N(R')$_2$, NR'C(O)R', SO$_2$R', SO$_2$N (R')$_2$, or NR'SO$_2$R', and wherein:

two substituents on adjacent positions of Ring A may be taken together to form a 5-7 membered saturated, partially unsaturated, or aryl ring having 0-3 heteroatoms independently selected from nitrogen, oxygen, or sulfur.

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group", as used herein, means a straight-chain or branched C$_1$-C$_8$ hydrocarbon chain that is completely saturated or that contains one or more units of unsaturation, or a monocyclic C$_3$-C$_8$ hydrocarbon or bicyclic C$_8$-C$_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR$^+$ (as in N-substituted pyrrolidinyl).

The term "unsaturated", as used herein, means that a moiety has one or more units of unsaturation, and includes aryl rings.

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

The term "hydrogen bond acceptor", as used herein, means an atom capable of accepting a hydrogen bond. A typical hydrogen bond acceptor is a sulfur, oxygen, or nitrogen atom, especially a nitrogen that is sp$^2$-hybridized, an ether oxygen, or a thioether sulfur. A preferred hydrogen bond acceptor is a nitrogen that is sp$^2$-hybridized.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention. Such compounds are useful, for example, as analytical tools or probes in biological assays.

Examples of suitable Ring A moieties are set forth in Table 1 below.

TABLE 1

| Structure | Label |
|---|---|
| 1-methyl-1H-pyrazol-3-yl | a |
| 1H-pyrazol-3-yl | b |
| 1H-imidazol-2-yl | c |
| 1H-imidazol-4-yl | d |
| 1-methyl-1H-1,2,3-triazol-4-yl | e |
| 1-methyl-1H-1,2,4-triazol-3-yl | f |
| 1H-1,2,4-triazol-3-yl | g |
| 1H-1,2,3-triazol-4-yl | h |
| 1H-tetrazol-5-yl | i |
| 1-methyl-1H-tetrazol-5-yl | j |
| 2-methyl-2H-tetrazol-5-yl | k |
| thiazol-2-yl | l |
| thiazol-4-yl | m |
| 1,3,4-thiadiazol-2-yl | n |

TABLE 1-continued

| Structure | Label |
|---|---|
| isothiazol-5-yl | o |
| 1,2,4-thiadiazol-3-yl | p |
| 1,2,4-thiadiazol-5-yl | q |
| 1,3,4-thiadiazol-2-yl | r |
| oxazol-2-yl | s |
| oxazol-4-yl | t |
| oxazol-5-yl | u |
| 1,2,4-oxadiazol-3-yl | v |
| 1,2,4-oxadiazol-5-yl | w |
| 1,3,4-oxadiazol-2-yl | x |
| pyridin-2-yl | y |
| pyrimidin-2-yl | z |
| pyrazin-2-yl | aa |
| pyrimidin-4-yl | bb |
| pyridazin-3-yl | cc |

TABLE 1-continued

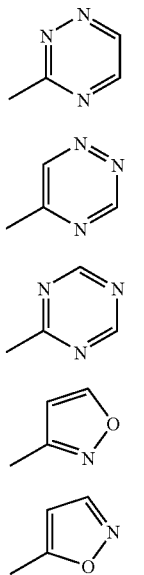

| | |
|---|---|
| | dd |
| | ee |
| | ff |
| | gg |
| | hh | wherein each Ring A is optionally substituted as defined above.

According to one embodiment, Ring A of formula I is a 5-membered heteroaryl ring having 1-4 heteroatoms independently selected from nitrogen, oxygen, or sulfur, provided that said ring has a hydrogen-bond acceptor in the position adjacent to the point of attachment to Ring B, wherein said Ring A is optionally substituted as defined herein supra.

According to another embodiment, Ring A of formula I is a 6-membered heteroaryl ring having 1-3 nitrogens, provided that said ring has a nitrogen atom in the position adjacent to the point of attachment to Ring B, wherein said Ring A is optionally substituted as defined herein supra.

In certain embodiments, Ring A moieties of formula I are selected from rings a, b, c, d, e, f, g, h, i, j, k, l, m, p, q, r, s, t, v, w, x, y, z, aa, bb, cc, dd, and ee, wherein each Ring A is optionally substituted as defined above.

In other embodiments, the Ring A moieties of formula I are selected from rings a, f, l, s, w, y, and z, wherein each Ring A is optionally substituted as defined above.

When Ring A of formula I is a bicyclic heteroaryl ring, preferred bicyclic Ring A moieties include benzothiazole, benzimidazole, benzoxazole, and quinoline.

According to one embodiment, substituents on Ring A of formula I, if present, are selected from oxo, N(R')$_2$, C(O)N(R')$_2$, CO$_2$R', halogen, N(R')SO$_2$R', C(O)R', OR', or R'. According to another embodiment, R' substituents on Ring A of formula I include methyl, ethyl, propyl, piperazinyl, piperidinyl, or morpholinyl, wherein said R' groups are optionally substituted with R°, N(R°)$_2$ or OR°.

According to one embodiment, the R$^1$ group of formula I is optionally substituted phenyl.

According to another embodiment, the R$^1$ group of formula I is an optionally substituted 5-membered heteroaryl ring having 1-3 heteroatoms independently selected from nitrogen, oxygen, or sulfur.

According to another embodiment, the R$^1$ group of formula I is an optionally substituted 5-membered heteroaryl ring having 1-3 nitrogens.

Yet another embodiment of the present invention relates to a compound of formula I wherein R$^1$ is an optionally substituted 6-membered heteroaryl ring having 1-2 nitrogens.

In certain embodiments, the R$^1$ group of formula I is selected from an optionally substituted phenyl or 5-6 membered heteroaryl ring having 1-2 nitrogens. In other embodiments, the R$^1$ group of formula I is selected from an optionally substituted pyrid-2-yl, pyrid-3-yl, pyrid-4-yl, pyridone, pyrimidin-2-yl, pyrimidin-4-yl, pyrimidin-5-yl, pyrimidin-6-yl, imidazol-1-yl, imidazol-2-yl, imidazol-4-yl, or imidazol-5-yl ring. According to yet another embodiment, the R$^1$ group of formula I is an optionally substituted ring selected from pyrid-3-yl, pyrid-4-yl, pyridone, pyrimidin-5-yl, or imidazol-1-yl.

In certain embodiments, substituents on the R$^1$ group of formula I, when present, are selected from halogen, oxo, -(T)$_y$-Ar, R', CO$_2$R', OR', N(R')$_2$, SR', C(O)N(R')$_2$, NR'C(O)R', SO$_2$R', SO$_2$N(R')$_2$, or NR'SO$_2$R'. According to other embodiments, substituents on the R$^1$ group of formula I, when present, are selected from oxo, fluoro, chloro, N(CH$_3$)$_2$, NHCH$_2$CH$_3$, NH-cyclopropyl, NH$_2$, NHC(O)CH$_3$, C(O)N-Hcyclopropyl, methyl, ethyl, t-butyl, isobutyl, cyclopropyl, isopropyl, CH$_2$phenyl, CH$_2$pyridin-3-yl, OH, OCH$_3$, OCH$_2$CH$_3$, OCH$_2$phenyl, OCH$_2$pyridin-3-yl, CH$_2$piperidinyl, CH$_2$cyclopropyl, or CH$_2$CH$_2$OCH$_3$.

According to one embodiment, R$^1$ is substituted with -(T)$_y$-Ar wherein T is a straight or branched C$_{1-3}$ alkylidene chain wherein one methylene unit of T is optionally replaced by —O—, —NH—, or —S—. According to another embodiment, T is a straight or branched C$_{1-3}$ alkylidene chain wherein one methylene unit of T is replaced by —O—, —NH—, or —S—. Yet another embodiment of the present invention relates to a compound of formula I wherein R$^1$ is substituted with -(T)$_y$-Ar and Ar is an optionally substituted 5-6 membered saturated ring having 1-2 heteroatoms independently selected from oxygen, nitrogen, or sulfur. According to another embodiment, the Ar group of formula I is an optionally substituted 5-membered heteroaryl ring having 1-3 heteroatoms independently selected from nitrogen, oxygen, or sulfur. According to yet another embodiment, the Ar group of formula I is an optionally substituted 6-membered heteroaryl ring having 1-3 nitrogens. Yet another embodiment relates to a compound of formula I wherein Ar is optionally substituted phenyl.

When the R$^1$ group of formula I is substituted with -(T)$_y$-Ar, examples of substituents on Ar include halogen, OR', R', CO$_2$R', SO$_2$R', oxo, and C(O)R'.

According to one embodiment, when two substituents on adjacent positions of R$^1$ of formula I are taken together to form an optionally substituted ring fused to R$^1$, rings formed thereby include 5-6 membered saturated, partially unsaturated, or aryl rings having 0-2 heteroatoms independently selected from nitrogen, oxygen, or sulfur. According to another embodiment, said ring fused to R$^1$ is selected from a 5-membered saturated ring having two oxygens or a 6-membered saturated ring having two oxygens. Examples of substituents on said ring fused to R$^1$ include halogen, such as fluorine.

One embodiment of the present invention relates to a compound of formula I wherein R$^2$ is selected from methyl, ethyl, isopropyl, or cyclopropyl. According to another embodiment, R$^2$ is methyl or ethyl. According to yet another embodiment, R$^2$ of formula I is ethyl.

According to one embodiment, the present invention relates to a compound of formula I wherein Z is NH.

According to another embodiment, the present invention relates to a compound of formula I wherein Z is O.

Compounds of the present invention fall within the genus of compounds described in PCT/US 01/48855. However, applicants have discovered that the presence of the Ring A moiety, as defined above, imparts surprising and unexpectedly increased gyrase inhibitory, TopoIV activity, and antimicrobial potency.

According to one embodiment, the present invention relates to a compound of formula II:

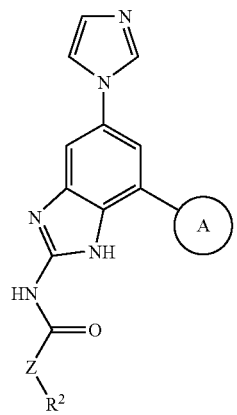

II or a pharmaceutically acceptable salt thereof, wherein Z, $R^2$ and Ring A are as defined above and the imidazole ring depicted is optionally substituted in the 4-position with C(O)N(R')$_2$ and/or substituted in the 2-position with R'. Accordingly, another embodiment of the present invention relates to a compound of formula II-a:

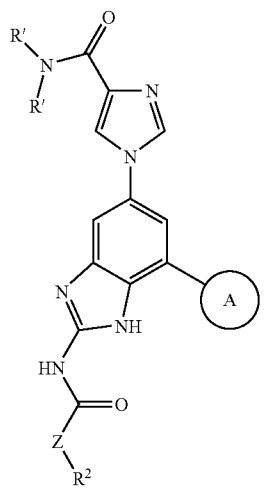

II-a or a pharmaceutically acceptable salt thereof, wherein Z, $R^2$, R', and Ring A are as defined above.

Other embodiments describing $R^2$ and Ring A groups of formula II-a are those described for formula I above.

Other embodiments describing R' groups of formula II-a are selected from hydrogen or $C_{1-4}$ aliphatic.

According to one embodiment, the present invention relates to a compound of formula II or II-a wherein Z is NH.

According to another embodiment, the present invention relates to a compound of formula II or II-a wherein Z is O.

According to another embodiment, the present invention relates to a compound of formula III:

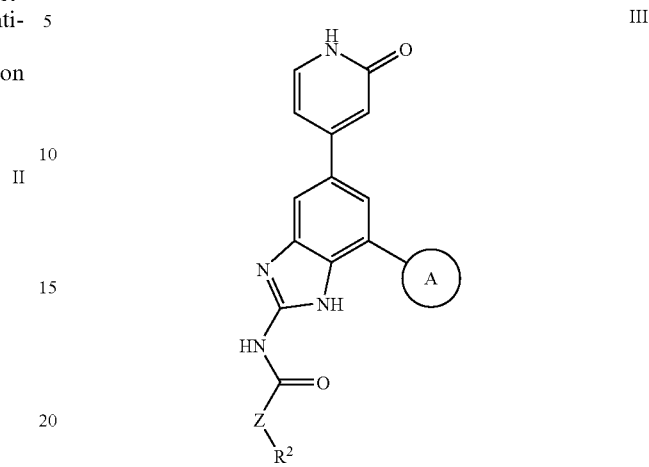

III or a pharmaceutically acceptable salt thereof, wherein Z, $R^2$ and Ring A are as defined above, and the pyridone ring depicted is substituted with 0-2 groups independently selected from —(CH$_2$)$_y$—Ar, halogen, oxo, R', CO$_2$R', OR', N(R')$_2$, SR', C(O)N(R')$_2$, NR'C(O)R', SO$_2$R', SO$_2$N(R')$_2$, or NR'SO$_2$R'.

Other embodiments describing $R^2$ and Ring A groups of formula III are those described for formula I above.

Other embodiments describing substituents on the pyridone ring of formula III are those described above as preferred substituents on $R^1$ of formula I.

According to one embodiment, the present invention relates to a compound of formula III wherein Z is NH.

According to another embodiment, the present invention relates to a compound of formula III wherein Z is O.

According to another embodiment, the present invention relates to a compound of formula III-a:

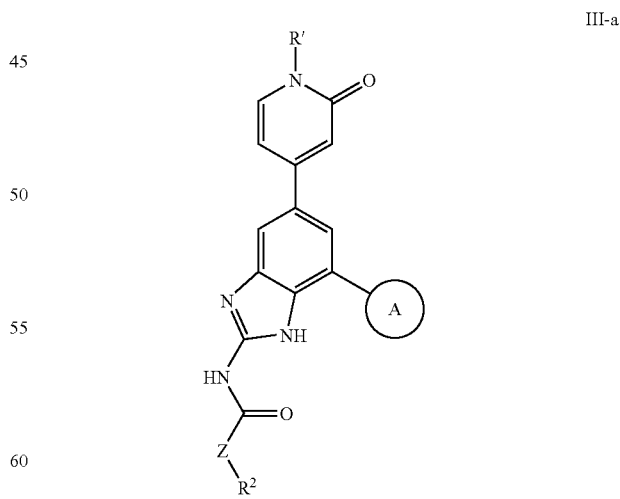

III-a or a pharmaceutically acceptable salt thereof, wherein Z, R', $R^2$ and Ring A are as defined above.

Other embodiments describing $R^2$ groups of formula III-a are those described for $R^2$ groups of formula I above.

Other embodiments describing Ring A groups of formula III-a are those described for Ring A groups of formula I above.

In certain embodiments, the R' substituents on the pyridone ring of formula III-a are selected from hydrogen or $C_{1-4}$ aliphatic wherein R' is optionally substituted with phenyl or pyridyl. In other embodiments, the R' substituents on the pyridone ring of formula III-a are selected from methyl, ethyl, t-butyl, isobutyl, cyclopropyl, isopropyl, $CH_2$phenyl, $CH_2$pyridin-3-yl, $CH_2$piperidinyl, $CH_2$cyclopropyl, or $CH_2CH_2OCH_3$.

According to one embodiment, the present invention relates to a compound of formula III-a wherein Z is NH.

According to another embodiment, the present invention relates to a compound of formula III-a wherein Z is O.

Yet another embodiment of the present invention relates to a compound of formula IV:

IV or a pharmaceutically acceptable salt thereof, wherein y, Z, T, Ar, $R^2$ and Ring A are as defined above.

Other embodiments describing Ring A and $R^2$ groups of formula IV are those set forth for those Ring A and $R^2$ groups of formula I, supra.

According to one embodiment, the Ar group of formula IV is an optionally substituted 5-6 membered saturated ring having 1-2 heteroatoms independently selected from oxygen, nitrogen, or sulfur.

According to another embodiment, the Ar group of formula IV is an optionally substituted 5-membered heteroaryl ring having 1-3 heteroatoms independently selected from nitrogen, oxygen, or sulfur.

According to another embodiment, the Ar group of formula IV is an optionally substituted 6-membered heteroaryl ring having 1-3 nitrogens.

Yet another embodiment relates to a compound of formula IV wherein Ar is optionally substituted phenyl.

According to one embodiment, the present invention relates to a compound of formula IV wherein Z is NH.

Examples of substituents on the Ar group of formula IV include halogen, OR', R', $CO_2R'$, $SO_2R'$, oxo, and C(O)R'.

According to another embodiment, the present invention relates to a compound of formula IV wherein Z is O.

Yet another embodiment of the present invention relates to a compound of formula V:

V or a pharmaceutically acceptable salt thereof, wherein y, Z, $R^2$ and $R^1$ are as defined above.

Other embodiments describing $R^1$ and $R^2$ groups of formula V are those set forth for those $R^1$ and $R^2$ groups of formula I, supra.

According to one embodiment, the present invention relates to a compound of formula V wherein Z is NH.

Examples of substituents on the Ar group of formula IV include halogen, OR', R', $CO_2R'$, $SO_2R'$, oxo, and C(O)R'.

According to another embodiment, the present invention relates to a compound of formula V wherein Z is O.

According to another embodiment of the present invention relates to a compound of formula VI:

VI or a pharmaceutically acceptable salt thereof, wherein y, Z, T, Ar, and $R^2$ are as defined above.

Other embodiments describing the $R^2$ group of formula VI are those set forth for the $R^2$ group of formula I, supra.

According to one embodiment, the Ar group of formula VI is an optionally substituted 5-6 membered saturated ring having 1-2 heteroatoms independently selected from oxygen, nitrogen, or sulfur.

According to another embodiment, the Ar group of formula VI is an optionally substituted 5-membered heteroaryl ring having 1-3 heteroatoms independently selected from nitrogen, oxygen, or sulfur.

According to another embodiment, the Ar group of formula VI is an optionally substituted 6-membered heteroaryl ring having 1-3 nitrogens.

Yet another embodiment relates to a compound of formula VI wherein Ar is optionally substituted phenyl.

According to one embodiment, the present invention relates to a compound of formula VI wherein Z is NH.

Examples of substituents on the Ar group of formula VI include halogen, OR', R', CO₂R', SO₂R', oxo, and C(O)R'.

According to another embodiment, the present invention relates to a compound of formula VI wherein Z is O.

Exemplary structures of formula I are set forth in Table 2 below.

TABLE 2

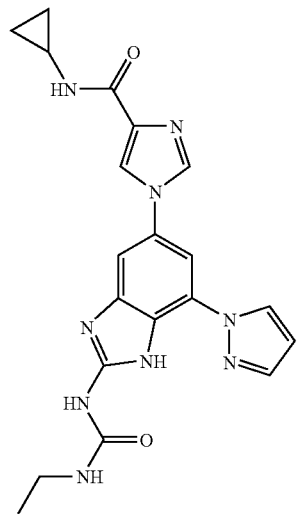

I-1

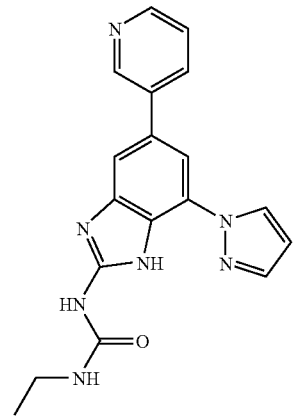

I-2

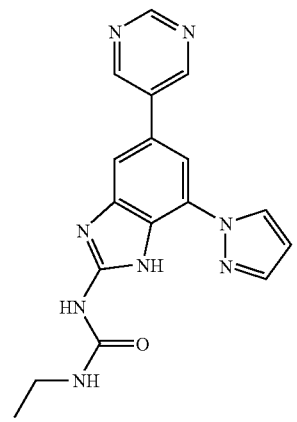

I-3

TABLE 2-continued

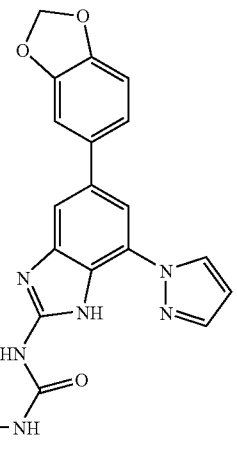

I-4

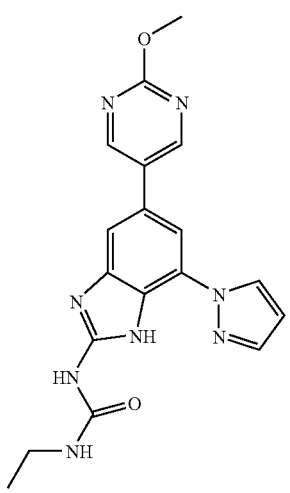

I-5

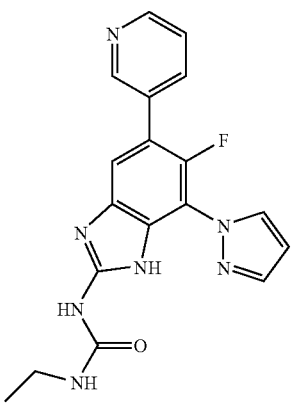

I-6

TABLE 2-continued
I-7
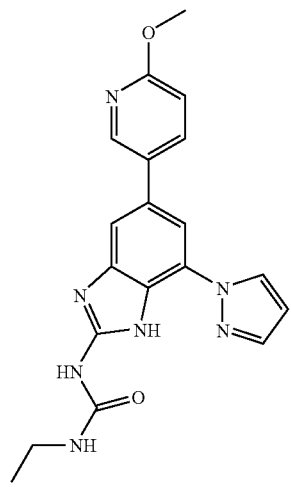
I-8
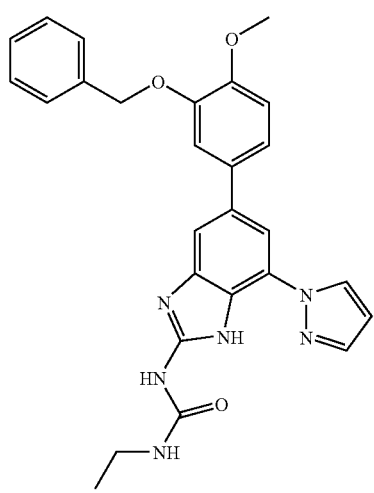
I-9
I-10
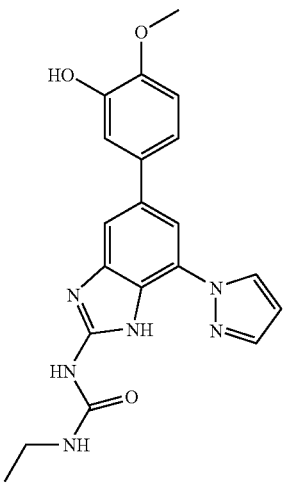
I-11
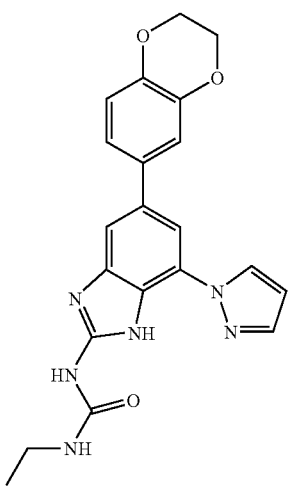
I-12
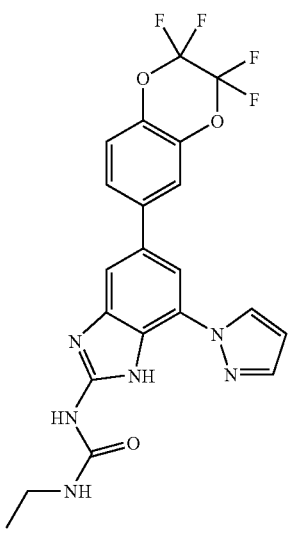

TABLE 2-continued
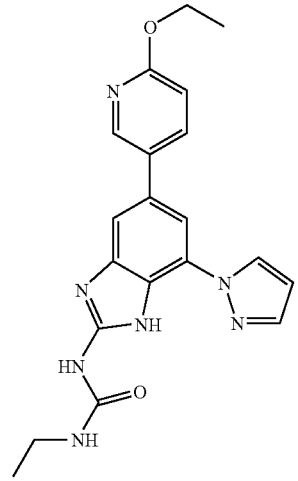
I-13
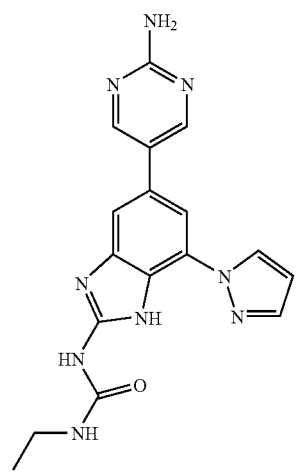
I-14
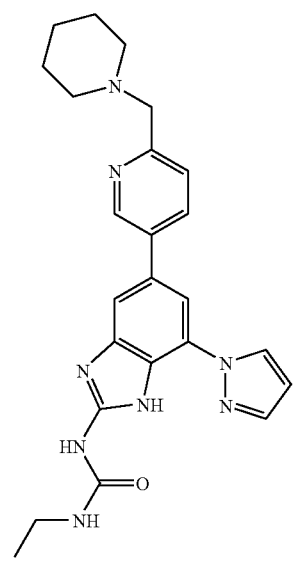
I-15
TABLE 2-continued
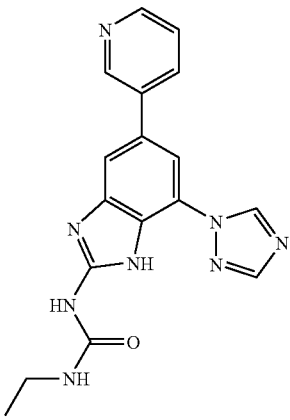
I-16
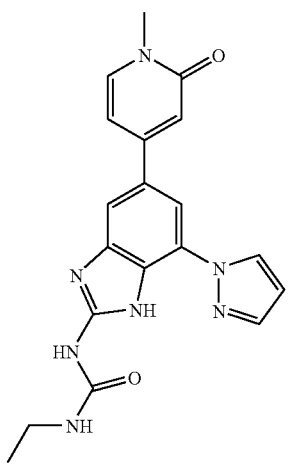
I-17
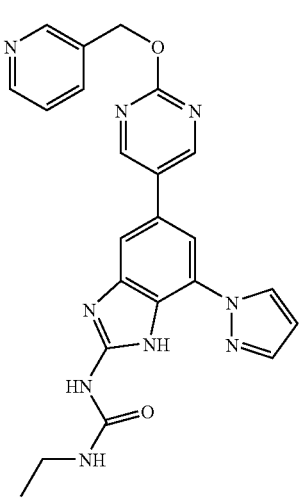
I-18

TABLE 2-continued
I-19
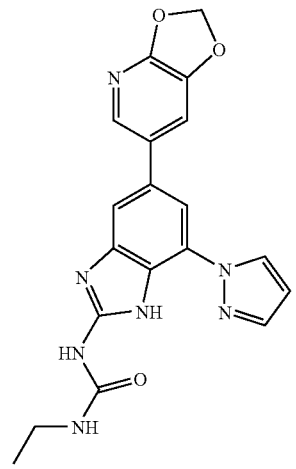
I-20
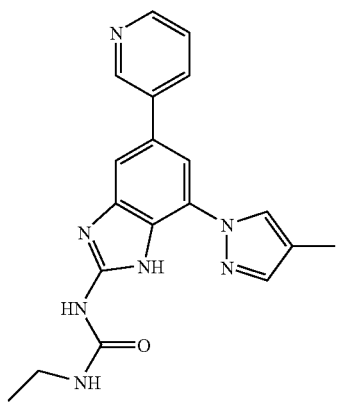
I-21
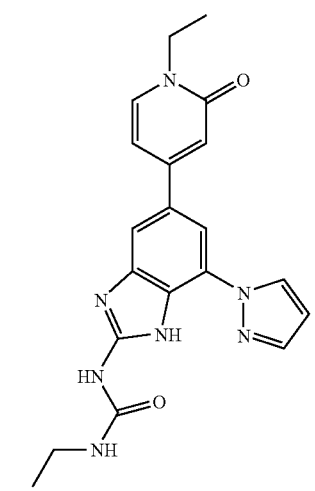
TABLE 2-continued
I-22
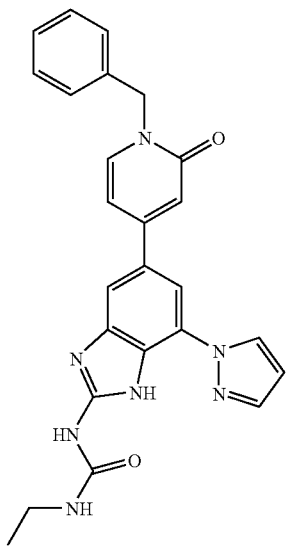
I-23
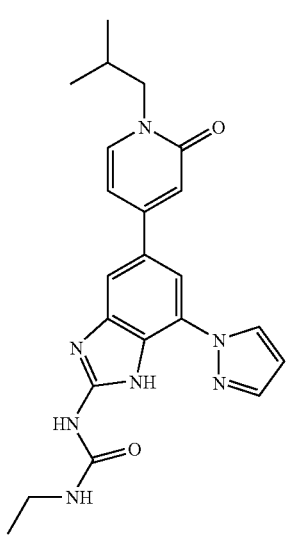
I-24
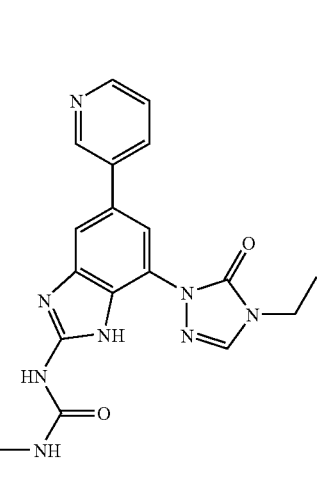

TABLE 2-continued
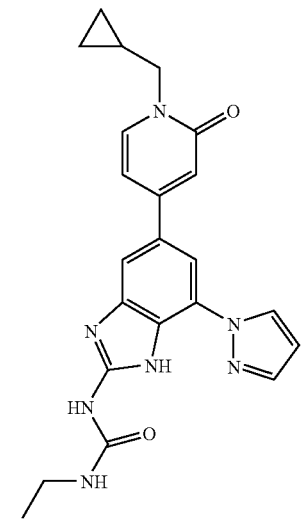
I-25
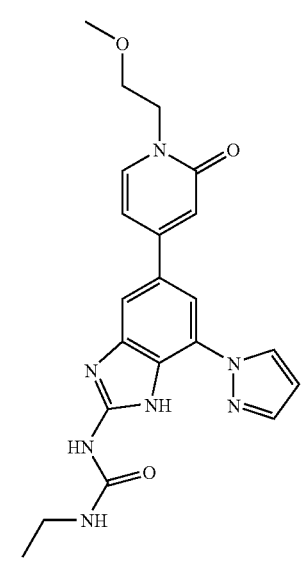
I-26
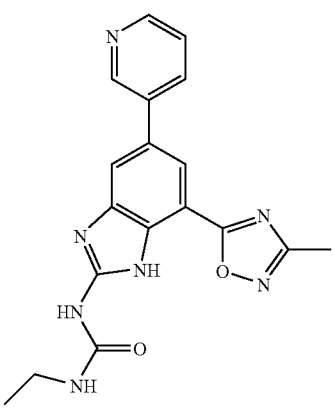
I-28
TABLE 2-continued
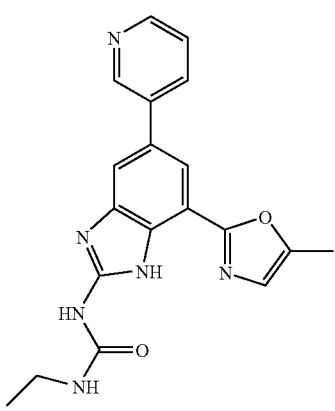
I-29
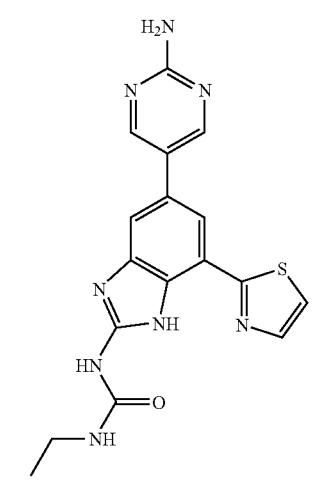
I-30
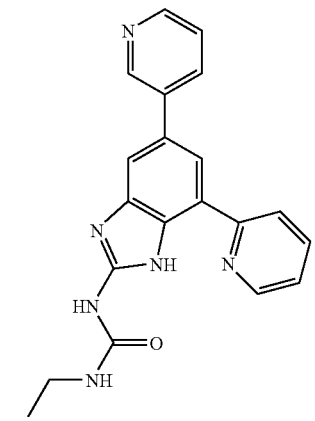
I-31

TABLE 2-continued
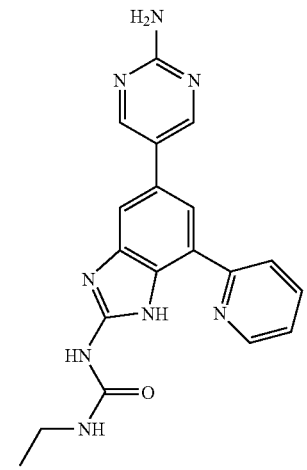
I-32
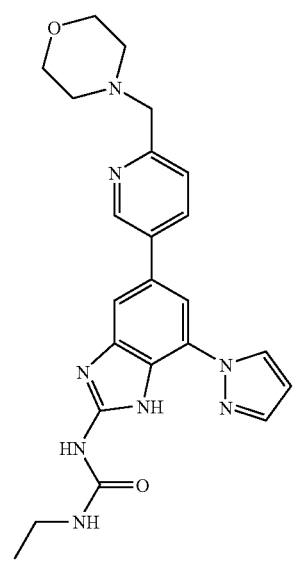
I-35
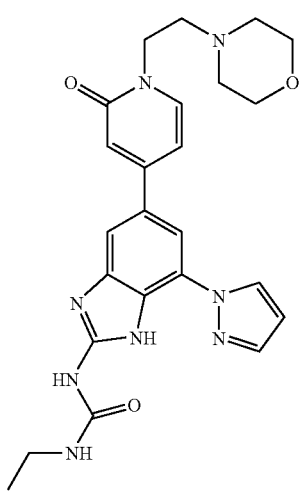
I-37
TABLE 2-continued
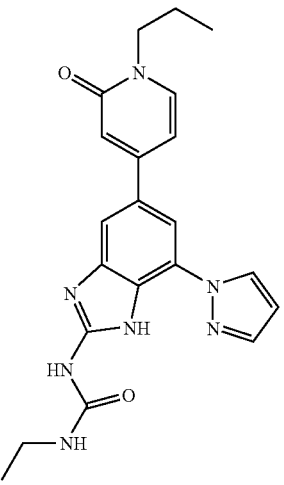
I-38
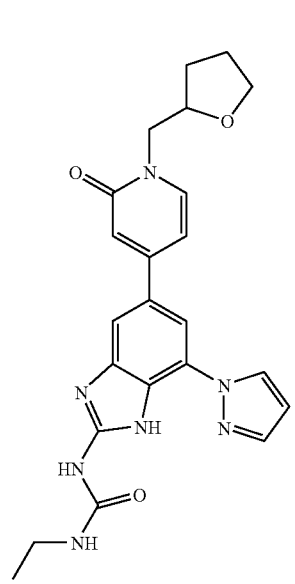
I-39
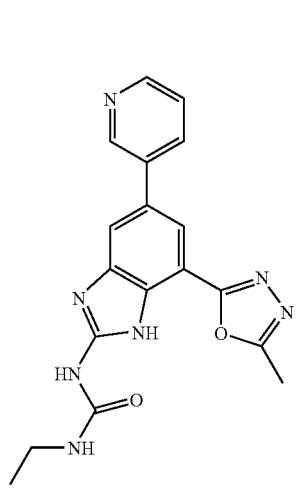
I-40

TABLE 2-continued
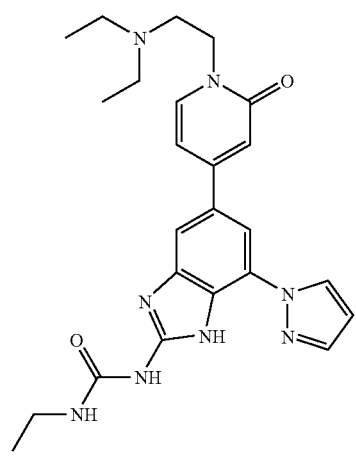
I-41
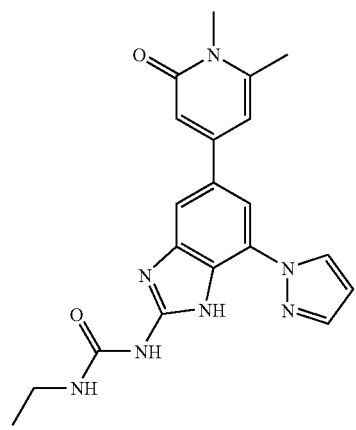
I-42
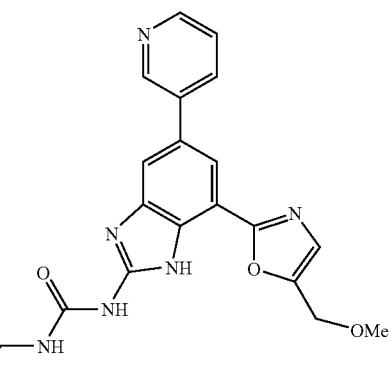
I-43
TABLE 2-continued
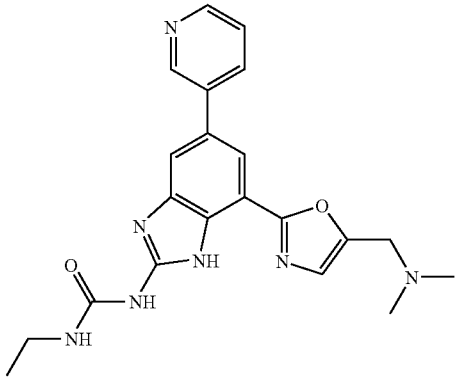
I-44
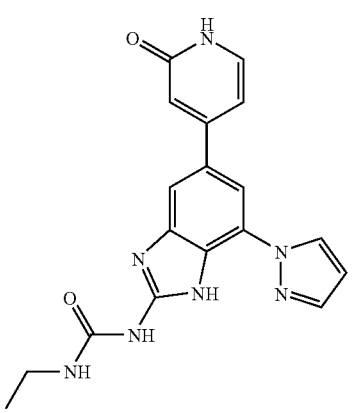
I-45
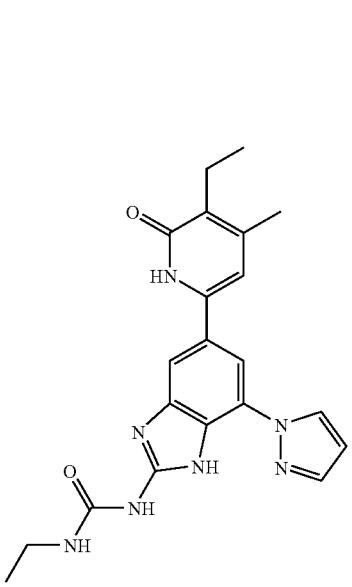
I-46

TABLE 2-continued
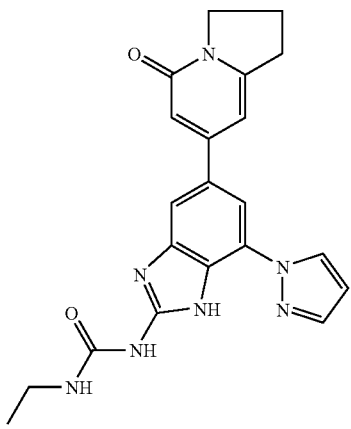
I-47
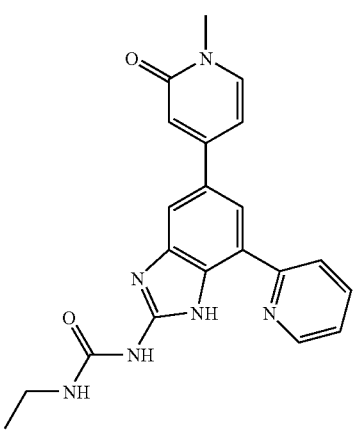
I-48
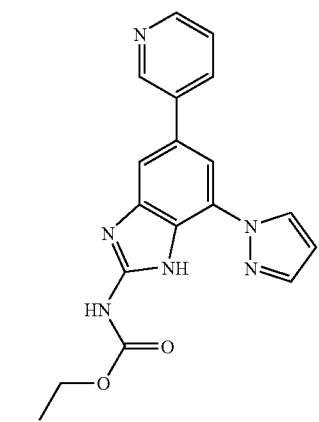
I-49
TABLE 2-continued
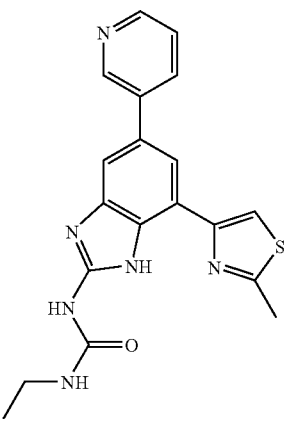
I-50
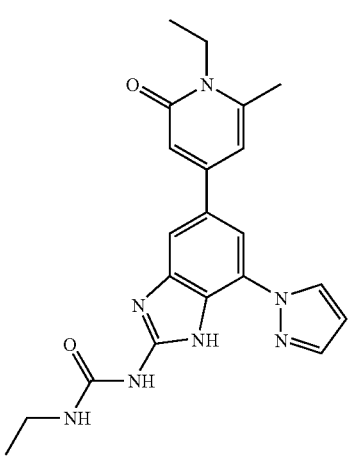
I-51
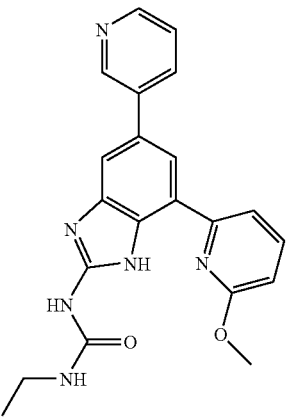
I-52

TABLE 2-continued
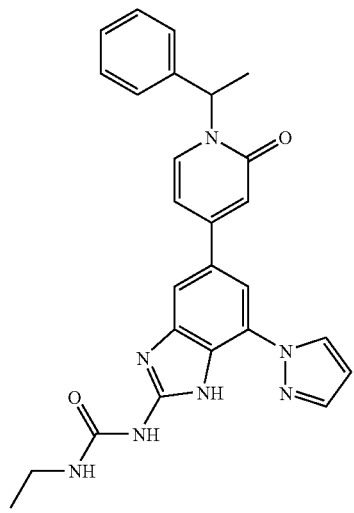
I-53
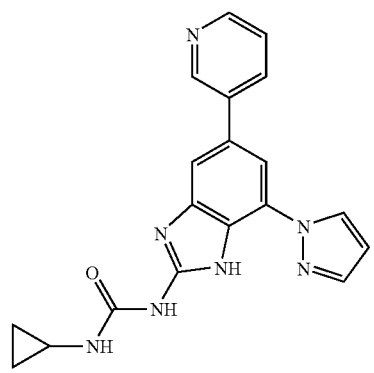
I-54
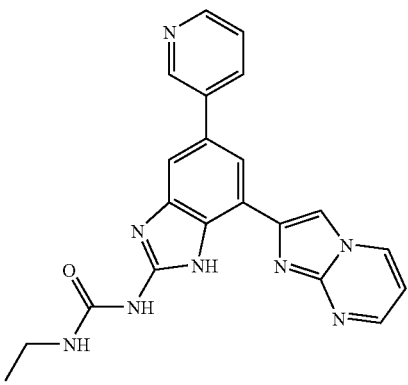
I-55
TABLE 2-continued

I-56
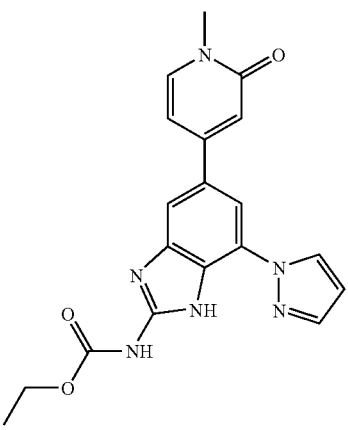
I-57
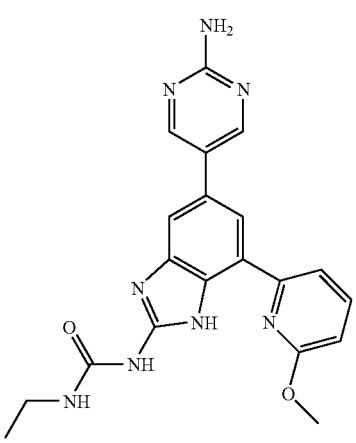
I-60

TABLE 2-continued
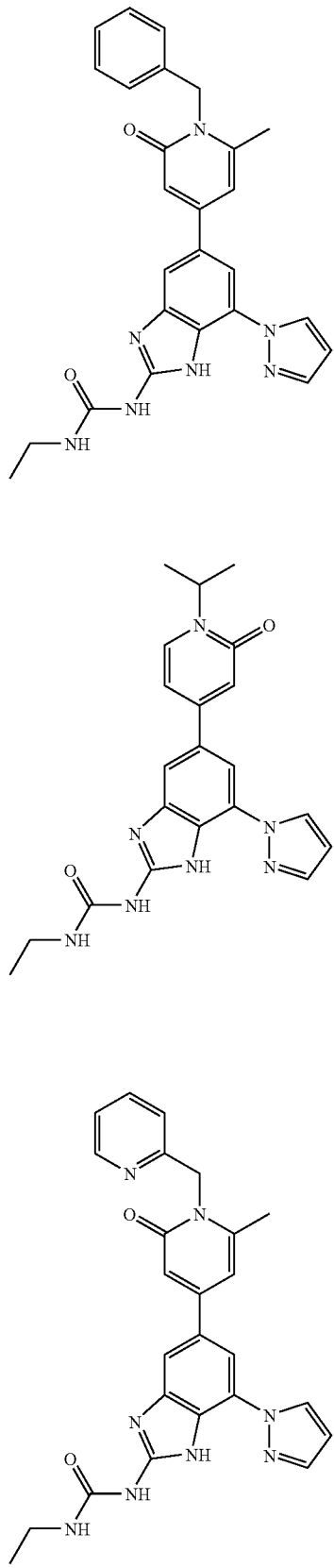
I-61
I-62
I-63
TABLE 2-continued
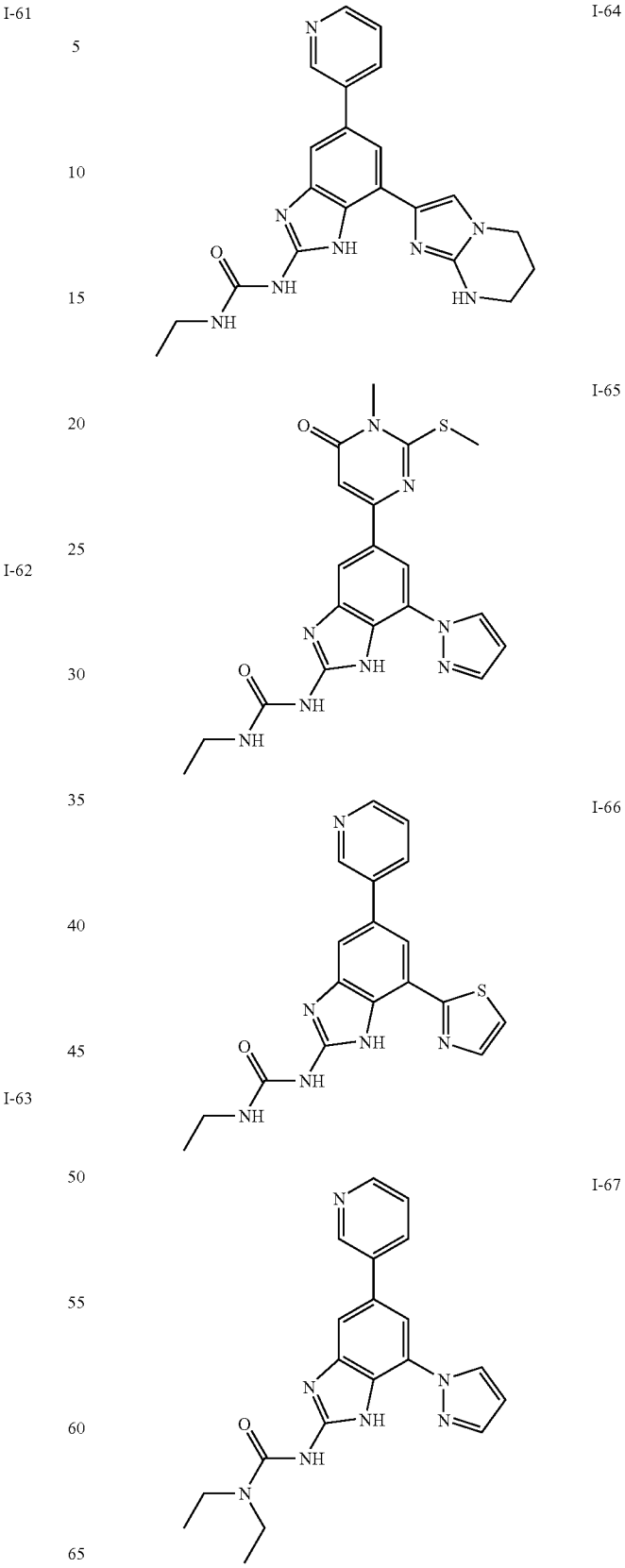
I-64
I-65
I-66
I-67

TABLE 2-continued
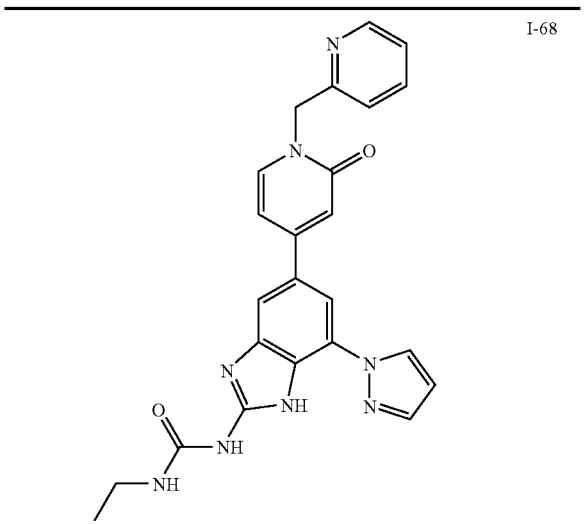
I-68
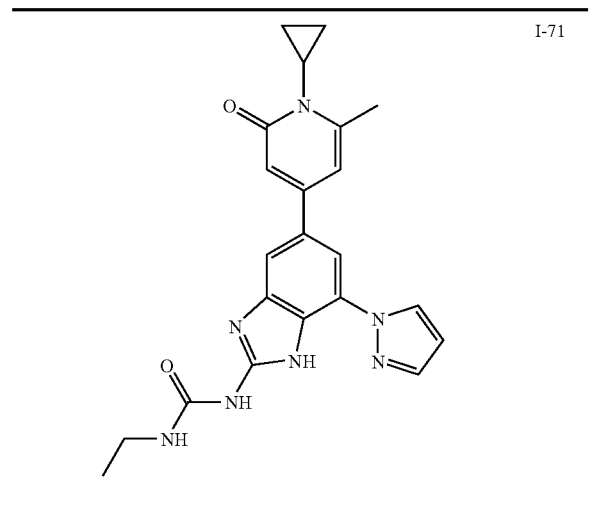
I-71
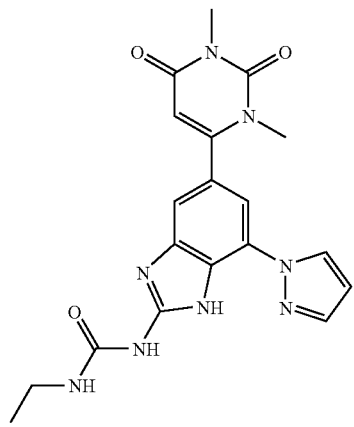
I-69
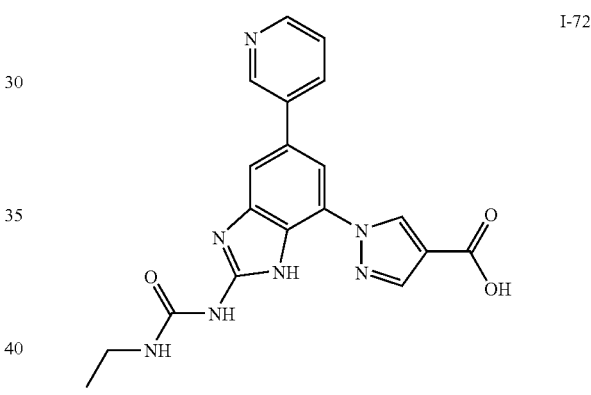
I-72
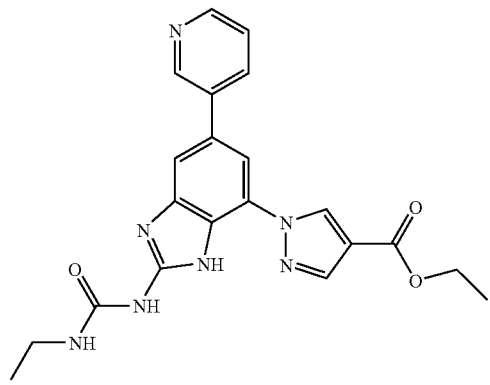
I-70
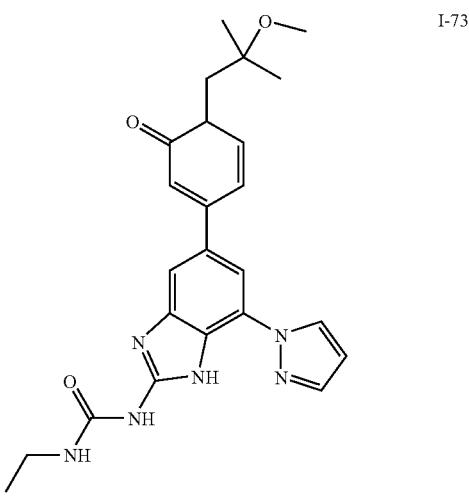
I-73

TABLE 2-continued
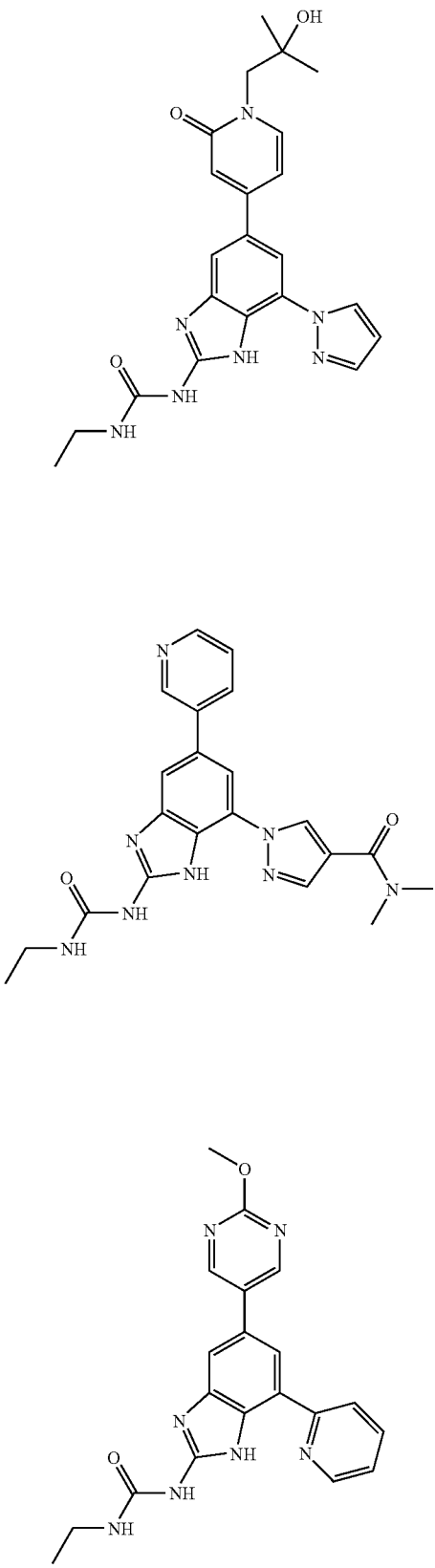
I-74
I-75
I-76
TABLE 2-continued
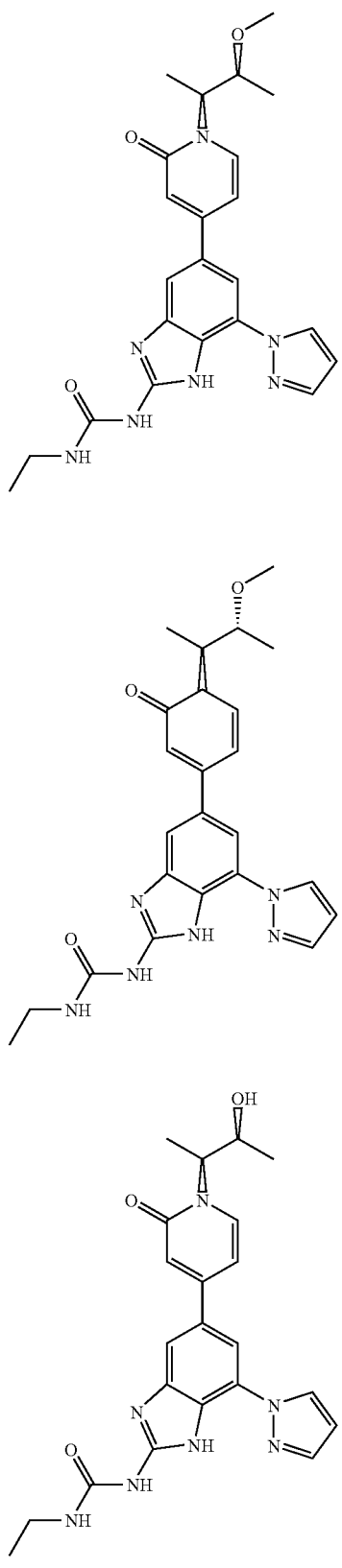
I-77
I-78
I-79

TABLE 2-continued
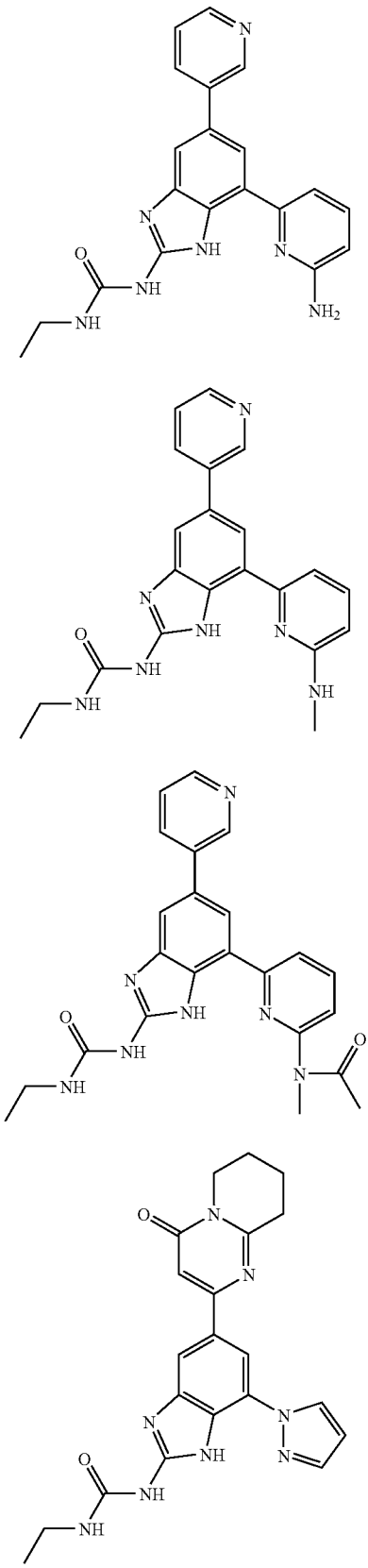
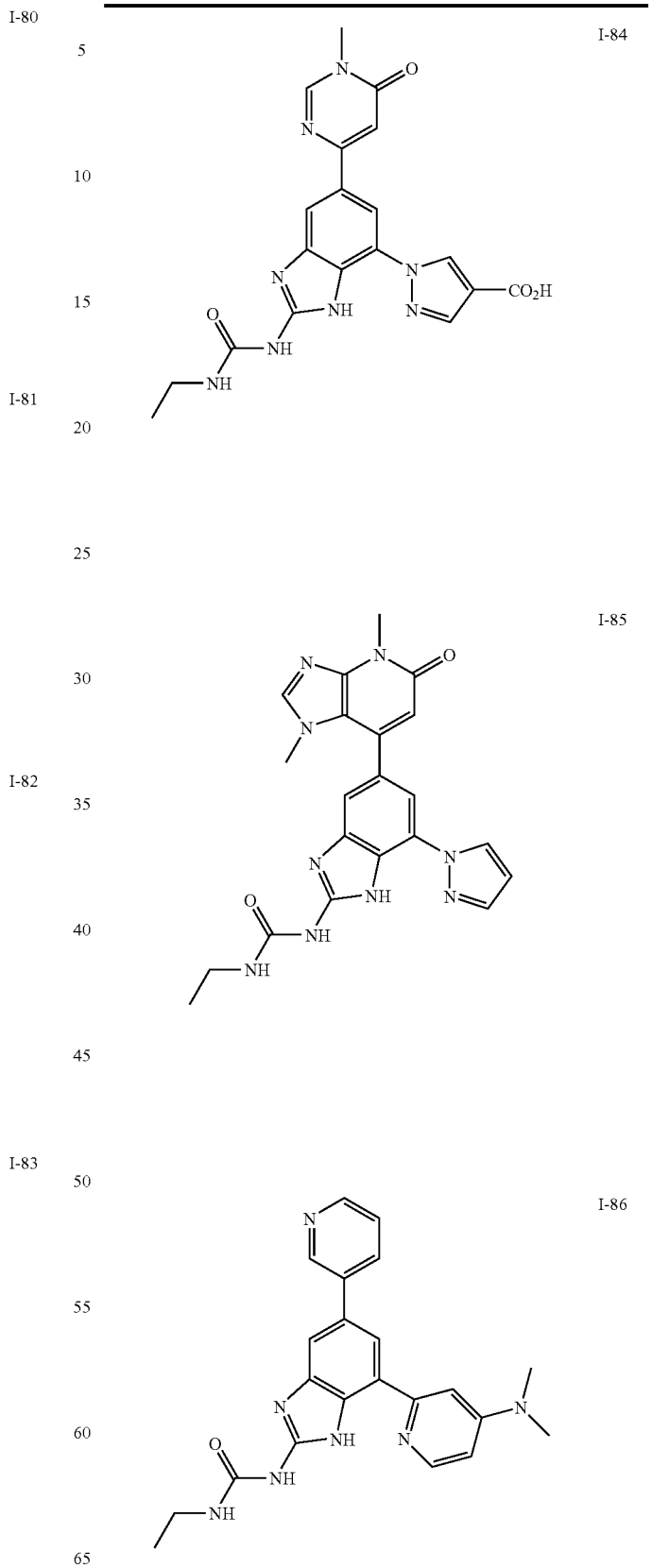

TABLE 2-continued
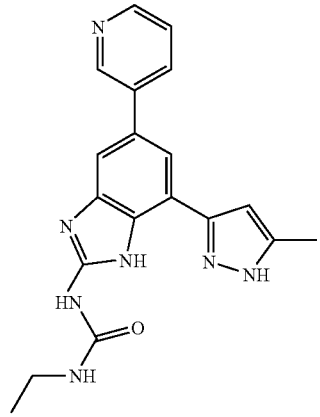
I-87
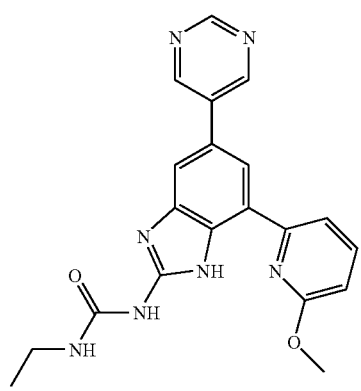
I-88
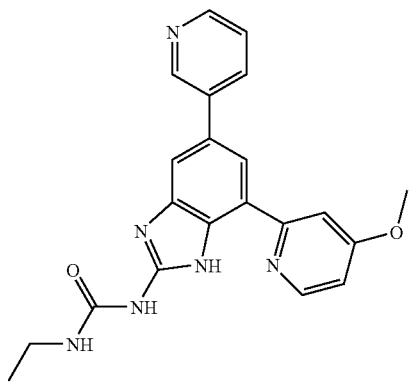
I-89
TABLE 2-continued
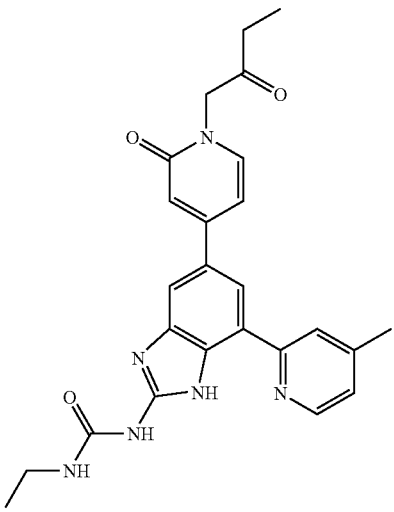
I-90
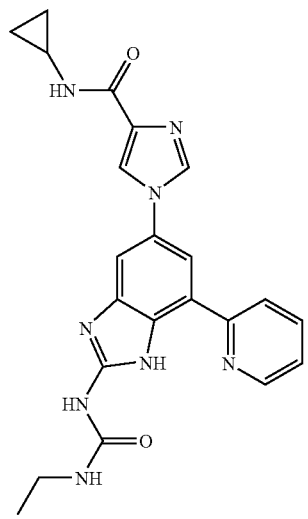
I-91
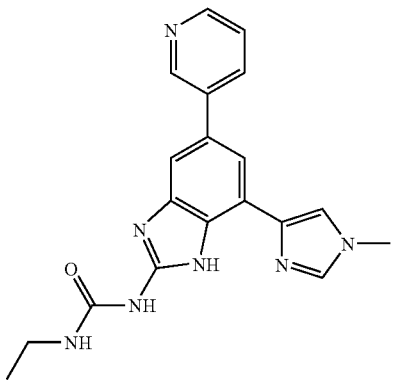
I-92

TABLE 2-continued
I-93
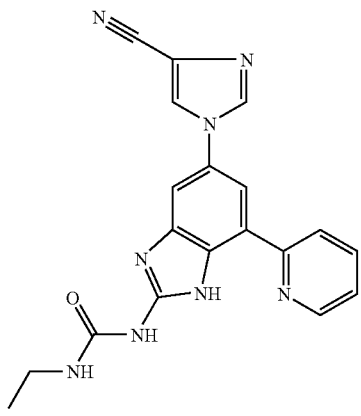
I-94
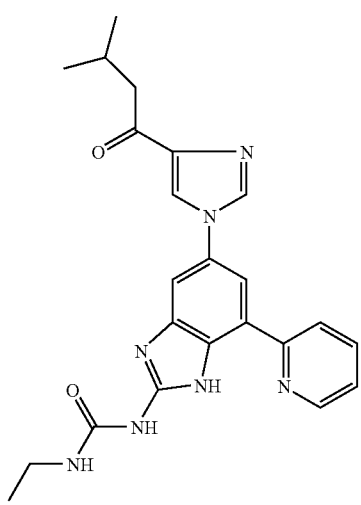
I-95
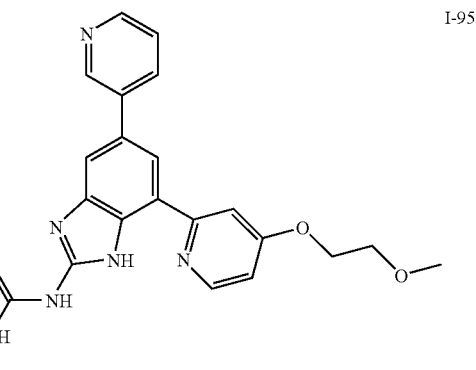
TABLE 2-continued
I-96
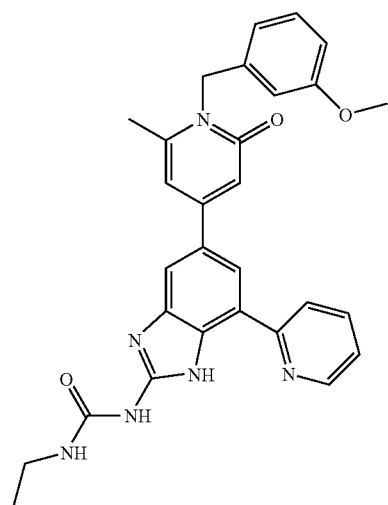
I-97
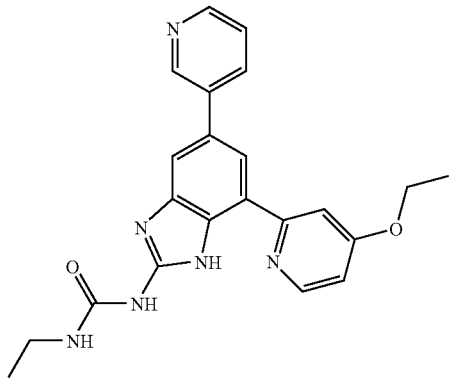
I-98
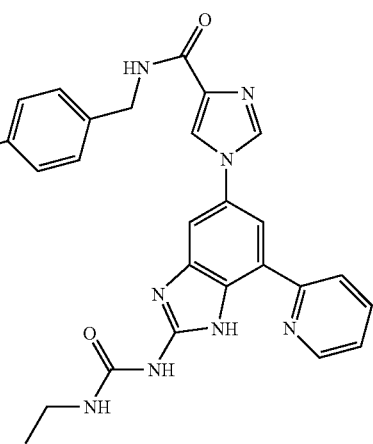

TABLE 2-continued
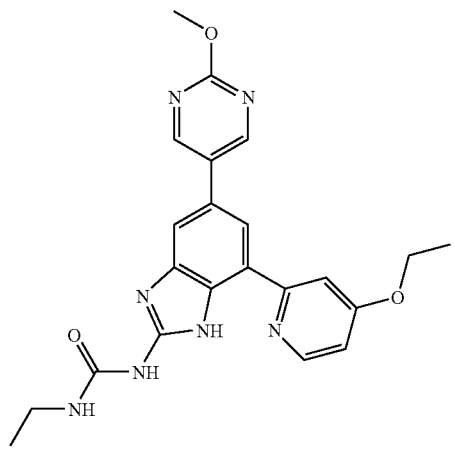
I-99
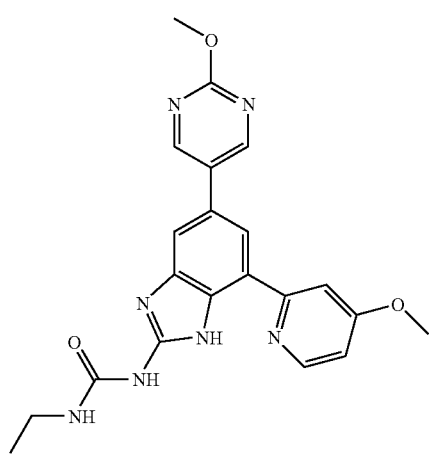
I-100
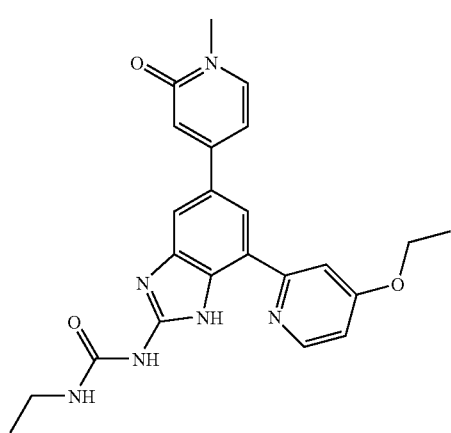
I-101
TABLE 2-continued
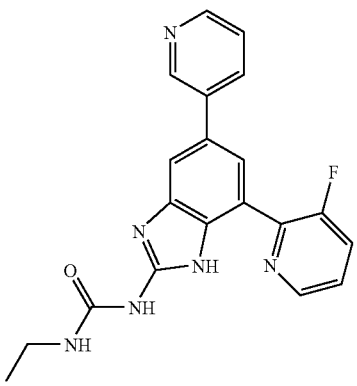
I-102
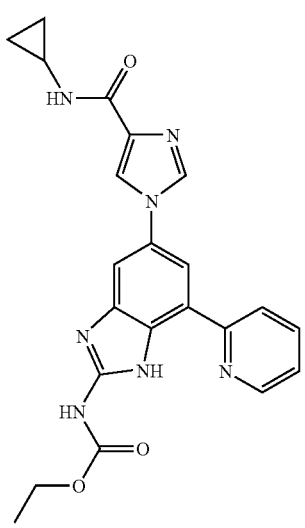
I-103
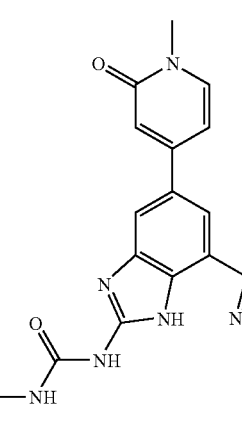
I-104

TABLE 2-continued
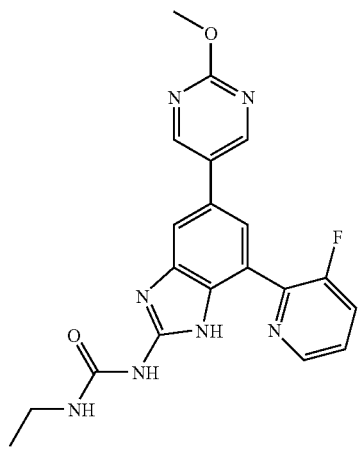
I-105
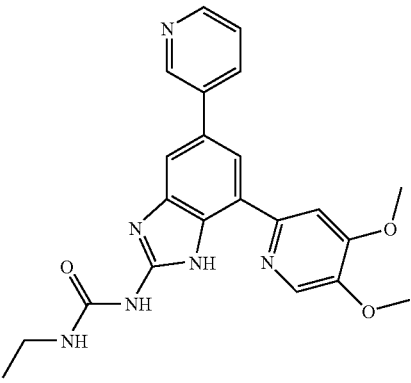
I-108
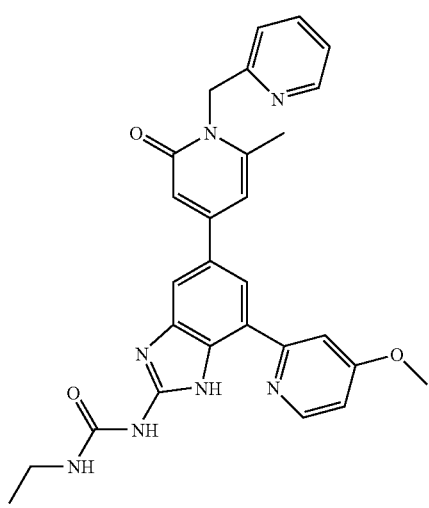
I-106
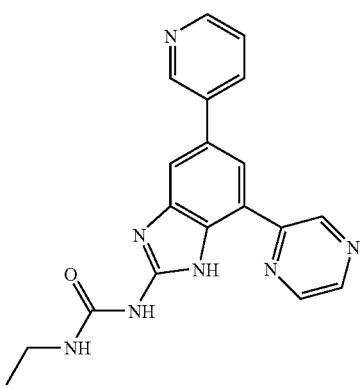
I-109
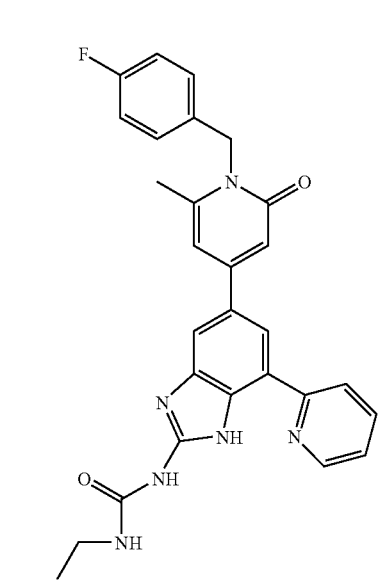
I-107
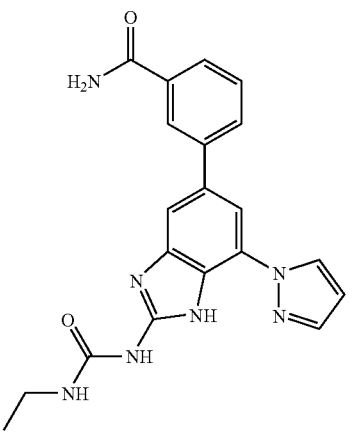
I-110

TABLE 2-continued
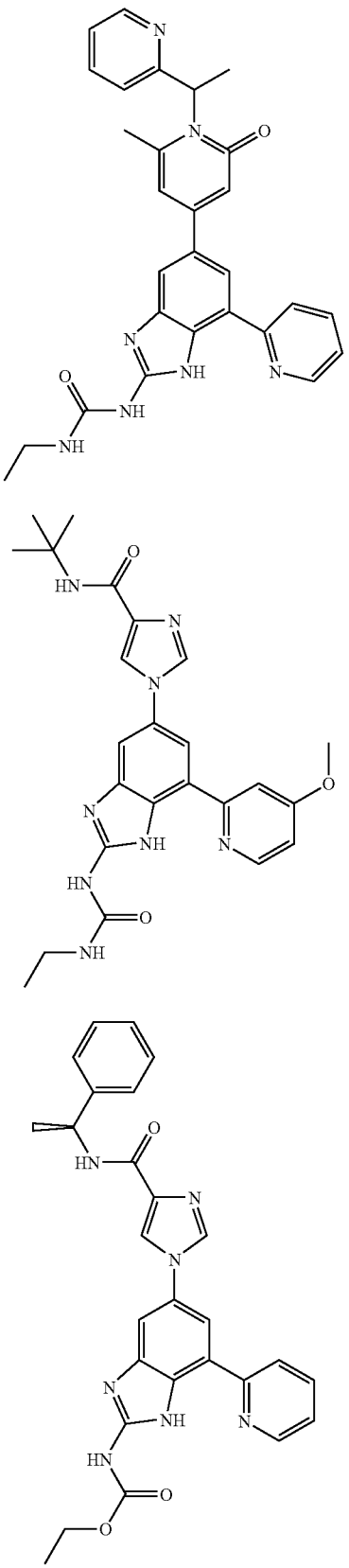
I-111
I-112
I-113
TABLE 2-continued
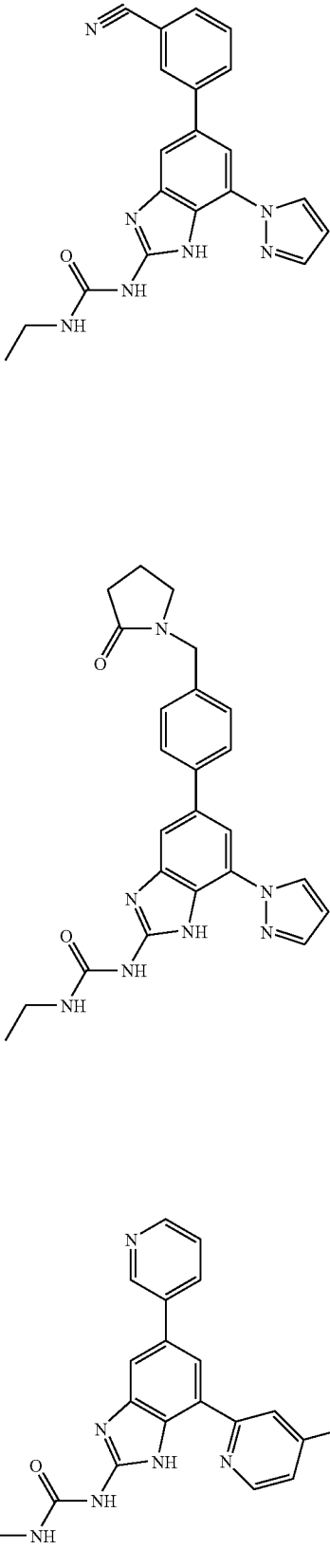
I-114
I-115
I-116

TABLE 2-continued
I-117
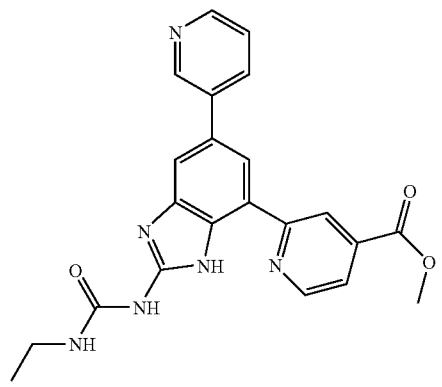
I-118
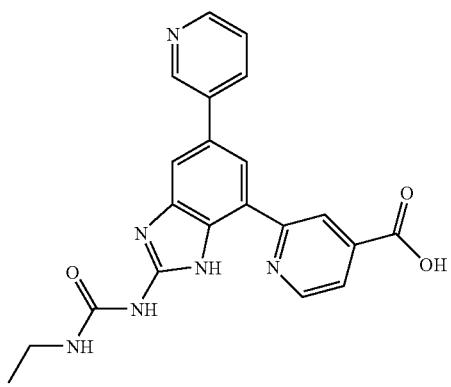
I-119
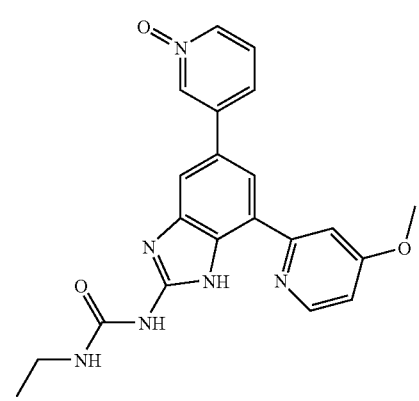
I-120
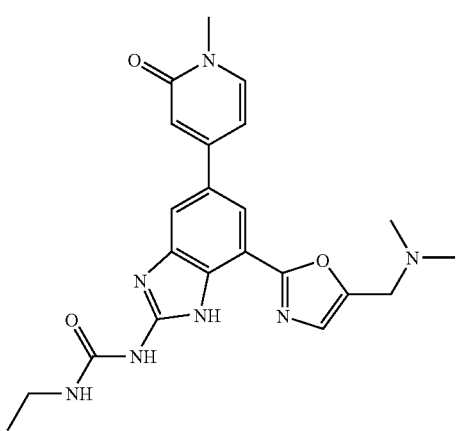
TABLE 2-continued
I-121
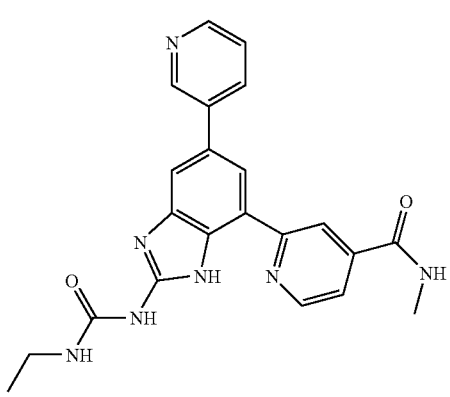
I-122
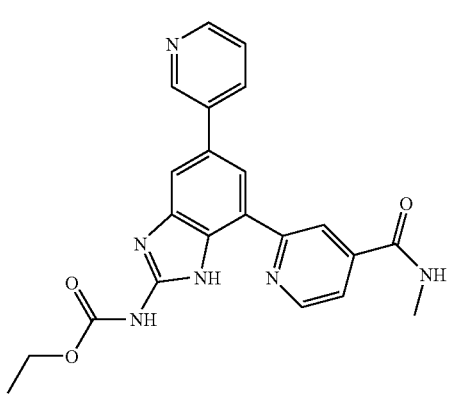
I-123
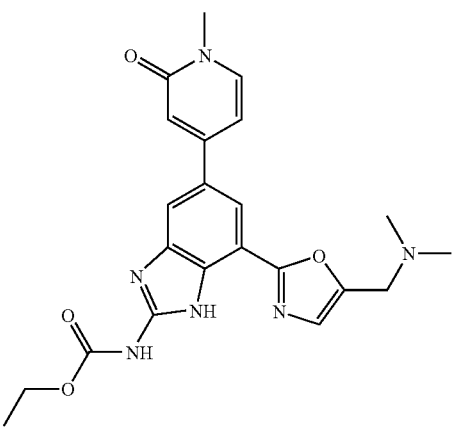

TABLE 2-continued
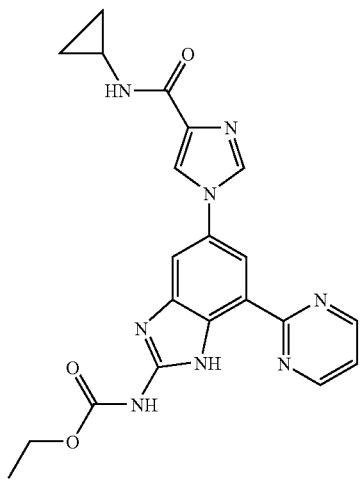
I-124
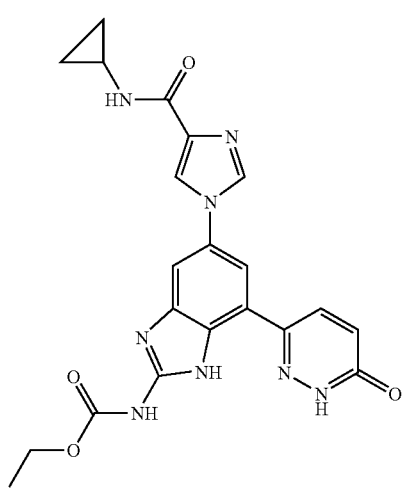
I-125
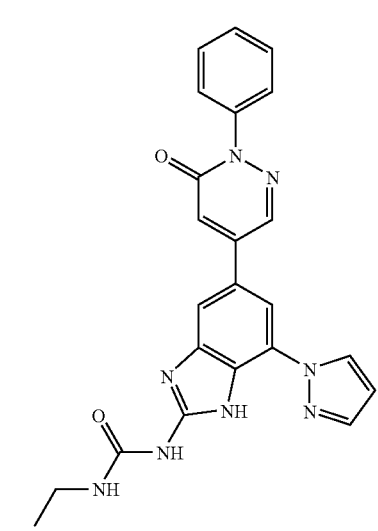
I-126
TABLE 2-continued
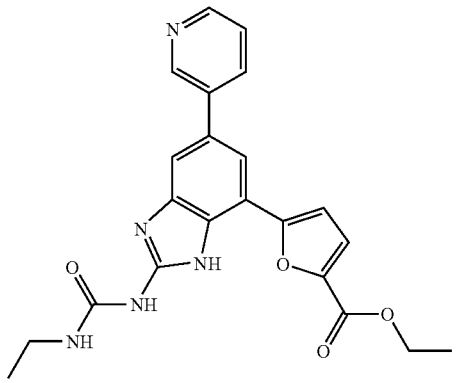
I-127
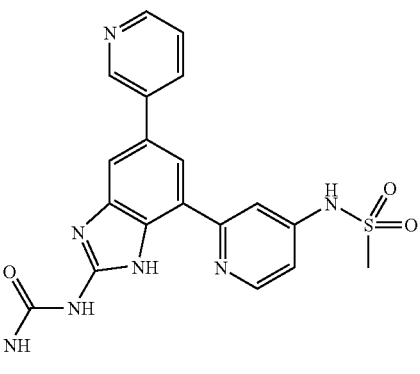
I-128
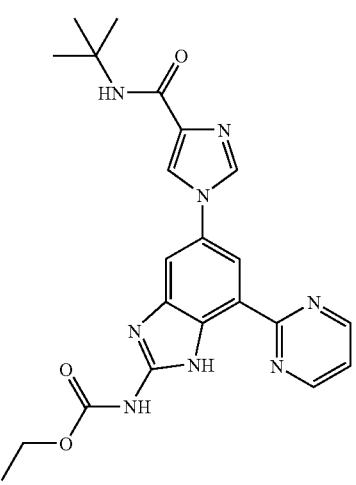
I-129

TABLE 2-continued
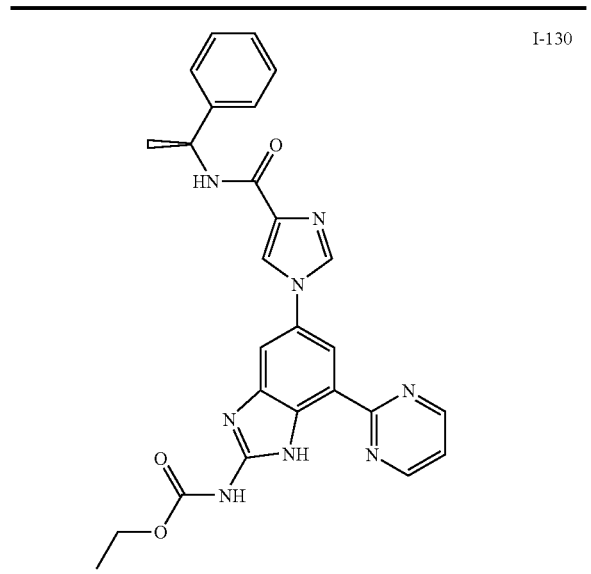
I-130
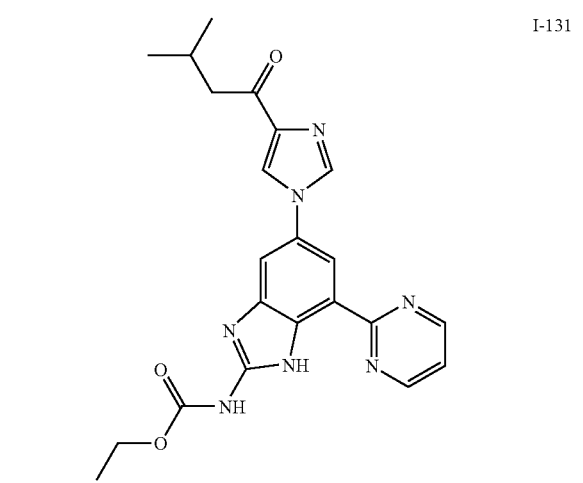
I-131
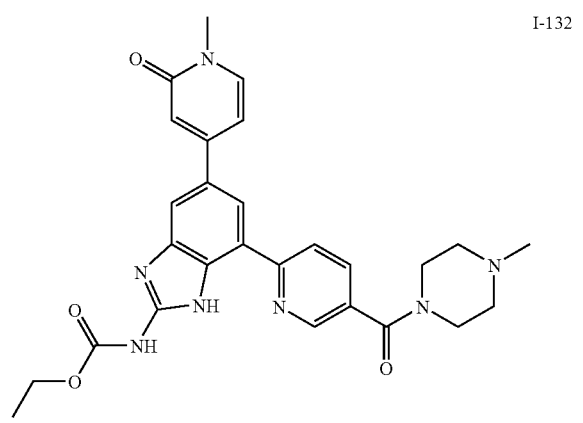
I-132
TABLE 2-continued
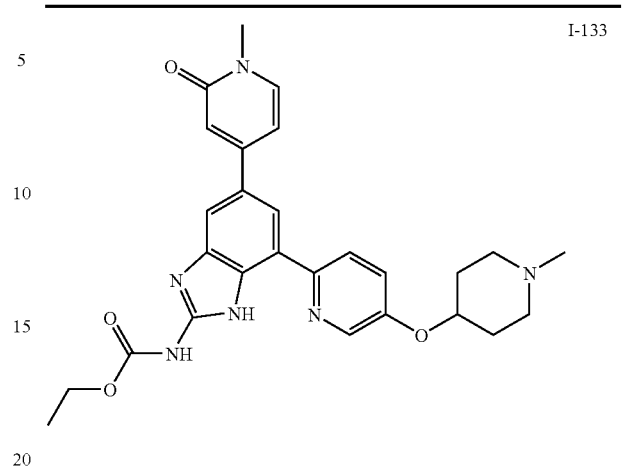
I-133
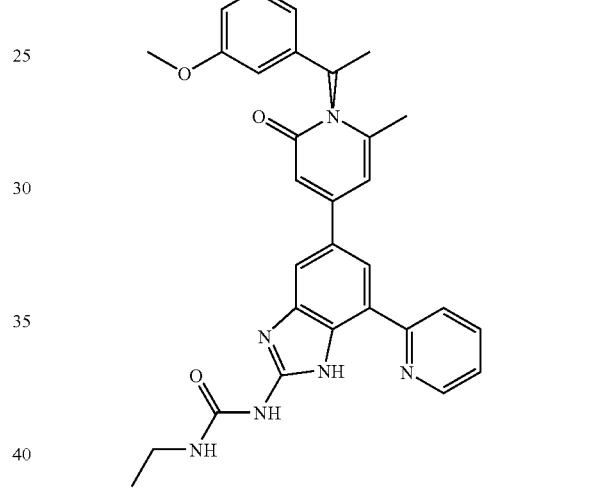
I-134
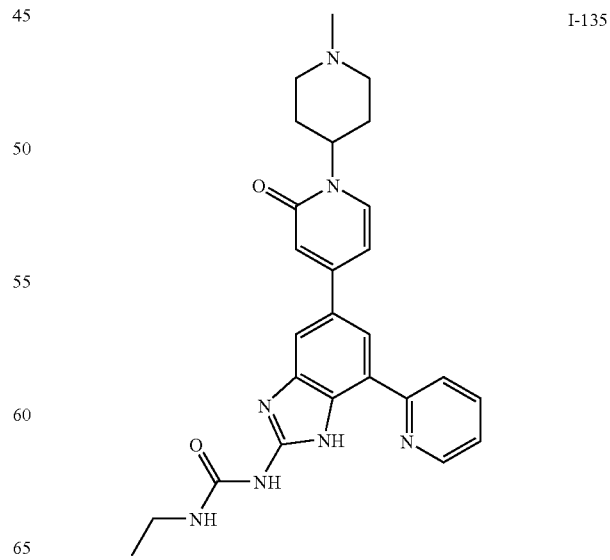
I-135

TABLE 2-continued
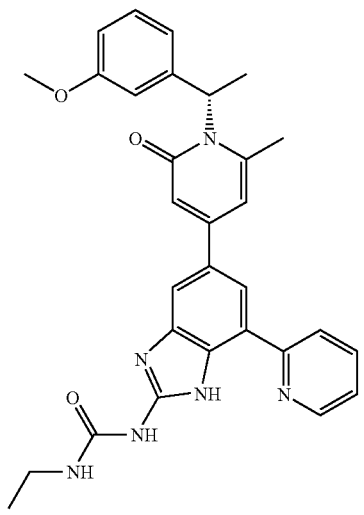
I-136
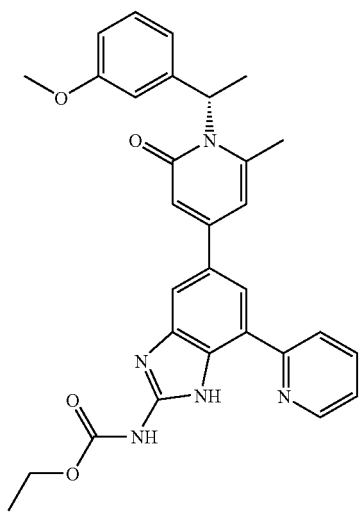
I-137
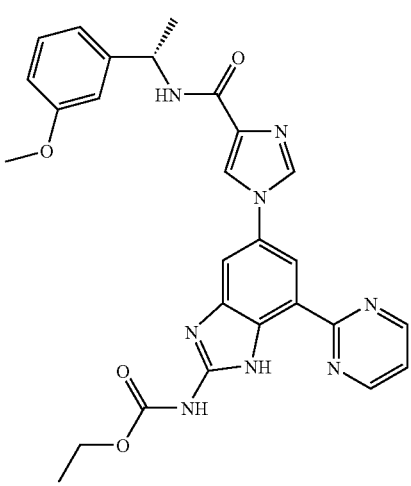
I-138
TABLE 2-continued
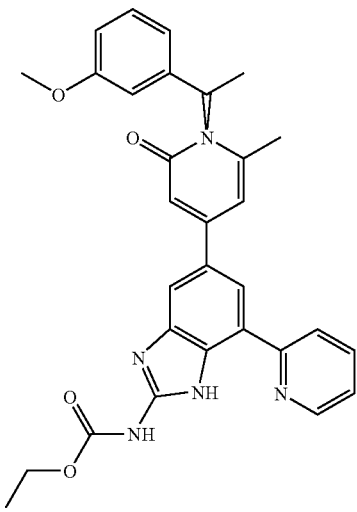
I-139
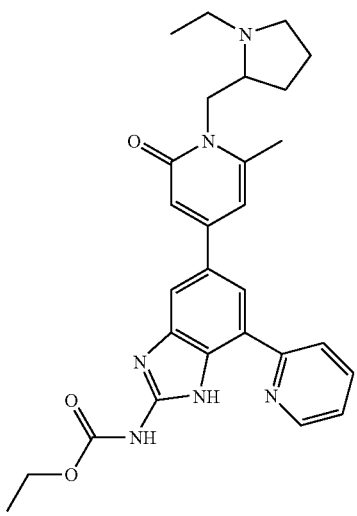
I-140
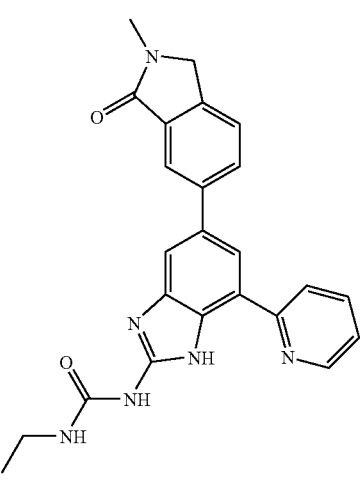
I-141

TABLE 2-continued
I-142
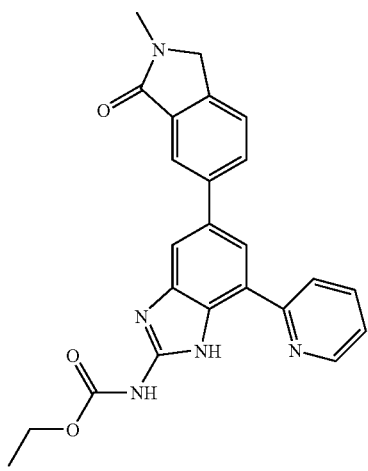
I-143
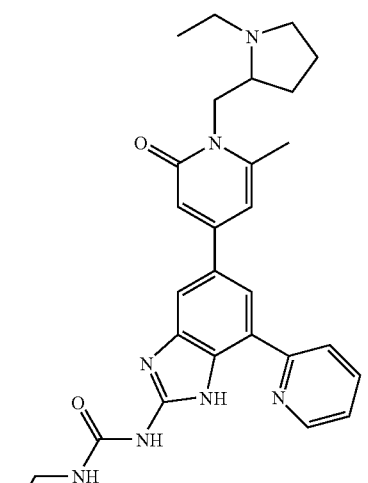
I-144
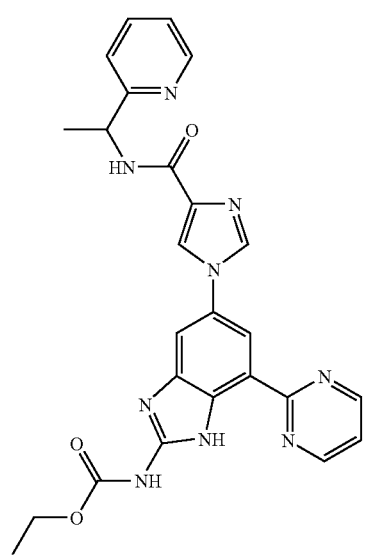
TABLE 2-continued
I-145
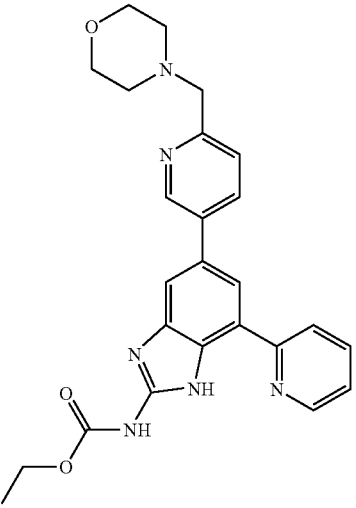
I-146
I-147
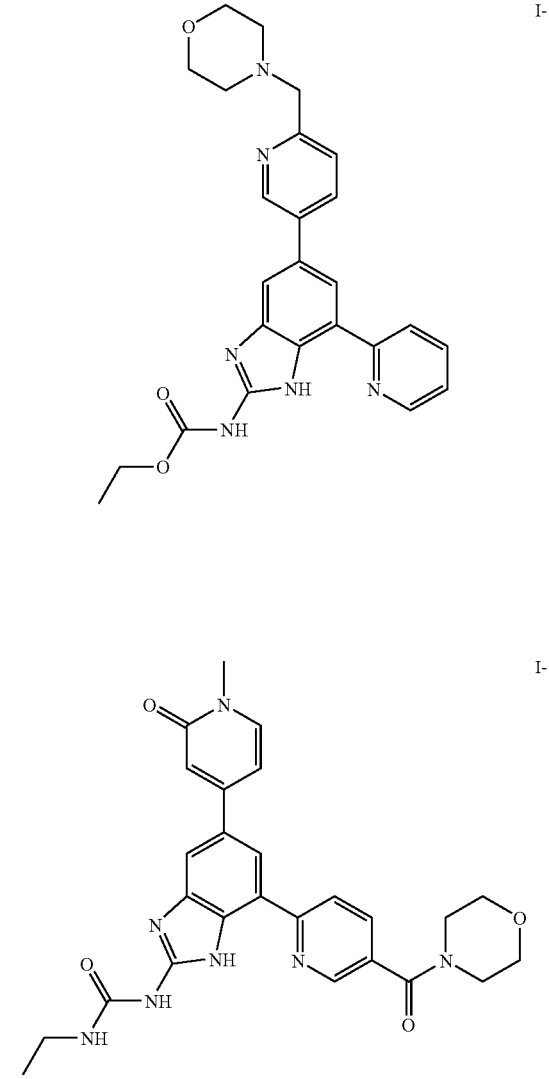

TABLE 2-continued
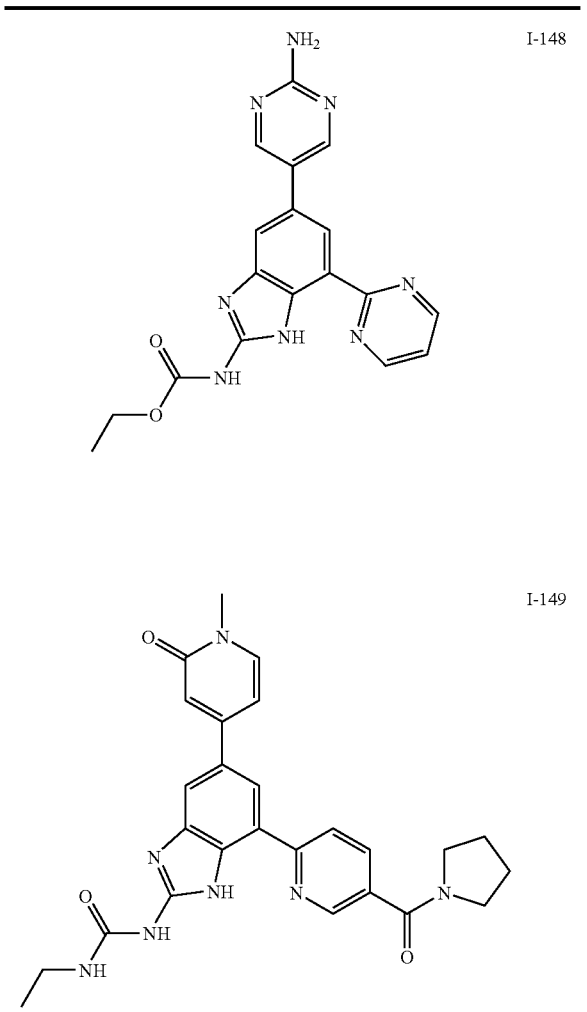
I-148
I-149
I-150
TABLE 2-continued
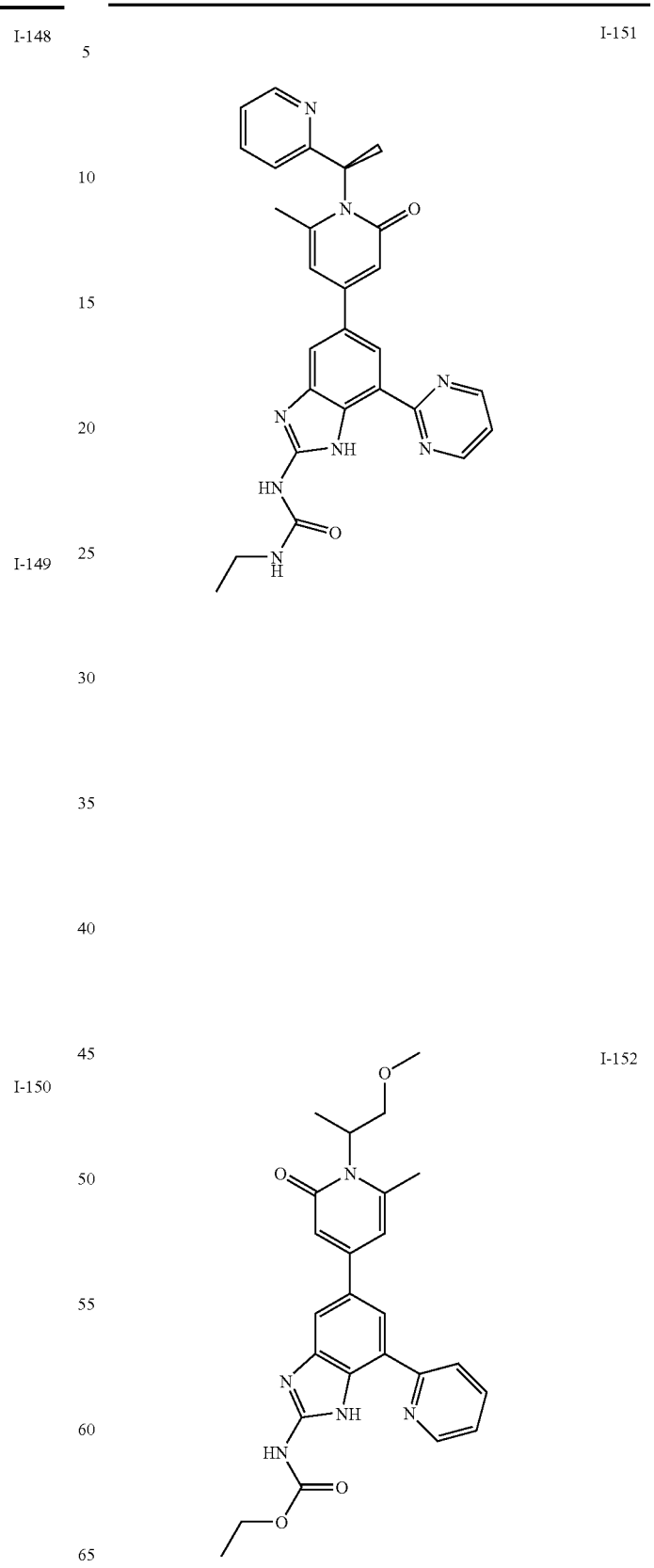
I-151
I-152

TABLE 2-continued
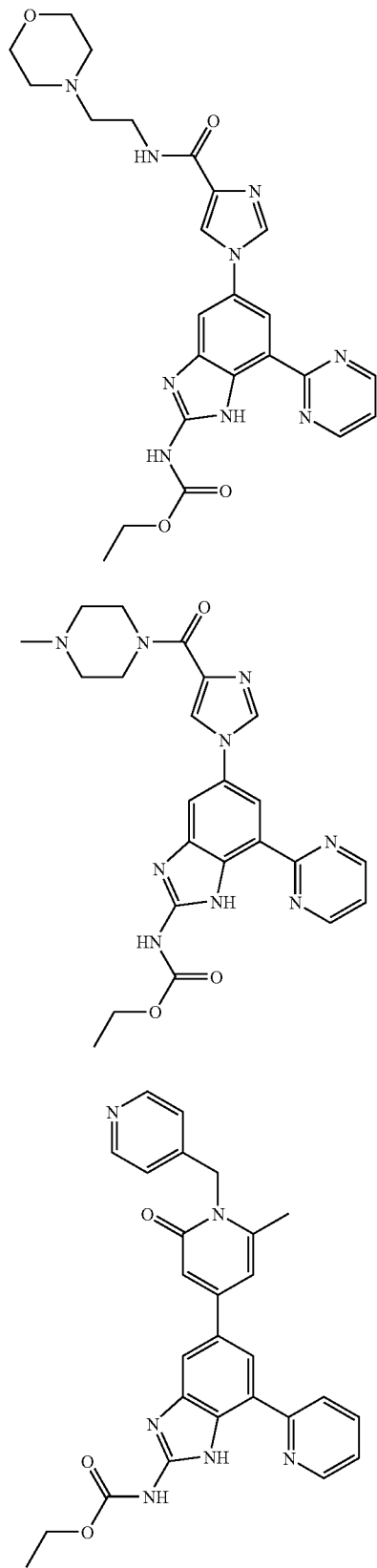
I-153
I-154
I-155
TABLE 2-continued
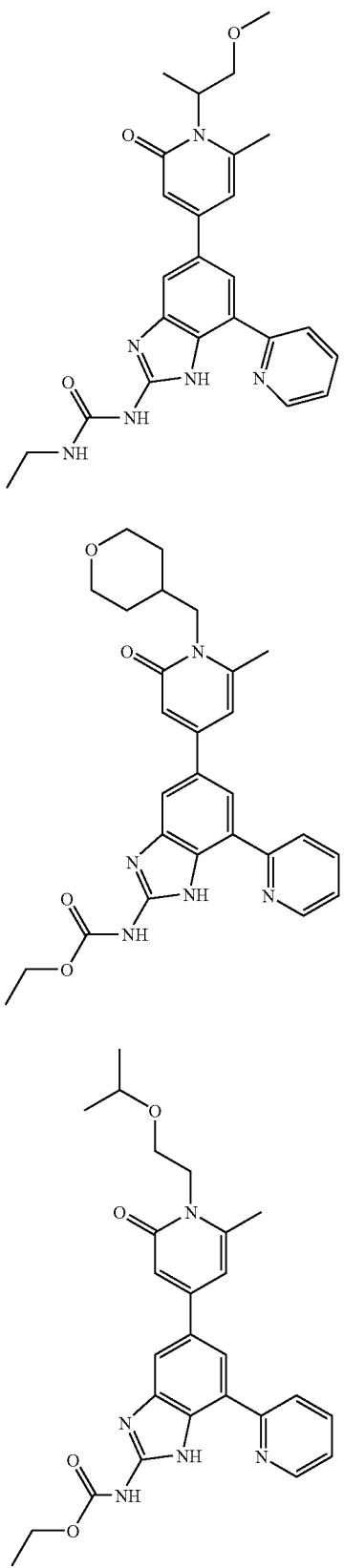
I-156
I-157
I-158

TABLE 2-continued
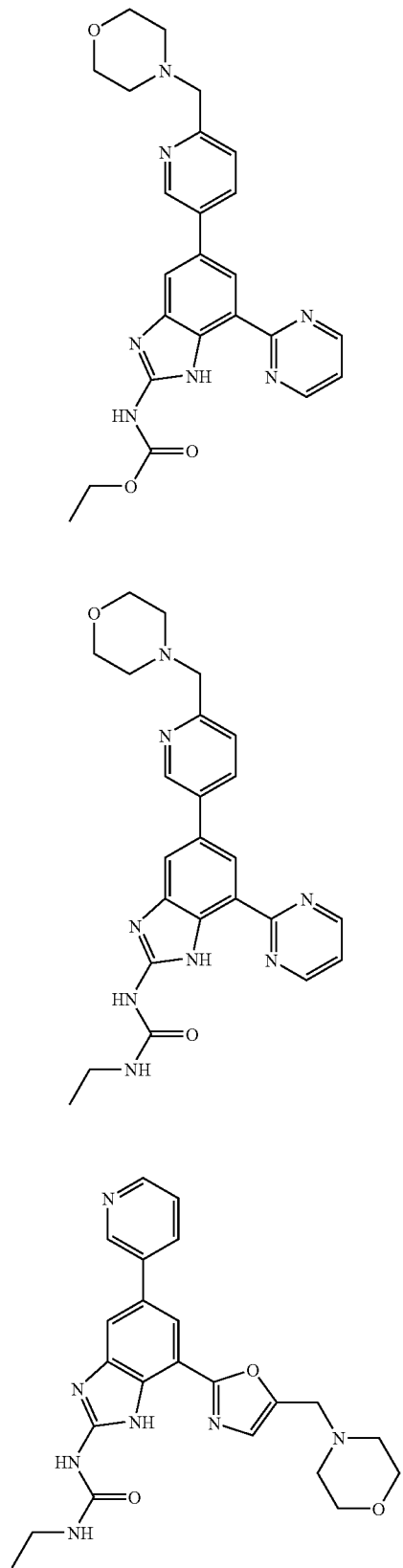
I-159
I-160
I-161
TABLE 2-continued
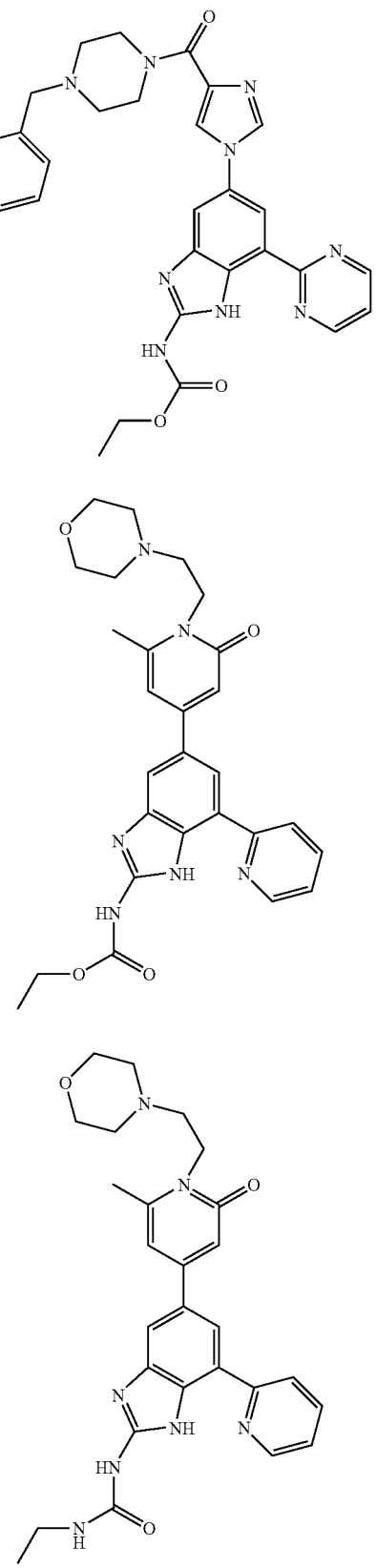
I-162
I-163
I-164

TABLE 2-continued
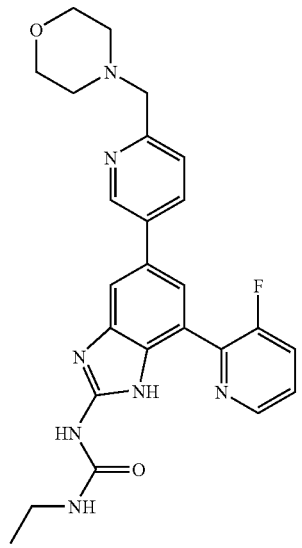
I-165
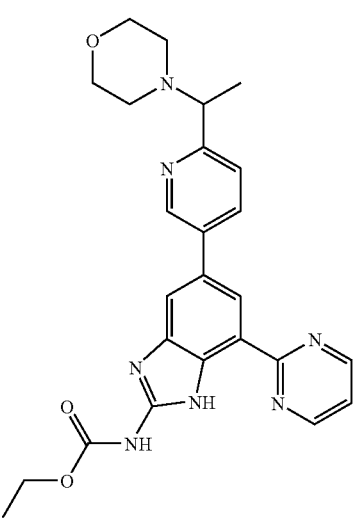
I-168
I-166
I-169
I-167
I-170
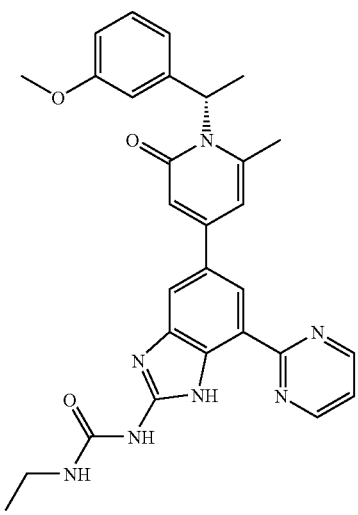

TABLE 2-continued
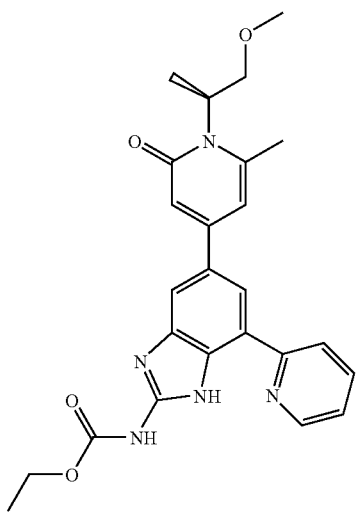
I-171
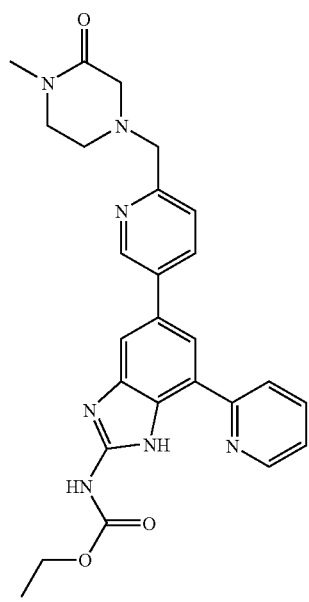
I-173
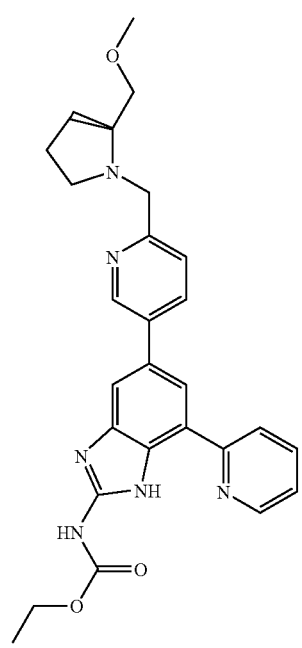
I-172
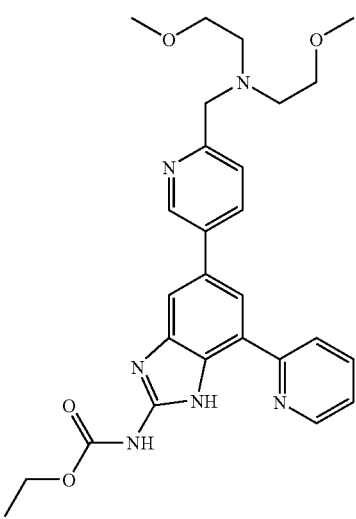
I-174

TABLE 2-continued
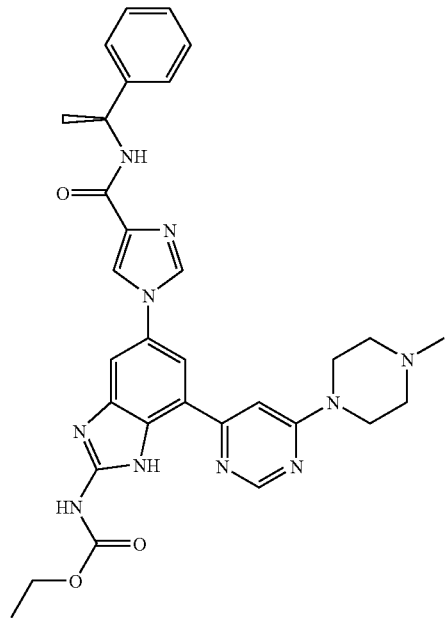
I-175
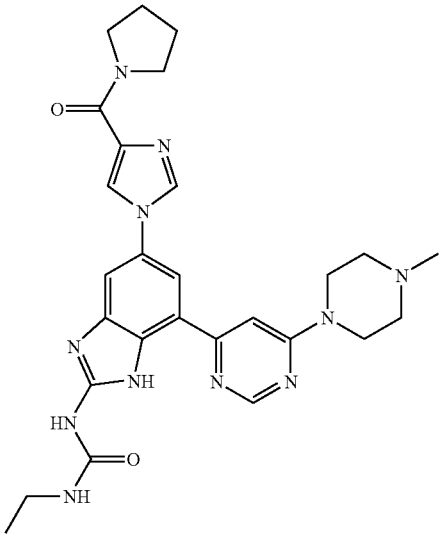
I-177
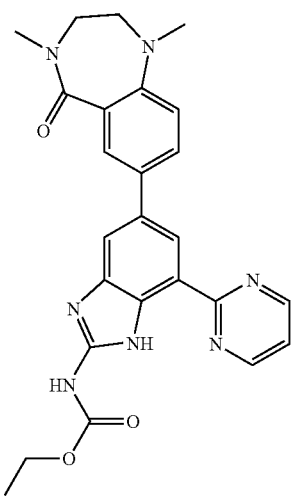
I-178
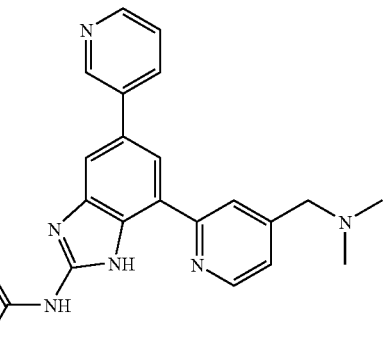
I-179
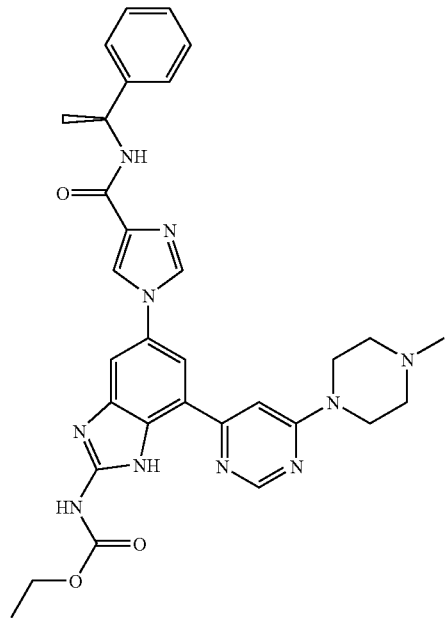
I-176

TABLE 2-continued
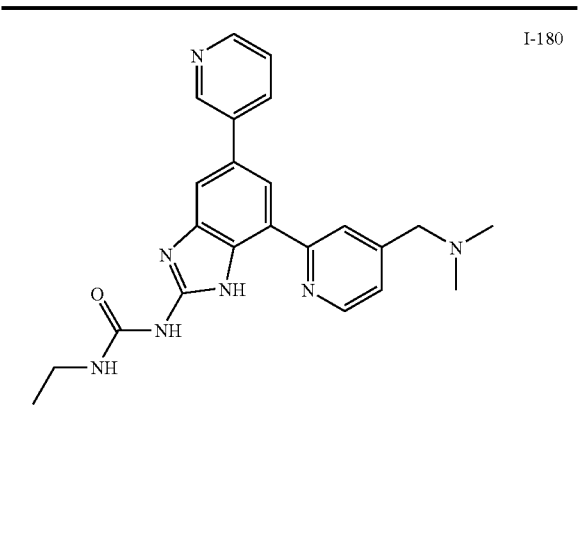
I-180
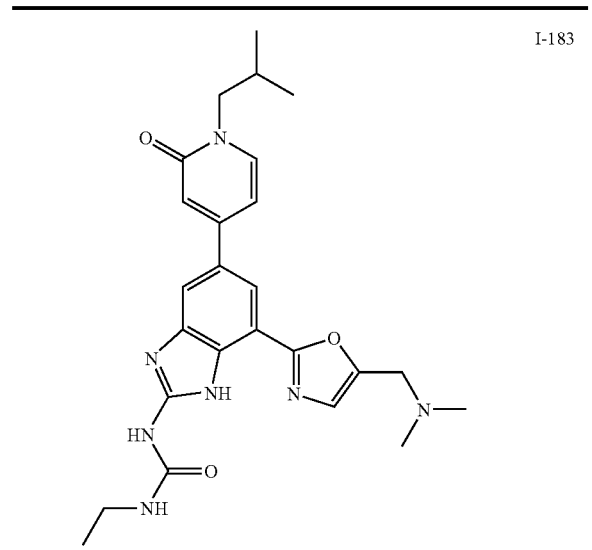
I-183
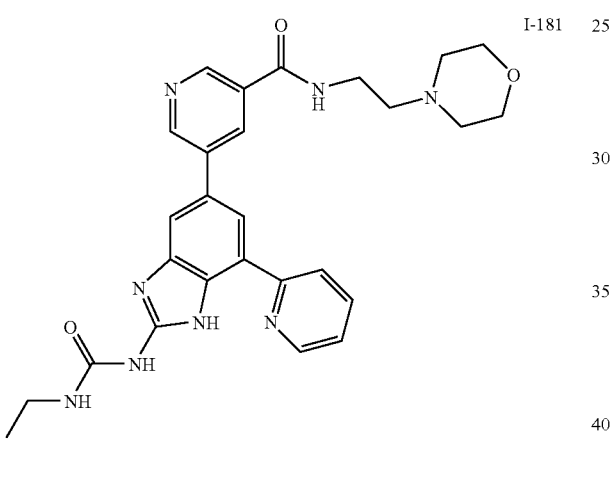
I-181
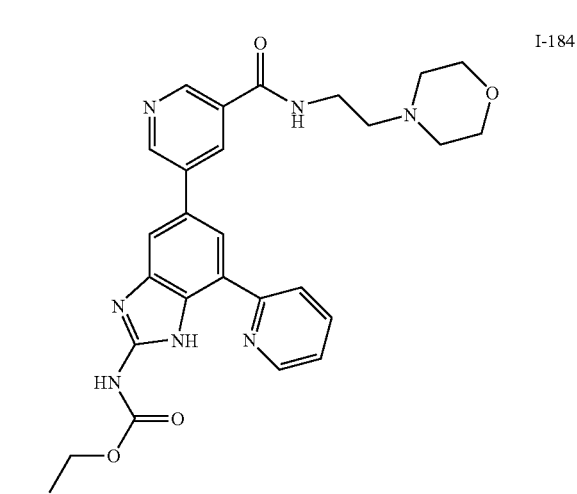
I-184
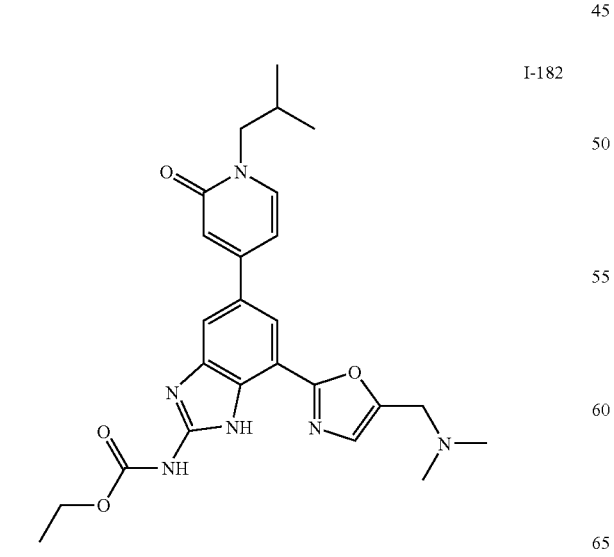
I-182
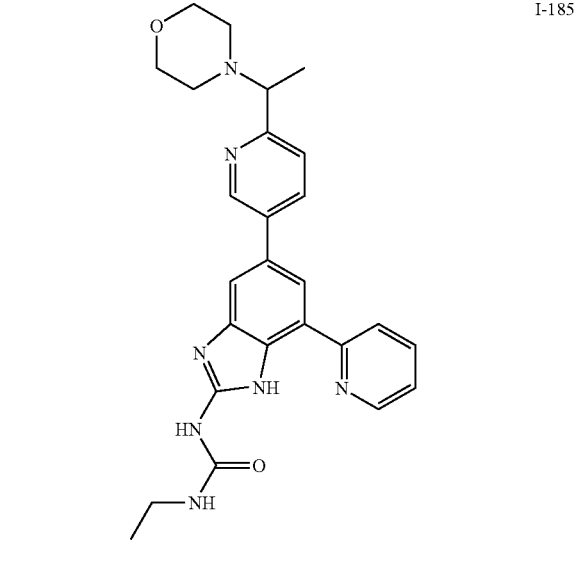
I-185

TABLE 2-continued
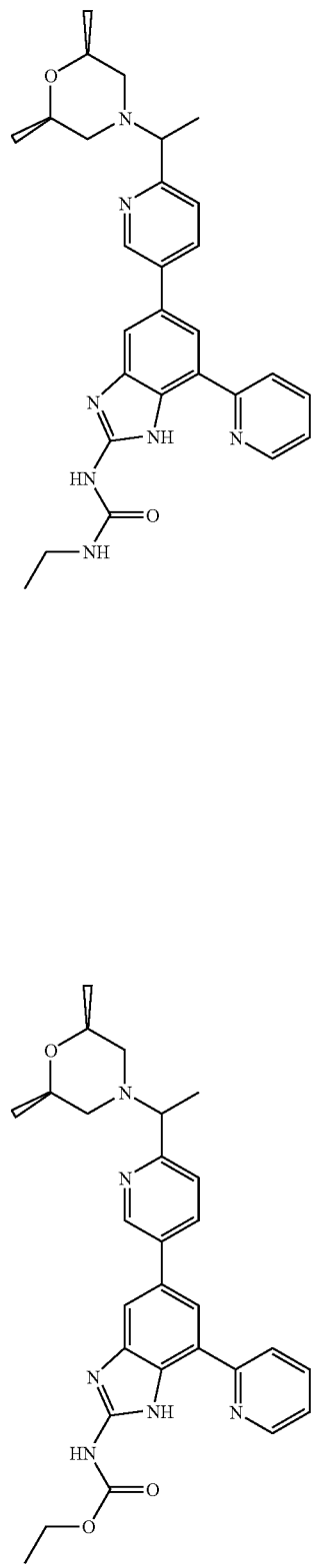
I-186
I-187
TABLE 2-continued
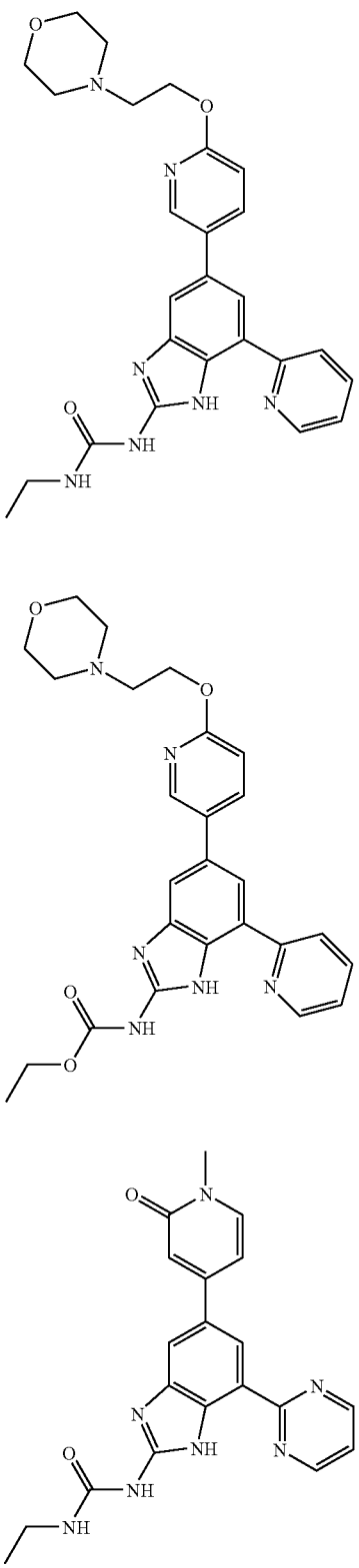
I-188
I-189
I-190

TABLE 2-continued
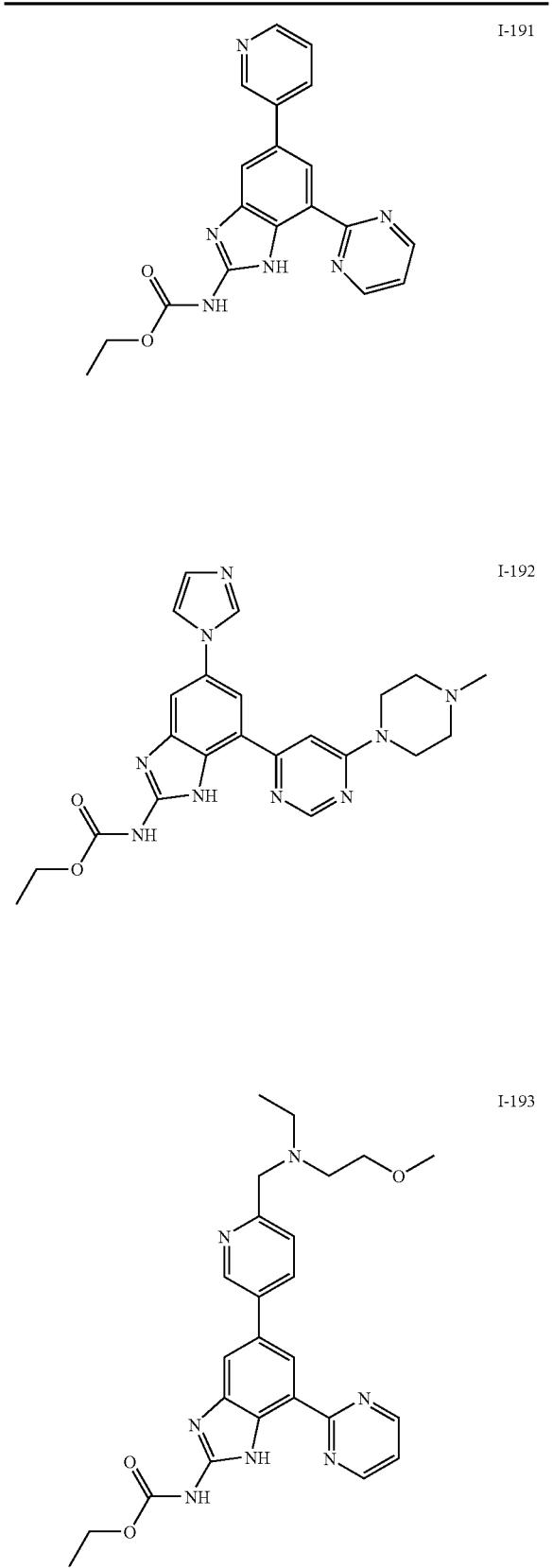
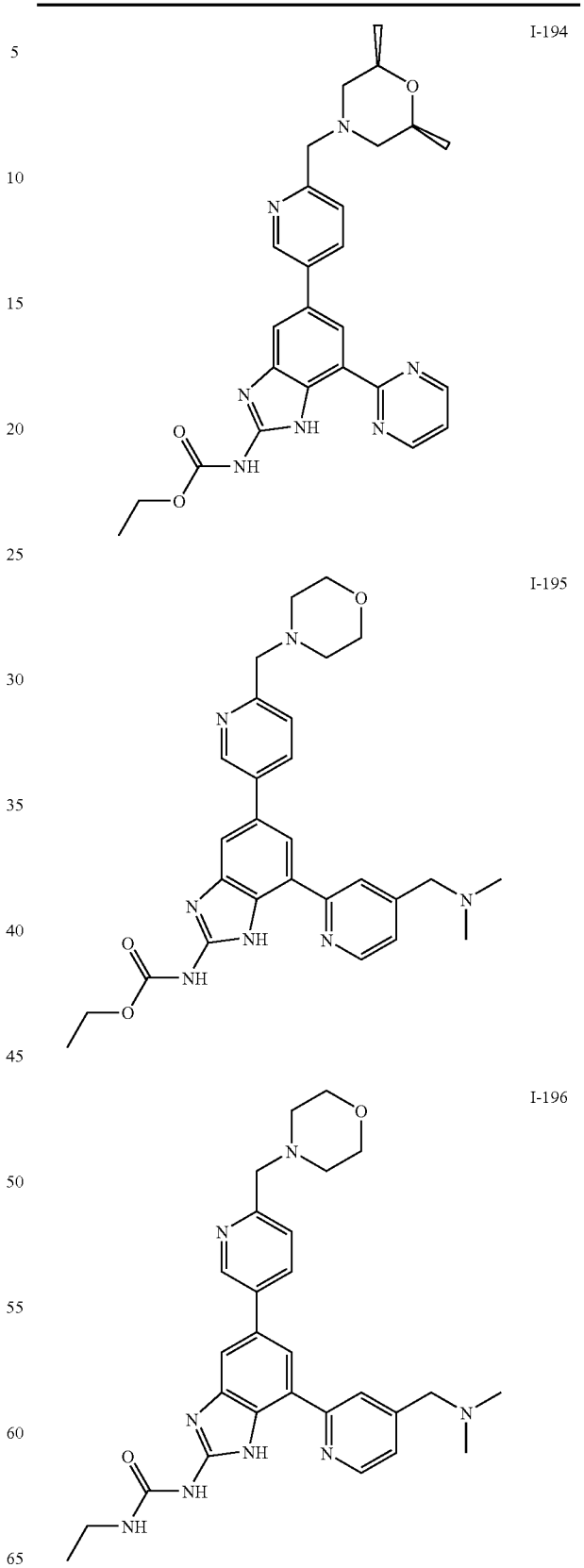

TABLE 2-continued
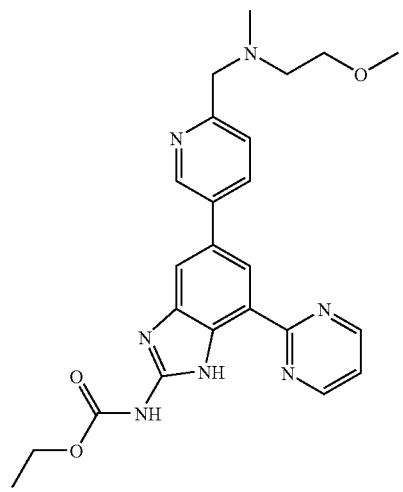
I-197
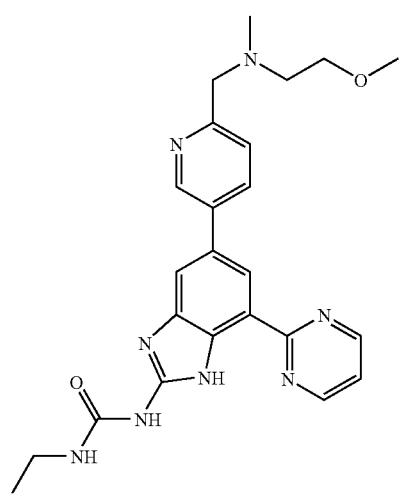
I-198
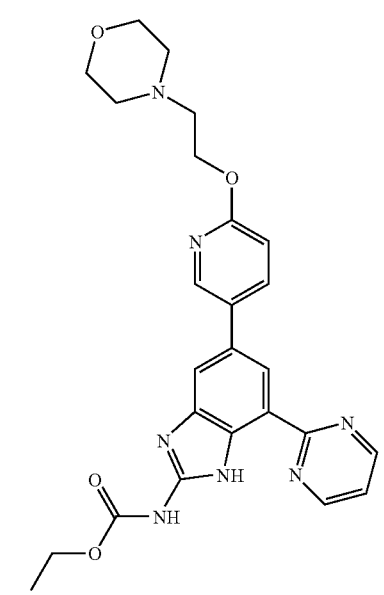
I-199
TABLE 2-continued
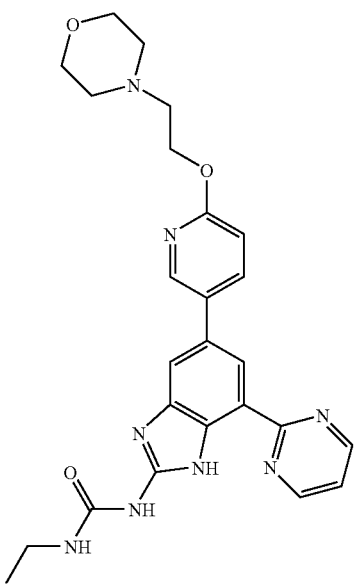
I-200
I-201

TABLE 2-continued
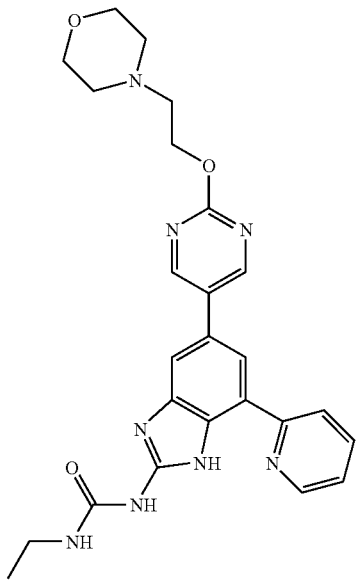
I-202
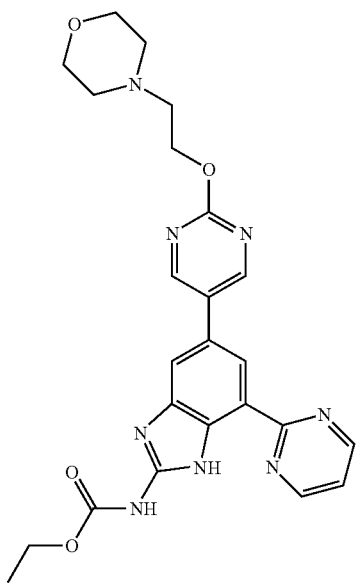
I-203
TABLE 2-continued
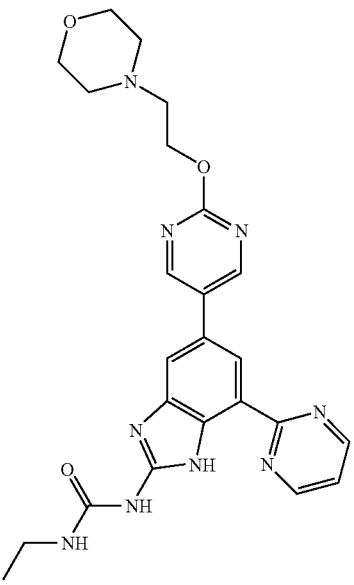
I-204
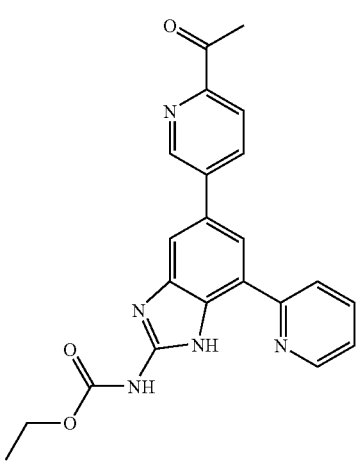
I-205
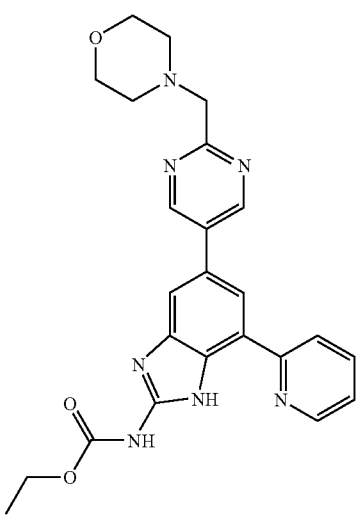
I-206

TABLE 2-continued
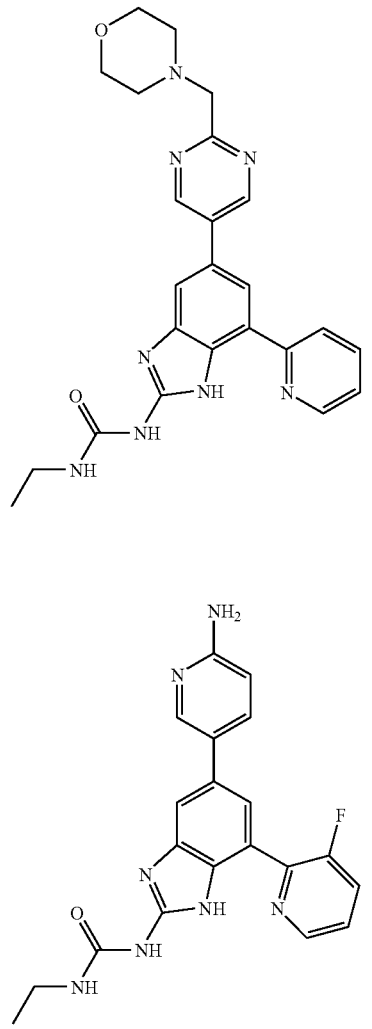
I-207
I-208
I-209
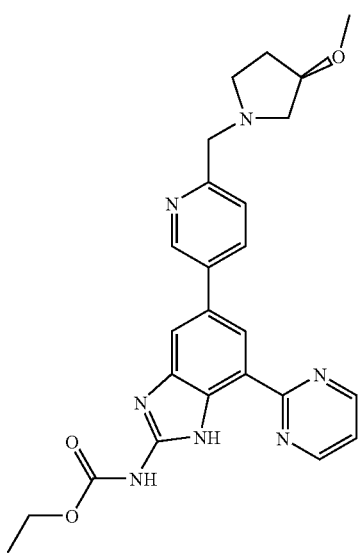
I-210
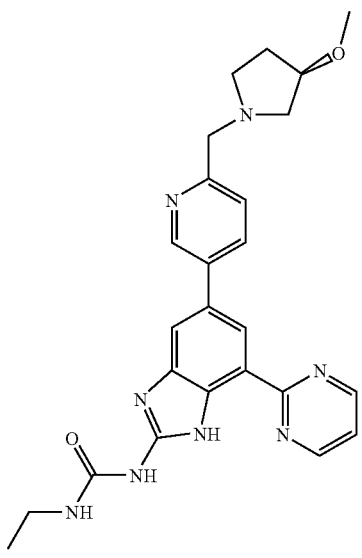
I-211

TABLE 2-continued
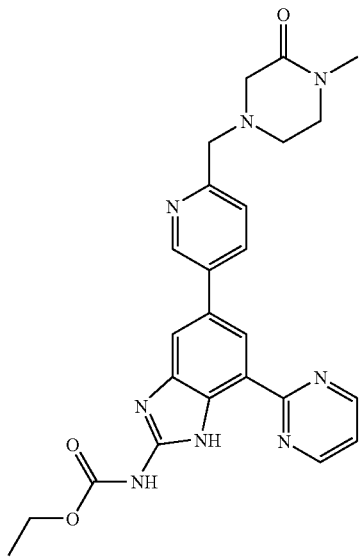
I-212
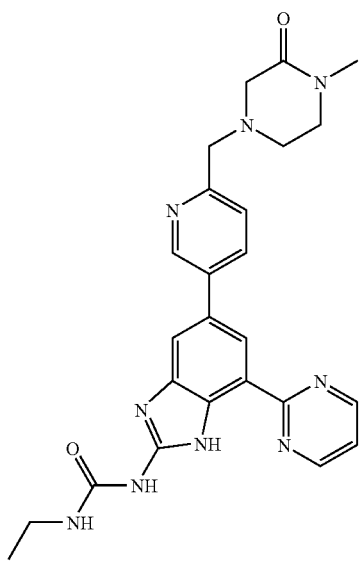
I-212
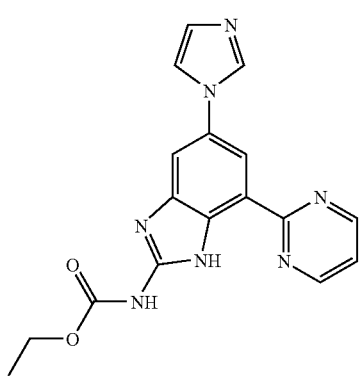
I-214
TABLE 2-continued
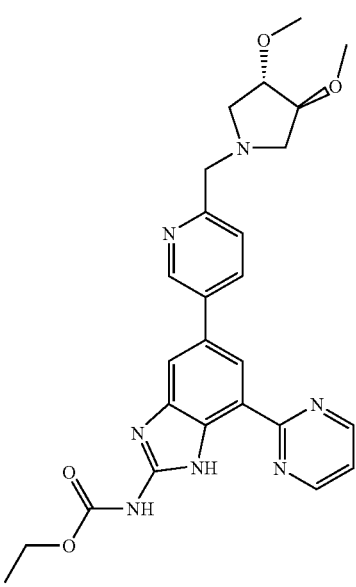
I-215
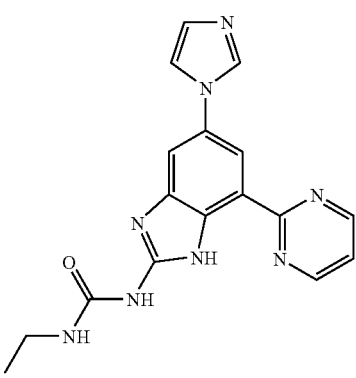
I-216
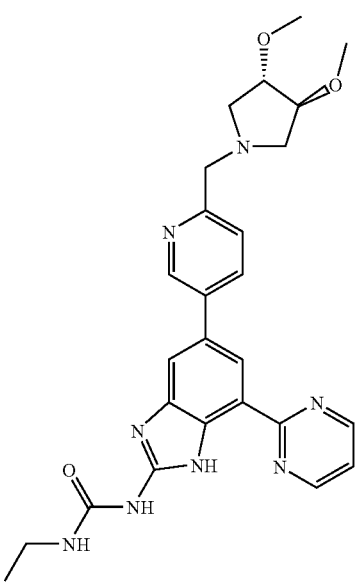
I-217

TABLE 2-continued
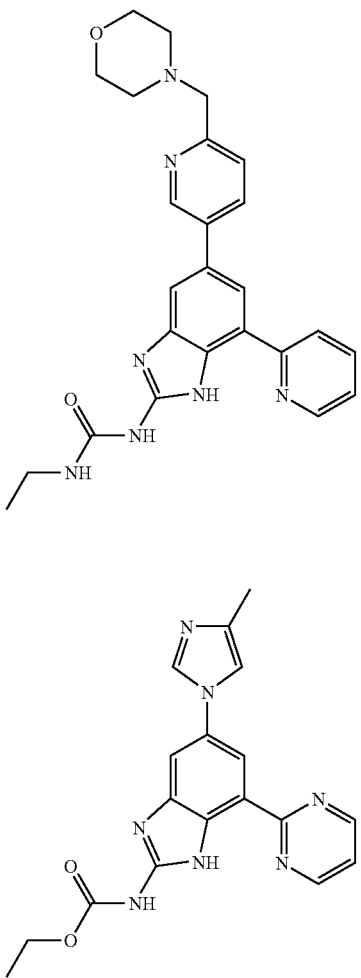
I-218
I-219
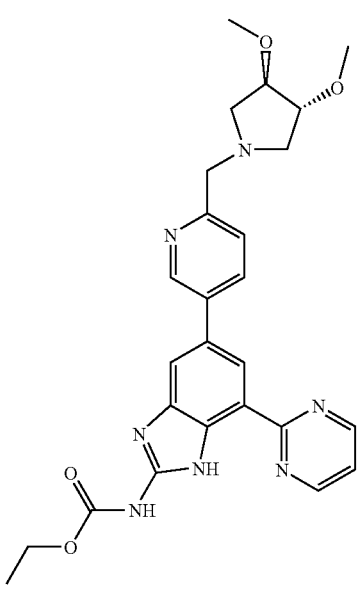
I-220
TABLE 2-continued
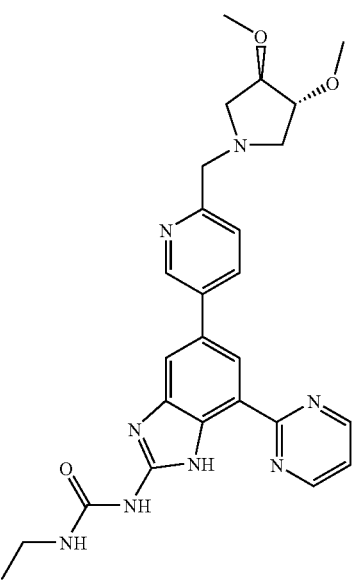
I-221
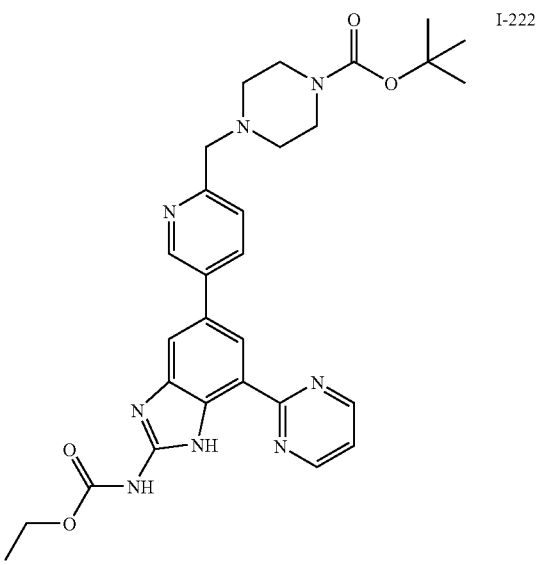
I-222

TABLE 2-continued
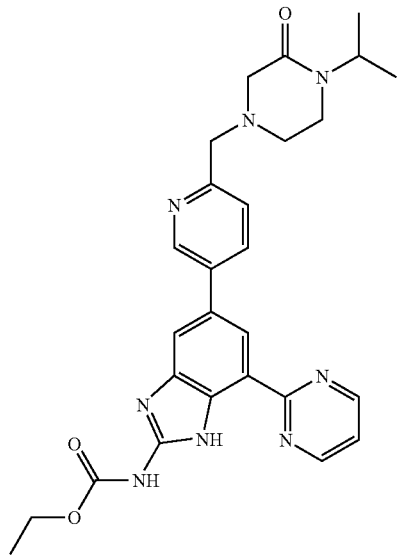
I-223
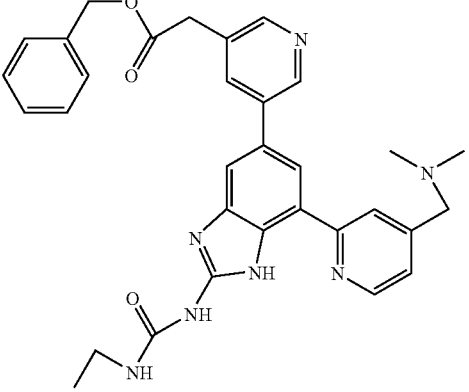
I-226
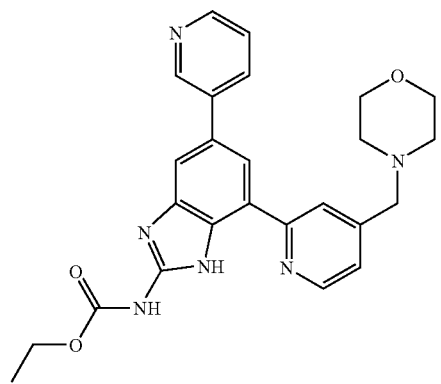
I-224
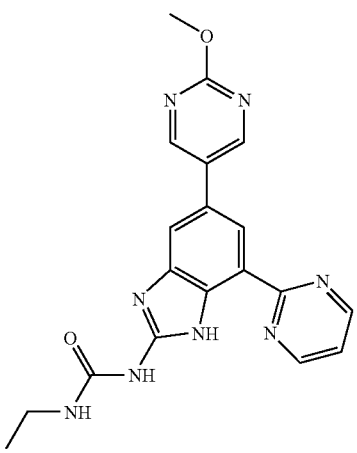
I-227
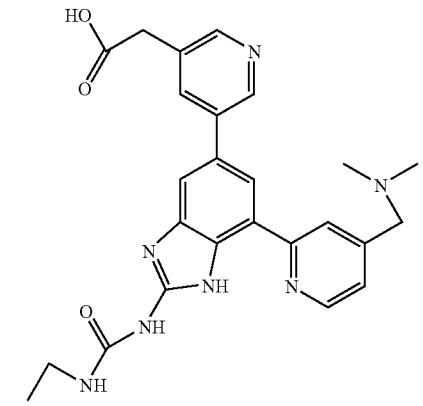
I-225
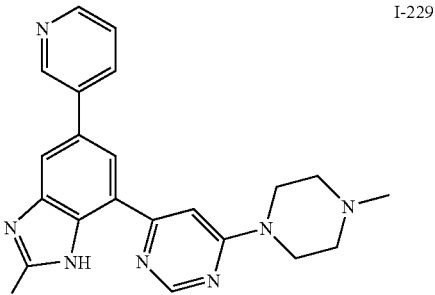
I-228
I-229

TABLE 2-continued
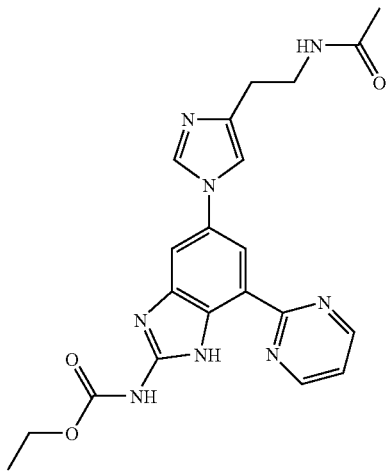
I-230
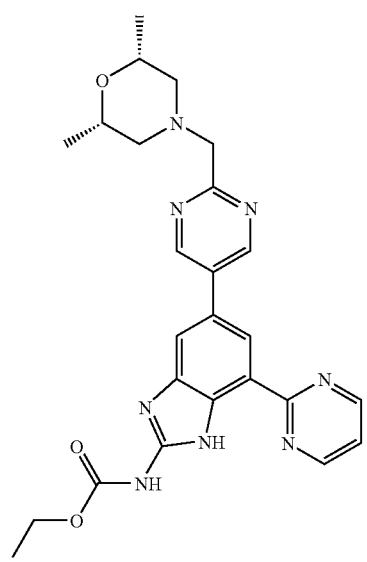
I-231
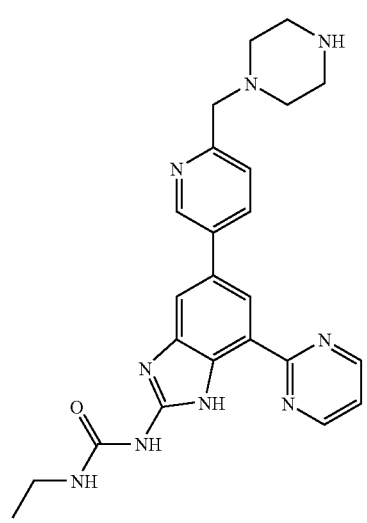
I-232
TABLE 2-continued
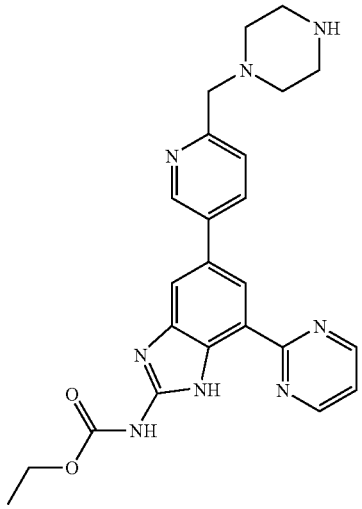
I-233
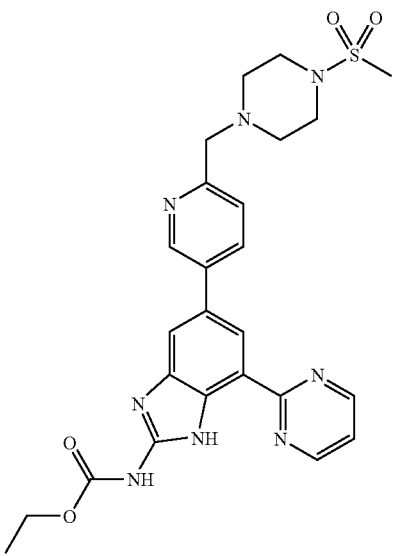
I-234
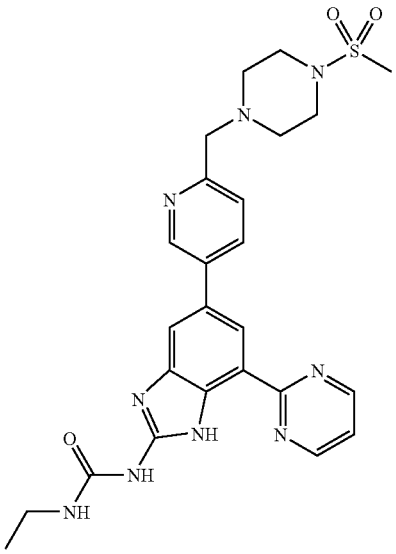
I-235

TABLE 2-continued
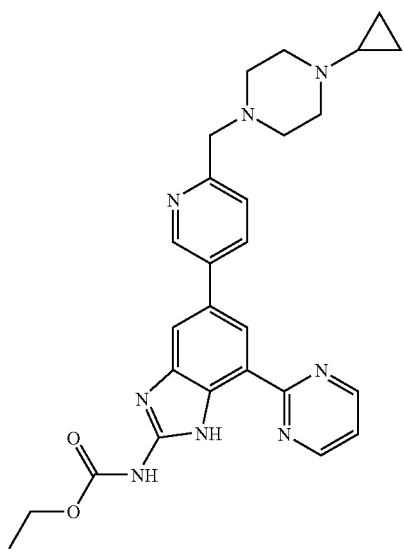 I-236
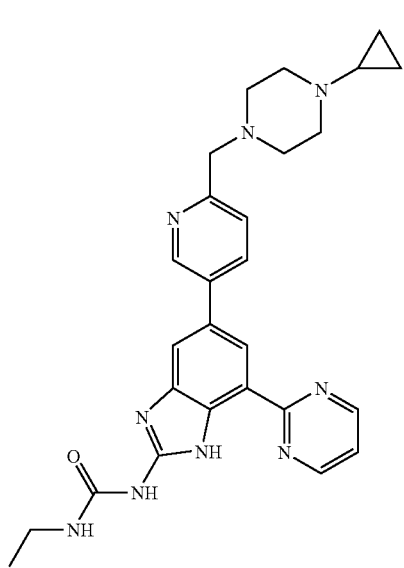 I-237
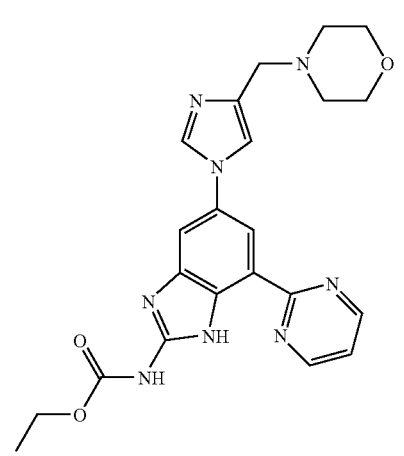 I-238
TABLE 2-continued
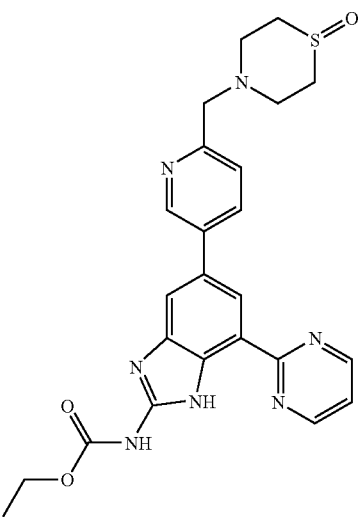 I-239
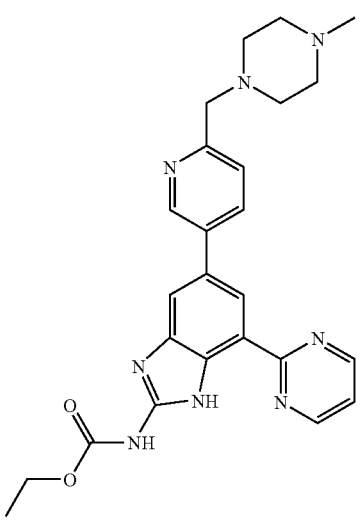 I-240
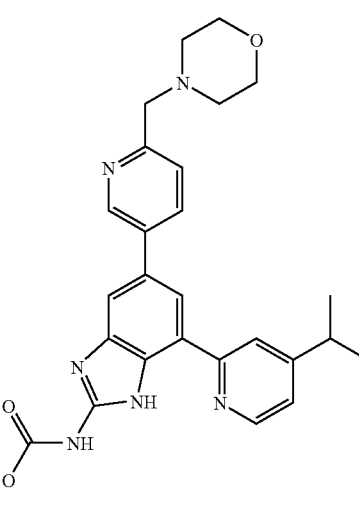 I-241

TABLE 2-continued
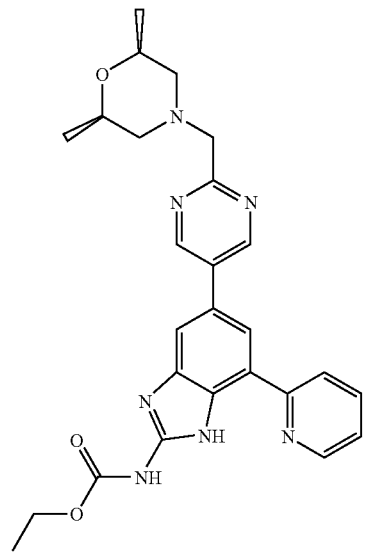
I-242
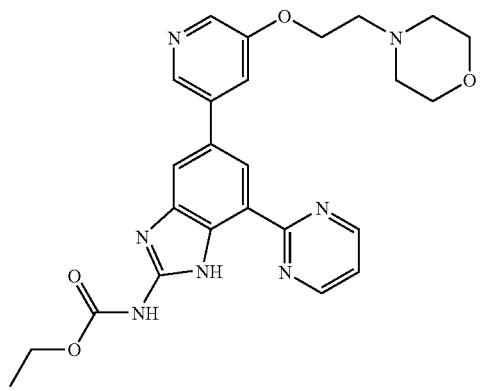
I-243
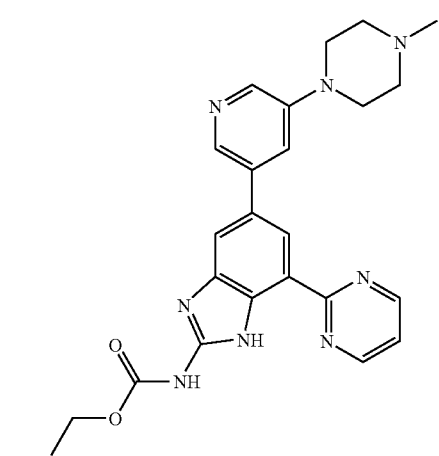
I-244
TABLE 2-continued
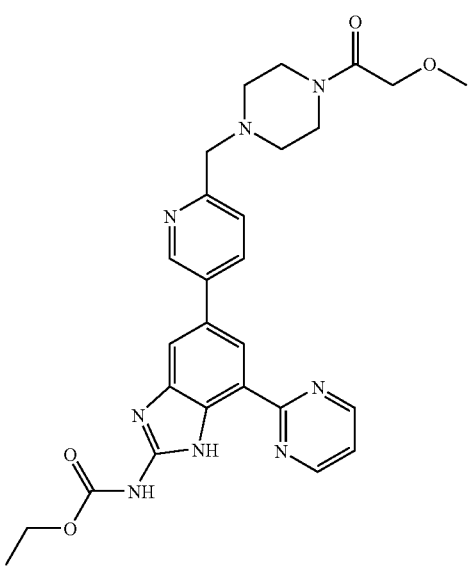
I-245
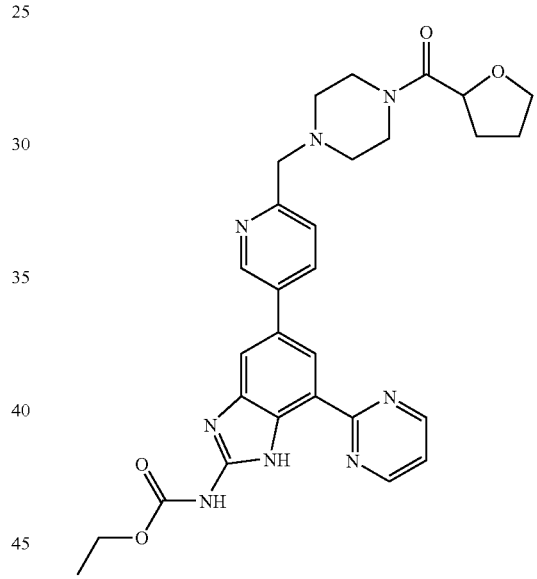
I-246
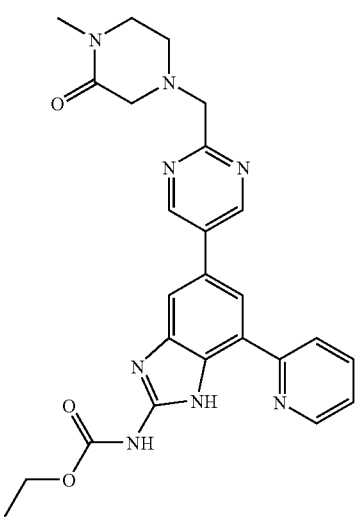
I-247

TABLE 2-continued
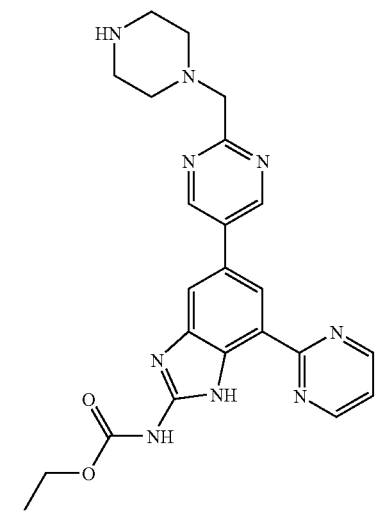
I-248
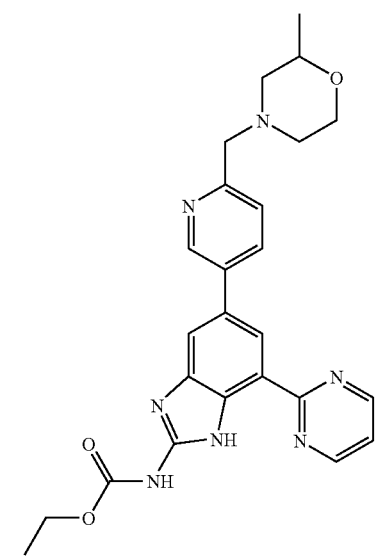
I-249
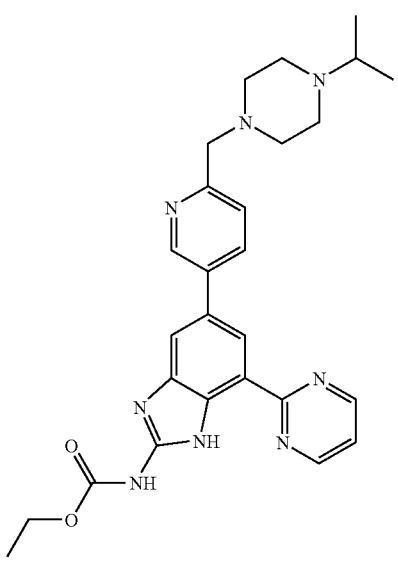
I-250
TABLE 2-continued
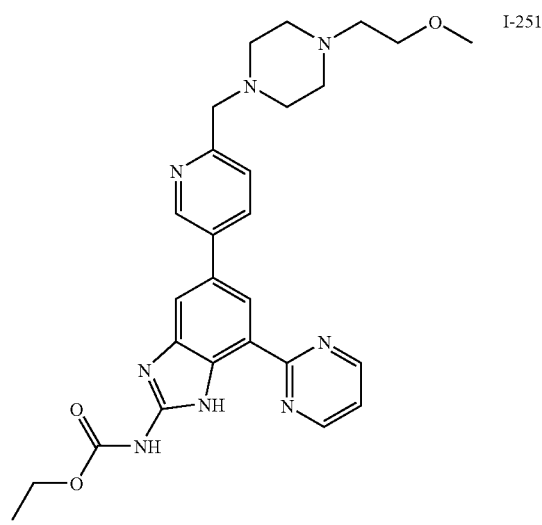
I-251
I-252
I-253

TABLE 2-continued
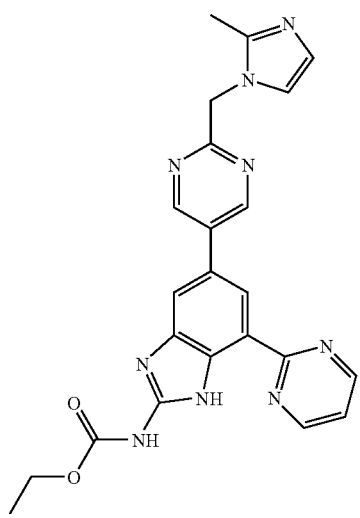
I-254
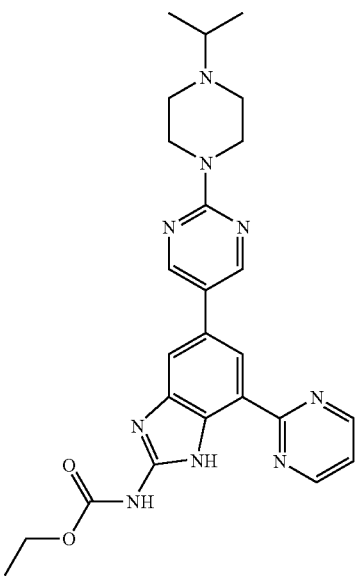
I-256
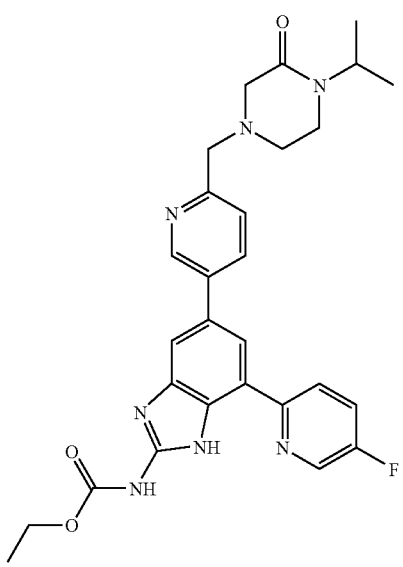
I-255
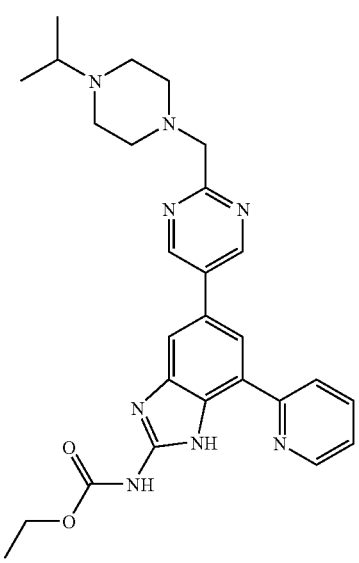
I-257

TABLE 2-continued
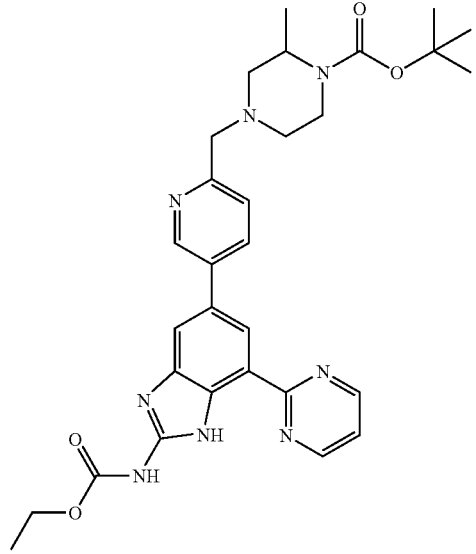
I-258
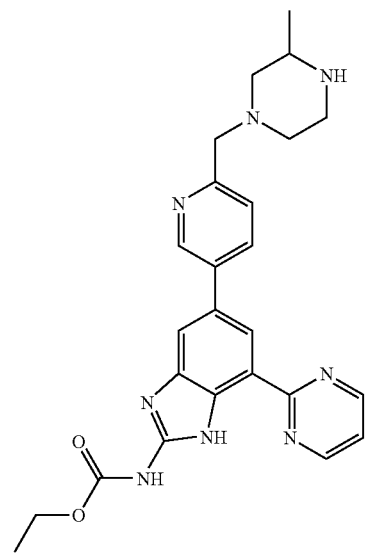
I-259
TABLE 2-continued
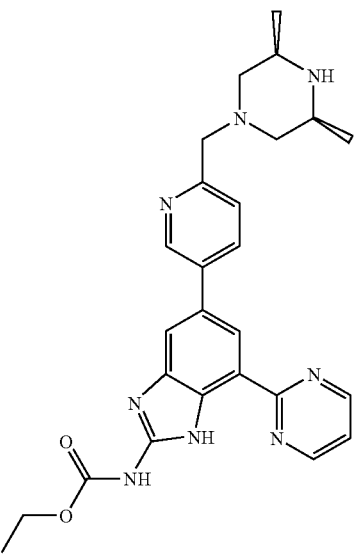
I-260
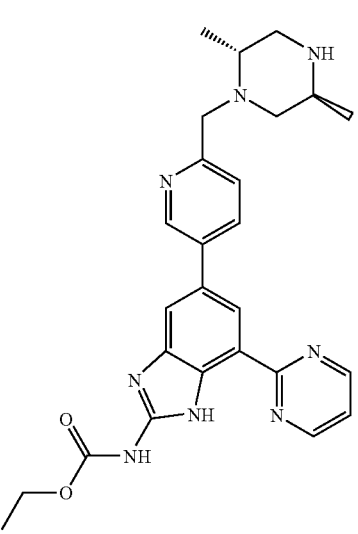
I-261
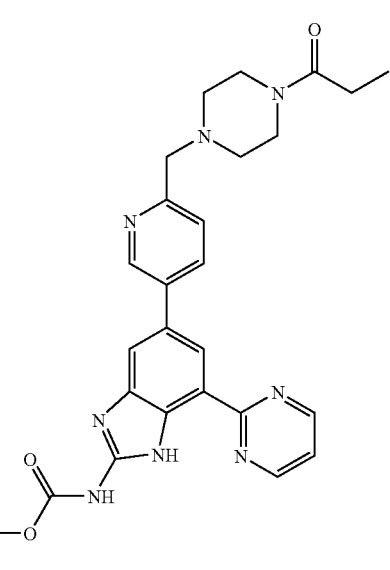
I-262

TABLE 2-continued
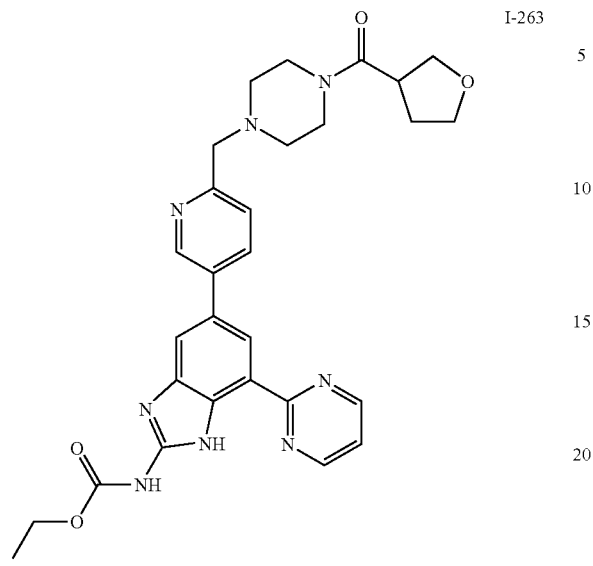
I-263
I-264
I-265
TABLE 2-continued
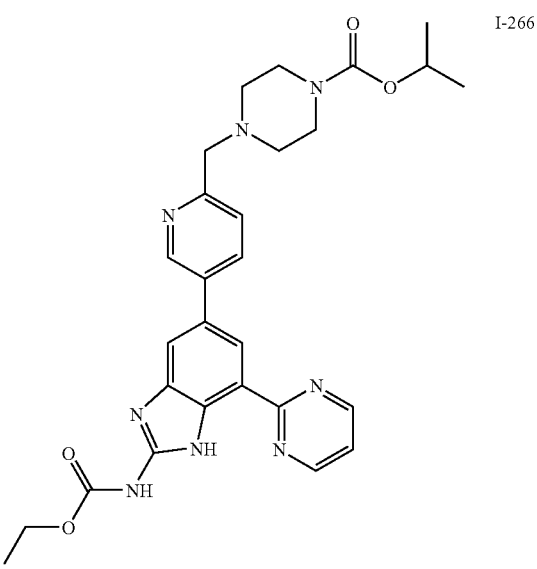
I-266
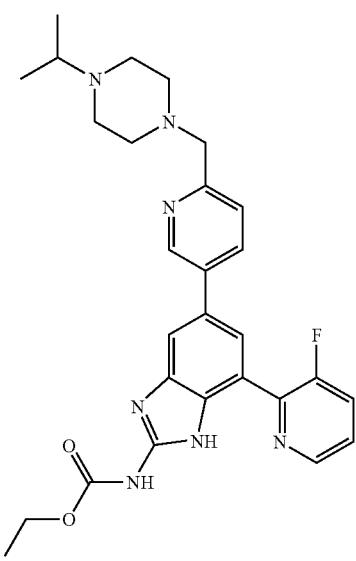
I-267

TABLE 2-continued
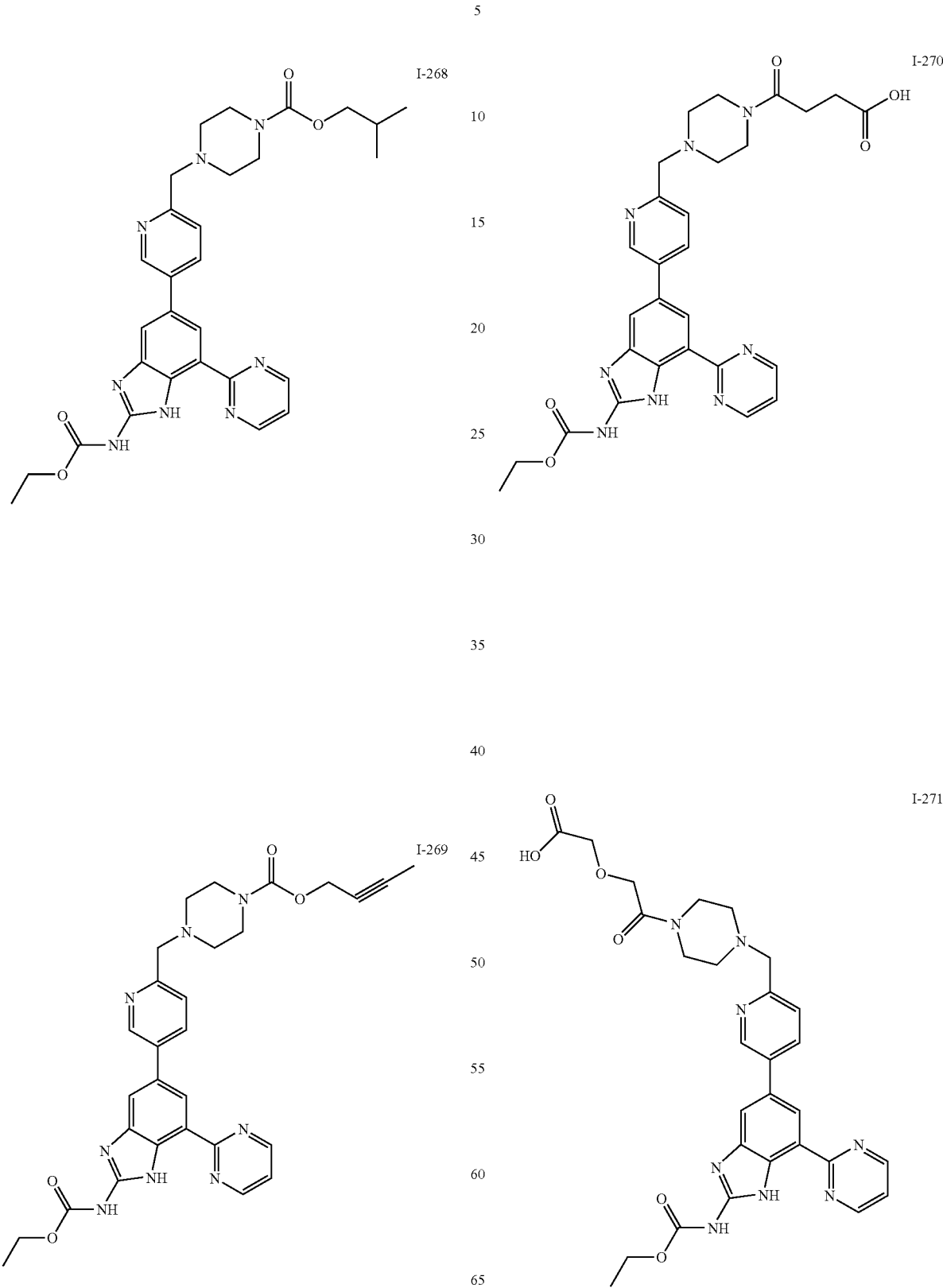

TABLE 2-continued
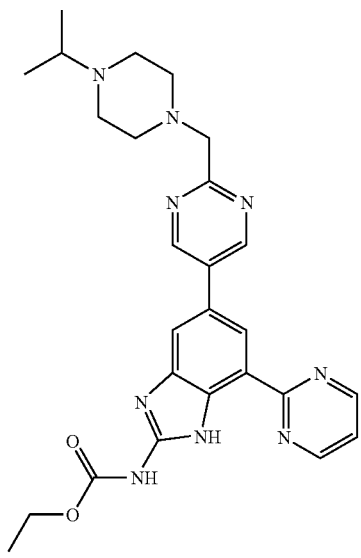
I-272
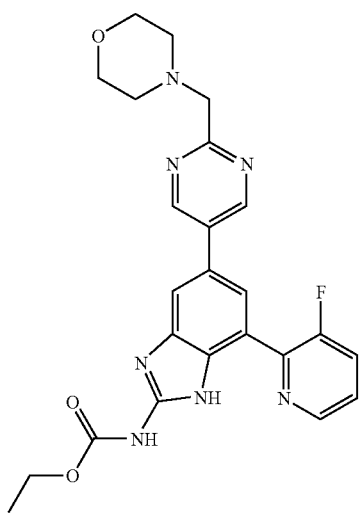
I-273
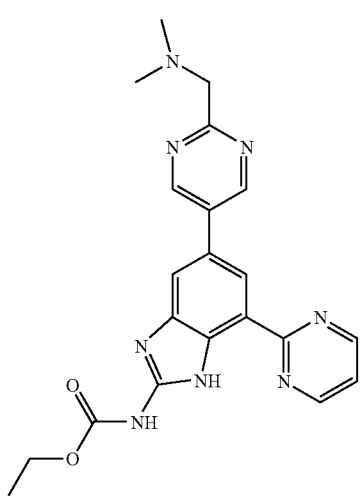
I-274
TABLE 2-continued
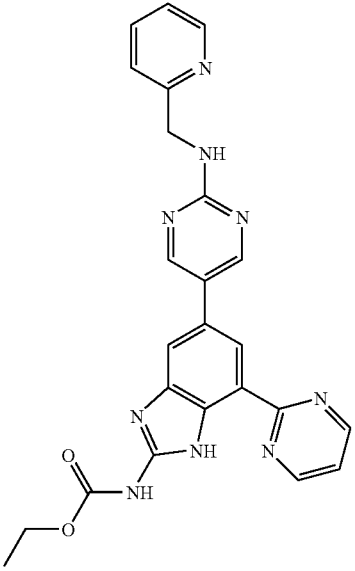
I-275
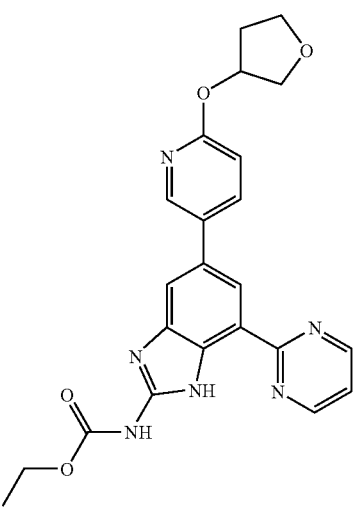
I-276
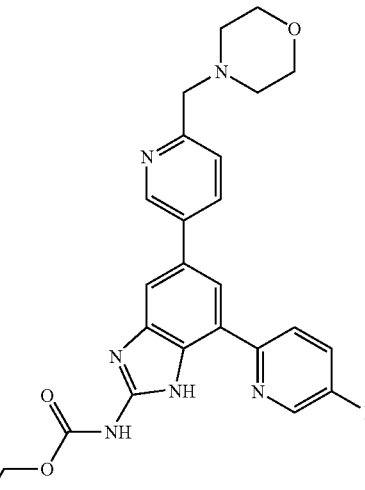
I-277

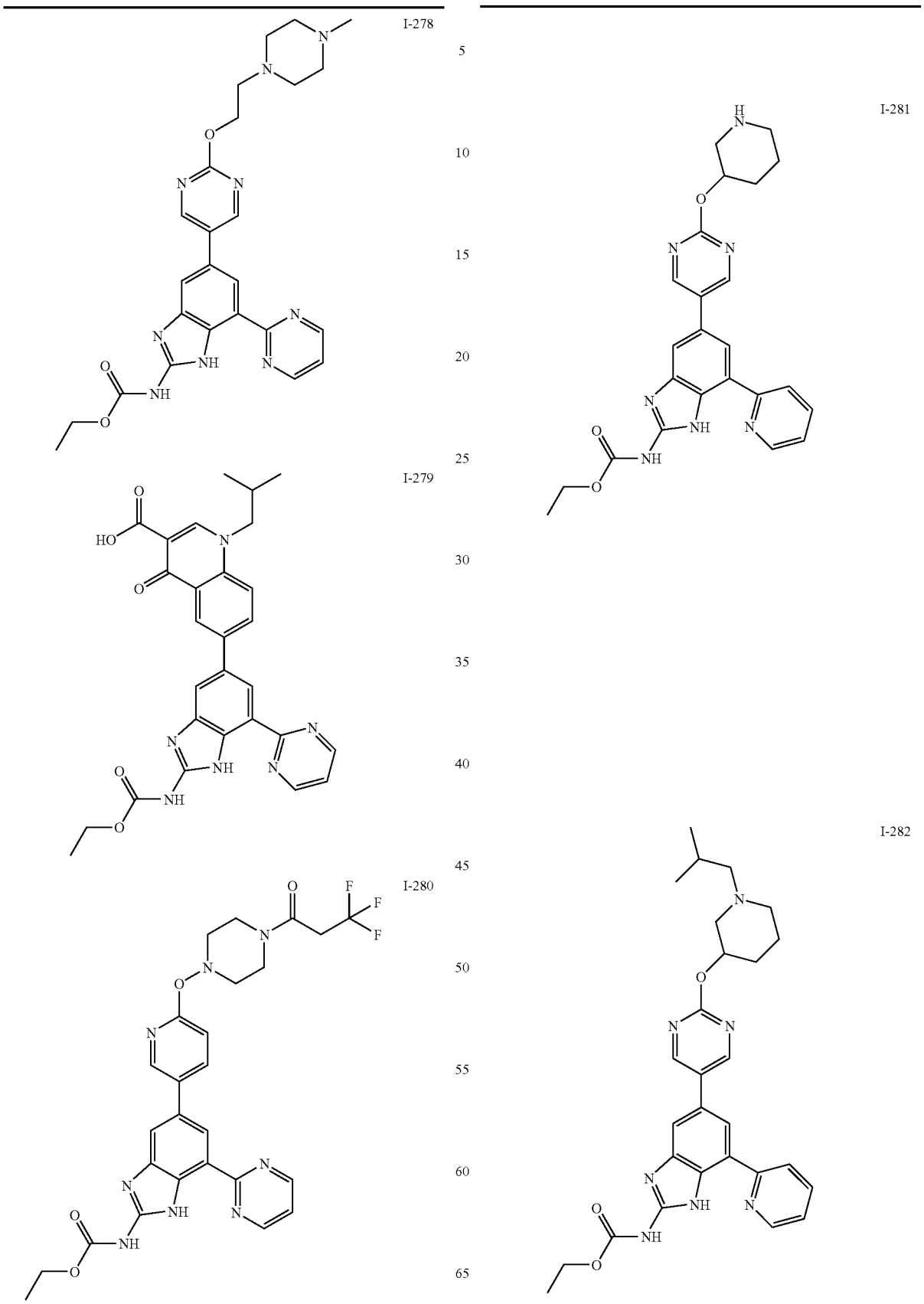

TABLE 2-continued
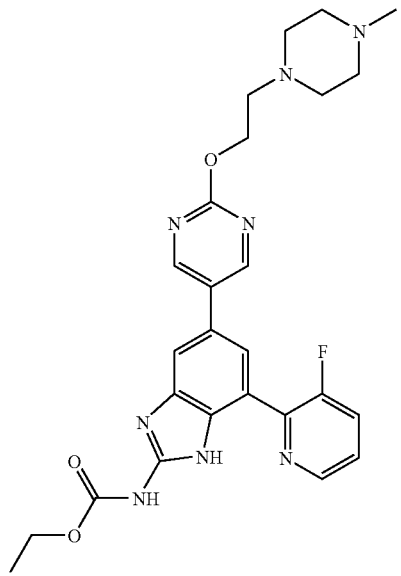
I-283
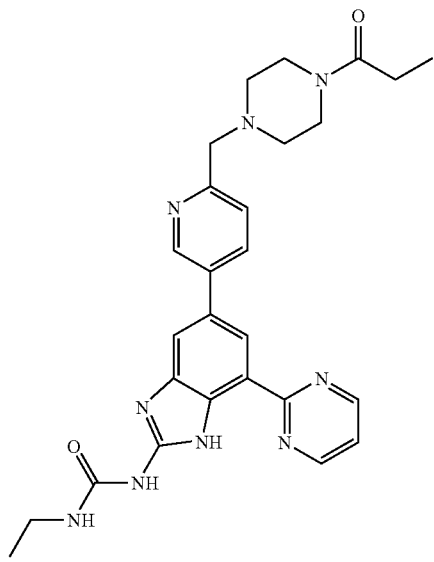
I-284
TABLE 2-continued
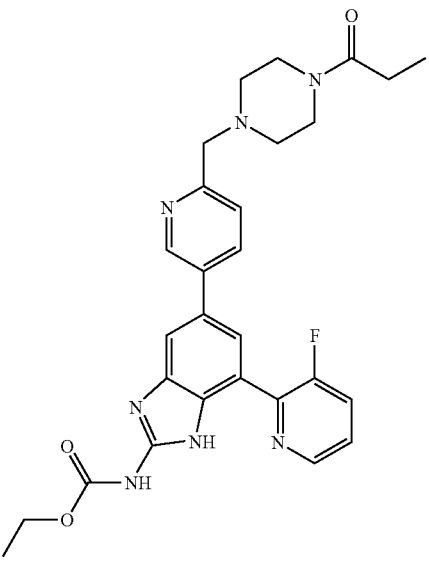
I-285
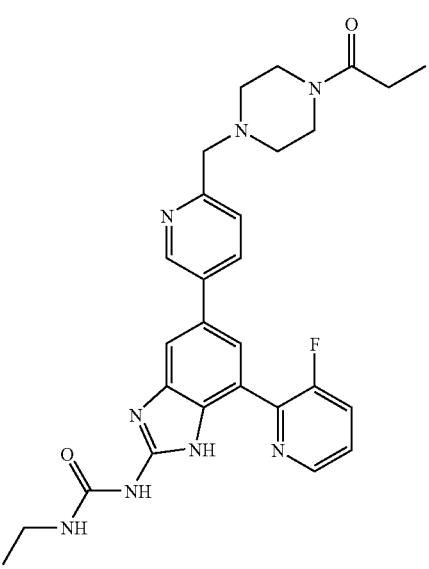
I-286
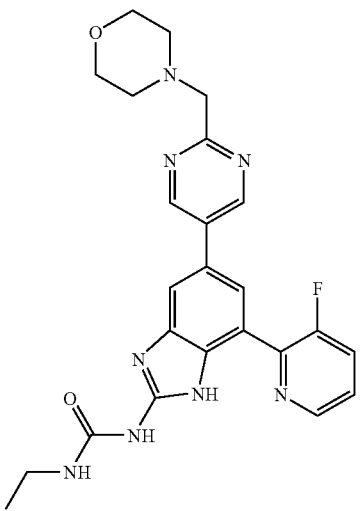
I-287

TABLE 2-continued
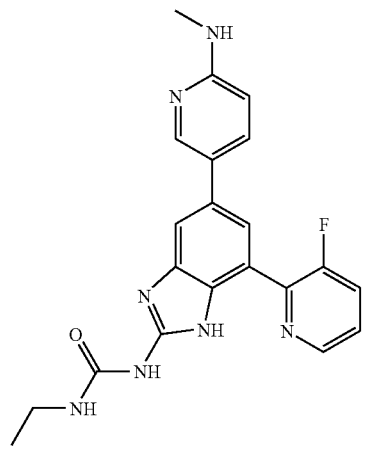
I-288
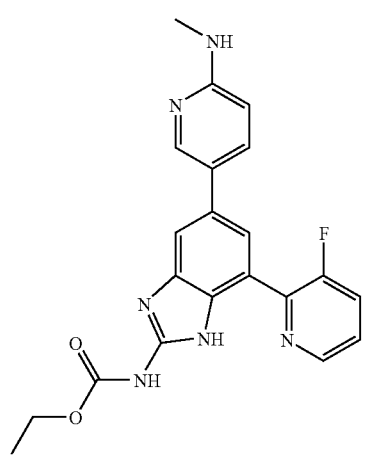
I-289
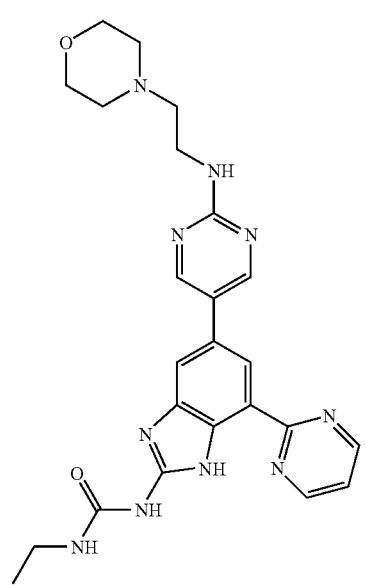
I-290
TABLE 2-continued
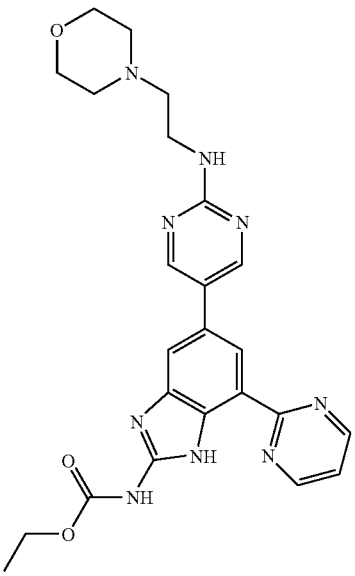
I-291
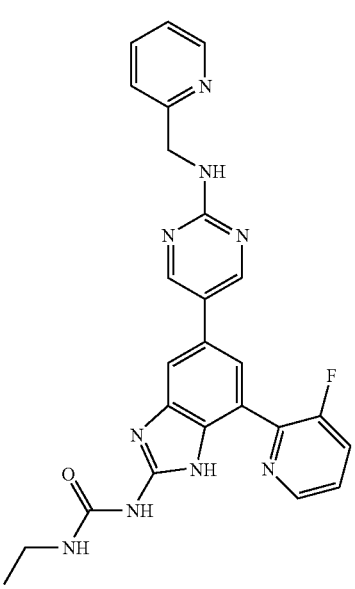
I-292

TABLE 2-continued

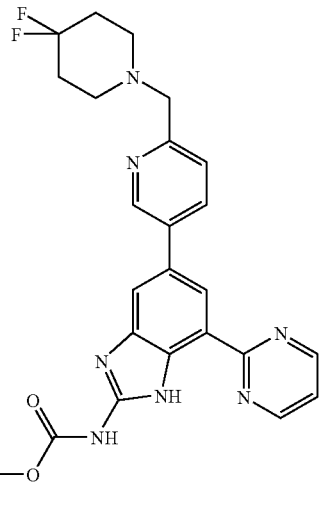
I-293

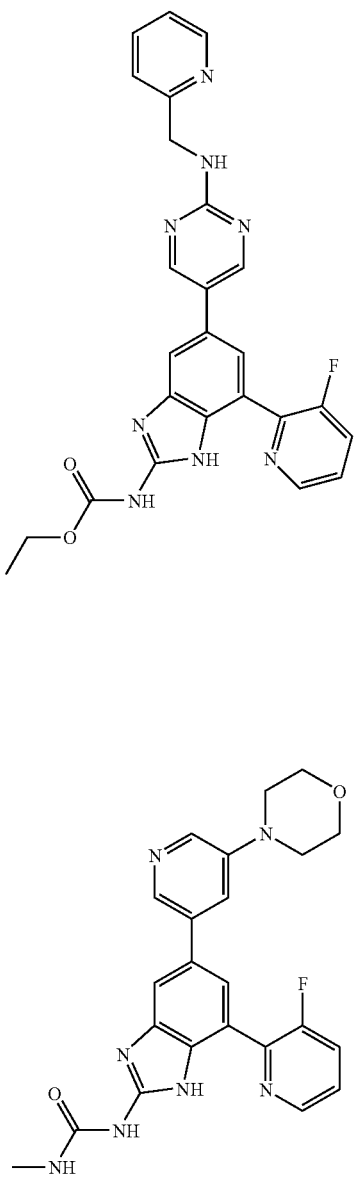
I-294

TABLE 2-continued

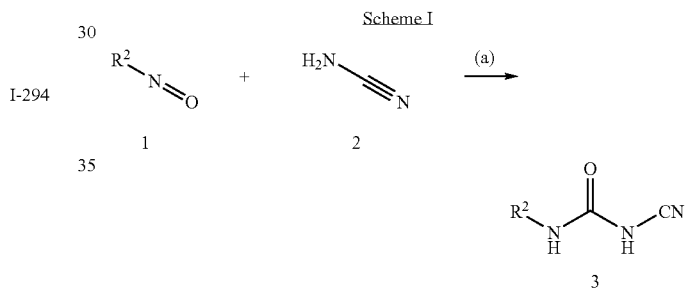
I-295

The compounds of this invention may be prepared in general by methods known to those skilled in the art for analogous compounds, as illustrated by the general Schemes I, II, III, and IV shown below and the Examples set forth infra.

Scheme I

R²—N=O + H₂N—C≡N —(a)→

R²—NH—C(O)—NH—CN

3

Scheme I above shows a general method for preparing N'-alkyl-N-cyanoureas (3) useful in the preparation of the compounds of the present invention wherein Z is NH. At step (a), cyanamide (2) is treated with an alkyl isocyanate in aqueous sodium hydroxide to afford, after acidification, compound 3. One of skill in the art would recognize that a variety of alkyl isocyanates would be amenable to the reaction conditions of Scheme I to form a variety of N'-alkyl-N-cyanoureas.

Scheme II

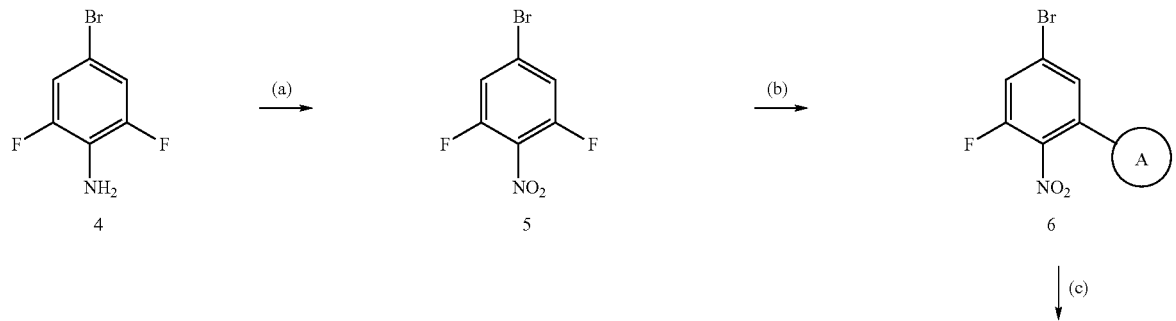

-continued

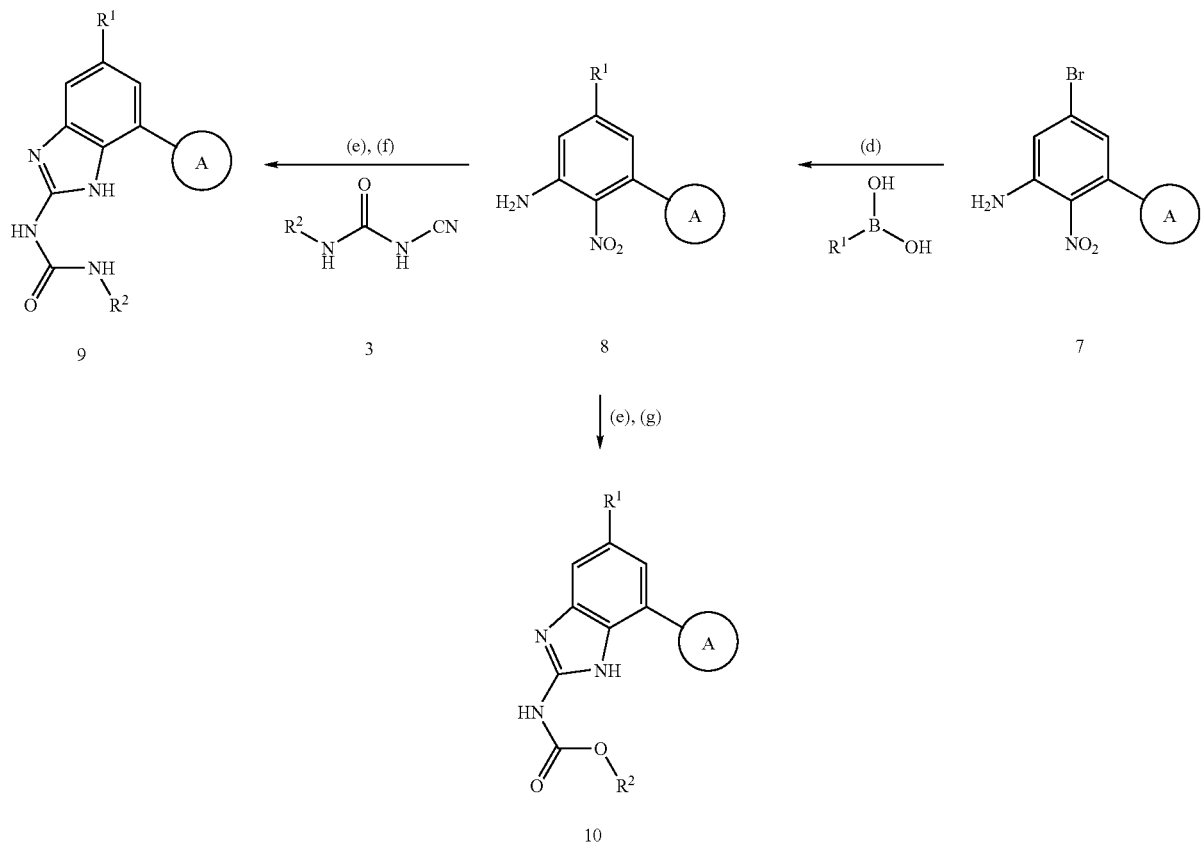

Reagents and conditions:
(a) sodium perborate, HOAC, 55° C.
(b) Ring A, NaH, THF;
(c) NH$_3$, MeOH, EtOH, 80° C.;
(d) R$^1$—B(OH)$_2$, Pd(PPh$_3$)$_4$, NaHCO$_3$, H$_2$O, THF, 70° C.;
(e) H$_2$, Pd/C, EtOAc;
(f) 3, H$_2$SO$_4$, 95° C.;
(g) 2-methyl-2-thiopseudourea, R$^2$-chloroformate.

Scheme II above shows a general method for preparing the benzimidazole compounds of the present invention wherein Z is NH or O. The bromo-aniline (4) is treated with sodium perborate and acetic acid to form the difluoro-nitro compound (5). Compound 5 is treated with Ring A in the presence of sodium hydride to afford the bi-aryl compound 6. The remaining fluoro group of compound 6 is displaced with ammonia to form the amino compound (7). The 2-nitro-5-bromoaniline (7) is then coupled to an aryl boronic acid, at step (d), in the presence of palladium to form the tri-aryl compound (8). The nitro group of compound 8 is reduced to form a diamino compound which is treated with an N'-alkyl-N-cyanourea (3) to form benzimidazole compound of formula I wherein Z is NH (9).

Alternatively, intermediate 8 may be used to form compounds of formula I wherein Z is O. Compound 10 is formed by treating 8, after reduction to the diamino compound, with 2-methyl-2-thiopseudourea and R$^2$-chloroformate according to the method described by L. I. Kruse et al, *J. Med. Chem.* 1989, 32, 409-417. One of ordinary skill in the art would recognize that the reactions depicted in Scheme II above are amenable to a variety of R$^1$ and Ring A groups of the present invention.

In an alternative method, intermediate 8 is treated with either N,N-diethlycarboxy-2-methyl-2-thiopseudourea or N,N-diethlyureamido-2-methyl-2-thiopseudourea to form compounds 10 and 9, respectively. The synthesese of both N,N-diethlycarboxy-2-methyl-2-thiopseudourea and N,N-diethlyureamido-2-methyl-2-thiopseudourea are described in the Examples set forth infra.

Scheme III

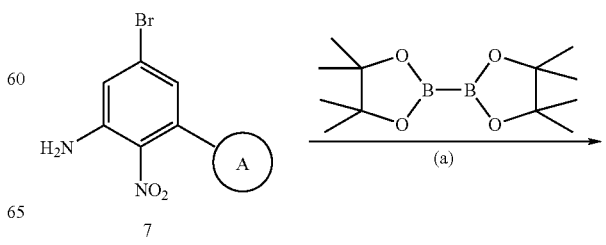

-continued

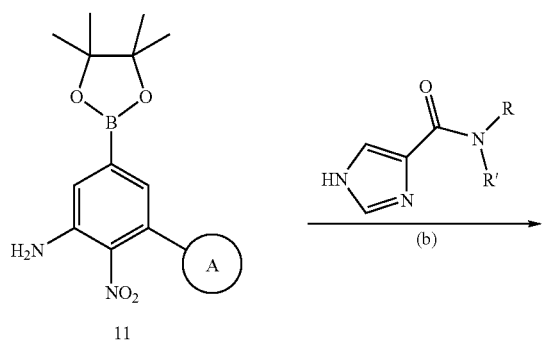

11

12

II-a

Reagents and conditions:
(a) PD(dppf)Cl₂/KOAc, DMSO, 80° C.; and
(b) Cu(OAc)₂/pyridine, DMF.

Scheme III above shows a general method for preparing compounds of formula II-a using methods substantially similar to those described by Kiyomori, A.; Marcoux, J.-F.; Buchwald, S. L., *Tetrahedron Letters*, vol. 40, (1999) 2657-2660. Compound 7 is treated with diboranic ester in the presence of Pd(dppf)/potassium acetate in DMSO at 80° C. to afford intermediate 11. Compound 11 is treated with 4-C(O)N(R')₂-imidazole in the presence of copper acetate to form the 4-C(O)N(R')₂-imidazol-1-yl compound 12. Compounds of formula II-a are prepared from compound 12 as described in Scheme II, steps (e), (f), and (g).

Although 4-C(O)N(R')₂-imidazole is used to exemplify, one of ordinary skill in the art would recognize that a variety of $R^1$ groups are amenable to the displacement reaction at step (c) to form a variety of compounds of the present invention. Generally, the boronate intermediate 11 may be treated with a variety of $R^1$-halides or $R^1$-triflates, using methods well known to one of ordinary skill in the art, to form intermediate compounds 12' as shown below. Using the methods recited herein and those known to one of ordinary skill in the art, compounds 12' are useful for preparing compounds 9 and 10 of the present invention as depicted above at Scheme II.

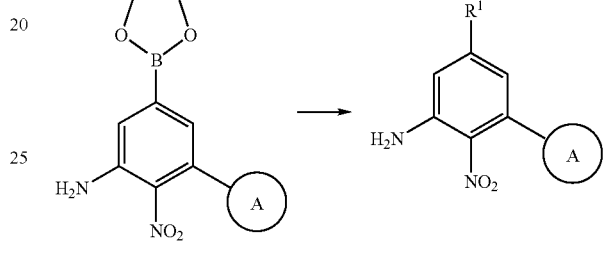

11                    12'

Scheme IV

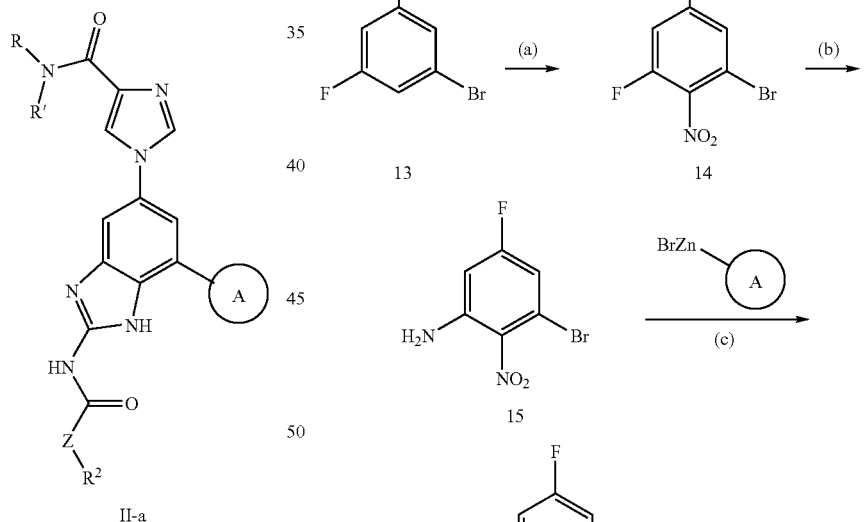

13              14

15

16

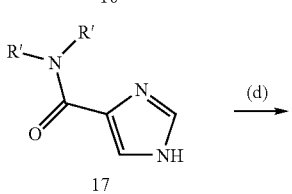

17

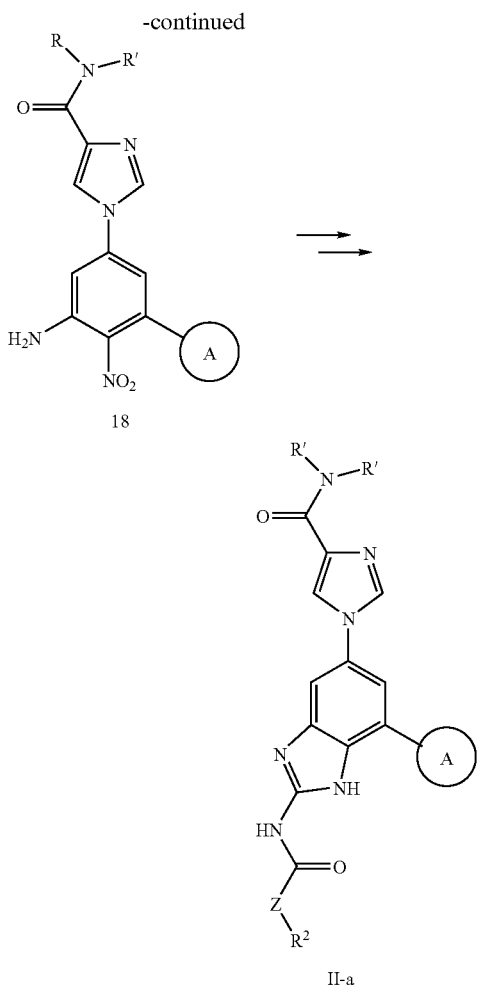

Reagents and conditions:
(a); (b) NH₄OH/dioxane, reflux;
(c) Pd(PPh₃)₄/THF, reflux; and
(d) Na₂CO₃/DMF, heat.

Scheme IV above shows an alternate method for preparing compounds of formula II-a. Compound 13 is nitrated to form 14. Compound 14 is treated with ammonium hydroxide to form the amino compound 15. The bromo group of compound 15 is treated with the BrZn-Ring A reagent in the presence of Pd(PPh₃)₄ in THF to form compound 16. Compound 16 is treated with the 4-C(O)N(R')₂-imidazole in the presence of sodium carbonate to form the 4-C(O)N(R')₂-imidazol-1-yl compound 18. Compounds of formula II-a are then prepared from compound 18 as described in Scheme II, steps (e), (f), and (g).

One of skill in the art would recognize that a variety of compounds of the present invention may be prepared according to the general method of Schemes I, II, III, and IV, methods known in the art, and the synthetic Examples set forth below.

The compounds of this invention are potent inhibitors of gyrase and Topo IV as determined by enzymatic assay. These compounds have also been shown to have antimicrobial activity in an antimicrobial susceptibility assay. The activity of a compound utilized in this invention as an inhibitor of gyrase or Topo IV may be assayed in vitro, in vivo or in a cell line according to methods known in the art. The details of the conditions used for both the enzymatic and the antimicrobial susceptibility assays are set forth in the Examples below.

According to another embodiment, the invention provides a composition comprising a compound of this invention or a pharmaceutically acceptable salt thereof and a pharmaceutically acceptable carrier, adjuvant, or vehicle. The amount of compound in the compositions of this invention is such that is effective to detectably inhibit gyrase, Topo IV, or to measurably decrease bacterial quantity, in a biological sample or in a patient. Preferably the composition of this invention is formulated for administration to a patient in need of such composition. Most preferably, the composition of this invention is formulated for oral administration to a patient.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of gyrase and/or Topo IV activity in a biological sample is useful for a variety of purposes that are known to one of skill in the art. Examples of such purposes include, but are not limited to, blood transfusion, organ-transplantation, biological specimen storage, and biological assays.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in gyrase, or Topo IV, activity between a sample comprising said composition and gyrase, or Topo IV, and an equivalent sample comprising gyrase, or Topo IV in the absence of said composition.

As used herein, the term "measurably decrease bacterial quantity", as used herein means a measurable change in the number of bacteria between a sample containing said composition and a sample containing only bacteria.

A "pharmaceutically acceptable salt" means any non-toxic salt of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of gyrase and/or Topo IV.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{ alkyl})_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of bacterial infections caused by bacteria such as *Streptococcus pneumoniae, Streptococcus pyogenes, Enterococcus faecalis, Enterococcus faecium, Klebsiella pneumoniae, Enterobacter* sps. *Proteus* sps. *Pseudomonas aeruginosa, E. coli, Serratia marcesens, Staphylococcus aureus, Coag. Neg. Staph, Haemophilus influenzae, Bacillus anthracis, Mycoplasma pneumoniae, Moraxella catarralis, Chlamydia pneumoniae, Legionella pneumophila, Mycobacterium tuberculosis, Staphylococcus epidermidis,* or *Helicobacter pylori*.

Typically, the pharmaceutical compositions of this invention will be administered from about 1 to 5 times per day or alternatively, as a continuous infusion. Or, alternatively, the compositions of the present invention may be administered in a pulsatile formulation. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated". Such agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, an anti-vascular hyperproliferation compound, or an agent which increases the susceptibility of bacterial organisms to antibiotics.

Agents which increase the susceptibility of bacterial organisms to antibiotics are known. For example, U.S. Pat. No. 5,523,288, U.S. Pat. No. 5,783,561 and U.S. Pat. No. 6,140,306 describe methods of using bactericidal/permeability-increasing protein (BPI) for increasing antibiotic susceptibility of gram-positive and gram-negative bacteria. Agents that increase the permeability of the outer membrane of bacterial organisms have been described by Vaara, M. in *Microbiological Reviews* (1992) pp. 395-411, and the sensitization of gram-negative bacteria has been described by Tsubery, H., et al, in *J. Med. Chem.* (2000) pp. 3085-3092.

According to another embodiment, the invention provides a method for treating or lessening the severity of a bacterial infection in a patient comprising the step of administering to said patient a composition according to the present invention.

According to another embodiment, the invention provides a method of inhibiting gyrase in a biological sample.

According to another embodiment, the invention provides a method of inhibiting Topo IV in a biological sample.

According to another embodiment, the invention provides a method of decreasing bacterial quantity in a biological sample.

According to another embodiment, the invention provides a method of decreasing bacterial quantity in a biological sample, but further comprising the step of contacting said biological sample with an agent which increases the susceptibility of bacterial organisms to antibiotics.

The pharmaceutical compositions and methods of this invention will be useful generally for controlling bacterial infections in vivo. Examples of bacterial organisms that may be controlled by the compositions and methods of this invention include, but are not limited to, the following organisms: *Streptococcus pneumoniae, Streptococcus pyogenes, Enterococcus faecalis, Enterococcus faecium, Kiebsiella pneumoniae, Enterobacter sps. Proteus sps. Pseudomonas aeruginosa, E. coli, Serratia marcesens, Staphylococcus aureus, Coag. Neg. Staph, Haemophilus infuenzae, Bacillus anthracis, Mycoplasma pneumoniae, Moraxella catarralis, H. influenzae, Chlamydia pneumoniae, Legionella pneumophila, Mycobacterium tuberculosis, Helicobacter pylori, Staphylococcus epidermidis. Chlamydia pneumoniae, Legionella pneumophila, Mycobacterium tuberculosis,* or *Helibacter pylori.*

The compositions and methods will therefore be useful for controlling, treating or reducing the advancement, severity or effects of nosocomial or non-nosocomial infections. Examples of nosocomial uses include, but are not limited to, urinary tract infections, respiratory infections such as pneumonia, surgical wound infections, and blood stream infections (also known as bacteremia). Examples of non-nosocomial uses include but are not limited to urinary tract infections, pneumonia, prostatitis, skin and soft tissue infections, intra-abdominal infections, and therapy for febrile neutropenic patients.

The term "pharmaceutically effective amount" refers to an amount effective in treating or ameliorating a bacterial infection in a patient. The term "prophylactically effective amount" refers to an amount effective in preventing or substantially lessening a bacterial infection in a patient.

The compounds of this invention may be employed in a conventional manner for controlling bacterial infections levels in vivo and for treating diseases or reducing the advancement or severity of effects which are mediated by bacteria. Such methods of treatment, their dosage levels and requirements may be selected by those of ordinary skill in the art from available methods and techniques.

For example, a compound of this invention may be combined with a pharmaceutically acceptable adjuvant for administration to a patient suffering from a bacterial infection or disease in a pharmaceutically acceptable manner and in an amount effective to lessen the severity of that infection or disease.

Alternatively, the compounds of this invention may be used in compositions and methods for treating or protecting individuals against bacterial infections or diseases over extended periods of time. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against bacterial infections or diseases.

The compounds of formula I may also be co-administered with other antibiotics to increase the effect of therapy or prophylaxis against various bacterial infections. When the compounds of this invention are administered in combination therapies with other agents, they may be administered sequentially or concurrently to the patient. Alternatively, pharmaceutical or prophylactic compositions according to this invention comprise a combination of a compound of formula I and another therapeutic or prophylactic agent.

The additional therapeutic agents described above may be administered separately, as part of a multiple dosage regimen, from the inhibitor-containing composition. Alternatively, these agents may be part of a single dosage form, mixed together with the inhibitor in a single composition.

In order that this invention be more fully understood, the following examples are set forth. These examples are for the purpose of illustration only and are not to be construed as limiting the scope of the invention in any way.

EXAMPLES

Example 1

5-Bromo-1,3-difluoro-2-nitro-benzene: To a suspension of sodium perborate tetrahydrate (1.04 g, 5 mmol) in acetic acid (20 mL), stirred at 55° C., was added a solution of 4-bromo-2,6-difluoroaniline in acetic acid (10 mL) over 1 hour in a dropwise fashion. After stirring at 55° C. for an additional 3 hours, the solution was allowed to cool to room temperature and filtered. The filtrate was poured into ice, and extracted twice with ethyl acetate. The combined organic extracts were washed successively with 5×100-mL portions of water, brine, dried ($MgSO_4$), and concentrated in vacuo. The resulting residue was purified by column chromatography over silica gel eluted with ethyl acetate:hexanes (1:20) to afford 780 mg of the title compound as a tan solid. $^1$H NMR ($CDCl_3$) δ 7.32 (dt, 2H).

Example 2

1-(5-Bromo-3-fluoro-2-nitro-phenyl)-1H-pyrazole: To a suspension of sodium hydride (44 mg, 1.1 mmol, 60% oil dispersion) in THF (4 mL), stirred at 0° C., was added a solution of pyrazole (72 mg, 1.05 mmol) in THF (1 mL). The resulting mixture was stirred at 0° C. for 5 minutes and a solution of 5-bromo-1,3-difluoro-2-nitro-benzene (238 mg, 1 mmol) in THF (1 mL) was added. The mixture was stirred at room temperature for 1 hour, quenched by addition of water (1 mL), then partitioned between water (20 mL) and ethyl acetate (50 mL). The organic layer was washed with brine, dried ($MgSO_4$), and concentrated in vacuo. The residue was purified by column chromatography over silica gel eluted with ethyl acetate:hexanes (1:6), to afford 240 mg (86%) of the title compound. $^1$H NMR ($CDCl_3$) δ 6.55 (t, 1H), 7.45 (d, 1H), 7.60 (s, 1H), 7.80 (m, 2H). MS M+1 287, M+1+2 289.

Example 3

5-Bromo-2-nitro-3-pyrazol-1-yl-phenylamine: To a solution of 1-(5-bromo-3-fluoro-2-nitro-phenyl)-1H-pyrazole (240 mg, 0.84 mmol) in ethanol (3 mL) was added ammonia (3 mL, 2N in methanol. The resulting mixture was heated in a sealed tube at 80° C. for 16 hours then concentrated in vacuo. The residue was purified by column chromatography over silica gel eluted with ethyl acetate:hexanes (1:3) to afford 205 mg (86%) of the title compound as a yellow solid. $^1$H NMR ($CDCl_3$) δ 5.20 (br s, 2H), 6.50 (t, 1H), 6.9 (d, 1H), 7.1 (d, 1H), 7.7 (d, 1H), 7.8 (d, 1H). MS M+1 283, M+1+2 285.

Example 4

2-Nitro-3-pyrazol-1-yl-5-pyridin-3-yl-phenylamine: To a solution of 5-bromo-2-nitro-3-pyrazol-1-yl-phenylamine (200 mg, 0.71 mmol) in THF (8 mL) was added, successively, 3-pyridyl-diethyl borane (157 mg), (tetrakistriphenylphosphine)palladium(0) (84 mg), and sodium carbonate (1.1 mL, 2.2 mmom of 2M aqueous). The resulting mixture was stirred at 70° C. overnight then cooled to room temperature. The reaction mixture was diluted with ethyl acetate (100 mL) and washed with water (50 mL), brine (50 mL), dried ($MgSO_4$) then concentrated in vacuo. The resulting residue was purified by column chromatography over silica gel eluted with a gradient of ethyl acetate:hexanes (1:3, 1:2, 1:0, 2:1, 4:1, 8:1), to afford 120 mg (60%) of the title compound as a yellow solid. $^1$H NMR (DMSO-$d_6$) δ 6.45 (br,s 2H), 6.55 (t, 1H), 7.1 (s, 1H), 7.25 (s, 1H), 7.55 (m, 1H), 7.7 (s, 1H), 8.1 (dt, 1H), 8.3 (d, 1H), 8.7 (d, 1H), 8.9 (s, 1H).

Example 5

1-Ethyl-3-(7-pyrazol-1-yl-5-pyridin-3-yl-1H-benzoimidazol-2-yl)-urea (I-2): A suspension of 2-nitro-3-pyrazol-1-yl-5-pyridin-3-yl-phenylamine (120 mg, 0.40 mmol) and 10% palladium on carbon (12 mg) in ethyl acetate (10 mL) was placed in a Parr hydrogenator under a hydrogen pressure of 45 psi. The mixture was shaken for 16 hours, filtered and the filtrate concentrated in vacuo. The resulting residue was diluted with $H_2SO_4$ (1.6 mL or 1N), and N'-ethyl-N-cyanourea (0.8 mL, 1M) was added. The mixture was heated at 95° C. for 4 hours then concentrated in vacuo. The residue was purified by preparative HPLC to afford 75 mg of the title compound as the bis-TFA salt which was converted to the free base to afford the title compound. $^1$H NMR (DMSO-$d_6$) δ 1.1 (t, 3H), 3.2 (m, 2H), 7.0 (m, 1H), 7.3 (d, 1H), 7.5 (m, 1H), 7.55 (s, 1H), 8.0 (d, 1H), 8.55 (dd, 1H), 8.85 (s, 1H), 10.1 (s, 1H), 12.0 (s, 1H). LC/MS one peak, M+1 348.23, M−1 346.18.

Example 6

N'-Ethyl-N-cyanourea: To a 20° C. solution of sodium hydroxide (1.5 M aqueous, 50 mL, 75.02 mmol) was added cyanamide (8.5 g, 202.25 mmol) then ethyl isocyanate (4 mL, 50.56 mmol) was added in a dropwise fashion over 10 minutes. After stirring for 30 minutes, additional sodium hydroxide (3M, 25 mL. 75.02 mmol) and ethyl isocyanate (4 mL, 50.56 mmol) were added. The resulting solution was then aged for a minimum of 30 minutes before using directly without isolation.

Example 7

4-(Pyridin-3-yl)-2-nitroaniline: To a solution of 4-bromo-2-nitroaniline (4.8 g, 22 mmol) in DME (100 mL) was added pyridine-3-boronic acid 1,3-propanediol cyclic ester (4 g, 24 mmol), sodium bicarbonate (45 mL, 1M), and tetrakis(triphenylphosphine)palladium (0.05 eq). The resulting mixture was heated at 90° C. for 8 hours then cooled to room temperature. The solids were collected, washed with water, 5% EtOAc in Hexane and dried to afford the title compound (5 g).

$^1$H NMR (CDCl$_3$) δ 8.8 (d, 1H), 8.55 (m, 1H), 8.35 (d, 1H), 7.85 (dd, 1H), 7.65 (dd, 1H), 7.35 (m, 1H), 6.95 (d, 1H), 6.25 (br s, 2H).

Example 8

2-Bromo-6-nitro-4-pyridin-3-yl-phenylamine: To a solution of 4-(pyridin-3-yl)-2-nitroaniline (1.3 g, 9 mmol) in HOAc (25 mL) was added bromine (1.58 g, 9.9 mmol) in HOAc (5 mL). The resulting mixture was stirred at room temperature for one hour and then quenched with ice-water. The solids were collected, washed with water and dried. The solids in EtOAc was then washed with NaOH (2N; 20 mL), water, brine and concentrated in vacuo. The concentrate was purified by chromatography [Silica Gel, ethyl acetate:hexanes (1:1)] to afford the title compound (0.8 g). $^1$H NMR (CDCl$_3$) δ 8.83 (d, 1H), 8.55 (m, 1H), 8.41 (d, 1H), 8.15 (d, 1H), 7.96 (m, 1H), 7.41 (m, 1H), 6.80 (br s, 2H). (M+1) 294.

Example 9

2-Nitro-6-pyridin-2-yl-4-pyridin-3-yl-phenylamine: A mixture of 2-bromo-6-nitro-4-pyridin-3-yl-phenylamine (100 mg, 1 eq), 2-pyridylznic bromide (6 eq) and tetrakis(triphenylphosphine)palladium (0.1 eq) in THF (10 mL) was heated at 100° C. for 18 hours. The reaction was quenched with water (2 mL). The product was extracted with EtOAc (20×3). The combined organic layer was then concentrated in vacuo and the residue was purified by chromatography (Silica Gel, EtOAC) to afford the title compound (75 mg) as a yellow solid. (M+1) 293.

Example 10

3-Pyridin-2-yl-5-pyridin-3-yl-benzene-1,2-diamine: To a solution of 2-nitro-6-pyridin-2-yl-4-pyridin-3-yl-phenylamine (75 mg, 0.26 mmol) in ethyl acetate (20 mL) was added 10% palladium on carbon (50 mg). The resulting suspension was placed in a Parr hydrogenation apparatus under 40 psi hydrogen gas while shaking at ambient temperature for one hour. The catalyst was removed by filtration and the filtrate concentrated in vacuo to afford compound the title compound (50 mg, 0.19 mmol).

Example 11

1-Ethyl-3-(7-pyridin-2-yl-5-pyridin-3-yl-1H-benzoindazol-2-yl)-urea (I-31): To a solution 3-pyridin-2-yl-5-pyridin-3-yl-benzene-1,2-diamine (50 mg, 0.19 mmol) and sulfuric acid (0.76 mL, 1 N) in water (1 mL) was added N'-ethyl-N-cyanourea (0.76 mL, 1 M). Enough sulfuric acid was added dropwise to achieve pH 3. The resulting mixture was heated at 100° C. for 8 hours. The reaction mixture was then cooled to ambient temperature. The solids were collected, washed with water and dried. The solids were purified by chromatography (Silica Gel, EtOAc, then 10% MeOH in EtOAc) to afford compound 5 (27 mg). $^1$H NMR (CDCl$_3$) δ 8.92 (d, 1H), 8.80 (m, 1H), 8.52 (m, 1H), 8.30 (m, 1H), 8.21 (d, 1H), 8.04 (s, 1H), 7.94 (m, 1H), 7.75 (s, 1H), 7.56 (d, 1H), 7.37 (m, 2H), 3.36 (q, 2H), 1.24 (t, 3H). (M+1) 359.

Example 12

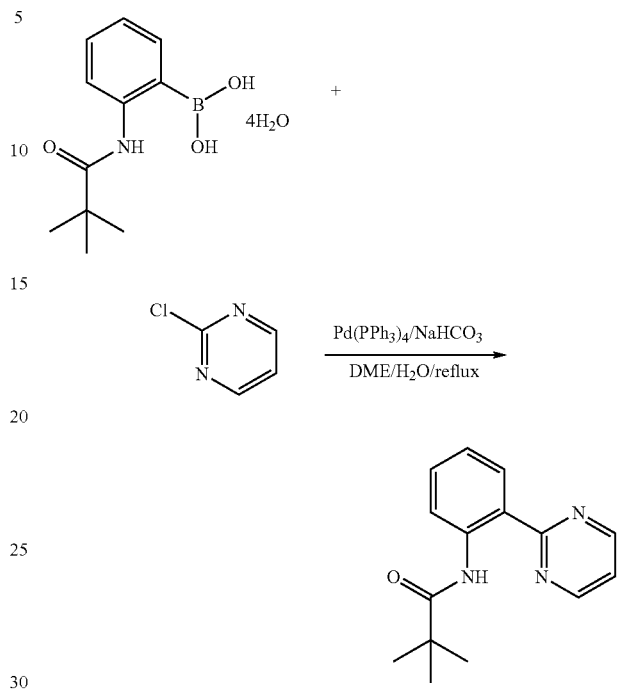

2,2-Dimethyl-N-(2-pyrimidin-2-yl-phenyl)-propionamide: A 5 L flask was charged with the above depicted boronic acid as a tetrahydrate (281.4 grams, 960 mmoles), 2-chloropyrimidine (100 g, 874 mmoles), NaHCO$_3$ (146.8 grams, 1.746 moles), and Pd(PPh$_3$)$_4$ (10.0 grams, 8.72 mmoles). Water (1 L) and dimethoxyethane (1 L) were added, and the mixture was heated slowly to 83° C. (internal temperature) over a 1 hour period with overhead stirring. After ~2 hours all solids had dissolved. The reaction was allowed to stir for 8 hours. The mixture was cooled to room temperature and stirred overnight after which time a thick precipitate had formed. The crude mixture was diluted with water (2 L) and stirred for an additional 2 hours after which time the mixture was filtered and the solids were washed sequentially with water, 0.1 N NaOH, and water again. The solids were then dried under high vacuum at 50° C. to afford the title compound (~233 grams) as a tan powder.

Example 13

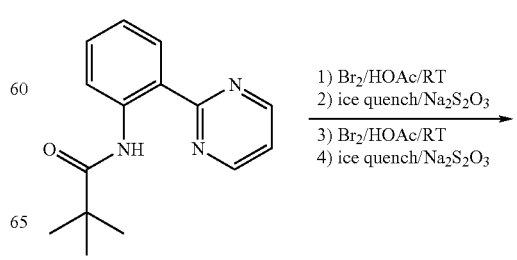

-continued

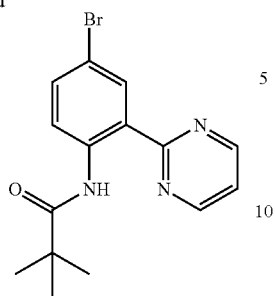

N-(4-Bromo-2-pyrimidin-2-yl-phenyl)-2,2-dimethyl-propionamide: To a room temperature suspension of 2,2-dimethyl-N-(2-pyrimidin-2-yl-phenyl)-propionamide (~117 grams, 437 mmoles) in acetic acid (1 L) was added bromine (67 mL, 1.31 moles) as a solution in 100 mL of acetic acid over a 1 hour period. The heterogenous mixture was stirred at room temperature for 5 hours over which time a thick precipitate formed. The mixture was then poured over ice, diluted with 1N $Na_2S_2O_3$ (2 L), and stirred for 1 hour. The solids were filtered, resuspended in water (2 L), stirred for 1 hour, then filtered and washed with water again. The resulting solids were pumped to dryness at 50° C., resuspended in HOAc (1 L), and treated with bromine (22 mL, 430 mmoles) in acetic acid solution (20 mL) over a 20 minute period. The resulting heterogenous mixture was stirred for 5 hours, then quenched and treated as described above. The resulting solids were vacuum dried at 50° C. to afford the title compound (165 grams) as a tan powder.

Example 14

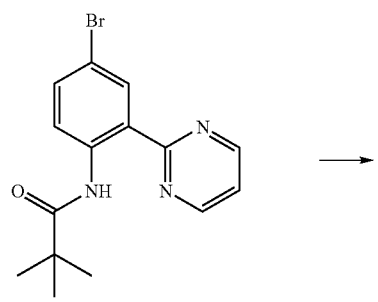

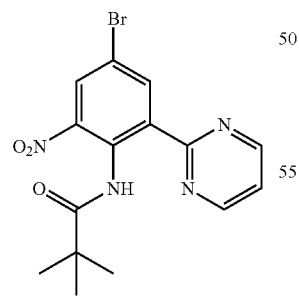

N-(4-Bromo-2-nitro-6-pyrimidin-2-yl-phenyl)-2,2-dimethyl-propionamide: To a 5° C. suspension of N-(4-bromo-2-pyrimidin-2-yl-phenyl)-2,2-dimethyl-propionamide (32.6 grams, 97.5 mmoles) in TFA (400 mL) was added 90% nitric acid (70 mL, 1.46 mmoles) over a 30 minute period. The mixture was then allowed to warm to room temperature and stir for a total of 2 hours. The crude reaction (now homogenous) was poured into ice producing a pasty mass. The mixture was diluted to 2 L total volume with water, treated with 500 mL of methanol, and vigorously stirred for 12 hours. The resulting solids were filtered, washed with copious amounts of water, then vacuum dried at 50° C. to afford the title compound (29.9 grams, 81% yield) as a tan powder.

Example 15

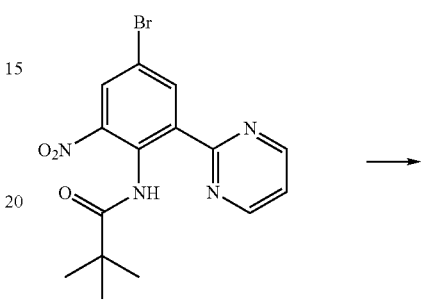

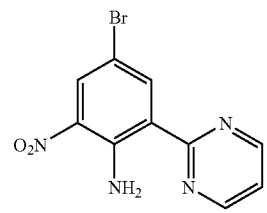

4-Bromo-2-nitro-6-pyrimidin-2-yl-pheylamine: A suspension of N-(4-bromo-2-nitro-6-pyrimidin-2-yl-phenyl)-2,2-dimethyl-propionamide (29.9 grams, 78.8 mmoles) in conc. HCl (200 mL) was refluxed for 8 hours. The partially homogeneous crude reaction was then cooled to room temperature, diluted with water (500 mL), and the resulting precipitate was stirred for 1 hour. The solids were then filtered, washed with water, and vacuum dried at 50° C. to afford the title compound (21.1 grams, 91% yield) as an orange powder.

Example 16

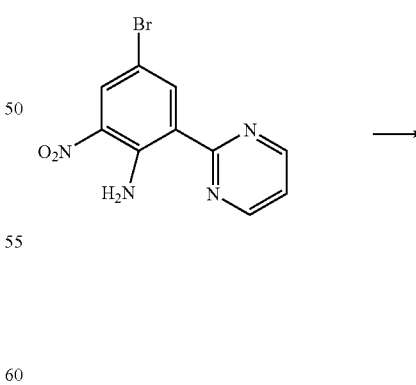

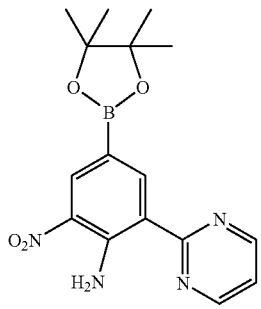

2-Nitro-6-pyrimidin-2-yl-4-(4,4,5,5-tetramethyl-[1,3,2]dioxaborolan-2-yl)-phenylamine: A mixture of 4-bromo-2-nitro-6-pyrimidin-2-yl-phenylamine (1.82 g, 6.2 mmol), bis(pinacolato)diboron (3.144 g, 12.4 mmol), PdCl$_2$dppf$_2$ (453 mg, 0.6 mmol) and KOAc (3.03 g, 31 mmol) in dioxane (60 ml) was heated at 105° C. for 2.5 hours. The reaction was filtered and washed with dichloromethane. The combined filtrates were concentrated under vacuum and water (100 ml) was added to the residue. Extraction with dichloromethane (3×50 ml), drying and concentration gave a residue, which was washed with ether-hexane to afford the title compound (2.07 g, 98%).

Example 17

Example 18

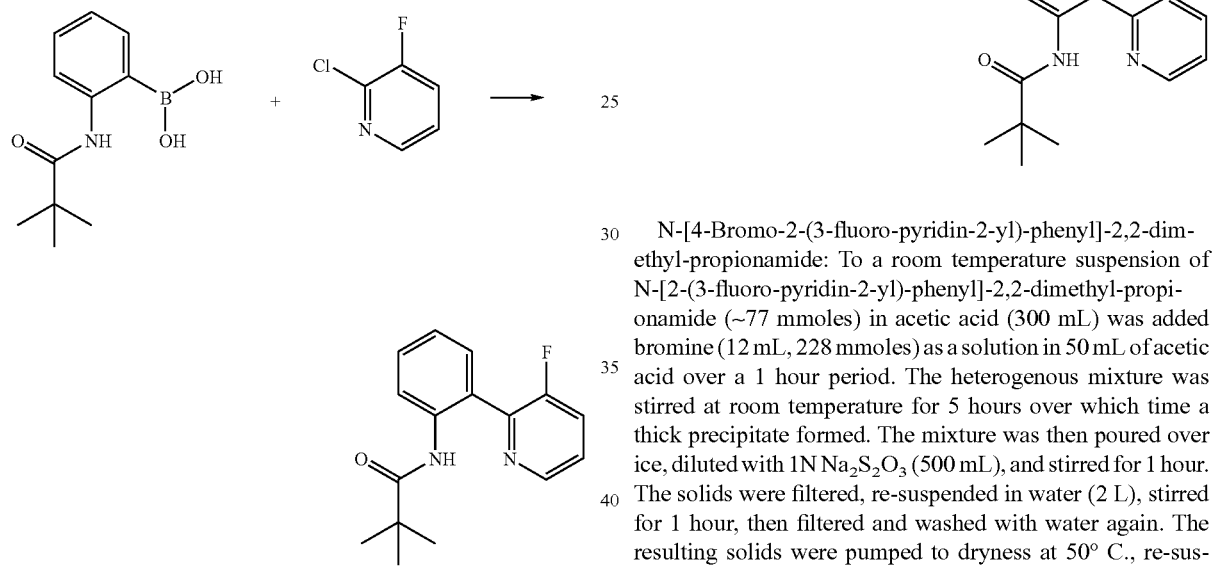

N-[2-(3-Fluoro-pyridin-2-yl)-phenyl]-2,2-dimethyl-propionamide: A 3 L flask was charged with the above depicted boronic acid as a tetrahydrate (92.1 grams, 314 mmoles), chlorofluoropyridine (37.6 g, 286 mmoles), NaHCO$_3$ (48.0 grams, 572 mmoles), and Pd(PPh$_3$)$_4$ (3.3 grams, 2.86 mmoles). Water (300 mL) and dimethoxyethane (300 mL) were added, and the mixture was heated slowly to 83° C. (internal temperature) over a 1 hour period with overhead stirring. After ~2 hours all solids had dissolved. The reaction was allowed to stir for 10 hours. The mixture was cooled to room temperature and stirred overnight after which time a thick gum had formed. The crude mixture was diluted with water (2 L) and stirred for an additional 2 hours. The mixture was then allowed to rest without stirring until the gum had settled to the bottom of the flask. The liquid phase was removed via vacuum, then replaced with 0.1 N NaOH and stirred for 15 minutes. The gum was allowed to settle and the liquid removed via vacuum. The gum was then similarly washed three times with water, then transferred to a 1 neck flask as an acetone solution. The mixture was concentrated in vacuo and azeotroped five times with ethyl acetate.

N-[4-Bromo-2-(3-fluoro-pyridin-2-yl)-phenyl]-2,2-dimethyl-propionamide: To a room temperature suspension of N-[2-(3-fluoro-pyridin-2-yl)-phenyl]-2,2-dimethyl-propionamide (~77 mmoles) in acetic acid (300 mL) was added bromine (12 mL, 228 mmoles) as a solution in 50 mL of acetic acid over a 1 hour period. The heterogenous mixture was stirred at room temperature for 5 hours over which time a thick precipitate formed. The mixture was then poured over ice, diluted with 1N Na$_2$S$_2$O$_3$ (500 mL), and stirred for 1 hour. The solids were filtered, re-suspended in water (2 L), stirred for 1 hour, then filtered and washed with water again. The resulting solids were pumped to dryness at 50° C., re-suspended in HOAc (400 mL), and treated with bromine (4 mL, 76 mmoles) in acetic acid solution (20 mL) over a 20 minute period. The resulting heterogenous mixture was stirred for 5 hours, then quenched and treated as described above. The resulting solids were vacuum dried at 50° C. to afford the title compound (19.1 grams, 72%) as a tan powder.

Example 19

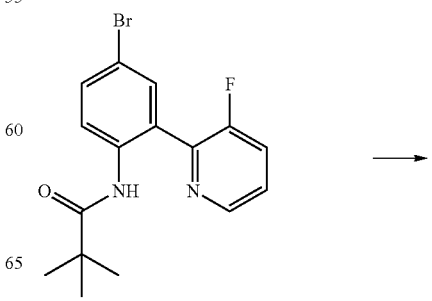

-continued

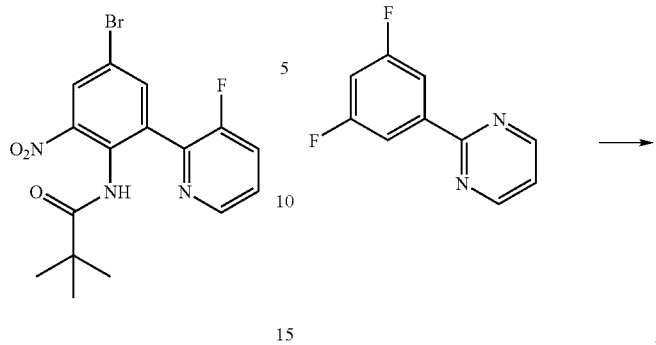

N-[4-Bromo-2-(3-fluoro-pyridin-2-yl)-6-nitro-phenyl]-2,2-dimethyl-propionamide: To a suspension of N-[4-bromo-2-(3-fluoro-pyridin-2-yl)-phenyl]-2,2-dimethyl-propionamide (6.45 grams, 18.4 mmoles) in TFA (100 mL) and TFAA (25.5 mL, 183.6 mmole), at 0° C., was added a TFA solution (30 mL) of 90% fuming nitric acid (2.46 mL, 55.1 mmoles) over a 45 minute period. The mixture was then stirred at 0° C. for a total of 4 hours. The crude reaction (now homogenous) was poured into ice producing a pasty mass. The mixture was diluted to 500 mL total volume with water, treated with 50 mL of methanol, and vigorously stirred for 12 hours. The resulting solids were filtered, washed with copious amounts of water, then dried in vacuo at 50° C. to afford the title compound (6.1 grams, 82% yield) as a tan powder.

Example 20

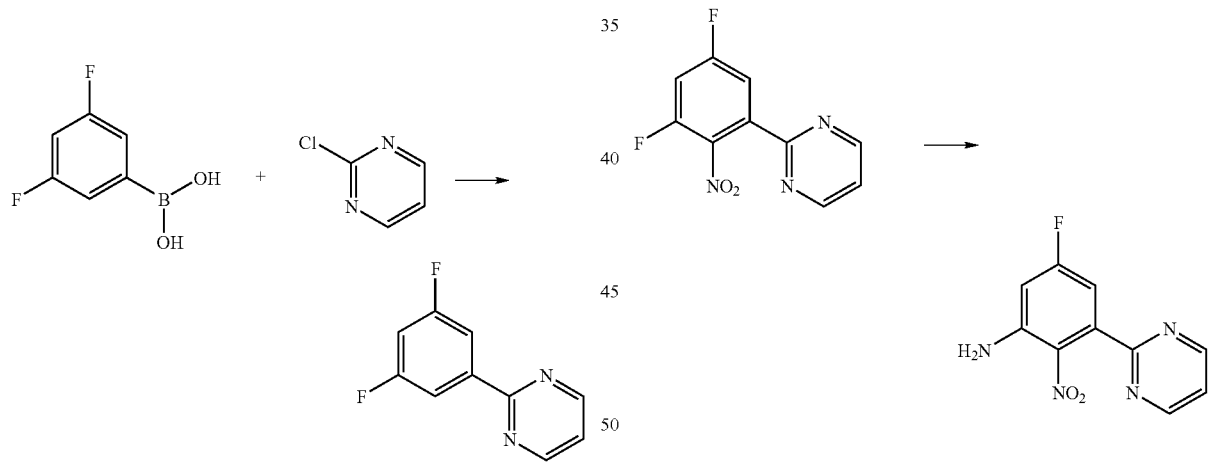

2-(3,5-Difluoro-phenyl)-pyrimidine: A solution of the difluoroboronic acid (5.4 g, 34.1 mmoles) and 2-chloropyrimidine (3.0 g, 26.2 mmoles) in ethanol (50 mL) was treated with Na$_2$CO$_3$ (3.6 g, 34.1 mmoles) and Pd(PPh$_3$)$_4$ (1.5 g, 1.31 mmoles) then heated at reflux for 3 days. The resulting mixture was then diluted with EtOAc, Silica gel added, and the resulting slurry stirred for 3 hours at room temperature. The crude mixture was then filtered through a silica gel pad with EtOAc, concentrated in vacuo, and flash chromatographed (silica gel, 19/1-14/1-9/1-7/1 hexanes/EtOAc gradient) to afford the title compound (1.38 g, 27%) as a white solid. $^1$H NMR (dmso-d$_6$, 500 MHz): 8.95 (d, 2H); 7.98 (m, 2H); 7.57 (dd, 1H); 7.48 (m, 1H).

Example 21

2-(3,5-Difluoro-2-nitro-phenyl)-pyrimidine: To a room temperature solution of 2-(3,5-difluoro-phenyl)-pyrimidine (1.2 g, 6.24 mmole) in H$_2$SO$_4$ (3 mL) was added 90% HNO$_3$ (0.375 mL, 9.37 mmoles) over 10 seconds via syringe. The resulting mixture was stirred at room temperature for 1 hour then poured into ice. The resulting heterogeneous mixture was then diluted with water, warmed to room temperature, and filtered. The solids were washed with water and dried in vacuo to afford the title compound (1.53 g, 100%) as a tan solid. $^1$H NMR (dmso-d$_6$, 500 MHz): 8.92 (d, 2H); 8.67 (m, 1H); 7.94 (m, 1H); 7.65 (dd, 1H).

Example 22

5-Fluoro-2-nitro-3-pyrimidin-2-yl-phenylamine: To a solution of 2-(3,5-difluoro-2-nitro-phenyl)-pyrimidine (1.5 g, 6.32 mmoles) in dioxane (10 mL) was added tBuNH$_2$ (6.6 mL, 63.24 mmoles) at room temperature. The mixture was heated to 100° C. in a sealed tube for 10 hours. The mixture was then cooled to room temperature, poured into water, and the solids stirred for 1 hour. The mixture was filtered, solids washed with water until filtrate was clear. The crude product was then diluted in MeOH, 6NHCl added, and the resulting mixture heated at reflux for 3 hours. The reaction was cooled to room temperature and poured into ice. The resulting heterogeneous mixture was warmed to room temperature, filtered, solids washed with water until filtrate ran clear, and dried in vacuo to afford the title compound (1.33 g, 90%) as an orange powder. $^1$H NMR (dmso-d$_6$, 500 MHz): 8.87 (d, 2H); 7.52 (dd, 1H); 7.08 (dd, 1H); 6.86 (dd, 1H); 6.60 (s, 2H).

Example 23

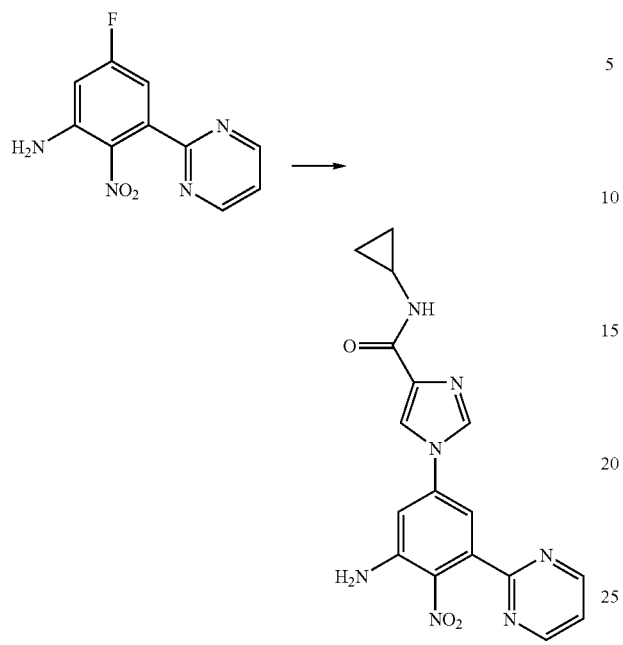

1-(3-Amino-4-nitro-5-pyrimidin-2-yl-phenyl)-1H-imidazole-4-carboxylic acid cyclopropylamide: To a mixture of 5-fluoro-2-nitro-3-pyrimidin-2-yl-phenylamine (650 mg, 2.77 mmole) in DMF (5 mL) was added 17 (545 mg, 3.6 mmoles) and Na$_2$CO$_3$ (381 mg, 3.60 mmoles) at room temperature. The resulting mixture was heated to 125° C. for 6 hours, then cooled to room temperature. The resulting mixture was diluted with water and the yellow precipitate was stirred for 1 hour. The crude reaction was filtered and the solids washed with water until the filtrate ran clear. The washed solids were then dried in vacuo to afford the title compound (960 mg, 95%) as a yellow powder. $^1$H NMR (dmso-d$_6$, 500 MHz): 8.91 (d, 1H); 8.42 (s, 1H); 8.29 (s, 1H); 8.08 (d, 1H); 7.52 (dd, 1H); 7.36 (d, 1H); 7.29 (d, 1H); 6.59 (s, 2H); 2.89 (m, 1H); 0.072 (m, 2H); 0.64 (m, 2H).

Example 24

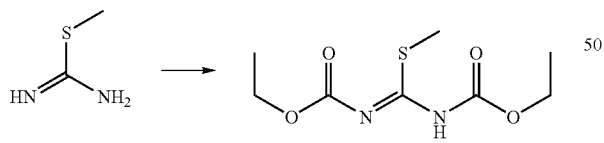

N,N-Diethlycarboxy-2-methyl-2-thiopseudourea: To a mixture of 2-methyl-2-thiopseudourea sulfate (22.8 g, 81.9 mmol) in methylene chloride (200 mL) was added triethylamine (34.5 mL, 245.7 mmol) and ethyl chloroformate (20.65 g, 245 mmol). After stirring over night the mixture was washed with water, brine then dried over sodium sulfate, filtered and concentrated in vacuo to a pungent oil which was flash chromatagraphed (10% ethyl acetate/hexanes) to provide the title compound (16.68 g, 86.9% Y) as a colorless oil which solidified on standing. $^1$H NMR (500 Mhz, CDCl$_3$) ∂1.3(q,6H), 2.41(s,3H), 4.22(m,4H).

Example 25

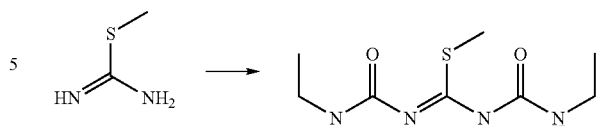

N,N-Diethlyureamido-2-methyl-2-thiopseudourea: To a mixture of 2-methyl-2-thiopseudourea sulfate (2.0 g, 7.18 mmol) in water (3 mL) was added ethyl isocyanate (1.137 mL, 14.37 mmol) followed by dropwise 6N NaOH to a stable pH 8. After 1 hour at pH8 the biphasic solution was diluted with aqueous saturated sodium bicarbonate and extracted into ethyl acetate (3×100 mL). The combined organic layers were washed with brine and dried over sodium sulfate, filtered then concentrated in vacuo to afford the title compound as a pungent oil (1.54 g, 92.7%). TLC (50% Ethyl acetate/methylene chloride) and $^1$H NMR suggests that the material is a mixture of mono and diacyl pseudourea. $^1$H NMR (500 Mhz, CDCl$_3$) ∂1.18(m2,6H), 2.31 and 2.41 (2s,3H), 3.28(m,4H).

Example 26

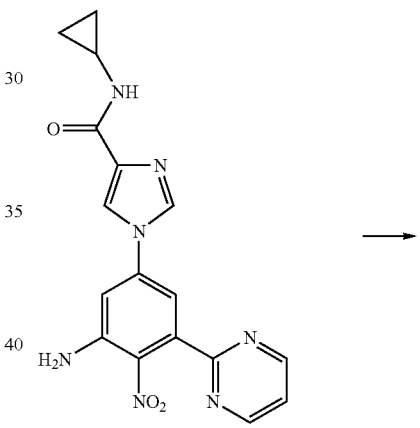

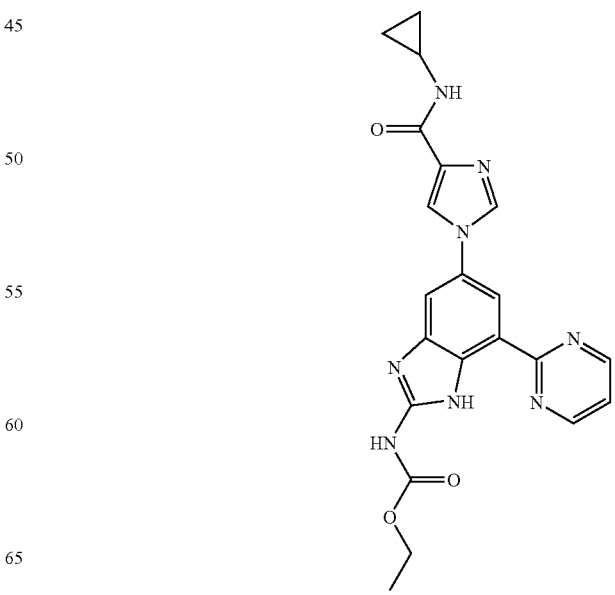

[5-(4-Cyclopropylcarbamoyl-imidazol-1-yl)-7-pyrimidin-2-yl-1H-benzoimidazol-2-yl]-carbamic acid ethyl ester: To a solution of 1-(3-amino-4-nitro-5-pyrimidin-2-yl-phenyl)-1H-imidazole-4-carboxylic acid cyclopropylamide (65 mg, 0.178 mmoles) in MeOH (10 mL) was added Ra—Ni (2 drops of water slurry, catalytic) and the resulting suspension was placed under 45 psi of H$_2$ (Parr shaker) for 2 hours. The resulting mixture was then filtered, concentrated, diluted with 3 mL of pH=3.5 buffer (made from 1M H$_2$SO$_4$ with enough NaOAc to raise pH to 3.5), and treated with N,N-diethlycarboxy-2-methyl-2-thiopseudourea (0.267 mL of a 1M solution of N,N-diethylcarboxy-2-methyl-2-thiopseudourea in dioxane) at room temperature. The resulting mixture was refluxed for 5 hours resulting in a heterogeneous suspension. The reaction was cooled to room temperature, diluted with water and enough NH$_4$OH to raise the pH to ~6.0. The solids were then filtered and washed sequentially with water, 2/1 water/ethanol, EtOAc, and then hexanes. The resulting solids were suspended in MeOH, 2 equivalents of methanesulfonic acid was added, and concentrated in vacuo to afford the title compound (75, 70%) as an off-white solid. $^1$H NMR (dmso-d$_6$, 500 MHz): 9.28 (s, 1H); 9.08 (d, 1H); 8.8-7.4 (v. broad s, 4H); 8.67 (s, 1H); 8.53 (s, 1H); 8.46 (d, 1H); 8.05 (d, 1H); 7.59 (dd, 1H); 4.33 (q, 2H); 2.88 (m, 1H); 2.35 (s, 6H); 1.34 (t, 3H); 0.76 (m, 2H); 0.61 (m, 2H).

Example 27

We have prepared other compounds of formula I by methods substantially similar to those described in Schemes I through IV, Examples 1 through 26, and by methods known in the art. The characterization data for these compounds is summarized in Table 3 below and includes LC/MS (observed) and $^1$H NMR data.

$^1$H NMR data is summarized in Table 3 below wherein $^1$H NMR data was obtained at 500 MHz in deuterated DMSO, unless otherwise indicated, and was found to be consistent with structure. Compound numbers correspond to the compound numbers listed in Table 2.

TABLE 3

Characterization Data for Selected Compounds of Formula I

| Compound No. I- | M − 1 (obs) | M + 1 (obs) | $^1$H NMR |
|---|---|---|---|
| 16 | 347.2 | 349.2 | 1.1(t, 3H) 3.2(q, 2H) 6.8(t, 1H) 7.5 (m, 1H), 7.7(s, 1H) 7.9(s, 1H) 8.1(d, 1H) 8.3(s, 1H) 8.6(d, 1H) 8.9(s, 1H) 9.6(s, 1H) 10.3(s, 1H) |
| 20 | 360.3 | 362.3 | (CD$_3$OD): 8.89(dd, 1H); 8.51(dd, 1H); 8.42-8.29(br. s, 1H), 8.18(ddd, 1H); 7.94-7.77(br. s, 1H); 7.63(br. s); 7.58 (br. s, 1H); 7.53(dd, 1H); 3.32(q, 2H); 2.21(s, 3H); 1.23(t, 3H) |
| 24 | 391.3 | 393.3 | 1.13(t, 3H), 1.3(t, 3H) 3.24(q, 2H), 3.37(q, 2H), 7.82(s, 1H), 7.82(s1H), 7.96(t, 1H) 8.19(s, 1H), 8.56(s, 1H), 8.62(d, 1H), 8.82(d, 1H), 9.15(s, 1H), 11.02(s, 1H) |
| 42 | 390.3 | 392.2 | 1.13(t, 3H) 2.45(s, 3H) 3.23(q, 2H) 3.46(s, 3H) 6.58(m, 4H), 7.78(m, 3H) 9.11(s, 1H) 10.51(s, 1H) 12.18(s, 1H) |
| 43 | — | — | 1.15(t, 3H), 3.25(m, 2H), 3.35(s, 3H), 4.6(s, 2H), 7.4(br s, 1H), 7.55(s, 1H), 7.8(m, 1H), 8.0(d, 1H), 8.05(d, 1H), 8.6(m, 1H), 8.7(m, 1H), 9.2(s, 1H), 10.4(br s, 1H) |
| 49 | — | — | 1.3(t, 3H), 4.3(q, 2H), 6.65(t, 1H), 7.75 (d, 1H), 7.85(dd, 1H), 7.9(s, 1H), 8.05 (d, 1H), 8.5(d, 1H), 8.75(dd, 1H), 9.1 (s, 1H0, 11.7(br s, 1H), |
| 50 | 377.2 | 379.1 | 1.23(t, 3H), 2.89(s, 3H), 3.36(q, 2H), 7.93(d, 1H), 8.16(d, 1H), 8.26(d, 1H), 8.33(d, 1H), 8.86(d, 1H), 8.97(d, 1H), 9.30(d, 1H) |
| 51 | — | — | 1.1(t, 3H), 1.25(t, 3H), 3.25(q, 2H), 3.37(s, 3H), 4.05(q, 2H), 6.6(m, 4H), 7.65(s, 1H), 7.9(m, 2H) 9.1(br s, 1H), 10.2(br s, 1H), 11.8(br s, 1H) |
| 54 | — | — | 0.5(m, 2H), 0.8(m, 2H), 2.7(m, 1H), 6.4(br s, 1H), 6.7(m, 1H), 7.75(s, 1H), 7.8(m, 1H), 7.85(s, 1H), 8.05(m, 1H), 8.5(brs, 1H), 8.7(m, 1H), 9.05(s, 1H), 9.15(s, 1H), 10.2(br s, 1H) |
| 55 | — | — | 1.15(t, 3H), 3.25(m, 2H), 7.25(m, 1H), 7.5(br s, 1H), 7.7(m, 1H), 7.85(s, 1H), 8.3(s, 1H), 8.4(m, 1H), 8.7(m, 2H), 8.85(s, 1H), 9.1(s, 1H), 9.15(dd, 1H), 10.5(br s, 1H), |
| 57 | 377.1 | 379.2 | 9.08(d, 1H); 8.48(br. s, 1h); 8.13, (d, 1H); 7.95(d, 1H); 7.88(s, 1H); 7.25(d, 1H); 6.75(d, 1H); 6.64(s, 1H);. 6.62(dd, |

TABLE 3-continued

Characterization Data for Selected Compounds of Formula I

| Compound No. I- | M − 1 (obs) | M + 1 (obs) | ¹H NMR |
|---|---|---|---|
| | | | 1H); 6.4-5.7(br. s, 2H); 5.69(q, 2H); 3.48(s, 3H); 1.48(t, 3H) |
| 61 | — | — | 1.13(t, 3H) 2.38(s, 3H) 3.24(q, 2H) 5.36(s, 2H) 6.71(m, 2H), 6.83(s, 1H) 7.18(d, 2H) 7.28(t, 1H) 7.38(m, 2H) 7.76(s, 1H) 7.92(s, 2H), 8.30(s, 1H) 9.08(s, 1H) 11.50(s, 1H) |
| 62 | 404.3 | 406.3 | 12.15, 11.81(s, 1H), 10.34, 9.99(s, 1H), 9.13, 8.99(s, 1H), 7.99-7.81(m, 3H), 7.68(s, 1H), 7.30-6.59(m, 4H), 5.09(m, 1H), 3.23(t, 2H), 1.339(d, 6H), 1.13(t, 3H) |
| 63 | — | — | 1.15(t, 3H) 2.44(s, 3H) 3.25(q, 2H) 5.44(s, 2H) 6.70(m, 3H) 7.40(d, 1H) 7.49(t, 1H) 7.75(s, 1H) 7.85(m, 1H) 7.97(s, 2H) 8.12(s, 1H) 8.60(d, 1H) 9.09(s, 1H) 11.21(s, 1H) |
| 64 | — | — | 1.2(t, 3H), 2.2(m, 2H), 3.3(m, 2H), 3.65(m, 2H), 4.1(t, 2H), 7.75(s, 1H), 7.84(s, 1H), 7.87(s, 1H), 7.8(m, 1H), 8.5(m, 1H), 8.65(m, 1H), 9.0(s, 1H) |
| 65 | 423.1 | 425.1 | (MeOH-d$_4$ & CDCl$_3$): 8.30-7.85(m, 4H), 6.78(s, 1H), 6.58(s, 1H), 3.60(s, 3H), 3.37(q, 2H), 2.80(s, 3H), 1.25(t, 3H) |
| 67 | — | — | 1.15(t, 6H), 3.45(q, 4H), 6.7(s, 1H), 7.7(m, 2H), 7.9(s, 1H), 8.1(s, 1H), 8.4 (m, 1H), 8.7(m, 1H), 9.1(m, 2H), 10.6 (br s, 1H), |
| 68 | 453.2 | 455.2 | 12.17, 11.81(s, 1H), 10.35, 9.99(s, 1H), 9.13, 9.00(s, 1H), 8.52(s, 1H), 7.99-7.69 (m, 5H), 7.32-7.27(m, 2H), 6.93-6.59 (m, 4H), 5.23(s, 2H), 3.22(q, 2H), 1.13(t, 3H) |
| 69 | 407.3 | 409.2 | (MeOH-d$_4$, HCl salt)): 8.62(s, 1H), 7.96-7.93(m, 2H), 7.59(s, 1H), 6.67(s, 1H), 5.81(s, 1H), 3.45, 3.39(s, 3H), 3.36(q, 2H), 3.28, 3.20(s, 3H), 1.23(t, 3H) |
| 70 | — | — | 1.15(t, 3H), 1.35(t, 3H), 3.25(q, 2H), 4.3(q, 2H), 7.1(br s, 1H), 7.85(s, 1H), 8.05(m, 1H), 8.2(s, 1H), 8.3(s, 1H), 8.8 (m, 1H), 8.85(d, 1H), 9.25(s, 1H), 9.65 (s, 1H), 10.7(br s, 1H), |
| 71 | 416.2 | 418.2 | 0.84(m, 2H) 1.14(m, 5H) 2.55(s, 3H) 2.91(m, 1H) 3.26(q, 2H) 6.59(s, 1H) 6.65(s, 1H) 6.69(s, 1H) 7.65(s, 1H) 7.81(m, 1H) 7.97(s, 1H) 8.07(s, 1H) 9.07(s, 1H) 11.59(s, 1H) |
| 72 | — | — | 1.1(t, 3H), 3.2(q, 2H), 7.1(br s, 1H), 7.8(s, 1H), 8.0(m, 1H), 8.2(s, 1H), 8.25 (s, 1H), 8.7(m, 1H), 8.8(m, 1H), 9.2(s, 1H), 9.6(s, 1H), 10.7(br s, 1H), |
| 73 | 448.2 | 450.2 | (CD$_3$OD): 1.18-1.26(m, 9H), 3.27(s, 3H), 3.36(q, 2H), 4.21(s, 2H), 6.65-6.68 (m, 1H), 6.90-6.94(m, 1H), 6.98-7.01 (m, 1H), 7.78-7.84(m, 2H), 7.93-7.96 (m, 1H), 8.09-8.11(m, 1H), 8.74-8.76 (m, 1H) |
| 74 | 434.3 | 436.3 | (CD$_3$OD): 1.21-1.27(m, 9H), 3.36(q, 2H), 4.17(s, 2H), 6.65-6.68(m, 1H), 6.95-6.99(m, 1H), 7.00-7.03(m, 1H), 7.79-7.82(m, 1H), 7.89(d, 1H), 7.94-7.96 (m, 1H), 8.09-8.11(m, 1H), 8.73-8.76(m, 1H) |
| 75 | — | — | 1.1(t, 3H), 3.0(br s, 3H), 3.25(m, 5H), 7.0(br s, 1H), 7.75(m, 2H), 8.05(s, 1H), 8.15(s, 1H), 8.45(m, 1H), 8.7(m, 1H), 9.1(s, 1H), 9.4(s, 1H), 10.4(br s, 1H), |
| 77 | 448.3 | 450.2 | (CD$_3$OD): d 1.24(t, 3H), 1.27(d, 3H), 1.47(d, 3H), 3.36(q, 2H), 3.37(s, 3H), 3.58-3.67(m, 1H), 5.21-5.28(m, 1H), 6.68-6.71(m, 1H), 7.80(d, 1H), 7.85(s, 1H), 7.95-7.99(m, 2H), 8.27(s, 1H), 8.38(d, 1H), 8.78-8.82(m, 1H). |

TABLE 3-continued

Characterization Data for Selected Compounds of Formula I

| Compound No. I- | M − 1 (obs) | M + 1 (obs) | ¹H NMR |
|---|---|---|---|
| 78 | 448.3 | 450.3 | (CD$_3$OD): d 1.24(t, 3H), 1.31(d, 3H), 1.51(d, 3H), 3.38(q, 2H), 3.42(s, 3H), 3.66-3.73(m, 1H), 5.44-5.51(m, 1H), 6.68-6.71(m, 1H), 7.94(d, 1H), 7.96-7.98(m, 1H), 8.03(s, 1H), 8.07(s, 1H), 8.32(s, 1H), 8.43(d, 1H), 8.81-8.86(m, 1H). |
| 79 | 434.3 | 436.2 | (CD$_3$OD): d 1.24(t, 3H), 1.32(d, 3H), 1.50(d, 3H), 3.37(q, 2H), 3.93-4.02(m, 1H), 5.14-5.22(m, 1H), 6.67-6.71(m, 1H), 7.90(d, 1H), 7.95-7.98(m, 1H), 8.02(s, 1H), 8.04(s, 1H), 8.32(s, 1H), 8.41(d, 1H), 8.81-8.85(m, 1H). |
| 82 | 428.2 | 430.1 | 9.0(m, 1H), 8.6(d, 1H), 8.4(m, 1H), 8.1-8.2(m, 2H), 8.0(m, 1H), 7.8(m, 1H), 7.5(m, 2H), 6.6(s, 1H), 4.8(s, 1H), 2.55(s, 3H), 3.25(m, 2H), 2.1(s, 3H), 1.1(t, 3H) |
| 83 | 417.1 | 419.1 | 11.01(br. s, 1H); 9.10(d, 1H); 8.37, (s, 1H); 8.19(s, 1H); 7.97(s, 1H); 7.78(br. s, 1H); 7.58(m, 1H); 7.08, (s, 1H); 6.68 (m, 1H); 3.88(dd, 2H); 3.22(dq, 2H); 2.99(dd, 2H);, 1.91(ddd, 2H); 1.85 (ddd, 2H); 1.11(t, 3H). |
| 84 | 377.2 | 379.2 | (MeOD-d$_3$): 8.72(br s, 1H), 8.58(s, 1H), 8.40(s, 1H), 8.19(s, 1H), 7.95(s, 1H), 7.14(s, 1H), 6.68(s, 1H), 3.60(s, 3H), 3.21(q, 2H), 1.24(t, 3H). |
| 85 | 430.2 | 432.2 | (MeOD-d$_3$, salt): 8.64(d, 1H), 8.14(s, 1H), 8.00(s, 1H), 7.97(d, 1H), 7.64(s, 1H), 6.66(dd, 1H), 6.51(s, 1H), 3.89(s, 3H), 3.48(s, 3H), 3.37(q, 2H), 1.24(t, 3H) |
| 87 | 360.1 | 362.1 | MeOD-d$_3$, 1.24(t, 3H), 2.42(s, 3H), 3.38 (q, 2H), 6.87(s, 1H), 7.94(s, 1H), 8.15 (m, 2H), 8.85(d, 1H), 8.98(d, 1H), 9.30 (s, 1H) |
| 88 | 388 | 390 | 9.27(s, 2H). 9.20(S, 1H), 8.27(s, 1H). 8.10(m, 1H), 7.94(s, H), 7.92(d, 1H), 6.95(d, 1H), 4.10(s, 3H), 3.25(m, 2H), 1.11(t, 3H) |
| 89 | 386.9 | 389.2 | (CD$_3$OD) 8.92-6.96(m, 9ArH), 3.99(s, 3H), 3.36(q, 2H), 1.24(t, 3H) |
| 90 | 457.1 | 459.2 | — |
| 91 | 429.2 | 431.2 | (CD$_3$OD): 8.97(s, 1H); 8.89(d, 1H); 8.49(d, 1H); 8.37(m, 2H); 8.22(ddd, 1H); 7.93(d, 1H); 7.64(dd, 1H); 3.38(q, 2H);2.91(m, 1H); 1.25(t, H): 0.88(m, 2H); 0.67(m, 2H). |
| 92 | 360.13 | 362.19 | 1.15(t, 3H), 3.25(m, 2H), 3.9(s, 3H), 7.15(m, 1H), 7.65(m, 1H), 7.8(s, 1H), 8.0(s, 1H), 8.2(m, 1H), 8.3(m, 1H), 8.65(m, 1H), 9.0(m, 2H), 10.3(br s, 1H) |
| 93 | 371 | 373 | 1.12(t, 3H), 3.25(m, 2H), 4.2(bs, 2H), 7.0.2-7.25(m, 1H), 7.5(m, 1H), 7.81(m, 1H), 8.08(t, 1H), 8.22(m, 1H), 8.61-8.48(m, 2H), 8.4(d, 1H), 8.46(s, 1H). |
| 94 | 430 | 432 | 0.92(d, 6H), 1.12(m, 3H), 2.23(m, 1H), 2.83(d, 2H), 3.35(m, 2H), 7.5(m, 1H), 7.61(bs, 1H), 7.89 (s, 1H), 8.1(m, 1H), 8.4(s, 1H), 8.58(m, 1H), 8.78(bs, 1H), 8.3(d, 1H). |
| 95 | 431.03 | 433.2 | (CD$_3$OD) 1.2(7, 3H), 3.3(q, 2H), 3.8 (m, 2H), 4.6(m, 2H), 7.4(m, 1H), 7.8 (m, 1H), 8.0(s, 1H), 8.3(m, 2H), 8.5(m, 1H), 8.7(m, 2H), 9.1(s, 1H) |
| 96 | 507.2 | 509.2 | (CD$_3$OD): 8.9(d, 1H), 8.55(d, 1H), 8.4(s, 1H), 8.3(m, 1H), 8.0(s, 1H), 7.7(m, 1H), 7.3(t, 1H), 7.0(s, 2H), 6.85(d, 1H), 6.7(d, 2H), 5.5(s, 2H), 3.7(s, 3H), 3.3(q, 2H), 2.5(s, 3H), 1.25(t, 3H) |
| 97 | 401 | 403 | 9.1(s, 1H), 8.6(d, 2H), 8.3(m, 1H), 8.1 (s, 1H), 7.9(s, 1H), 7.8(s, 1H) 7.5(m, |

TABLE 3-continued

Characterization Data for Selected Compounds of Formula I

| Compound No. I- | M − 1 (obs) | M + 1 (obs) | ¹H NMR |
|---|---|---|---|
| 98 | 497.03 | 499.18 | 1H), 7.0(d, 1H), 4.3(m, 2H), 3.3(m, 2H), 1.4(t, 3H), 1.1(t, 3H). , 1.16(t, 3H) 3.25(q, 2H) 4.44(d, 2H) 7.17(t, 2H) 7.38(t, 2H)7.53(t, 1H) 7.79(m, 1H) 7.87(s, 1H) 8.10(t, 1H) 8.32(s, 1H) 8.51(s, 1H) 8.57(d, 1H) 8.77(s, 1H) 8.82(d, 1H) 8.94(t, 1H) 11.10(br s, 1H) |
| 99 | 432 | 434 | — |
| 100 | 418.25 | 420.15 | 1.1(t, 3H), 3.2(m, 2H), 3.95(s, 3H), 4.1 (s, 2H), 7.2(br s, 1H), 7.25(brs, 1H), 7.9 (s, 1H), 8.2(m, 1H), 8.25(s, 1H), 8.7(d, 1H), 9.05(s, 2H), 10.4(br s, 1H) |
| 101 | 431 | 433 | 8.65(d, 1H), 8.28(s, 1H), 8.24(s, 1H), 7.98(d, 1H), 7.78(d, 1H), 7.38(m, 1H), 6.93(s, 1H), 6.89(dd, 1H), 4.51(q, 2H), 3.63(s, 3H), 3.35(q, 2H), 1.55(t, 3H), 1.22(t, 3H) |
| 102 | 375 | 377 | 8.86(d, 1H), 8.69(m, 1H), 8.52(d, 1H), 8.16(m, 2H), 7.79(m, 2H), 7.56(m, 1H), 7.50(m, 1H), 3.55(m, 2H) 1.23, (t, 3H) |
| 103 | 430 | 432.1 | 8.87(br. s, 1H); 8.81(d, 1H); 8.66(br. s., 1H); 8.49(s, 1H); 8.39(br. s., 1H); 8.25 (d, 1H); 8.09(ddd, 1H); 7.87(d, 1H); 7.52(dd, 1H); 5.3(very br. s, 5 H); 4.29 (q, 2H); 2.85(m, 1H); 1.31(t, 3H); 0.72 (m, 2H); 0.63(m, |
| 104 | 417.19 | 419.14 | 1.1(t, 3H), 3.2(q, 2H), 3.45(s, 3H), 4.1 (s, 3H), 6.7(dd, 1H), 6.85(d, 1H), 7.15 (br s, 1H), 7.35(br s, 1H), 7.8(d, 1H), 7.95(s, 1H), 8.2(s, 1H), 8.4(br s, 1H), 8.7(d, 1H), 10.5(br s, 1H) |
| 105 | 406 | 408 | 8.97(br. s, 2H); 8.60(d, 1H); 7.99(br. s., 1H); 7.96(m, 1H); 7.81(br. s., 1H); 7.57(m, 1H); 3.98(s, 3H); 3.25(m, 2H); 1.11(t, 3H). |
| 106 | 508.2 | 510.2 | 1.1(t, 3H), 2.4(s, 3H), 3.2(q, 2H), 4.1 (s, 3H), 5.4(s, 2H), 6.65(s, 1H), 6.75(s, 1H), 7.15(br s, 1H), 7.3(m, 2H), 7.35 (m, 1H), 7.8(m, 1H), 7.95(s, 1H), 8.25 (s, 1H), 8.35(br s, 1H), 8.5(m, 1H), 8.75 (m, 1H), 10.5(br s, 1H) |
| 107 | 495.2 | 497.2 | 8.8(m, 1H), 8.2(m, 1H), 7.9(s, 1H), 7.8(m, 1H), 7.4(m, 2H), 7.35(d, 2H), 7.25(d, 2H), 6.7-6.8(m, 2H), 5.3(2, 2H), 4.0(m, 1H), 3.4(q, 2H), 2.4(s, 3H), 1.1(t, 3H) |
| 108 | 417 | 419 | 9.12(br. s, 1H); 8.60(d, 1H); 8.39(m, 1H); 8.36(s, 1H); 8.25(s, 1H); 7.89(s, 1H); 7.70(dd, 1H); 7.41(m, 1H); 4.13 (s, 3H); 3.98(s, 3H); 3.26(m, 2H); 1.15 (t, 3H). |
| 109 | 358.3 | 360.1 | (CD₃OD) 9.61(d, 1H), 9.22(d, 1H), 8.83-8.79(m, 3H), 8.65(d, 1H), 8.47(d, 1H), 8.02(dd, 1H), 8.00(s, 1H), 3.37(q, 2H), 1.24(t, 3H) |
| 110 | 388.3 | 390.2 | (CDCl₃) 14.05(br s, 1H), 12.85(br s, 1H), 8.37(t, 1H), 7.97(d, 1H), 7.88(d, 1H), 7.79-7.74(m, 2H), 7.63(dd, 1H), 7.46(d, 1H), 6.62(dd, 1H), 5.75(br s, 1H), 3.45-3.40(m, 2H), 1.27(t, 3H) |
| 111 | 492.3 | 494.1 | 10.3(s, 1H), 8.9(d, 1H), 8.6(m, 1H), 8.5(d, 1H), 8.2(s, 1H), 8.05(t, 1H), 7.8-7.9(m, 2H), 7.5(m, 2H), 7.4(d, 1H), 7.3(m, 1H), 6.7(s, 1H), 6.6(s, 1H), 3.3(q, 2H), 1.9(d, 3H), 1.1-1.2(t, 3H). |
| 112 | 475.2 | 477.2 | 10.62(s, 1H); 8.74(d, 1H); 8.65(s, 1H); 8.40(s, 1H); 8.28(s, 1H); 8.23(s, 1H); 7.87(s, 1H); 7.43(s, 1H); 7.32(m, 2H); 5.52-4.41(br. s, 3H); 4.10(s, 3H); 3.24 (dt, 2H); 1.41(s, 9H); 1.13(t, 3H). |
| 113 | 494.2 | 496.2 | (CD₃OD) 9.06(s, 1H); 8.93(d, 1H); 8.71 (d, 1H); 8.50(m, 2H); 8.39(s, 1H); 8.00 (s, 1H); 7.87(dd, 1H); 7.42(d, 2H); 7.35 |

TABLE 3-continued

Characterization Data for Selected Compounds of Formula I

| Compound No. I- | M − 1 (obs) | M + 1 (obs) | $^1$H NMR |
|---|---|---|---|
| 114 | 370.2 | 372.2 | (dd, 2H); 7.25(dd, 1H); 5.27(q, 1H); 4.41(q, 2H); 1.62(d, 3H); 1.42(t, 3H) 12.09 & 12.74(s, 1H), 10.25 & 9.94(s, 1H), 9.12 & 8.94(s, 1H), 8.35-6.58(m, 9H), 3.24(m, 2H), 1.13(t, 3H) |
| 115 | 442.1 | 444.3 | (CD$_3$OD) 8.65(d, 1H), 7.94(s, 1H), 7.91 (d, 1H), 7.72(d, 2H), 7.66(s, 1H), 7.40 (d, 2H), 6.63(dd, 1H), 4.52(s, 2H), 3.40 (t, 2H), 3.35(q, 2H), 2.47(t, 2H), 2.09-2.03(m, 2H), 1.24(t, 3H) |
| 116 | 382 | 384 | — |
| 117 | 415 | 417 | 9.17(br. s, 1H); 9.0(m, 1H); 8.98(d, 1H); 8.72(d, 1H); 8.55(m, 1H); 8.38(s, 1H); 7.94(s, 1H); 7.86(d, 1H); 7.79(m, 1H); 3.97(s, 3H); 3.27(m, 2H); 1.15(t, 3H). |
| 118 | 401 | 403 | — |
| 119 | 403.3 | 405.2 | (CD$_3$OD): 8.78(s, 1H), 8.67(d, 1H), 8.37(d, 1H), 8.24(d, 1H), 8.22(s, 1H), 8.04(d, 1H), 7.91(s, 1H), 7.67(dd, 1H), 7.40(dd, 1H), 4.22(s, 3H), 3.34(q, 2H), 1.23(t, 3H) |
| 120 | 434.32 | 436.23 | 1.1(t, 3H), 2.8(s, 6H), 3.2(m, 2H), 3.4 (s, 3H), 4.6(s, 2H), 6.6(d, 1H), 6.8(s, 1H), 7.2(br s, 1H), 7.6(s, 1H), 7.8(d, 1H), 7.9(s, 1H), 7.95(s, 1H), 10.0(br s, 1H), 10.2(br s, 1H) |
| 121 | 414 | 416 | (CD$_3$OD): 9.40(br. s, 1H); 9.07(d, 1H); 8.98(d, 1H); 8.91(d, 1H); 8.80(s, 1H); 8.60(s, 1H); 8.24(dd, 1H); 8.11(d, 1H); 7.84(dd, 1H); 3.35(m, 2H); 3.01 (s, 3H); 1.25(t, 3H). |
| 122 | 415 | 417 | — |
| 123 | 435.28 | 437.26 | 1.3(t, 3H), 2.8(s, 6H), 3.5(s, 3H), 4.2 (q, 2H), 4.6(s, 2H), 6.6(dd, 1H), 6.7(s, 1H), 7.7(s, 1H), 7.8(d, 1H), 8.0(m, 2H), 10.1(br s, 1H), 11.7(br s, 1H) |
| 124 | 431.2 | 433.2 | 9.28(s, 1H); 9.08(d, 1H); 8.8-7.4(v. broad s, 4H); 8.67(s, 1H); 8.53(s, 1H); 8.46(d, 1H); 8.05(d, 1H); 7.59(dd, 1H); 4.33(q, 2H); 2.88(m, 1H); 2.35(s, 6H); 1.34(t, 3H); 0.76(m, 2H); 0.61(m, 2H). |
| 125 | 447.4 | — | 9.10(s, 1H); 8.60(d, 1H); 8.47(m, 2H); 7.95(s, 1H); 7.83(s, 1H); 7.12(d, 1H); 5.2-3.6(br. m, 7H); 2.86(M, 1H); 1.30 (t, 3H); 0.75(m, 2H); 0.64(m, 2H) |
| 126 | 439.2 | 441.2 | (CDCl$_3$) 13.89(br s, 1H), 12.89(br s, 1H), 8.28(d, 1H), 8.25(d, 1H), 7.96(d, 1H), 7.74(s, 1H), 7.69-7.43(m, 6H), 7.40(s, 1H), 6.64(dd, 1H), 6.11(br s, 1H), 3.46-3.40(m, 2H), 1.27(t, 3H) |
| 127 | 418.2 | 420.2 | (CD$_3$OD) 9.72(d, 1H), 8.87(d, 1H), 8.82(d, 1H), 8.11(d, 1H), 8.09(d, 1H), 7.85(d, 1H), 7.39(d, 1H), 7.36(d, 1H), 4.43(q, 2H), 3.35(q, 2H), 1.44(t, 3H), 1.24(t, 3H) |
| 128 | 449.8 | 452.1 | (CD$_3$OD) 9.21(d, 1H), 8.83(ddd, 1H), 8.81(dd, 1H), 8.68(d, 1H), 8.26(d, 1H), 8.18(d, 1H), 8.07(dd, 1H), 8.05(d, 1H), 7.50(dd, 1H), 3.36(q, 2H), 3.34(s, 3H), 1.23(t, 3H) |
| 129 | — | — | 9.31(s, 1H); 9.08(d, 2H); 8.63(s, 1H); 8.43(d, 1H); 8.02(d, 1H); 7.89(s, 1H); 7.57(t, 1H); 8.8-6.6(very br. s, 4H); 4.31(q, 2H); 2.32(s, 6H); 1.42(s, 9H); 1.33(t, 3H). |
| 130 | 495.4 | 497.2 | 9.07(d, 2H); 8.73(d, 1H); 8.56(s, 1H); 8.44(d, 1H); 8.03(d, 1H); 7.57(t, 3H); 7.44(d, 2H); 7.36(dd, 2H); 7.26(dd, 1H); 6.95-5.90(very broad s., 5H); 5.18 (dt, 1H); 4.32(q, 2H); 2.32(s, 6H); 1.53 (d, 3H); 1.33(t, 3H). |
| 131 | 432 | 434 | (CD$_3$OD) 1.08(d, 6H), 1.43(t, 3H), 2.33(m, 1H), 2.91(d, 2H), 4.45(q, 2H), |

TABLE 3-continued

Characterization Data for Selected Compounds of Formula I

| Compound No. I- | M − 1 (obs) | M + 1 (obs) | $^1$H NMR |
|---|---|---|---|
| | | | 7.53(t, 1H), 8.08(s, 1H), 8.79(s, 1H) <8.94(s, 1H), 9.05(d, 2H), 9.5(s, 1H). |
| 132 | 514.23 | 516.23 | 8.84(d, 1H), 8.81-8.83(m, 1H), 8.35(s, 1H), 8.06(dd, 1H), 7.90(dd, 1H), 7.80(d, 1H), 6.80(br s, 1H), 6.70(d, 1H), 4.30(q, 2H), 3.42-3.54(m, 4H), 3.48(s, 3H), 3.12-3.17(m, 4H), 2.81(d, 3H), 1.32(t, 3H)ppm |
| 133 | 501.33 | 503.26 | — |
| 134 | 521.6 | 523.2 | (CD$_3$OD) 8.82(s, 1H),m 8.46(d, 1H), 8.30(s, 1H), 8.13(dd, 1H), 7.90(s, 1H), 7.55(dd, 1H), 7.28(dd, 1H), 6.86-6.77(m, 4H), 6.74(s, 1H), 3.77(s, 3H), 3.36(q, 2H), 2.41(br s, 3H), 1.97(d, 3H), 1.24(t, 3H) |
| 135 | 470.3 | 472.5 | (CD$_3$OD) 8.85(br s, 1H), 8.45(d, 1H), 8.34(dd, 1H), 8/26(dd, 1H), 8.13(ddd, 1H), 7.96(dd, 1H), 7.56(dd, 1H), 7.43(dd, 1H), 7.29 & 7.20(s, 1H), 5.49(m, 1H), 3.66-3.25(m, 4H), 3.38(q, 2H), 2.94(2s, 3H), 2.52(m, 1H), 2.38(m, 1H), 2.15(m, 1H) |
| 136 | 521.3 | 523.3 | (CD$_3$OD) 8.81(d, 1H), 8.43(d, 1H), 8.27(s, 1H), 8.11(ddd, 1H), 7.88(s, 1H), 7.54(dd, 1H), 7.28(dd, 1H), 6.87(d, 1H), 6.84(d, 1H), 6.81(s, 1H), 4.42(q, 2H), 3.78(s, 3H), 2.50(br s, 3H), 2.00(d, 3H), 1.41(t, 3H) |
| 137 | 522.6 | 524.2 | (CD$_3$OD) 8.90(d, 1H), 8.81(d, 1H), 8.49(dd, 1H), 8.41(s, 1H), 8.06(s, 1H), 7.84(dd, 1H), 7.29(dd, 1H), 6.99(br s, 1H), 6.92(s, 1H), 6.87(d, 1H), 6.84(d, 1H), 6.81(s, 1H), 4.42(q, 2H), 3.78(s, 3H), 2.50(br s, 3H), 2.00(d, 3H), 1.41(t, 3H) |
| 138 | 525 | 527 | 1.2(t.3H). 1.5(d, 3H), 3.73(s, 3H), 4.3(q, 2H), 5.13(m, 1H), 6.8(d, 1H), 7.0(m, 2H), 7.24(t, 1H), 7.53(t, 1H), 7.93(s, 1H), 8.24(s, 1H), 8.32(m, 2H), 8.4(s, 1H), 9.08(s, 1H), 11.79(bs, 1H), 12.18(s, 1H). |
| 139 | 522.5 | 524.2 | (CD$_3$OD): 8.86(d, 1H), 8.74(d, 1H), 8.41(dd, 1H), 8.35(s, 1H), 7.99(s, 1H), 7.78(dd, 1H), 7.28(dd, 1H), 6.85(d, 1H), 6.83(d, 1H), 6.80(s, 2H),m 6.76(s, 1H), 4.41(q, 2H), 3.77(s, 3H), 2.41(br s, 3H), 1.97(d, 3H), 1.41(t, 3H) |
| 140 | 499 | 501 | — |
| 141 | 425.3 | 427.2 | (CD$_3$OD) 8.8(d, 1H), 8.35(d, 1H), 8.2(s, 1H), 8.1(t, 1H), 8.0(s, 1H), 7.9(d, 1H), 7.8(s, 1H), 7.65-7.7(dd, 1H), 7.5(t, 1H), 7.49(d, 1H), 4.6(s, 2H), 4.45(s, 1H), 3.4(q, 2H), 3.2(s, 3H), 3.15(s, 1H), 1.2(t, 3H) |
| 142 | 426.3 | 428.2 | (CD$_3$OD): 8.8(d, 1H), 8.6(d, 1H), 8.3(m, 2H), 8.1(s, 1H), 8.0(d, 1H), 7.9(s, 1H), 7.7(d, 1H), 4.6(s, 2H), 4.45(s, 1H), 4.4-4.5(q, 2H), 3.3(s, 3H), 3.15(s, 1H), 1.4(t, 3H) |
| 143 | 498 | 500 | — |
| 144 | 497 | 499 | (CD$_3$OD) 1.42(t, 3H), 1.84(d.3H), 4.49(q, 2H), 6.43(q, 1H). 7.58(t, 1H), 8.03(t, 1H), 8.08(s, 1H), 8.23(d, 1H), 8.67(t, 1H), 8.73(s, 1H), 8.39(d, 2H), 8.88(d, 2H), 9.06(s, 2H). |
| 145 | 457 | 459 | (CD$_3$OD) 1.4(t, 3H), 3.48(s, 4H), 3.99(s, 4H), 4.41(s, 2H), 7.7(d, 1H), 8.07(s, 1H) 8.05(m, 3H), 8.73(s, 1H), 8.9(s, 1H), 9.12(s, 1H). |
| 146 | — | 502.21 | (CD$_3$OD) 8.89(s, 1H), 8.49(d, 1H), 8.45(s, 1H), 8.22(d, 1H), 8.11(d, 1H), 8.06 |

TABLE 3-continued

Characterization Data for Selected Compounds of Formula I

| Compound No. I- | M − 1 (obs) | M + 1 (obs) | $^1$H NMR |
|---|---|---|---|
| 147 | — | 487.2 | (s, 1H), 7.47(br d, 1H), 7.36(br s, 1H), 3.91(s, 3H), 3.68-3.89(br m, 8H), 3.38 (q, 2H), 1.25(t, 3H)ppm (CD$_3$OD) 8.99(s, 1H), 8.54(d, 1H), 8.46 (s, 1H), 8.27(d, 1H), 8.01(s, 1H), 7.85 (br s, 1H), 6.97(br s, 1H), 6.91(br s, 1H), 4.47(q, 2H), 3.66-3.69(m, 5H), 3.59-3.62(m, 2H), 2.01-2.06(m, 2H), 1.96-2.00(m, 2H), 1.43(t, 3H) ppm |
| 148 | 375 | 377 | (CD$_3$OD): 9.02(t, 2H), 8.98(s, 2H), 8.82(d, 1H), 8.05(d, 1H), 7.54(t, 1H), 4.48(q, 2H), 1.44(t, 3H) |
| 149 | — | 486.22 | (CD$_3$OD) 8.98(s, 1H), 8.44(m, 1H), 8.38(br s, 1H), 8.19(br d, 1H), 8.02(br s, 1H), 7.98(br s, 1H), 7.15(br s, 1H), 7.13(br s, 1H), 3.79(br s, 3H), 3.67(m, 2H), 3.61(m, 2H), 3.37(q, 2H), 2.05(m, 2H), 2.00(m, 2H), 1.25(t, 3H) p |
| 150 | 494.3 | 496.2 | (CD$_3$OD) 9.0(d, 2H), 8.8(s, 1H), 8.6(d, 1H), 8.2(t, 1H), 7.95(s, 1H), 7.8(d, 1H), 7.65(t, 1H), 7.5(t, 1H), 6.9(s, 1H), 6.6(s, 1H), 6.1(m, 1H), 4.4(q, 2H), 2.7(s, 3H), 2.05(d, 3H), 1.4(t, 3H) |
| 151 | 493.4 | 495.2 | (CD$_3$OD) 8.95(d, 2H), 8.6(s, 1H), 8.5(d, 1H), 8.1(t, 1H), 7.8(s, 1H), 7.7(d, 1H), 7.5(t, 1H), 7.4(1, 1H), 6.8(s, 1H), 6.6(s, 1H), 6.0(m, 1H), 3.35(q, 2H), 2.6(s, 3H), 2.0(d, 3H), 1.2(t, 3H) |
| 152 | — | 462.21 | (CD$_3$OD) 8.90(d, 1H), 8.81(d, 1H), 8.49(m, 1H), 8.39(d, 1H), 8.04(d, 1H), 7.85(m, 1H), 7.02(br s, 1H), 6.90(d, 1H), 4.82(m, 1H, underneath water peak), 4.42(q, 2H), 4.29(m, 1H), 3.72 (m, 1H), 3.35(s, 3H), 2.65 & 2.90(s, 3H), 1 |
| 153 | 504.3 | 506.3 | 12.14(s, 1H); 11.11(s, 1H);9.59(s, 1H); 9.08(d, 2H); 8.38(s, 1H); 8.33(d, 1H); 8.22(s, 1H); 7.95(d, 1H);7.56(dd, 1H); 4.32(q, 2H); 4.12(br. s, 4H); 3.62 (br. s, 4H); 2.46(br. s, 2H); 1.31(dd, 2H); 1.22(t, 3H). |
| 154 | 474.3 | 476.3 | 10.31(s, 1H); 9.09(d, 2H); 8.79(s, 1H); 8.44(s, 1H); 8.42(s, 1H); 8.00(s, 1H); 7.68(t, 2H); 7.7-6.6(br. s, 3H); 4.32(q, 2H); 3.55(m, 4H); 3.12(m, 4H); 2.34(s, 6H); 1.32(t, 3H). |
| 155 | 479.3 | 481.2 | 1.33(t, 3H) 2.36(s, 3H) 4.35(q, 2H) 5.60(s, 2H) 6.84(s, 1H) 6.88(s, 1H) 7.68(t, 1H) 7.81(d, 2H) 7.99(s, 1H) 8.26(t, 1H) 8.35(s, 1H) 8.78(d, 1H) 8.89(d, 3H) 11.75(br s, 2H) |
| 156 | — | 461.22 | (CD$_3$OD) 8.83(m, 1H), 8.44(d, 1H), 8.25(d, 1H), 8.12(m, 1H), 7.88(d, 1H), 7.54(m, 1H), 6.70(s, 1H), 6.68(s, 1H), 4.68(m, 1H), 4.32(m, 1H), 3.70(m, 1H), 3.38(q, 2H), 3.35(s, 3H), 2.56(s, 3H), 1.60(d, 3H), 1.24(t, 3H) ppm |
| 157 | 486.3 | 488.3 | (CD$_3$OD) 1.37(t, 3H) 1.57(m, 4H) 2.27(m, 1H) 2.82(s, 3H) 3.41(t, 2H) 3.96(d, 2H) 4.29(d, 2H) 4.43(q, 2H) 7.27(s, 1H) 7.50(s, 1H) 7.90(t, 1H) 8.17(s, 1H) 8.55(s, 1H) 8.659(t, 1H) 8.95(d, 1H) 9.09(d, 1H) |
| 158 | 474.3 | 476.3 | (CD$_3$OD) 1.08(d, 6H) 1.42(t3H) 2.76(s, 3H) 3.57(m, 1H) 2.82(t, 2H) 4.42(m, 4H) 6.98(s, 1H) 7.05(s, 1H) 7.86(t, 1H) 8.09(s, 1H) 8.41(s, 1H) 8.51(t, 1H) 8.82(d, 1H) 8.91(d, 1H) |
| 159 | 458 | 460 | (CD$_3$OD) 1.43(t, 3H), 3.48(bs, 24H), 3.99(bs, 4H), 4.48(t, 2H), 4.63(s, 2H), 7.55(t, 1H), 7.71(d, 1H), 8.1(s, 1H), 8.33(d, 1H), 8.9(1H), 9.03(d, 2H), 9.13(s.1H). |

TABLE 3-continued

Characterization Data for Selected Compounds of Formula I

| Compound No. I- | M − 1 (obs) | M + 1 (obs) | $^1$H NMR |
|---|---|---|---|
| 160 | 457 | 459 | (CD$_3$OD) 1.35(t, 3H), 3.3-3.5(m, 6H), 3.99(bs, 4H), 4.62(s, 2H), 7.52(t, 1H), 7.7(d, 1H), 8.08(s, 1H), 8.32(d, 1H), 8.88(s, 1H), 9.05(d, 2H) 9.1(s, 1H). |
| 161 | 446.28 | 448.2 | 1.2(t, 3H), 3.2(m, 2H), 3.3(br s, 4H), 3.9(br s, 4H), 4.7(s, 2H), 7.7(s, 1H), 7.8(br s, 1H), 7.95(m, 1H), 8.1(s, 1H), 8.25(s, 1H), 8.7(m, 1H), 8.8(m, 1H), 9.2(s, 1H), 10.6(br s, 1H) |
| 162 | 550.3 | 552.3 | 12.32(s, 1H); 11.18(s, 1H); 9.08(d, 2H); 8.62(s, 1H); 8.39(s, 1H); 8.37(s, 1H); 7.98(s, 1H); 7.62(m, 2H); 7.58 (dd, 1H); 7.48(m, 3H); 6.4-5.9(br. s, 3H); 4.38(s, 2H); 4.33(q, 2H); 3.42(m, 4H); 3.15(m, 4H); 1.35(t, 3H). |
| 163 | 501.3 | 503.3 | (CD$_3$OD) 9.1(d, 1H), 8.8(t, 1H), 8.5(d, 1H), 8.4(s, 1H), 8.3(s, 1H), 8.2(t, 1H), 7.7(s, 1H), 7.5(s, 1H), 4.8(t, 2H), 4.4(q, 2H), 4.1(d, 2H), 3.9(t, 2H), 3.75(d, 2H), 3.7(t, 2H), 3.4(m, 2H), 3.3(s, 2H), 2.85(s, 3H), 2.0(s, 5H), 1.4(t, 3H) |
| 164 | 500.4 | 502.3 | (CD$_3$OD) 8.75(d, 1H), 8.3(d, 1H), 8.2(s, 1H), 8.0-8.05(1, 1H), 7.8(s, 1H), 7.5(t, 1H), 6.8(s, 1H), 6.7(s, 1H), 4.5-4.6(1, 2H), 4.0(brd s, 4H), 3.5-3.6(1, 4H), 3.4(q, 2H), 3.3(t, 2H), 2.6(s, 3H), 1.2-1.3(1, 3H) |
| 165 | 474 | 476 | (CD$_3$OD) 9.04(d, 1H), 8.71(d, 1H), 8.34(d, 1H), 8.23(dd, 1H), 7.94(d, 1H), 7.84(m, 1H), 7.65(d, 1H), 7.57(m, 1H), 4.56(s, 2H), 3.98(t, 4H), 3.45(t, 4H), 3.37(q, 2H), 1.24(t, 3H) |
| 166 | 475 | 477 | (CD$_3$OD): 9.07(d, 1H), 8.72(d, 1H), 8.49(d, 1H), 8.28(dd, 1H), 8.04(d, 1H), 7.92(m, 1H), 7.69(d, 1H), 7.63(m, 1H), 4.63(s, 2H), 4.47(q, 2H), 3.99(m, 4H), 3.44(m, 4H), 1.43(t, 3H) |
| 167 | 522.3 | 524.4 | (CD$_3$OD) 8.94(d, 2H), 8.65(s, 1H), 7.85 (s, 1H), 7.44(dd, 1H), 7.27(dd, 1H), 6.84(d, 2H), 6.80(s, 1H), 6.70(s, 1H), 6.64(s, 1H), 3.77(s, 3H), 3.36(q, 2H), 2.39(br s, 3H), 1.96(d, 3H), 1.24(t, 3H) |
| 168 | — | 474.3 | (CD$_3$OD) 1.45(t, 3H) 1.80(d, 3H) 2.69(m, 2H) 3.50(m, 2H) 3.97(m, 4H) 4.49(q, 2H) 4.72(m, 1H)7.55(t, 1H) 7.71(d, 1H) 1.15(s, 1H) 8.33(d, 1H) 8.91(s, 1H) 9.08(d, 2H) 9.17(s, 1H) |
| 169 | 445.44 | 447.24 | 1.3(t, 3H), 2.9(br s, 6H), 3.6(brs, 2H), 4.3(q, 2H), 4.6(m, 2H), 7.1(m, 1H), 7.6 (m, 1H), 7.9(s, 1H), 8.2(m, 1H), 8.25 (s, 1H), 8.3(m, 1H), 8.6(d, 1H), 8.7(d, 1H), 9.1(s, 1H), 9.7(br, s, !H) |
| 170 | 444.43 | 446.22 | 1.2(t, 3H), 2.9(br s, 6H), 3.25(m, 2H), 3.6(br s, 2H), 4.6(m, 2H), 7.1(m, 1H), 7.4(br s, 1H), 7.6(m, 1H), 7.9(s, 1H), 8.1(br s, 1H), 8.2(s, 1H), 8.3(m, 1H), 8.6(d, 1H), 8.7(d, 1H), 9.1(s, 1H), 9.8 (br s, 1H), 10.5(br s, 1H) |
| 171 | 460.2 | 462.2 | (CD$_3$OD) 8.95(d, 1H), 8.86(d, 1H), 8.57(dt, 1H), 8.46(d, 1H), 8.17(d, 1H), 7.93(t, 1H), 7.62(br s, 1H), 7.33(d, 1H), 5.14(m, 1H), 4.42(q, 2H), 4.26(m, 1H), 3.75(dd, 1H), 3.36(s, 3H), 2.81(s, 3H), 1.42(d, 3H), 1.30(t, 3H) ppm |
| 172 | 485 | 487 | (CD$_3$OD) 1.45-1.12(m, 3H), 1.9(m, 1H), 2.1(m, 2H), 2.32(m, 1H), 3.5-3.3(m, 5H), 3.7(m, 4H), 3.99(bs, 1H), 4.4(q, 2H), 4.57(bd, 1H), 7.58(d, 1H), 7.8(t, 1H), 8.03(s, 1H), 8.32(d, 1H), 8.42(m, 2H), 8.75(d, 1H), 8.88(s, 1H) 9.1(s, 1H). |
| 173 | 484 | 486 | (CD$_3$OD) 1.15(t, 3H), 1.4(t, 3H), 3.02(s, 2H), 3.6(m, 2H), 3.68(m, 2H), 3.95(s, 2H), 4.4(m, 2H), 4.61(s, 2H), |

TABLE 3-continued

Characterization Data for Selected Compounds of Formula I

| Compound No. I- | M − 1 (obs) | M + 1 (obs) | ¹H NMR |
|---|---|---|---|
| 174 | 503.2 | 505.2 | 7.8(m, 2H), 8.08(s, 1H), 8.48(m, 3H), 8.78(d, 1H), 8.9(d, 1H), 9.17(s, 1H). (CDCl₃) 8.94(d, 1H), 8.87(d, 1H), 8.15 (d, 1H), 8.11(d, 2H), 7.95(ddd, 1H), 7.90(s, 1H), 7.70(d, 1H), 7.42(dd, 1H), 4.76(s, 2H), 4.46(q, 2H), 3.82(t, 4H), 3.64(t, 4H), 3.40(s, 6H), 1.45(t, 3H) |
| 175 | 593.4 | 595.3 | 10.85(s, 1H); 8.84(s, 1H); 8.72(s, 1H); 8.58(d, 1H); 8.52(s, 1H); 8.30(d, 1H); 8.08(s, 1H); 7.92(d, aH); 7.44(d, 2H); 7.34(dd, 2H); 7.24(t, 1H); 6.05-4.9(br. s); 5.21(dq, 1H); 4.78(d, 2H); 4.31(q, 2H); 3.58(d, 2H); 3.52( |
| 176 | 543.5 | 545.3 | 11.76(s, 1H);9.59(s, 1H); 8.89(d, 1H); 8.78(s, 1H); 8.65(s, 1H); 8.40(s, 1H); 8.05(d, 1H); 7.9-6.2(br. s, 2H); 4.87(d, 2H); 4.32(q, 2H); 3.96(dd, 2H); 3.68 (dd, 2H); 3.58(m, 4H);3.20(m, 2H); 2.94(d, 3H); 1.98(m, 2H); 1.88 |
| 177 | 542.5 | 544.3 | 11.12(s, 1H); 10.84(s, 1H); 9.08(s, 1H); 8.87(d, 1H); 8.66(s, 1H); 8.41(s, 1H); 8.01(s, 1H); 7.96(d, 1H); 7.58(s, 1H); 6.3-4.6(br. s, 6H); 4.82(d, 2H); 3.96(dd, 2H); 3.58(m, 6H); 3.26(m, 2H); 3.15(m, 2H); 2.84(d, 3H); 1.96( |
| 178 | 470.4 | 472.3 | 9.05(d, 2H); 8.54(s, 1H); 7.89(s, 1H); 8.01(s, 1H); 7.78(d, 1H); 7.55(t, 1H); 7.05(d, 1H); 5.5-4.2(br. s, 1H); 4.33(q, 2H); 3.50(dd, 2H); 3.36(dd, 2H); 3.12 (s, 3H); 2.85(s, 3H); 1.33(t, 3H). |
| 179 | 415.4 | 417.3 | (CD₃OD) 9.54(d, 1H), 9.21(m, 1H), 9.15(s, 1H), 8.97(d, 1H), 8.92(d, 1H), 8.83(d, 1H), 8.28(dd, 1H), 8.20(d, 1H), 7.69(m, 1H), 4.62(s, 2H), 4.48(q, 2H), 3.00(s, 6H), 1.44(t, 3H) ppm |
| 180 | 414.4 | 416.3 | (CD₃OD) 9.54(d, 1H), 9.22(m, 1H), 9.05(s, 1H), 8.97(d, 1H), 8.93(d, 1H), 8.79(d, 1H), 8.28(dd, 1H), 8.17(d, 1H), 7.62(m, 1H), 4.59(s, 2H), 3.39(q, 2H), 2.99(s, 6H), 1.25(t, 3H) ppm |
| 181 | 513 | 515 | (CD₃OD): 9.14(d, 1H), 9.06(d, 1H), 8.85(t, 1H), 8.67(t, 1H), 8.46(d, 1H), 8.37(d, 1H) 8.11(m, 1H), 7.97(d, 1H), 7.55(m, 1H), 4.07(brs, 2H), 3.88(t, 4H), 3.71(brs, 2H), 3.48(t, 4H), 3.36(q, 2H), 1.24(t, 3H) |
| 182 | 477.4 | 479.37 | 0.9(d, 6H), 1.3(t, 3H), 2.1(m, 1H), 2.9 (s, 6H), 3.75(d, 2H), 4.3(q, 2H), 4.6(s, 2H), 6.6(dt, 1H), 6.7(d, 1H), 7.7(s, 1H), 7.8(d, 1H), 7.95(s, 1H), 8.010.2 (br s, 1H)(s, 1H), |
| 183 | 476.42 | 478.41 | 0.9(d, 6H), 1.1(t, 3H), 2.1(m, 1H), 2.9 (s, 6H), 3.2(m, 2H), 3.8(d, 2H), 4.6(s, 2H), 6.6(dt, 1H), 6.7(d, 1H), 7.3(br s, 1H), 7.7(s, 1H), 7.8(d, 1H), 7.95(s, 1H), 8.0(s, 1H), 10.2(br s, 1H) |
| 184 | 514 | 516 | — |
| 185 | 470.4 | 472.2 | (CD₃OD) 1.25(t, 3H) 1.78(d, 3H) 3.30(m, 2H) 3.35(q, 2H) 3.50(m, 2H) 3.93 (m, 4H) 4.73(q, 1H) 7.72(t, 1H) 7.45(d, 1H) 8.01(s, 1H) 8.27(t, 1H) 8.35(m, 2H) 8.52(d, 1H) 8.91(d, 1H) 9.18(s, 1H) |
| 186 | 498.4 | 500.3 | (CD₃OD) 1.16(m, 3H) 1.26(m, 6H) 1.80(d, 3H) 2.82(t, 2H) 3.20(d, 1H) 3.35(q, 2H) 3.72(d, 1H) 3.91(m, 1H) 4.04(m, 1H) 4.68(q, 1H) 7.65(t, 1H) 7.71(d, 1H) 8.01(s, 1H) 8.22(t, 1H) 8.35(m, 2H) 8.49(d, 1H) 8.89(d, 1H) 9.18(s, 1H) |
| 187 | 499.5 | 501.3 | (CD₃OD) 1.16(m, 3H) 1.29(d, 3H) 1.41(t, 3H) 1.79(d, 3H) 2.82(t, 2H) 3.20(d, 1H) 3.74(d, 1H) 3.92(m, 1H) 4.04(m, 1H) 4.43(q, 2H) 4.69(q, 1H) 7.70(d, 1H) 7.87(t, 1H) 8.11(s, 1H) |

TABLE 3-continued

Characterization Data for Selected Compounds of Formula I

| Compound No. I- | M − 1 (obs) | M + 1 (obs) | $^1$H NMR |
|---|---|---|---|
| | | | 8.35(d, 1H) 8.46(m, 2H) 8.75(d, 1H) 8.92(d, 1H) 9.34(s, 1H) |
| 188 | 486 | 488 | (CD$_3$OD): 8.91(m, 1H), 8.65(m, 1H), 8.47(m, 1H), 8.31(m, 2H), 8.29(m, 1H), 7.96(m, 1H) 7.73(m, 1H), 7.19(m, 1H), 4.08(m, 2H), 3.90(m, 2H), 3.72(m, 4H), 3.66(m, 4H), 3.37(m, 2H), 1.24(t, 3H) |
| 189 | 487 | 489 | (CD$_3$OD): 8.89(d, 1H), 8.69(d, 1H), 8.61(d, 1H), 8.41(t, 1H), 8.32(d, 1H), 8.20(dd, 1H) 7.95(d, 1H), 7.78(t, 1H), 7.10(d, 1H), 4.42(q, 2H), 4.09(m, 2H), 3.86(m, 2H), 3.70(m, 4H), 3.33(m, 4H), 1.24(t, 3H) |
| 190 | 388.38 | 390.19 | 1.2(t, 3H), 3.3(m, 2H), 3.5(s, 3H), 6.6 (dd, 1H), 6.7(d, 1H), 7.6(t, 1H), 7.8(d, 1H), 7.95(br s, 1H), 8.0(s, 1H), 8.6(s, 1H), 9.05(d, 2H) |
| 191 | 359.3 | 361.2 | — |
| 192 | 446.4 | 448.3 | — |
| 193 | 474.2 | 476.4 | (CD$_3$OD) 9.14(s, 1H), 9.08(d, 2H), 8.91 (s, 1H), 8.39(d, 1H), 8.14(s, 1H), 7.78 (s, 1H), 7.55(dd, 1H), 4.72(s, 2H), 4.48 (q, 2H), 3.81(t, 2H), 3.56(t, 2 H), 3.46 (q, 2H), 3.41(s, 3H), 1.44(t, 3H), 1.43 (t, 3H) |
| 194 | 486.1 | 488.1 | (CDCl$_3$) 12.31(br s, 1H), 8.95(s, 1H), 8.93(d, 2H), 8.58(s, 1H), 8.05(s, 1H), 8.01(d, 1H), 7.50(d, 1H), 7.24(dd, 1H), 4.46(q, 2H), 3.78(m, 2H), 3.72(s, 2H), 2.78(d, 2H), 1.91(dd, 2H), 1.41(t, 3H), 1.17(d, 6H) |
| 195 | — | — | 11.5(br s, 1H), 9.19(br s, 1H), 8.97(s, 1H), 8.88(d, 1H), 8.45(m, 1H), 8.40(s, 1H), 7.98(d, 1H), 7.77(d, 1H), 7.60(d, 1H), 4.57(s, 2H), 4.47(br d, 2H), 4.32 (q, 2H), 3.90(br m, 4H), 3.32(br s, 4H), 2.80(br, 6H), 1.34 |
| 197 | 460.2 | 462.2 | (CD$_3$OD & CDCl$_3$): 8.98(d, 2H), 8.85(d, 1H), 8.60(d, 1H), 8.16(dd, 1H), 7.86(d, 1H), 7.67(d, 1H), 7.40(dd, 1H), 4.37(q, 2H), 3.81(s, 2H), 3.60(t, 2H), 3.37(s, 3H), 2.74(t, 2H), 2.38(s, 3H), 1.41(t, 3H) |
| 198 | 459.3 | 461.2 | (CD$_3$OD): 8.95(d, 2H), 8.83(s, 1H), 8.54(s, 1H), 8.15(d, 1H), 7.82(s, 1H), 7.65(d, 1H), 7.39(dd, 1H), 3.79(s, 2H), 3.59(t, 2H), 3.36(q, 2H), 3.35(s, 3H), 2.72(t, 2H), 2.36(s, 3H), 1.24(t, 3H) |
| 199 | 488 | 490 | — |
| 200 | 487 | 489 | — |
| 201 | 488 | 490 | — |
| 202 | 487 | 489 | — |
| 203 | 489 | 491 | 9.06(m, 4H), 8.50(d, 1H), 7.98(d, 1H), 7.54(t, 1H), 4.79(t, 2H), 4.31(q, 2H), 4.01(m, 2H), 3.79(m, 2H), 3.67(m, 2H), 3.56(m, 2H), 3.25(m, 2H) 1.33(t, 3H) |
| 204 | 488 | 490 | (CD$_3$OD): 9.02(m, 4H), 8.75(s, 1H), 7.97(d, 1H), 7.52(m, 1H), 4.88(m, 2H), 3.75-3.73(m, 10H), 3.35(m, 2H), 1.25(t, 3H) |
| 205 | 400.1 | 402.1 | 1.31(t, 3H) 2.70(s, 3H) 4.32(q, 2H) 7.55(t, 1H) 8.00(s, 1H) 8.09(d, 1H) 8.14(t, 1H) 8.39(s, 1H) 8.44(d, 1H) 8.70(d, 1H) 8.81(d, 1H) 9.19(s, 1H) |
| 206 | 458.1 | 460 | (CD$_3$OD) 9.41(d, 2H), 8.92(m, 1H), 8.80(d, 1H), 8.48(m, 2H), 8.10(br s, 1H), 7.84(m, 1H), 4.76(s, 2H with water peak), 4.42(q, 2H), 4.11(br m, 2H), 3.95(nr m, 2H), 3.71(br m, 2H), 3.45(br m, 2H), 1.42(t, 3H) ppm. |
| 207 | 457.2 | 459.1 | (CD$_3$OD) 9.33(s, 2H), 8.89(d, 1H), 8.53 (d, 1H), 8.44(d, 1H), 8.20(m, 1H), 8.04 |

TABLE 3-continued

Characterization Data for Selected Compounds of Formula I

| Compound No. I- | M − 1 (obs) | M + 1 (obs) | $^1$H NMR |
|---|---|---|---|
| | | | (d, 1H), 7.63(m, 1H), 4.76(s, 2H, with water peak), 4.12(br m, 2H), 3.94(br m, 2H), 3.71(br m, 2H), 3.44(br m, 2H), 3.39(q, 2H), 1.25(t, 3H) ppm |
| 208 | 391 | 393 | — |
| 209 | 441.1 | 443 | (CD$_3$OD) 1.43(t, 3H) 4.50(s, 2H) 4.89(s, 2H) 7.55(t, 1H) 8.10(d, 1H) 8.20(s, 1H) 8.87(d, 1H) 9.01(s, 1H) 9.10(d, 2H) 9.30(s, 1H) |
| 210 | 472.4 | 474.2 | (CD$_3$OD) 9.25(s, 1H), 9.02(d, 2H), 8.87 (d, 1H), 8.65(d, 1H), 8.18(s, 1H), 8.08 (d, 1H), 7.54(dd, 1H), 4.88(s, 2H), 4.49 (q, 2H), 4.27(br s, 1H), 3.68(m, 4H), 3.40(s, 3H), 2.32(m, 2H), 1.45(t, 3H) |
| 211 | 471.2 | 473.1 | (CD$_3$OD) 9.16(s, 1H), 8.98(d, 2H), 8.76 (d, 1H), 8.48(d, 1H), 8.05(s, 1H), 7.91 (d, 1H), 7.50(dd, 1H), 4.81(s, 2H), 4.27 (br s, 1H), 3.69(m, 4H), 3.40(s, 3H), 3.38(q, 2H), 2.32(m, 2H), 1.26(t, 3H) |
| 212 | 485.2 | 487.3 | (CD$_3$OD) 9.16(s, 1H), 9.03(d, 2H), 8.87 (s, 1H), 8.50(d, 1H), 8.14(s, 1H), 7.92 (d, 1H), 7.54(dd, 1H), 4.75(s, 2H), 4.49 (q, 2H), 4.06(s, 2H), 3.74(br s, 4H), 3.06(s, 3H), 1.45(t, 3H) |
| 213 | 484.2 | 486.2 | (CD$_3$OD) 9.16(s, 1H), 9.01(d, 2H), 8.78 (s, 1H), 8.52(d, 1H), 8.07(s, 1H), 7.96 (d, 1H), 7.52(dd, 1H), 4.77(s, 2H), 4.07 (s, 2H), 3.75(br s, 4H), 3.38(q, 2H), 3.06(s, 3H), 1.26(t, 3H) |
| 214 | | 350.1 | 12.28(br. s, 1H); 11.77(br. s, 1H); 9.73 (s, 1H); 9.08(d, 2H); 8.49(d, 1H); 8.37 (m, 1H); 8.08(d, 1H); 7.94(m, 1H); 7.59 (t, 1H); 4.32(q, 2H); 2.30(s, 3H); 1.32 (t, 3H). |
| 215 | 502.4 | 504.1 | (CD$_3$OD) 9.17(s, 1H), 9.02(d, 2H), 8.85 (s, 1H), 8.48(d, 1H), 8.15(s, 1H), 7.90 (d, 1H), 7.53(dd, 1H), 4.81(d, 1H), 4.77 (d, 1H), 4.48(q, 2H), 4.18(br s, 2H), 3.75(m, 4H), 3.47(s, 6H), 1.45(t, 3H) |
| 216 | 347.2 | 349.1 | 12.28(br. s, 1H); 10.22(br. s, 1H); 9.53 (s, 1H); 9.08(d, 2H); 8.41(d, 1H); 8.29 (m, 1H); 7.98(d, 1H); 7.83(m, 1H); 7.57 (t, 1H); 7.22(m, 1H); 3.26(dq, 2H); 2.31 (s, 3H); 1.15(t, 3H). |
| 217 | 501.4 | 503.1 | (CD$_3$OD) 9.15(s, 1H), 9.03(d, 2H), 8.85 (s, 1H), 8.43(d, 1H), 8.10(s, 1H), 7.83 (d, 1H), 7.53(dd, 1H), 4.78(d, 1H), 4.74 (d, 1H), 4.18(br s, 2H), 3.74(m, 4H), 3.47(s, 6H), 3.38(q, 2H), 1.26(t, 3H) |
| 218 | 456 | 458 | (CD$_3$OD) 1.24(t, 3H), 3.38(m, 2H), 3.57(bs, 4H), 3.99(bs, 4H), 4.63(s, 2H), 7.68(m, 1H), 7.73(m, 1H), 8.02(s, 1H), 8.24(t, 1H), 8.48(m, 1H), 8.49(d, 1H), 8.9(d, 1H), 9.13(s, 1H). |
| 219 | — | — | 12.25(s, 1H); 11.75(s, 1H); 9.61(d, 1H); 9.07(d, 2H); 8.45(d, 1H); 8.11(s, 1H); 8.02(d, 1H); 7.59(t, 1H); 4.31(q, 2H); 2.38(s, 3H); 2.29(s, 3H); 1.32(t, 3H). |
| 220 | 502.3 | 504.2 | (CD$_3$OD) 9.10(d, 1H), 9.05(d, 2H), 8.91(d, 1H), 8.32(dd, 1H), 8.11(d, 1H), 7.69(d, 1H), 7.55(dd, 1H), 4.73(d, 1H), 4.69(d, 1H), 4.49(q, 2H), 4.17(br s, 2H), 3.70(m, 4H), 3.46(s, 6H), 1.44(t, 3H) |
| 221 | 501.3 | 503.2 | (CD$_3$OD) 9.09(s, 1H), 9.05(d, 2H), 8.86 (s, 1H), 8.29(d, 1H), 8.09(s, 1H), 7.67 (d, 1H), 7.54(dd, 1H), 4.72(d, 1H), 4.67 (d, 1H), 4.17(br s, 2H), 3.71(m, 4H), 3.47(s, 6H), 3.39(q, 2H), 1.26(t, 3H) |
| 222 | — | 559 | (CDCl$_3$) 12.29(br s, 1H), 8.94(s, 1H), 8.94(d, 2H), 8.60(s, 1H), 8.04(s, 1H), 8.02(d, 1H), 7.50(d, 1H), 7.25(dd, 1H), |

TABLE 3-continued

Characterization Data for Selected Compounds of Formula I

| Compound No. I- | M − 1 (obs) | M + 1 (obs) | ¹H NMR |
|---|---|---|---|
| 223 | 513.2 | 515.14 | 4.46(q, 2H), 3.75(s, 2H), 3.50(m, 4H), 2.51(m, 4H), 1.47(s, 9H), 1.41(t, 3H) 1.1(d, 6H), 1.3(t, 3H), 3.5(m, 4H), 3.7 (br s, 2H), 4.3(q, 2H), 4.5(br s, 2H), 4.65(m, 1H), 7.5(t, 1H), 7.7(d, 1H), 8.0 (d, 1H), 8.3(dd, 1H), 8.5(d, 1H), 9.0(d, 2H), 9.05(d, 1H) |
| 224 | 457.207 | 459.207 | (CD$_3$OD) 9.54(s, 1H), 9.28(s, 1H), 9.22 (d, 1H), 8.97(d, 1H), 8.93(d, 1H), 8.85 (br s, 1H), 8.27(t, 1H), 8.20(br s, 1H), 7.71(d, 1H), 4.63(s, 2H), 4.48(q, 2H), 4.05(br s, 4H), 3.44(br m, 4H), 1.44(t, 3H) ppm |
| 225 | 472.2 | 474.49 | (CD$_3$OD) 9.0(d, 1H), 8.95(m, 1H), 8.6(s, 1H), 8.5(s, 1H), 8.4(s, 1H), 8.3(s, 1H), 7.9(s, 1H), 7.55(m, 1H), 4.5(s, 2H), 3.9(s, 2H), 3.4(q, 2H), 3.0(s, 6H), 1.3(t, 3H). |
| 226 | 562.3 | 564.2 | (CD$_3$OD) 9.0(d, 1H), 8.9(m, 1H), 8.6(s, 1H), 8.5(s, 1H), 8.3(s, 1H), 8.25(s, 1H), 7.9(s, 1H), 7.55(m, 1H), 7.3-7.4(m, 5H), 5.2(s, 2H), 4.5(s, 2H), 4.0(s, 2H), 3.4(q, 2H), 3.0(s, 6H), 1.3(t, 3H) |
| 227 | 389 | 391 | |
| 228 | 457.3 | 459.1 | — |
| 229 | 456.3 | 458.1 | — |
| 230 | 433.3 | 435.1 | — |
| 231 | 487 | 489 | (CD$_3$OD) 9.30(s, 2H), 9.04(d, 2H), 8.89 (d, 1H), 8.11(d, 1H), 7.54(t, 1H), 4.46 (q, 2H), 4.02(m, 2H), 3.59(m, 2H), 2.89 (m, 2H), 1.44(t, 2H), 1.13(t, 3H) ppm. |
| 232 | 456.3 | 458.3 | (CD$_3$OD) 9.22(s, 1H), 9.05(d, 2H), 8.92 (s, 1H), 8.78(d, 1H), 8.17(s, 1H), 8.08 (d, 1H), 7.54(dd, 1H), 4.42(s, 2H), 3., 52 (m, 4H), 3.39(q, 4H), 3.28(m, 4H), 1.26 (t, 3H) |
| 233 | — | 459.1 | (CD$_3$OD) 9.22(s, 1H), 9.06(d, 2H), 8.96 (s, 1H), 8.77(d, 1H), 8.22(s, 1H), 8.07 (d, 1H), 7.56(dd, 1H), 4.49(q, 2H), 4.42 (s, 2H), 3., 52(m, 4H), 3.29(m, 4H), 1.45(t, 3H) |
| 234 | | 537 | (CD$_3$OD) 9.22(s, 1H), 9.04(d, 2H), 8.90 (s, 1H), 8.54(d, 1H), 8.16(s, 1H), 7.99 (d, 1H), 7.54(dd, 1H), 4.78(s, 2H), 4.49 (q, 2H), 3.69 & 3.63(m, 8H), 3.00(s, 3H), 1.45(t, 3H) |
| 235 | 534.2 | 536.1 | (CD$_3$OD) 9.20(s, 1H), 9.02(d, 2H), 8.82 (s, 1H), 8.52(d, 1H), 8.09(s, 1H), 7.98 (d, 1H), 7.52(dd, 1H), 4.78(s, 2H), 3.69 &3.62(m, 8H), 3.39(q, 2H), 3.00(s, 3H), 1.25(t, 3H) |
| 236 | 496.4 | 498.3 | (CD$_3$OD) 9.28(s, 1H), 9.06(br s, 2H), 8.96(s, 1H), 8.85(br s, 1H), 8.24(s, 1H), 8.15(br s, 1H), 7.56(br s, 1H), 4.49 (q, 2H), 4.42(s, 2H), 3.73(br s, 4H), 3.35 (br s, 4H), 3.01(br s, 1H), 1.45(t, 3H), 1.20(br s, 2H), 1.00(br s 2H) |
| 237 | 496.4 | 498.3 | (CDCl$_3$) 11.82(br s, 1H), 8.88(s, 1H), 8.71(br s, 2H), 8.48(s, 1H), 7.89(d, 1H), 7.79(s, 1H), 7.42(d, 1H), 7.05(br s, 1H), 3.71(s, 2H), 3.46(q, 2H), 2.70 & 2.55(m, 8H), 1.28(t, 3H), 0.45-0.41(m, 4H) |
| 238 | 447.2 | 449 | 12.35(s, 1H); 9.07(d, 2H); 8.82(s, 1H); 8.41(d, 1H); 8.13(s, 1H); 7.95(d, 1H); 7.57(t, 1H); 6.7-5.2(br. s, 4H); 4.38(s, 2H); 4.32(q, 2H); 3.92(br. d, 4H); 3.32 (br. d, 4H); 1.33(t, 3H). |
| 239 | 490.1 | 492.2 | (CD$_3$OD) 9.21(s, 1H), 9.05(d, 2H), 8.92 (s, 1H), 8.54(d, 1H), 8.17(s, 1H), 7.97 (d, 1H), 7.55(dd, 1H), 4.78(s, 2H), 4.49 (q, 2H), 4.01(br dd, 2H), 3.74(br d, 2H), 3.43(br dd, 2H), 3.27(br d, 2H), 1.45(t, 3H) |

TABLE 3-continued

Characterization Data for Selected Compounds of Formula I

| Compound No. I- | M − 1 (obs) | M + 1 (obs) | $^1$H NMR |
|---|---|---|---|
| 240 | 471.3 | 473 | (CD$_3$OD) 9.28(s, 1H), 9.05(br s, 2H), 8.96(s, 1H), 8.89(s, 1H), 8.25(s, 1H), 8.17(s, 1H), 7.55(br s, 1H), 4.49(q, 2H), 4.39(s, 2H), 3.64-3.13(m, 8H), 3.00(s, 3H), 1.45(t, 3H) |
| 241 | — | 531.01 | 1.3(t, 3H), 1.55(d, 3H), 3.3(br s, 4H), 3.9(br s, 4H), 4.0(q, 1H), 4.35(q, 2H), 4.6(s, 2H), 7.6(dd, 1H), 7.8(d, 1H), 8.0 (s, 1H), 8.4(d, 1H), 8.42(s, 1H), 8.7(s, 1H), 8.8(d, 1H), 9.15(s, 1H), 11 . . . 2(br s, 1H) |
| 242 | 486.2 | 488.1 | (CD$_3$OD) 9.33(s, 2H), 8.92(d, 1H), 8.79 (d, 1H), 8.47(m, 2H), 8.09(d, 1H), 7.84 (m, 1H), 4.42(q, 2H), 4.05(m, 2H), 3.67 (m, 2H), 3.39(m, 2H, underneath solvent peak), 3.00(m, 2H), 1.42(t, 3H), 1.28(d, 6H)ppm |
| 243 | 488.2 | 490.05 | 1.3(t, 3H), 3.2(m, 2H), 3.5(m, 2H), 3.7 (m, 2H), 3.9(m, 2H), 4.0(m, 2H), 4.3 (q, 2H), 4.8(m, 2H), 7.6(7, 1H), 8.1(d, 1H), 8.2(br s, 1H), 8.6(d, 1H), 8.65(d, 1H), 8.8(d, 1H), 9.05(d, 2H), 11.6(br s, 1H), 12.7(br s, 1H) |
| 244 | 457.21 | 459.09 | 1.35(t, 3H), 2.8(br s, 3H), 3.2(m, 2H), 3.4(m, 2H), 3.55(m, 2H), 4.3(m, 2H), 4.35(q, 2H), 7.6(t, 1H), 8.1(d, 1H), 8.3 (br s, 1H), 8.55(d, 1H), 8.6(d, 1H), 8.7 (d, 1H), 9.05(d, 2H), 11.2(br s, 1H), 12.4(br s, 1H) |
| 245 | 529.2 | 531.1 | (CD$_3$OD) 9.08(d, 1H), 9.01(d, 2H), 8.82(d, 1H), 8.30(d, 1H), 8.04(d, 1H), 7.68(d, 1H), 7.51(dd, 1H), 4.63(s, 2H), 4.47(q, 2H), 4.22(s, 2H), 3.91(br s, 4H), 3.49(br s, 4H), 3.43(s, 3H), 1.44(t, 3H) |
| 246 | 555.3 | 557.1 | (CD$_3$OD) 9.23(s, 1H), 9.04(d, 2H), 8.90 (s, 1H), 8.56(d, 1H), 8.17(s, 1H), 8.00 (d, 1H), 7.55(dd, 1H), 4.77(s, 2H), 4.49 (q, 2H), 4.12-3.84(m, 6H), 3.57(br s, 4H), 3.48(br s, 1H), 2.18(m, 2H), 1.97 (m, 2H), 1.45(t, 3H) |
| 247 | 485.1 | 487 | (CD$_3$OD) 9.34(s, 2H), 8.93(d, 1H), 8.80 (d, 1H), 8.48(m, 2H), 8.10(d, 1H), 7.85 (t, 1H), 4.88(s, 2H), 4.44(q, 2H), 4.21 (s, 2H), 3.86(m, 2H), 3.79(m, 2H), 3.09 (s, 3H), 1.42(t, 3H)ppm. |
| 248 | 458.15 | 460.02 | 1.23(t, 3H) 3.17(m, 4H) 3.65(m, 4H) 4.34(q, 2H) 4.77(s, 2H) 7.57(t, 1H) 8.11(s, 1H) 8.61(s, 1H) 9.06(d, 2H) 9.39(s, 2H) 9.87(br s, 2H) |
| 249 | 472.3 | 474 | (CD$_3$OD) 9.17(s, 1H), 9.04(d, 2H), 8.92 (s, 1H), 8.45(d, 1H), 8.15(s, 1H), 7.87 (d, 1H), 7.55(dd, 1H), 4.68(s, 2H), 4.69 (q, 2H), 4.11(dd, 1H), 4.02-3.95(m, 2H), 3.57(m, 2H), 3.03(dd, 1H), 1.44(t, 3H), 1.26(d, 3H) |
| 250 | 499.2 | 501.3 | (CD$_3$OD) 9.25(s, 1H), 9.06(d, 2H), 8.97 (s, 1H), 8.84(d, 1H), 8.23(s, 1H), 8.12 (d, 1H), 7.56(dd, 1H), 4.49(q, 2H), 4.37 (s, 2H), 3.65-3.12(m, 9H), 1.46-1.43(m, 9H) |
| 251 | 514.9 | 517 | (CD$_3$OD) 9.27(s, 1H), 9.05(d, 2H), 8.95 (s, 1H), 8.86(d, 1H), 8.25(s, 1H), 8.16 (d, 1H), 7.56(dd, 1H), 4.49(q, 2H), 4.46 (s, 2H), 3.81-3.50(m, 12 H), 3.44(s, 3H), 1.45(t, 3H) |
| 252 | 527.2 | 529 | (CD$_3$OD) 9.06(s, 1H), 8.97(d, 2H), 8.76 (s, 1H), 8.28(d, 1H), 8.00(s, 1H), 7.69 (d, 1H), 7.49(dd, 1H), 4.65(s, 2H), 4.45 (q, 2H), 3.99(br s, 4H), 3.49(br s, 4H), 2.99(hept, 1H), 1.44(t, 3H), 1.14(d, 6H) |
| 253 | 502 | 504 | (CD$_3$OD) 9.08(d, 2H), 8.73(s, 1H), 8.51 (s, 1H), 8.38(dd, 1H), 8.07(d, 1H), 7.92 (m, 1H), 7.77(d, 1H), 7.64(m, 1H), 4.67 |

TABLE 3-continued

Characterization Data for Selected Compounds of Formula I

| Compound No. I- | M − 1 (obs) | M + 1 (obs) | ¹H NMR |
|---|---|---|---|
| | | | (s, 2H), 4.48(q, 2H), 4.01(s, 2H), 3.65 (m, 4H), 3.06(m, 2H), 1.43(t, 2H), 1.13 (t, 3H)ppm. |
| 254 | 454.17 | 456.02 | 14.52(s, 1H); 9.22(s, 2H); 9.05(d, 2H); 8.56(d, 1H); 8.04(d, 1H); 7.74(s, 1H); 7.62(s, 1H); 7.55(t, 1H); 6.8-5.6(br. s); 5.79(s, 2H); 4.33(q, 2H); 2.62(s, 3H); 1.33(t, 3H). |
| 255 | 530.17 | 532.03 | 1.1(d, 6H), 1.35(t, 3H), 2.3(s, 6H), 3.5 (m, 2H), 3.6(m, 2H), 3.9(s, 2H), 4.3(q, 2H), 4.6(s, 2H), 4.65(m, 1H), 7.7(d, 1H), 7.9(s, 1H), 8.0(dt, 1H), 8.3(s, 1H), 8.4(dd, 1H), 8.8(d, 1H), 8.85(m, 1H), 9.1(s, 1H) |
| 256 | 486.23 | 488.05 | 1.3(d, 6H), 1.35(t, 3H), 3.1(m, 2H), 3.5 (m, 1H), 3.6(m, 4H), 4.3(q, 2H), 4.8 (m, 2H), 7.6(t, 1H), 7.9(s, 1H), 8.5(s, 1H), 8.9(s, 2H), 9.05(d, 1H), 10.5(br s, 1H) |
| 257 | 499.2 | 501.1 | (CD₃OD) 9.34(s, 2H), 8.93(m, 1H), 8.81(d, 1H), 8.49(m, 2H), 8.11(d, 1H), 7.85(t, 1H), 4.87(s, 2H), 4.42(q, 2H), 4.11(br s, 2H), 3.87(br m, 4H), 3.71(m, 3H), 1.48(d, 6H), 1.42(t, 3H) ppm. |
| 258 | 571.3 | 573.1 | (CDCl₃) 12.75(br 1H), 12.29(s, 1H), 8.94(d, 2H), 8.92(s, 1H), 8.60(s, 1H), 8.05(s, 1H), 8.04(d, 1H), 7.59(d, 1H), 7.25(dd, 1H), 4.46(q, 2H), 4.23(br s, 1H), 3.86(d, 1H), 3.80(d, 1H), 3.65(d, 1H), 3.19(ddd, 1H), 2.86(d, 1H), 2.66 (d, 1H) |
| 259 | — | 473 | (CD₃OD) 9.24(s, 1H), 9.04(d, 2H), 8.94 (s, 1H), 8.81(d, 1H), 8.22(s, 1H), 8.11 (d, 1H), 7.55(dd, 1H), 4.49(q, 2H), 4.42 (s, 2H), 3.77-2.89(m, 7H), 1.45(t, 3H), 1.41(d, 3H) |
| 260 | 485.3 | 487.3 | (CD₃OD) 9.24(s, 1H), 9.06(d, 2H), 8.96 (s, 1H), 8.83(d, 1H), 8.23(s, 1H), 8.11 (d, 1H), 7.56(dd, 1H), 4.49(q, 2H), 4.39 (s, 2H), 3.76(m, 2H), 3.40(d, 2H), 2.80 (d, 2H), 1.45(t, 3H), 1.40(d, 6H) |
| 261 | 485.2 | 487 | (CD₃OD) 9.23(s, 1H), 9.06(d, 2H), 8.97 (s, 1H), 8.82(d, 1H), 8.24(s, 1H), 8.13 (d, 1H), 7.56(dd, 1H), 4.74(d, 2H), 4.49 (q, 2H), 4.25(d, 1H), 3.80-2.92(m, 6H), 1.45(t, 3H), 1.36(d, 6H) |
| 262 | 513.2 | 515 | (CD₃OD) 9.10(s, 1H), 9.02(d, 2H), 8.85 (s, 1H), 8.31(d, 1H), 8.06(s, 1H), 7.68 (d, 1H), 7.52(dd, 1H), 4.62(s, 2H), 4.46 (q, 2H), 3.92-3.16(m, 8 H), 2.48(q, 2H), 1.86(m, 2H), 1.44(t, 3H), 1.14(t, 3 H) |
| 263 | — | 557.3 | (CD₃OD) 9.11(s, 1H), 9.03(d, 2H), 8.85 (s, 1H), 8.32(d, 1H), 8.07(s, 1H), 7.69 (d, 1H), 7.52(dd, 1H), 4.63(s, 2H), 4.47 (q, 2H), 3.99-3.79(m, 8 H), 3.50-3.45 (m, 5H), 2.15(m, 2H), 1.44(t, 3H) |
| 264 | — | 501.1 | (CD₃OD) 9.10(s, 1H), 9.03(d, 2H), 8.85 (s, 1H), 8.62(d, 1H), 8.08(s, 1H), 7.94 (d, 1H), 7.52(dd, 1H), 4.46(q, 2H), 4.12 (s, 2H), 3.46-3.01(m, 10H), 1.80(m, 2H), 1.43(t, 3H), 1.04(t, 3H) |
| 265 | — | 531.1 | (CD₃OD) 9.21(s, 1H), 8.96(d, 2H), 8.82 (s, 1H), 8.59(d, 1H), 8.12(s, 1H), 8.06 (d, 1H), 7.48(dd, 1H), 4.75(s, 2H), 4.42 (q, 2H), 4.12(q, 2H), 3.83(br s, 4H), 3.47(br s, 4H), 1.38(t, 3H), 1.23(t, 3H) |
| 266 | 543.2 | 545 | (CD₃OD) 9.33(s, 1H), 8.99(d, 2H), 8.83 (s, 1H), 8.79(br s, 1H), 8.18(s, 1H), 7.54(br s, 1H), 4.93(m, 1H), 4.89(s, 2H), 4.49(q, 2H), 3.90(br s, 4H), 3.57 (br s, 4H), 1.45(t, 3H), 1.29(d, 6H) |
| 267 | 516 | 518 | — |
| 268 | 557.3 | 559.2 | (CD₃OD) 9.08(s, 1H), 8.969(d, 2H), 8.78(s, 1H), 8.29(d, 1H), 8.01(s, 1H), |

TABLE 3-continued

Characterization Data for Selected Compounds of Formula I

| Compound No. I- | M − 1 (obs) | M + 1 (obs) | ¹H NMR |
|---|---|---|---|
| | | | 7.67(d, 1H), 7.49(dd, 1H), 4.62(s, 2H), 4.45(q, 2H), 3.93(d, 2H), 3.85(br s, 4H), 3.46(br s, 4H), 1.96(m, 1H), 1.43 (t, 3 H), 0.98(d, 6 H) |
| 269 | 553.3 | 555.1 | (CD$_3$OD) 9.15(s, 1H), 9.05(d, 2H), 8.91 (s, 1H), 8.39(d, 1H), 8.14(s, 1H), 7.79 (d, 1H), 7.55(dd, 1H), 4.71(q, 2H), 4.68 (s, 2H), 4.49(q, 2H), 3.88(br s, 4H), 3.49(br s, 4H), 1.82(t, 3H), 1.44(t, 3 H) |
| 270 | 557.3 | 559.2 | (CD$_3$OD) 9.11(s, 1H), 9.03(d, 2H), 8.84 (s, 1H), 8.31(d, 1H), 8.05(s, 1H), 7.68 (d, 1H), 7.52(dd, 1H), 4.63(s, 2H), 4.46 (q, 2H), 3.96(br s, 4H), 3.52(br s, 2H), 3.44(br s, 2H), 2.71(t, 2H), 2.65(t, 2H), 1.43(t, 3H) |
| 271 | 573.2 | 575.2 | (CD$_3$OD) 9.12(s, 1H), 9.05(d, 2H), 8.86 (s, 1H), 8.32(d, 1H), 8.07(s, 1H), 7.68 (d, 1H), 7.53(dd, 1H), 4.63(s, 2H), 4.46 (q, 2H), 4.37(s, 2H), 4.21(s, 2H), 3.98 (br s, 4H), 3.52(br s, 2H), 3.47(br s, 2H), 1.44(t, 3H) |
| 272 | 500.23 | 502.05 | 1.21(m, 9H) 3.17(s, 1H) 3.61(m, 8H) 4.32(q, 2H) 4.65(s, 2H) 7.56(t, 1H) 8.10(s, 1H) 8.58(s, 1H) 9.07(d, 2H) 9.30(s, 2H) |
| 273 | 476 | 478 | 9.29(s, 2H), 8.66(s, 1H), 8.02(s, 1H), 7.95(m, 2H), 7.59(m, 1H), 4.76(s, 2H), 4.30(m, 2H), 3.94-3.68(m, 4H), 3.50-3.17(m, 4H), 1.30(t, 3H) |
| 274 | 417.1 | 419 | 9.1(s, 2H), 9.0(s, 2H), 8.4(s, 1H), 7.8(s, 1H), 7.5(t, 1H), 4.1-4.2(q, 2H), 3.7(s, 2H), 2.3(s, 6H), 1.3(t, 3H). |
| 275 | 466 | 468 | — |
| 276 | 445.1 | 447 | 1.33(t, 3H) 2.06(m, 1H) 2.26(m, 1H) 3.88(m, 4H) 4.33(q, 2H) 5.85(m, 1H) 6.97(d, 1H) 7.55(t, 1H) 7.91(s, 1H) 8.08(d, 1H) 8.52(m, 2H) 9.05(d, 2H) 12.44(br s, 1H) |
| 277 | 475.1 | 477 | 1.3(t, 3H), 2.3(s, 6H), 3.35(m, 4H), 3.9 (m, 4H), 4.3(q, 2H), 4.6(s, 2H), 7.7(d, 1H), 7.9(s, 1H), 8.0(dt, 1H), 8.3(s, 1H), 8.35(dd, 1H), 8.75(d, 1H), 8.8(br s, 1H), 9.1(d, 1H), 10.4(br s, 1H) |
| 278 | 502.1 | 504 | 1.3(t, 3H), 3.2(s, 3H), 3.4(br s, 4H), 3.7 (br s, 4H), 3.8(br s, 2H), 4.3(q, 2H), 4.8 (br s, 2H), 7.55(t, 1H), 8.0(d, 1H), 8.5 (d, 1H), 9.0(s, 2H), 9.05(d, 2H), 11.8 (br s, 1H), 12.6(br s, 1H) |
| 279 | 525.2 | 527 | — |
| 280 | 567.2 | 569 | (CD$_3$OD) 9.11(s, 1H), 9.03(d, 2H), 8.83 (s, 1H), 8.33(d, 1H), 8.06(s, 1H), 7.68 (d, 1H), 7.52(dd, 1H), 4.63(s, 2H), 4.46 (q, 2H), 3.94(m, 4H), 3.59(q, 2H), 3.47 (m, 4H), 1.44(t, 3H) |
| 281 | 458.15 | 459.98 | 9.11(br. s, 2H); 9.09(s, 1H); 8.82(d, 1H); 8.78(br. s, 1H); 8.64(d, 1H); 8.28 (s, 1H); 8.10(dd, 1H); 7.88(s, 1H); 7.52 (dd, 1H); 5.38(m, 1H); 5.5-4.2(br. s, 4H); 4.32(q, 2H); 3.45(m, 2H); 3.37(m, 1H); 3.12(m, 2H); 2.05(M, 1 |
| 282 | 514.2 | 516 | 10.05(m, 1H); 9.24(m, 1H); 9.15(d, 2H); 8.82(d, 1H); 8.67(d, 1H); 8.31(s, 1H); 8.12(m, 1H); 7.90(s, 1H); 7.53(m, 1H); 5.52(m, 1H); 4.32(q, 2H); 3.78(m, 1H); 3.55-2.88(m, 4H); 2.12(m, 1H); 2.02(m, 1H); 1.88(m, 1H); 1.33(t |
| 283 | 519.15 | 521.02 | 1.3(t, 3H), 2.35(s, 12H), 2.8(s, 3H), .3.0-3.7(br s, 10H), 4.3(q, 2H), 4.7(br s, 2H), 7.6(m, 1H), 7.9(s, 1H), 7.95(m, 2H), 8.65(m, 1H), 9.0(s, 2H) |
| 290 | 487.1 | 489 | — |
| 291 | — | 490 | — |
| 292 | 482.1 | 484 | — |
| 293 | 483 | 484.9 | — |

TABLE 3-continued

Characterization Data for Selected Compounds of Formula I

| Compound No. I- | M − 1 (obs) | M + 1 (obs) | $^1$H NMR |
|---|---|---|---|
| 294 | 460.11 | 461.96 | 1.15(t, 3H), 2.3(s, 9H), 3.25(m, 2H), 3.5(m, 4H), 3.8(m, 4H), 7.5(br s, 1H), 7.6(m, 1H), 7.95(m, 1H), 8.0(s, 1H), 8.1(m, 1H), 8.2(m, 1H), 8.4(d, 1H), 8.6 (s, 1H), 8.7(d, 1H), 10.3(br s, 1H) |
| 295 | — | — | (CD$_3$OD) 9.13(d, 1H), 9.05(d, 2H), 8.92(d, 1H), 8.37(m, 1H), 8.13(d, 1H), 7.75(dt, 1H), 7.55(t, 1H), 4.70(s, 2H), 4.49(q, 2H), 3.62(m, 4H), 2.47(m, 4H), 1.44(t, 3H) ppm |

Example 27

Gyrase ATPase Assay

The ATP hydrolysis activity of DNA gyrase was measured by coupling the production of DP through pyruvate kinase/lactate dehydrogenase to the oxidation of NADH. This method has been described previously (Tamura and Gellert, 1990, *J. Biol. Chem.*, 265, 21342).

ATPase assays are carried out at 30° C. in buffered solutions containing 100 mM TRIS ph 7.6, 1.5 mM MgCl$_2$, 150 mM KCl. The coupling system contains (final concentrations) 2.5 mM phosphoenol pyruvate, 200 µM nicotinamide adenine dinucleotide (NADH), 1 mM DTT, 30 ug/ml pyruvate kinase, and 10 ug/ml lactate dehydrogenase. 40 nanomolar enzyme (374 kDa Gyr A2B2 subunit from *Staphylococcus aureus*) and a DMSO solution of the inhibitor to a final concentration of 4% are added and the reaction mixture is allowed to incubate for 10 minutes at 30° C. The reaction is then started by the addition of ATP to a final concentration of 0.9 mM and the rate of NADH disappearance at 340 nanometers is measured over the course of 10 minutes. The K$_i$ values determined from rate versus concentration profiles.

Compounds of the present invention were found to inhibit gyrase. In certain embodiments, compounds of the present invention inhibit gyrase with a K$_i$ value of less than 50 nM in the above assay.

Example 28

Topo IV ATPase Assay

The conversion of ATP to ADP by Topo4 enzyme is coupled to the conversion of NADH to NAD+ and measured by the change in absorbance at 340 nm. Topo4 is incubated with inhibitor (4% DMSO final) in buffer for 10 minutes at 30° C. Reaction is initiated with ATP and rates are monitored continuously for 20 minutes at 30° C. on a Molecular Devices SpectraMAX plate reader. The inhibition constant, Ki, is determined from plots of rate vs. [Inhibitor] fit to the Morrison Equation for tight binding inhibitors.

*S. aureus* Topo4 Buffer:
100 mM Tris 7.5, 2 mM MgCl2, 200 mM K. Glutamate, 2.5 mM phosphoenol pyruvate, 0.2 mM NADH, 1 mM DTT, 4.25 µg/mL linearized DNA, 50 µg/mL BSA, 30 µg/mL pyruvate kinase, and 10 µg/mL lactate dehyrodgenase (LDH).

*E. coli* Topo4 Buffer:
100 mM Tris 7.5, 6 mM MgCl2, 20 mM KCl, 2.5 mM phosphoenol pyruvate, 0.2 mM NADH, 10 mM DTT, 5.25 µg/mL linearized DNA, 50 µg/mL BSA, 30 µg/mL pyruvate kinase, and 10 µg/mL lactate dehyrodgenase (LDH).

Compounds of the present invention were found to inhibit TopoIV. In certain embodiments, compounds of the present invention inhibit TopoIV with a K$_i$ value of less than 50 nM in the above assay.

Example 29

Susceptibility Testing in Liquid Media

Compounds of this invention were also tested for antimicrobial activity by susceptibility testing in liquid media. Such assays were performed within the guidelines of the latest NCCLS document governing such practices: "M7-A5 Methods for dilution Antimicrobial Susceptibility Tests for Bacteria that Grow Aerobically; Approved Standard—Fifth Edition (2000)". Other publications such as "Antibiotics in Laboratory Medicine" (Edited by V. Lorian, Publishers Williams and Wilkins, 1996) provide essential practical techniques in laboratory antibiotic testing. Essentially, several discrete bacterial colonies of *Staphylococcus aureus* (3 to 7) from a freshly streaked plate were transferred to an appropriate rich broth medium such as MHB, supplemented where appropriate for the more fastidious organisms. This was grown overnight to high density followed by a 1 or 2-thousand-fold dilution to give an inoculation density of between 5×10$^5$ and 5×10$^6$ CFU per mL. Alternatively, the freshly picked colonies can be incubated at 37° C. for about 4 to 8 hours until the culture equals or exceeds a turbidity of a 0.5 McFarland standard (approximately 1.5×10$^8$ cells per mL) and diluted to give the same CFU per mL as above. In a more convenient method, the inoculum was prepared using a commercially available mechanical device (the BBL PROMPT System) that involves touching five colonies directly with a wand, containing crosshatch grooves at its bottom, followed by suspension of the bacteria in an appropriate volume of saline. Dilution to the appropriate inoculum cell density was made from this cell suspension. The broth used for testing consists of MHB supplemented with 50 mg per L of Ca$^{2+}$ and 25 mg per L of Mg$^{2+}$. Standard dilution panels of control antibiotics were made and stored as in the NCCLS standard M7-A5, the dilution range typically being in the 128 µg per mL to 0.015 µg per mL (by 2-fold serial dilution). The test compounds were dissolved and diluted fresh for experimentation on the same day; the same or similar ranges of concentration as above being used. The test compounds and controls were dispensed into a multiwell plate and test bacteria added such that the final inoculation was approximately 5×10$^4$ CFU per well and the final volume was 100 µL. The plates were incubated at 35° C. overnight (16 to 20 hours) and checked by eye for turbidity or quantitated with a multiwell plate reader. The endpoint minimal inhibitory concentration (MIC) is the lowest concentration of drug at which the microorganism tested (*Staphylococcus aureus*) does not grow. Such determinations were also compared to the appropriate tables contained in the above two publications to ensure that the range of antibacterial activity is within the acceptable range for this standardized assay.

Compounds of the present invention were found to have antimicrobial activity in the above-described *S. aureus* MIC assay.

While we have described a number of embodiments of the present invention, it is apparent that our basic constructions may be altered to provide other embodiments which utilize the products and processes of this invention.

What is claimed is:

1. A compound of formula I:

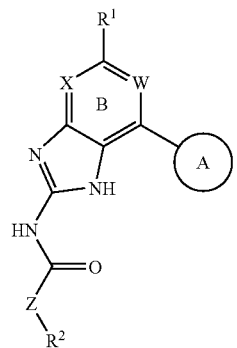

I or a pharmaceutically acceptable salt thereof, wherein:
W is selected from CH or CF;
X is selected from CH or CF;
Z is O or NH;
$R^1$ is phenyl or a 5-6 membered heteroaryl ring having 1-3-heteroatoms independently selected from oxygen, nitrogen, or sulfur, wherein:
  $R^1$ is substituted with 0-3 groups independently selected from -(T)$_y$-Ar, R', oxo, C(O)R', CO$_2$R', OR', N(R')$_2$, SR', NO$_2$, halogen, CN, C(O)N(R')$_2$, NR'C(O)R', SO$_2$R', SO$_2$N(R')$_2$, or NR'SO$_2$R';
y is 0 or 1;
T is a straight or branched C$_{1-4}$ alkylidene chain, wherein one methylene unit of T is optionally replaced by —O—, —NH—, or —S—;
each R' is independently selected from hydrogen, C$_{1-4}$ aliphatic, or a 5-6 membered saturated, unsaturated, or aryl ring having 0-3 heteroatoms independently selected from nitrogen, oxygen, or sulfur, wherein:
  R' is substituted with 0-3 groups independently selected from halogen, oxo, R°, N(R°)$_2$, OR°, CO$_2$R°, NR°C(O)R°, C(O)N(R°)$_2$, SO$_2$, R°, SO$_2$N(R°)$_2$, or NR°SO$_2$R°, wherein:
    each R° is independently selected from hydrogen, C$_{1-4}$ aliphatic, or a 5-6 membered saturated, unsaturated, or aryl ring having 0-3 heteroatoms independently selected from nitrogen, oxygen, or sulfur, and wherein:
      two substituents on adjacent positions of $R^1$ may be taken together to form a 5-7 membered saturated, partially unsaturated, or aryl ring having 0-3 heteroatoms independently selected from nitrogen, oxygen, or sulfur;
Ar is a 3-8 membered saturated, unsaturated, or aryl ring, a 3-7 membered heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur, wherein:
  Ar is substituted with 0-3 groups independently selected from R', oxo, CO$_2$R', OR', N(R')$_2$, SR', NO$_2$, halogen, CN, C(O)N(R')$_2$, NR'C(O)R', SO$_2$R', C(O)R', SO$_2$N(R')$_2$, or NR'SO$_2$R';
$R^2$ is selected from hydrogen or a C$_{1-3}$ aliphatic group; and
Ring A is a 5-6 membered heteroaryl ring having 1-4 heteroatoms independently selected from nitrogen, oxygen, or sulfur, provided that said ring has a hydrogen-bond acceptor in the position adjacent to the point of attachment to Ring B, wherein:
  Ring A is substituted with 0-3 groups independently selected from R', oxo, CO$_2$R', OR', N(R')$_2$, SR', NO$_2$, halogen, CN, C(O)N(R')$_2$, NR'C(O)R', SO$_2$R', SO$_2$N(R')$_2$, or NR'SO$_2$R', and wherein:
    two substituents on adjacent positions of Ring A may be taken together to form a 5-7 membered saturated, partially unsaturated, or aryl ring having 0-3 heteroatoms independently selected from nitrogen, oxygen, or sulfur.

2. The compound according to claim 1, wherein Ring A is selected from the following optionally substituted rings:

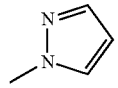

a

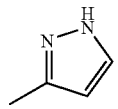

b

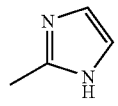

c

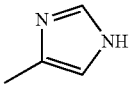

d

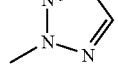

e

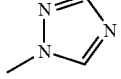

f

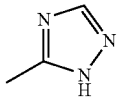

g

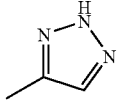

h

-continued
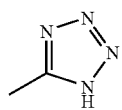 i
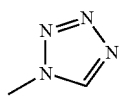 j
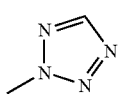 k
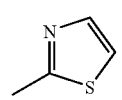 l
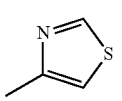 m
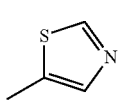 n
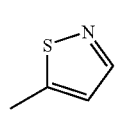 o
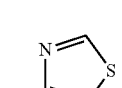 p
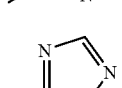 q
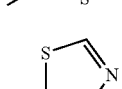 r
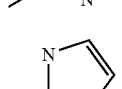 s
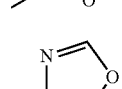 t
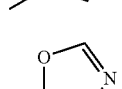 u
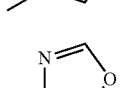 v
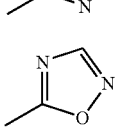 w
-continued
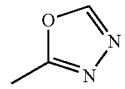 x
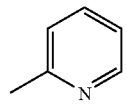 y
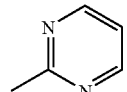 z
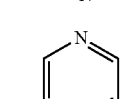 aa
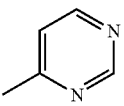 bb
cc
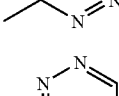 dd
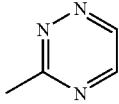 ee
ff
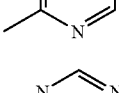 gg
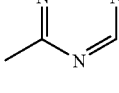 or
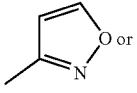.
3. The compound according to claim 2, wherein Ring A is an optionally substituted ring selected from rings a, f, l, s, w, y, or z:
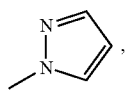 a
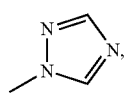 f -continued

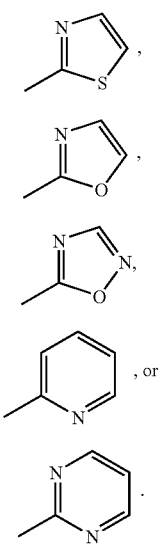

4. The compound according to claim 1, wherein:
$R^1$ is selected from an optionally substituted phenyl or 5-6 membered heteroaryl ring having 1-2 nitrogens.

5. The compound according to claim 4, wherein $R^1$ is an optionally substituted ring selected from pyrid-2-yl, pyrid-3-yl, pyrid-4-yl, pyrimidin-2-yl, pyrimidin-4-yl, pyrimidin-5-yl, pyrimidin-6-yl, imidazol-1-yl, imidazol-2-yl, imidazol-4-yl, or imidazol-5-yl.

6. The compound according to claim 5, wherein $R^1$ is substituted with 0-2 groups independently selected from halogen, oxo, R', $CO_2R'$, OR', $N(R')_2$, SR', $C(O)N(R')_2$, NR'C(O)R', $SO_2R'$, $SO_2N(R')_2$, or $NR'SO_2R'$.

7. The compound according to claim 6, wherein $R^2$ is selected from methyl, ethyl, isopropyl, or cyclopropyl.

8. The compound according to claim 1, wherein said compound is of formula II-a:

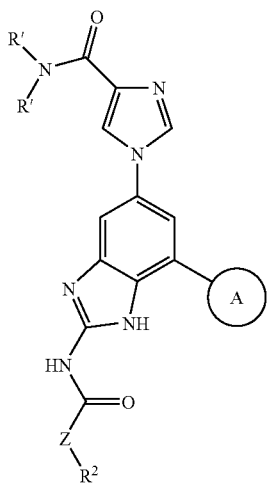

or a pharmaceutically acceptable salt thereof.

9. The compound according to claim 1, wherein said compound is of formula III:

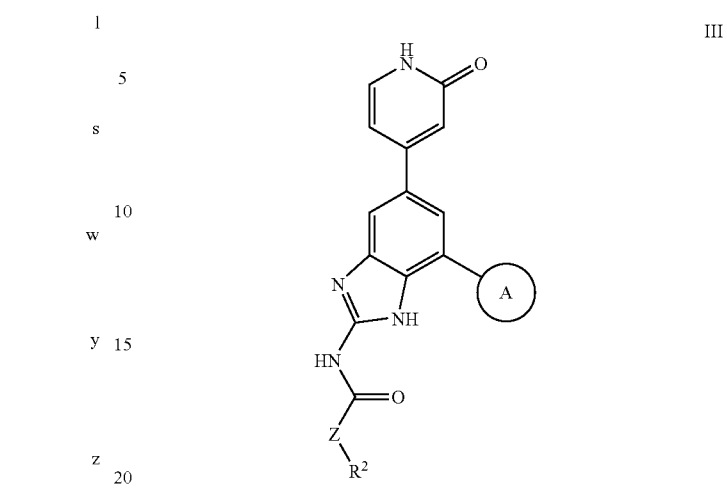

or a pharmaceutically acceptable salt thereof, wherein:
the pyridone ring depicted is substituted with 0-2 groups independently selected from halogen, oxo, R', $CO_2R'$, OR', $N(R')_2$, SR', $C(O)N(R')_2$, NR'C(O)R', $SO_2R'$, $SO_2N(R')_2$, or $NR'SO_2R'$.

10. The compound according to claim 9, wherein said compound is of formula III-a:

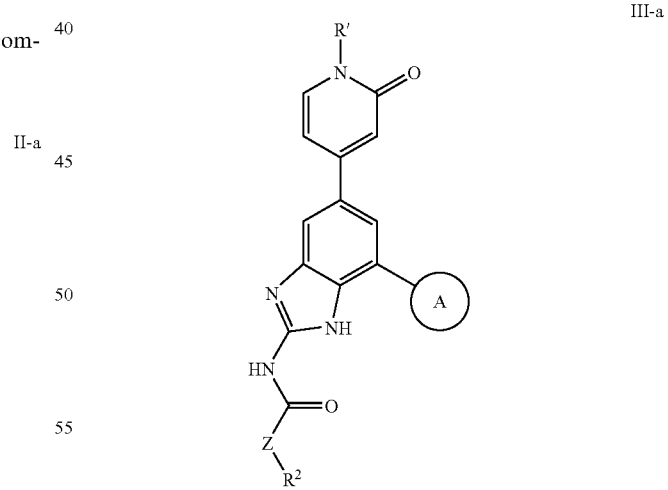

or a pharmaceutically acceptable salt thereof.

11. The compound according to claim 10, wherein:
R' is hydrogen or $C_{1-4}$ aliphatic, and wherein:
R' is optionally substituted with phenyl or pyridyl.

12. The compound according to claim 1, wherein said compound is of formula IV:

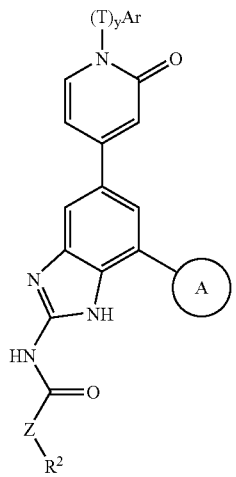

or a pharmaceutically acceptable salt thereof.

13. The compound according to claim 12, wherein Ar is an optionally substituted 5-6 membered saturated ring having 1-2 heteroatoms independently selected from oxygen, nitrogen, or sulfur.

14. The compound according to claim 12, wherein Ar is an optionally substituted 5-membered heteroaryl ring having 1-3 heteroatoms independently selected from nitrogen, oxygen, or sulfur.

15. The compound according to claim 12, wherein Ar is an optionally substituted 6-membered heteroaryl ring having 1-3 nitrogens.

16. The compound according to claim 12, wherein Ar is optionally substituted phenyl.

17. The compound according to claim 1, wherein said compound is of formula V:

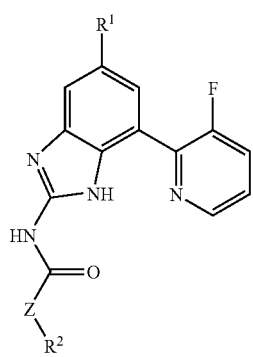

or a pharmaceutically acceptable salt thereof.

18. The compound according to claim 17, wherein said compound is of formula VI:

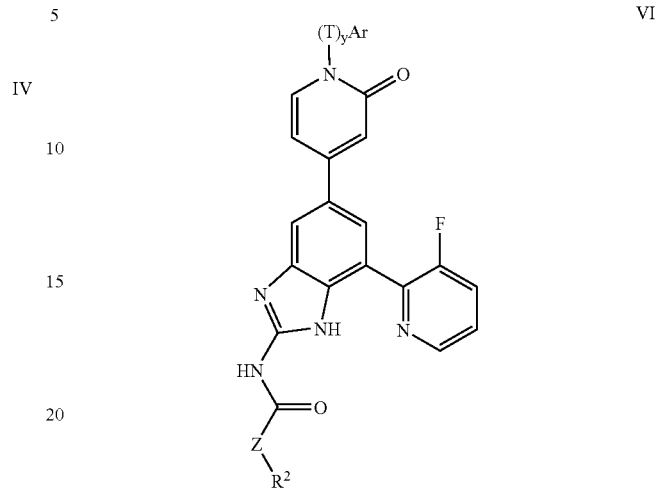

or a pharmaceutically acceptable salt thereof.

19. The compound according to any one of claims 8, 11, 12, or 17 wherein $R^2$ is ethyl.

20. A compound selected from the group consisting of:

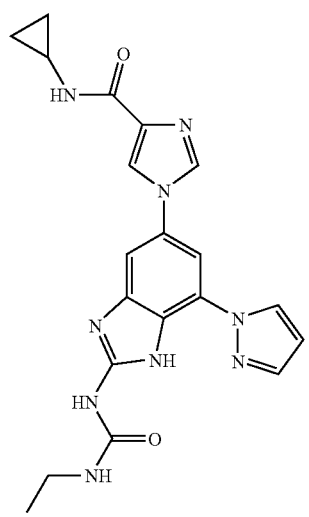

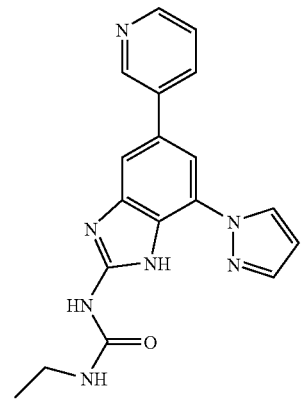

-continued
I-3
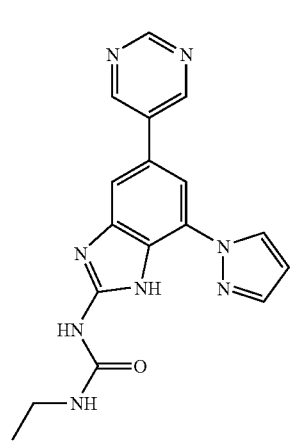
I-4
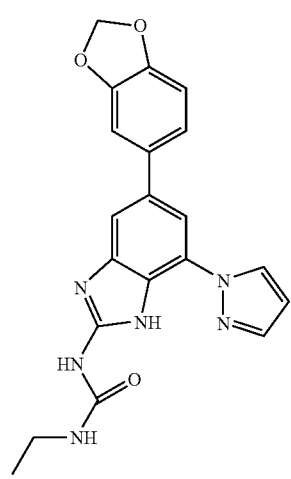
I-5
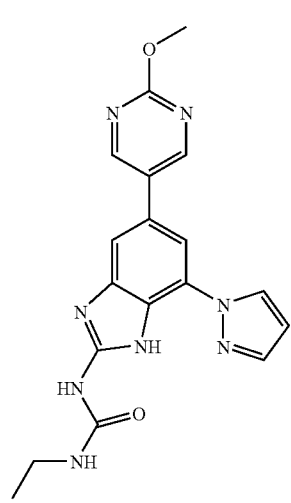
-continued
I-6
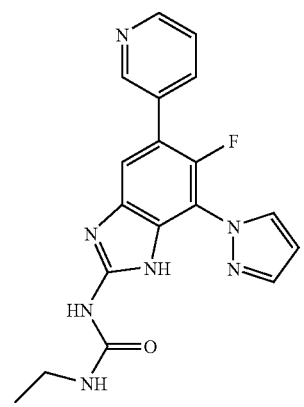
I-7
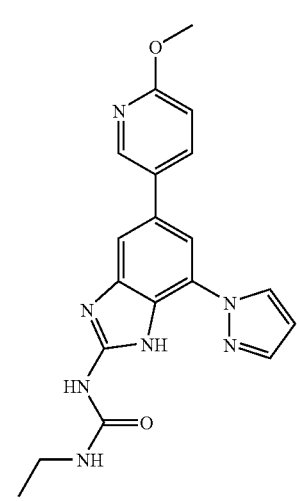
I-8
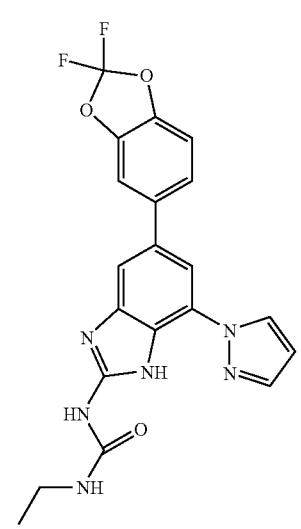

-continued
I-9
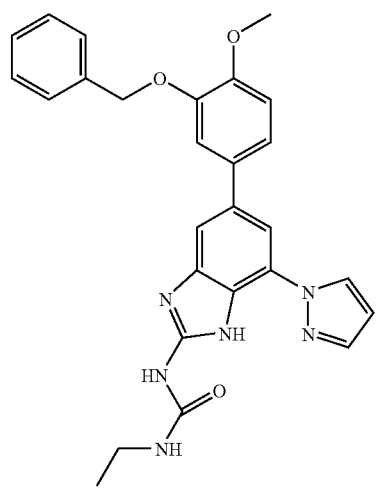
I-10
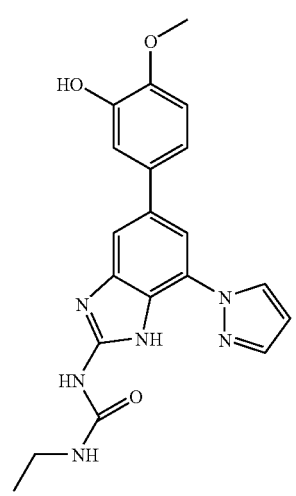
I-11
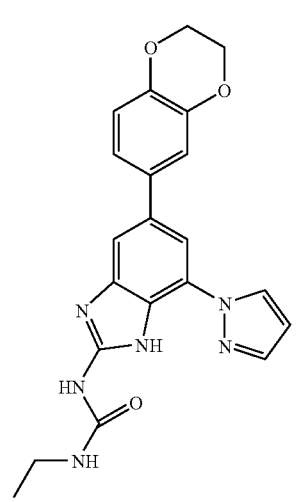
-continued
I-12
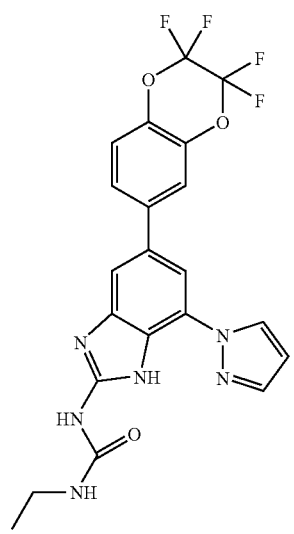
I-13
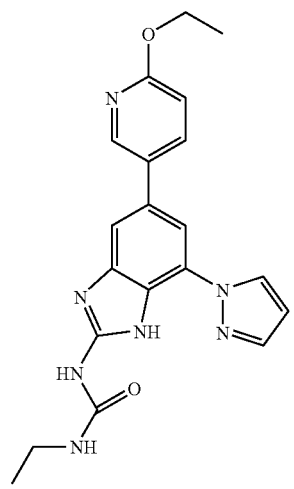
I-14
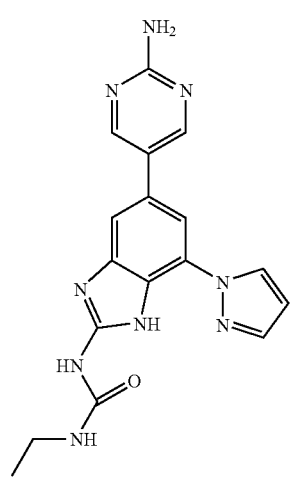

-continued
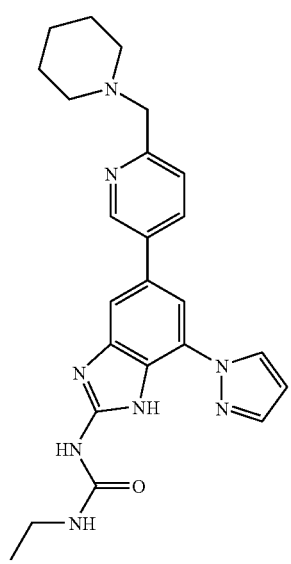
I-15
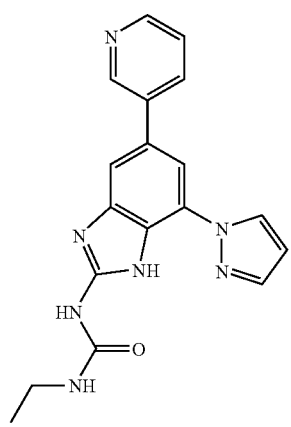
I-16
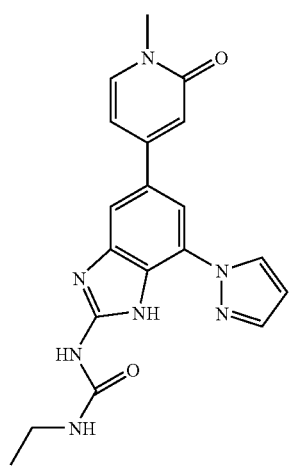
I-17
-continued
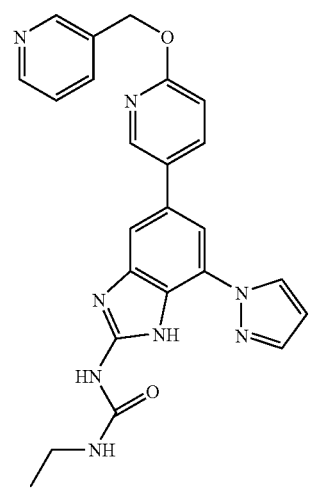
I-18
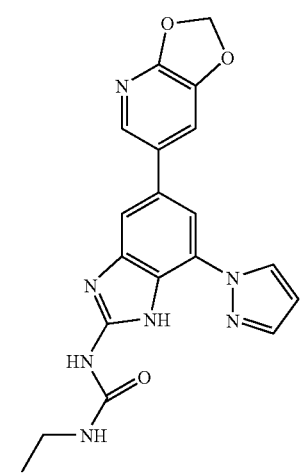
I-19
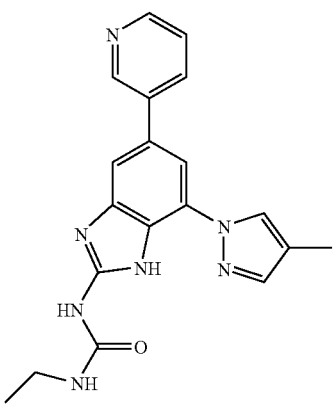
I-20

I-21
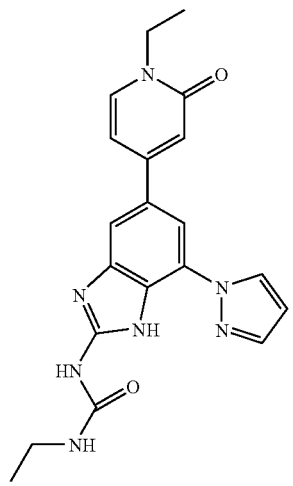
I-22
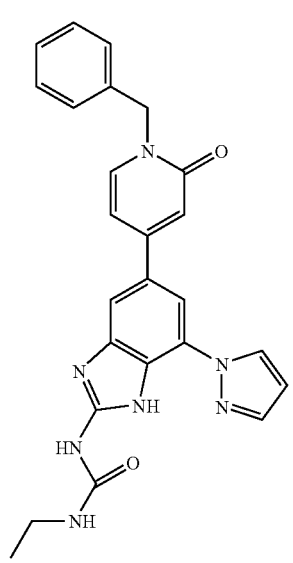
I-23
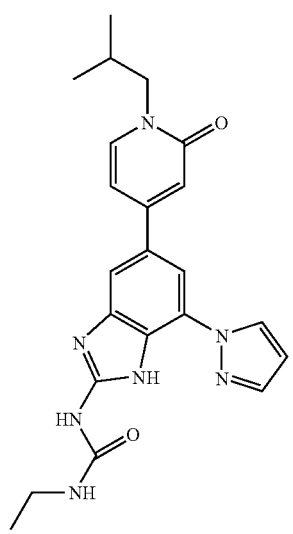
I-24
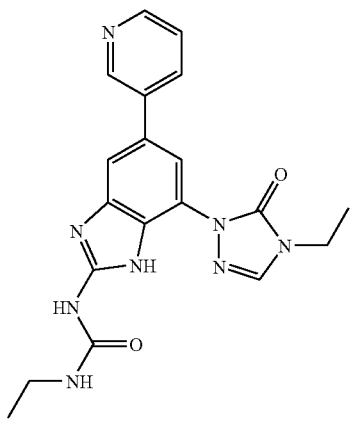
I-25
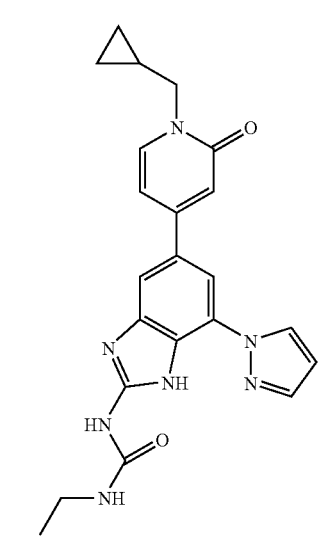
I-26
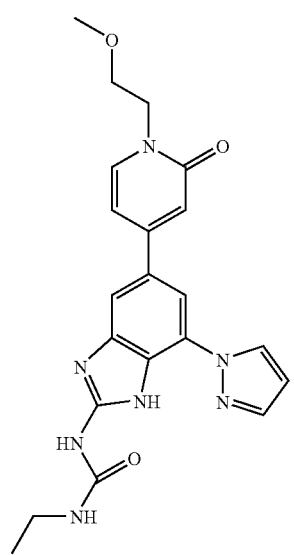

-continued
I-28
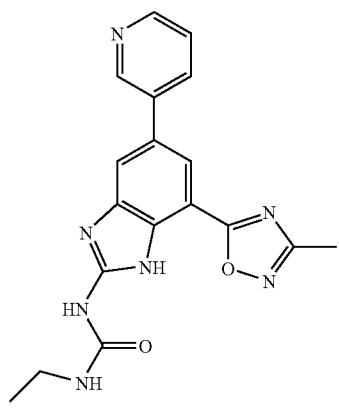
I-29
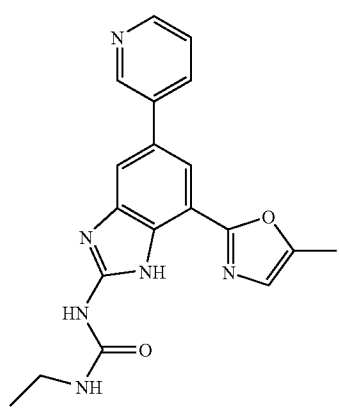
I-30
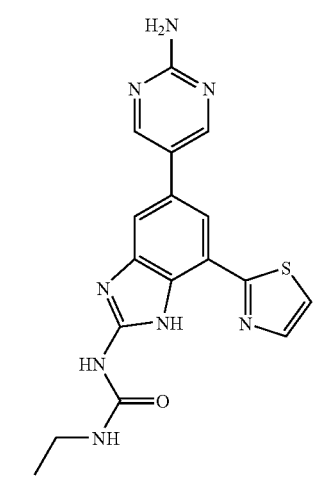
-continued
I-31
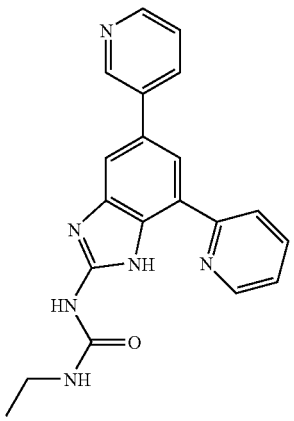
I-32
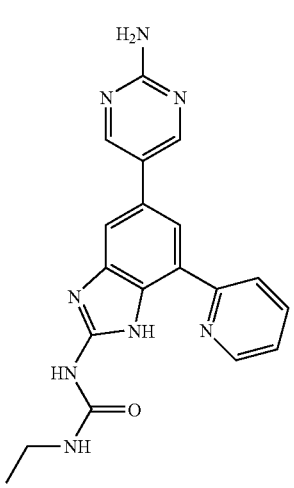
I-35
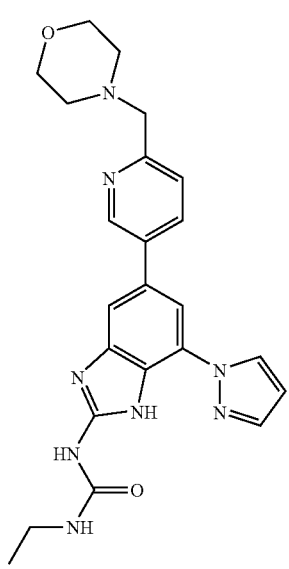

I-37
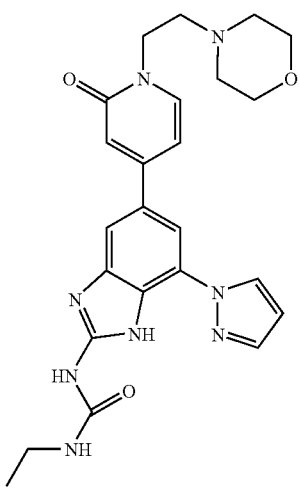
I-38
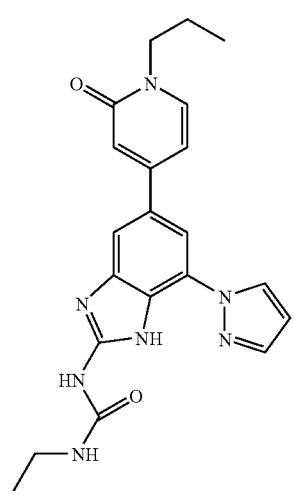
I-39
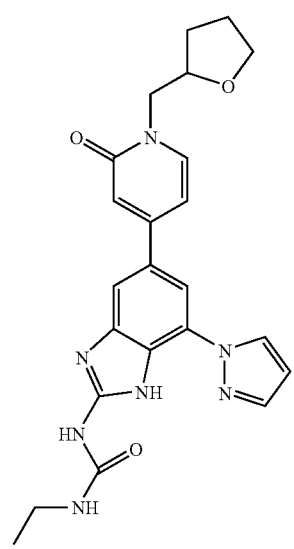
I-40
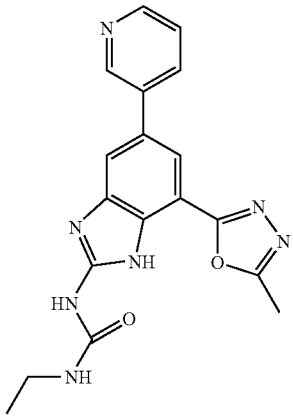
I-41
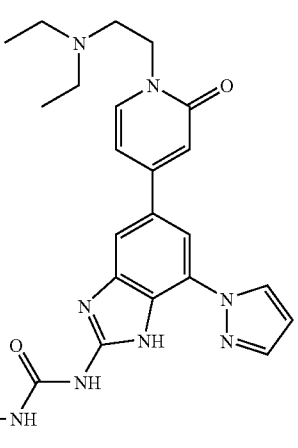
I-42
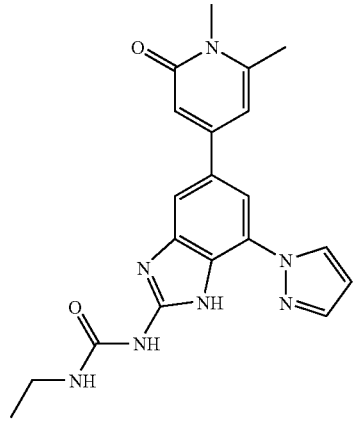

-continued
I-43
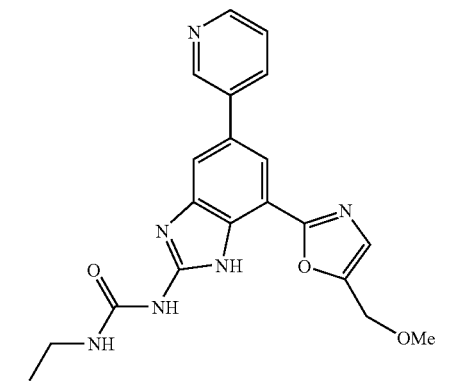
I-44
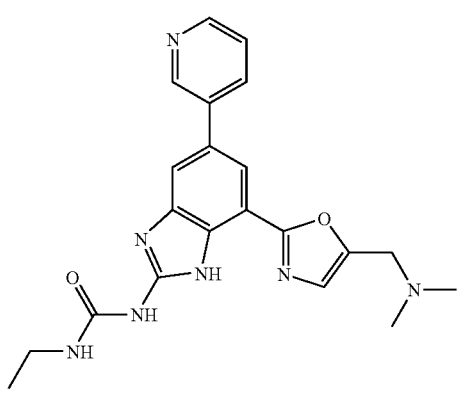
I-45
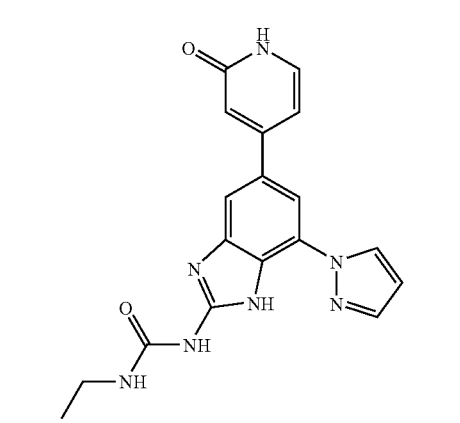
I-46
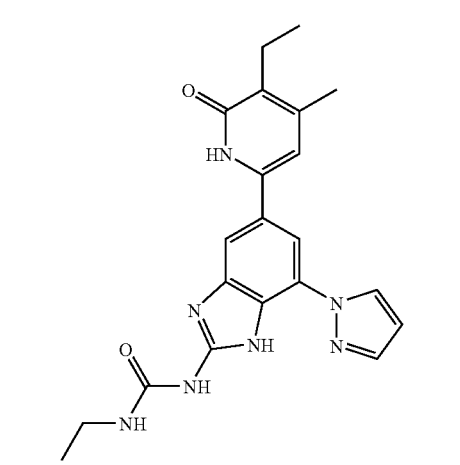
-continued
I-47
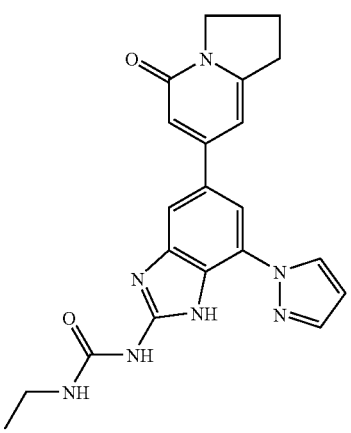
I-48
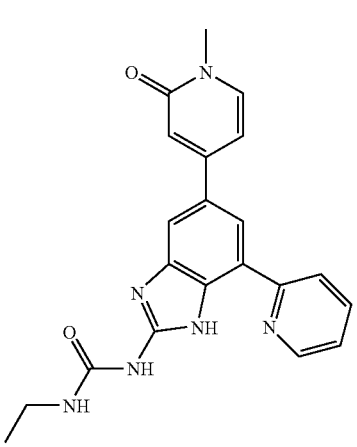
I-49
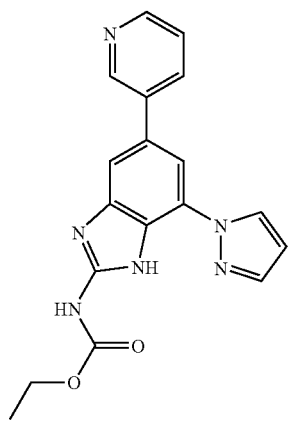

-continued
I-50
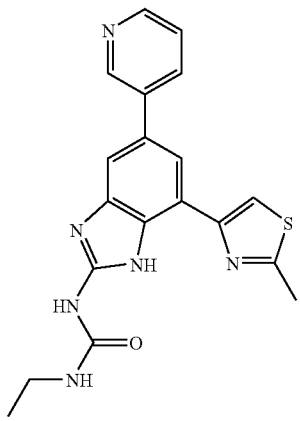
I-51
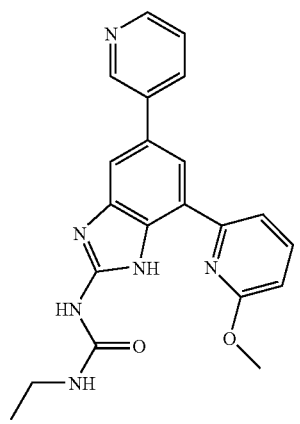
I-52
-continued
I-53
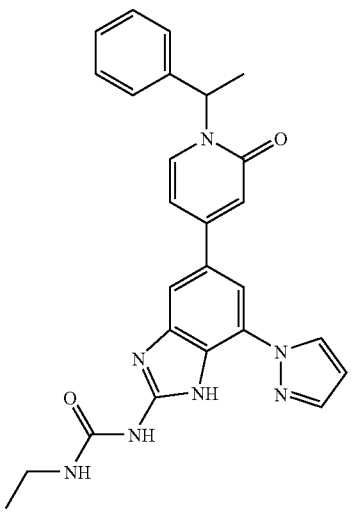
I-54
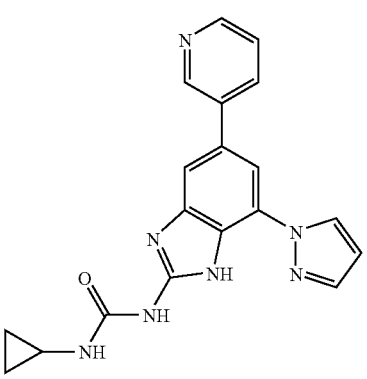
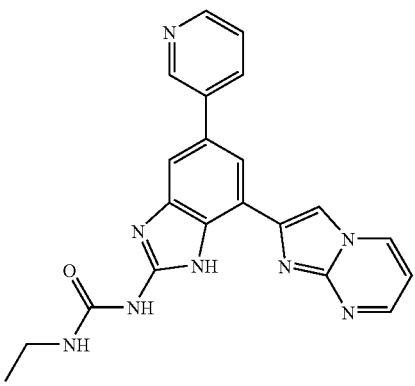

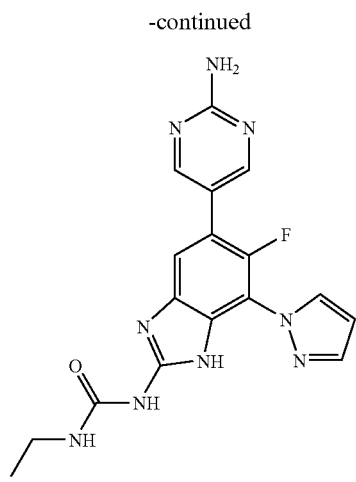
I-56
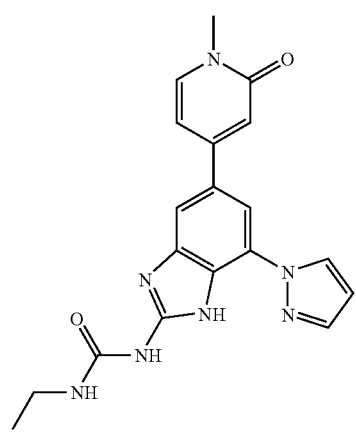
I-57
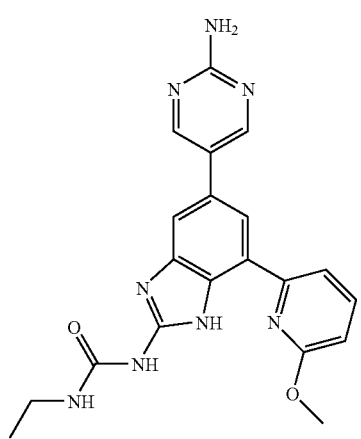
I-60
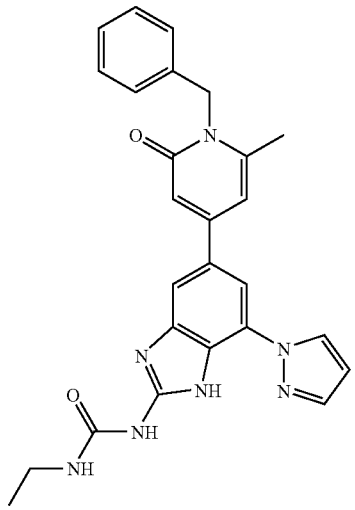
I-61
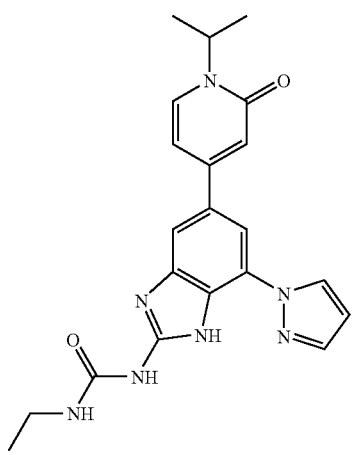
I-62
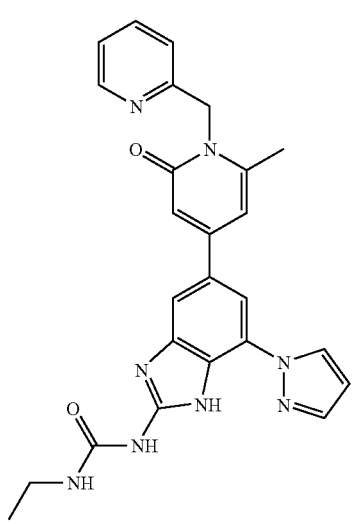
I-63

-continued
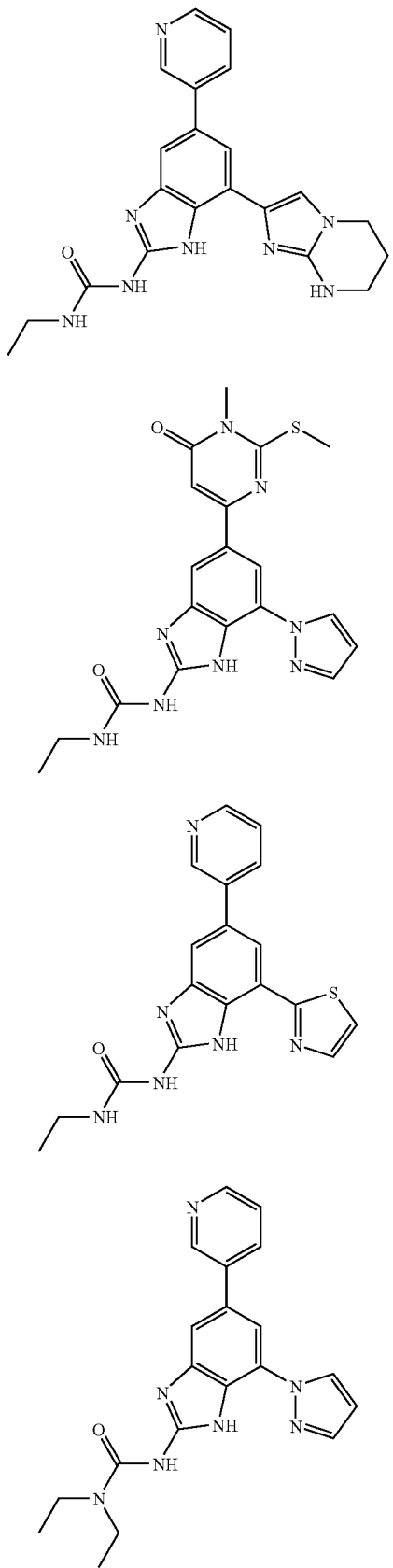
I-64
I-65
I-66
I-67
-continued
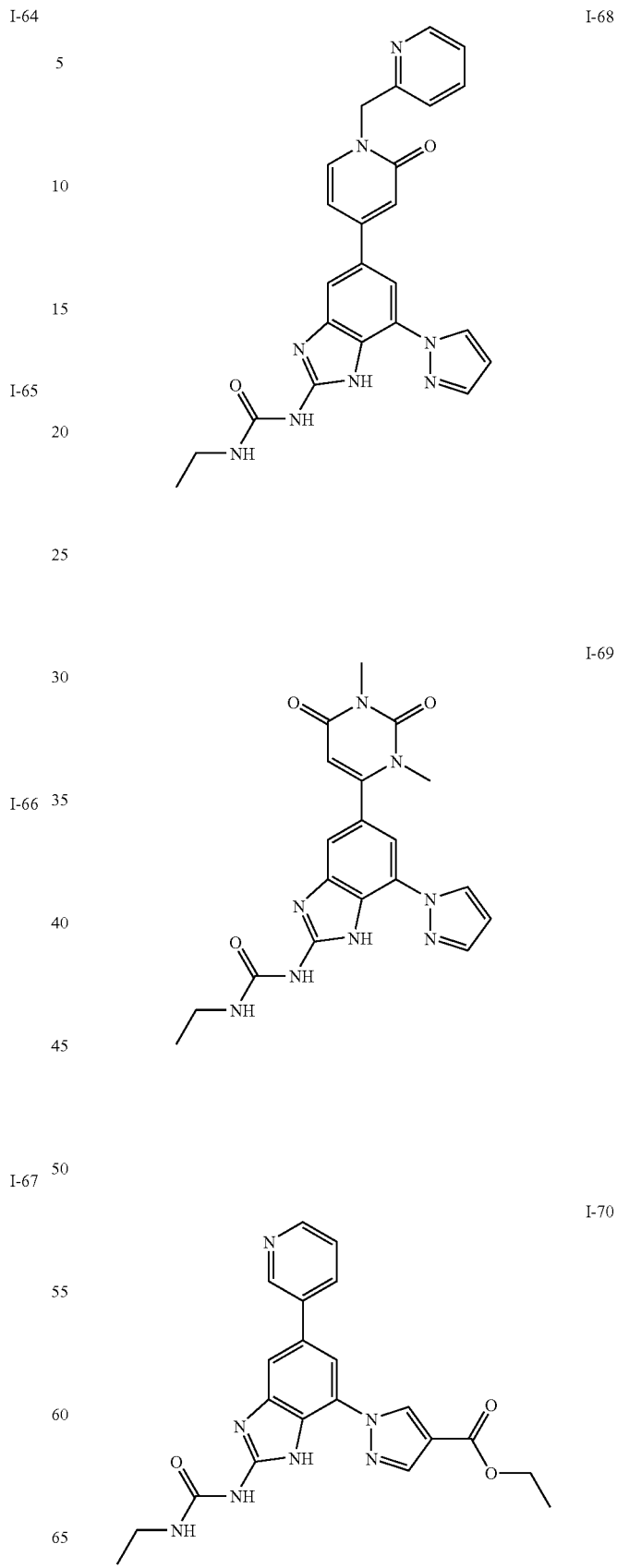
I-68
I-69
I-70

-continued
I-71
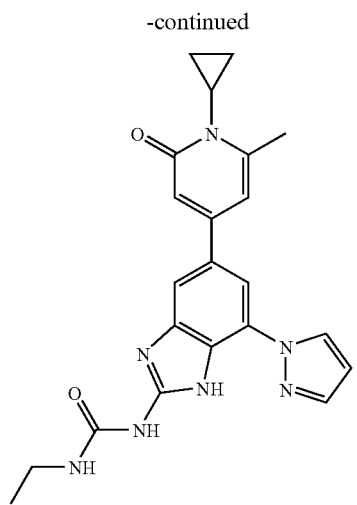
I-72
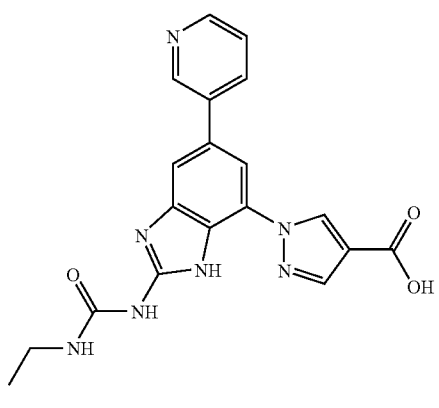
I-73
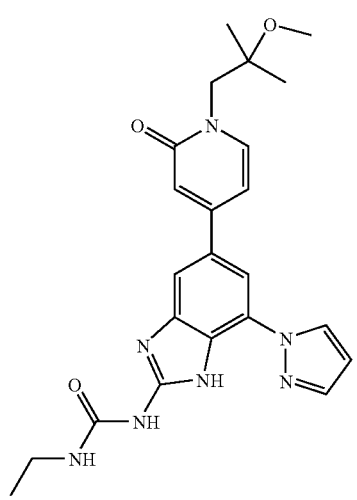
-continued
I-74
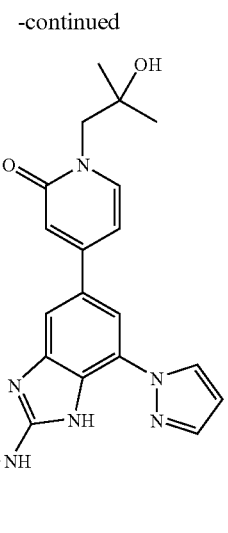
I-75
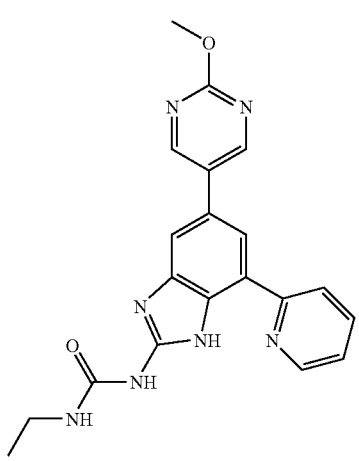
I-76

-continued
I-77
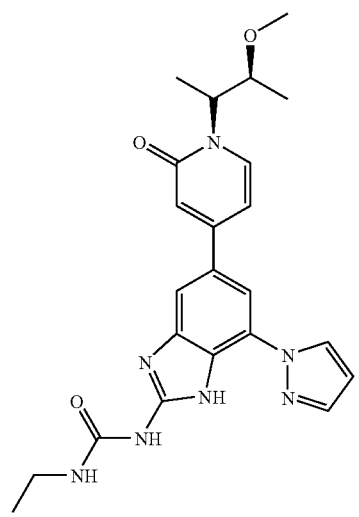
I-78
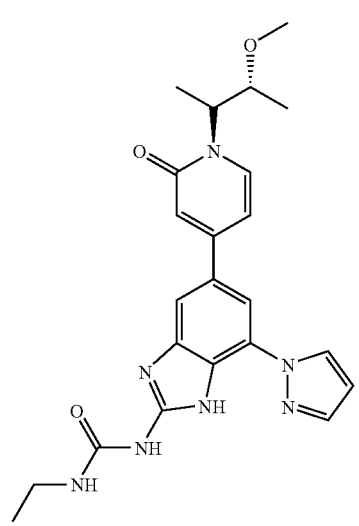
I-79
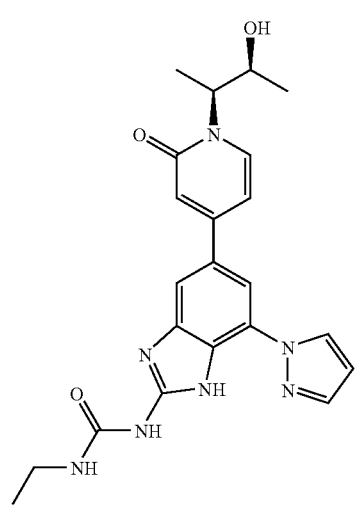
-continued
I-80
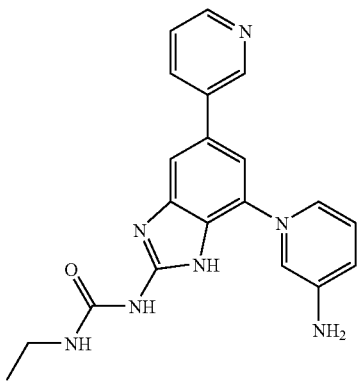
I-81
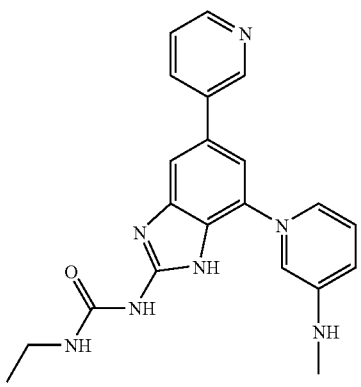
I-82
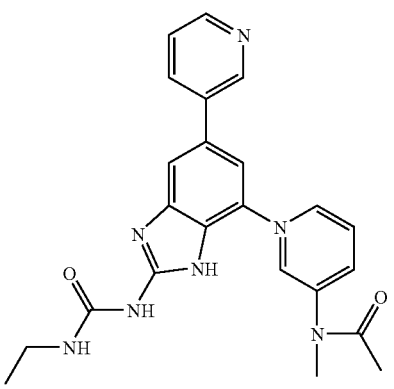
I-83
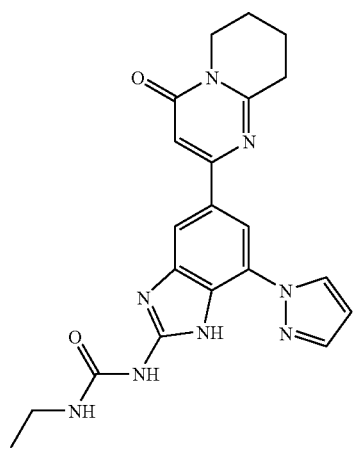

I-84
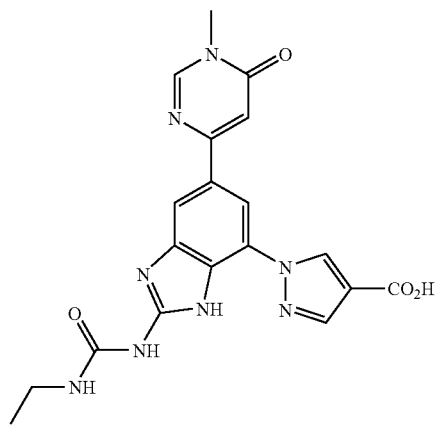
I-85
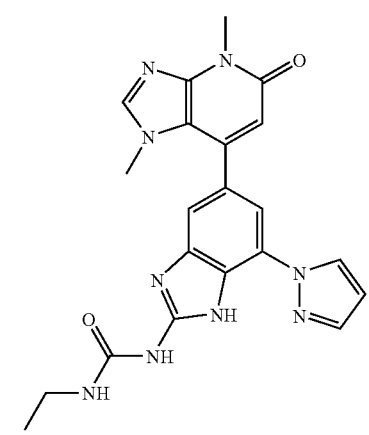
I-86
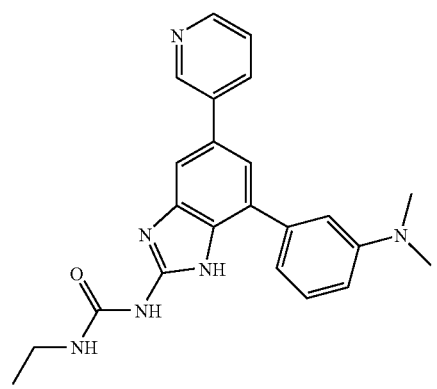
I-87
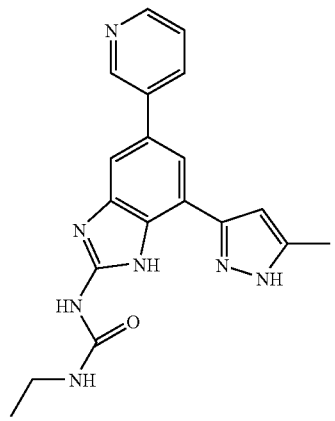
I-88
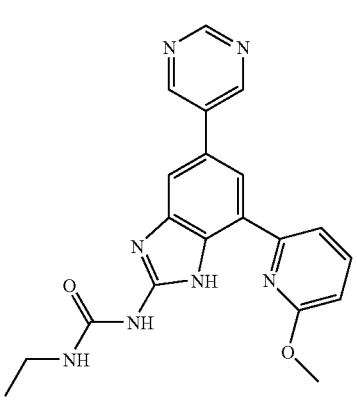
I-89
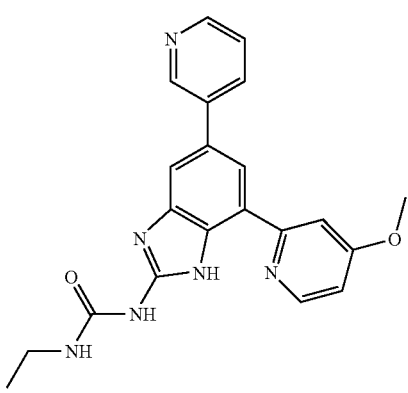

I-90
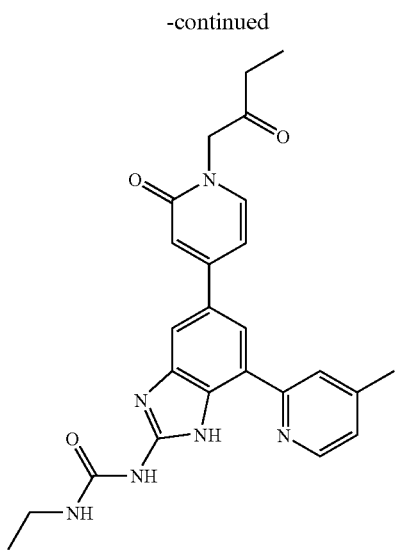
I-91
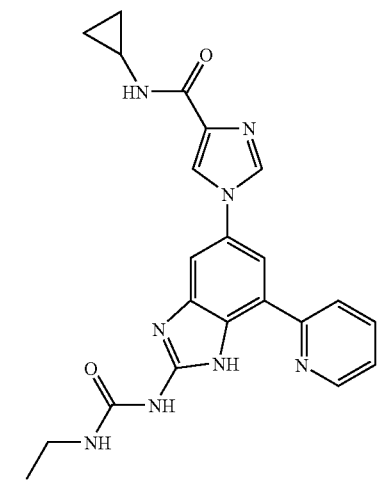
I-92
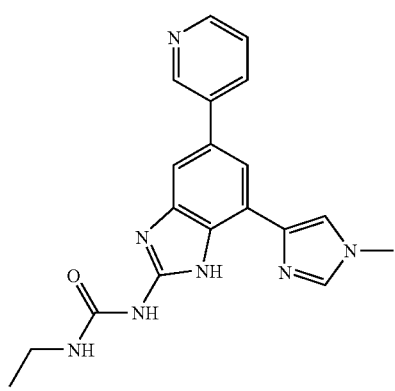
I-93
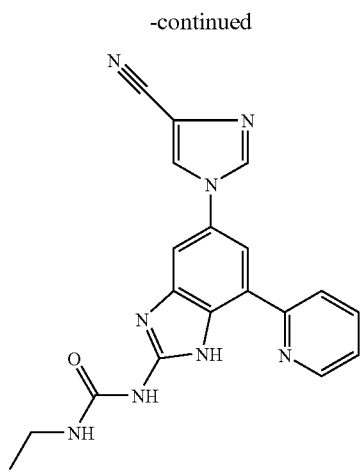
I-94
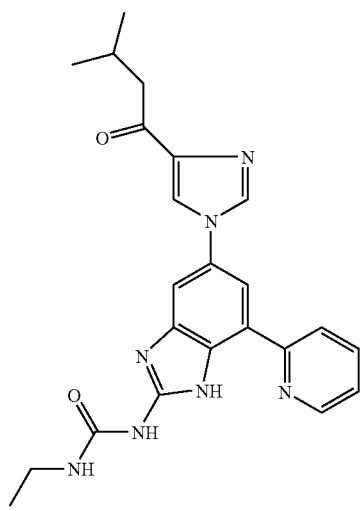
I-95
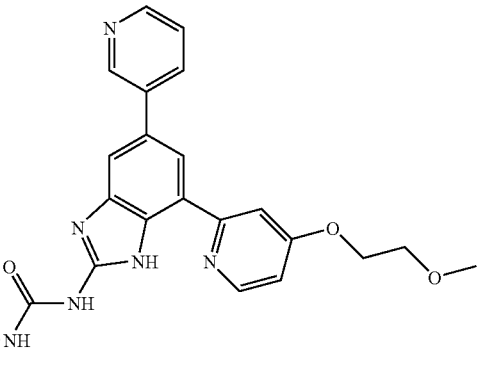

-continued
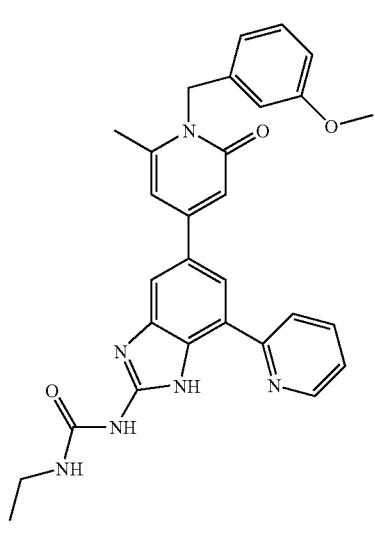
I-96
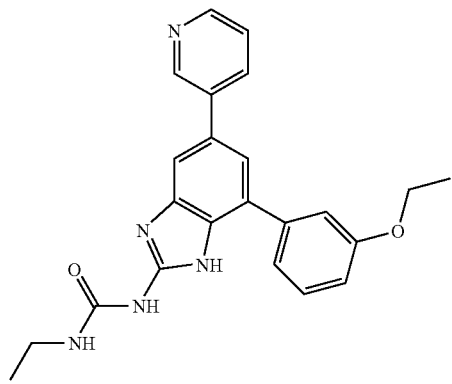
I-97
-continued
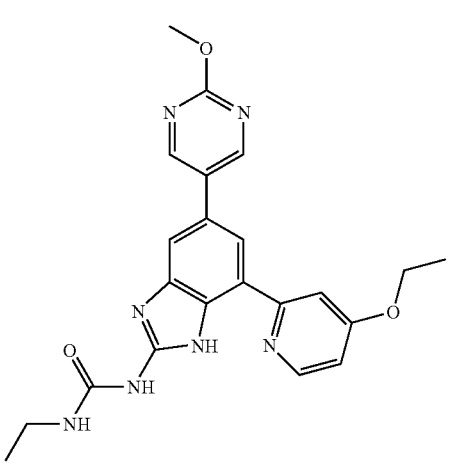
I-99
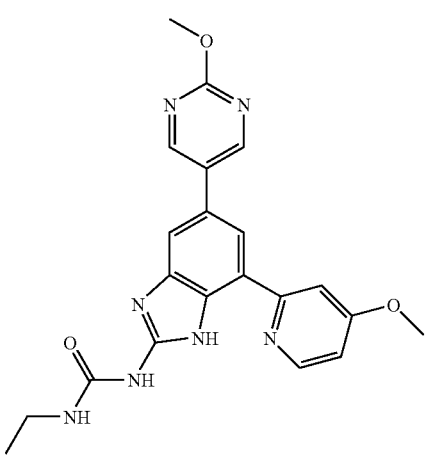
I-100
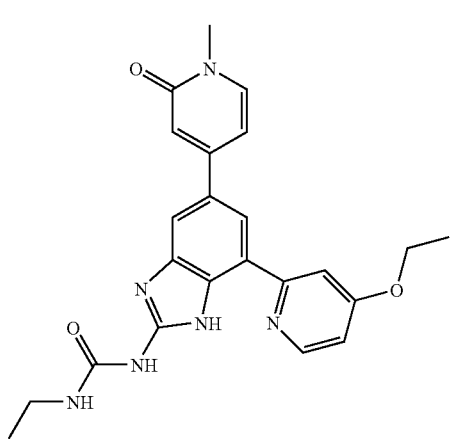
I-101

-continued
I-102
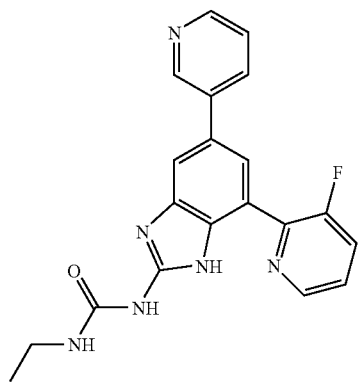
I-103
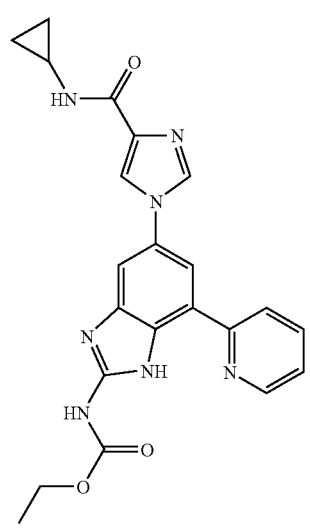
I-104
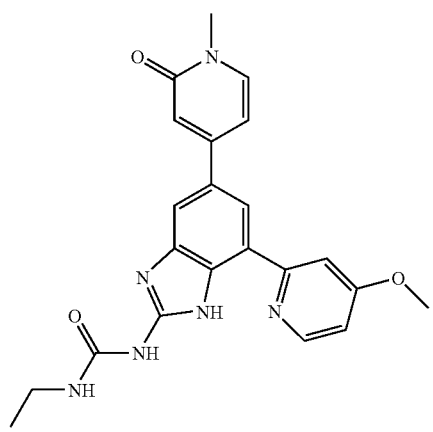
-continued
I-105
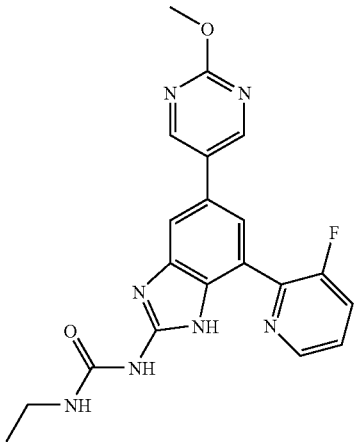
I-106
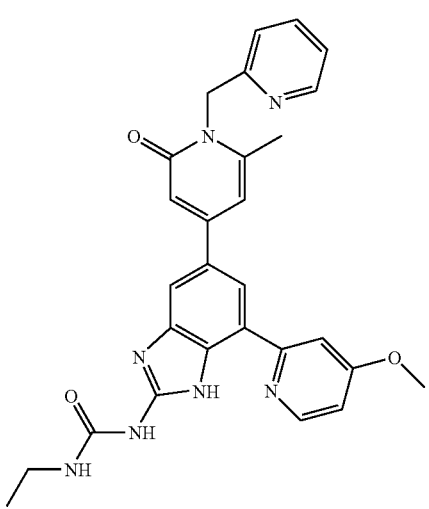
I-107
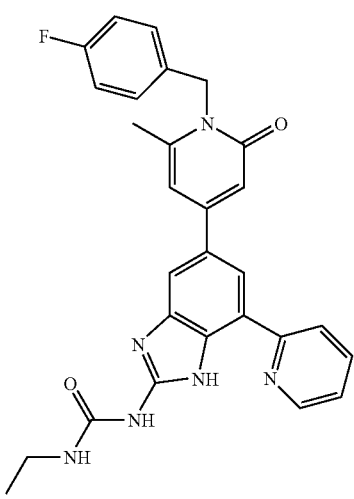

I-108
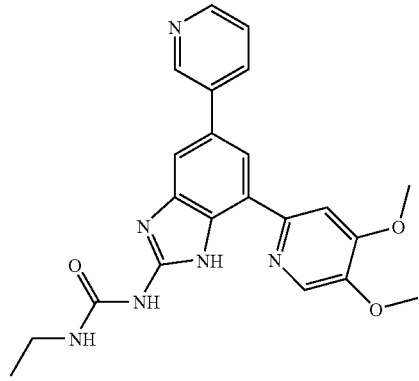
I-109
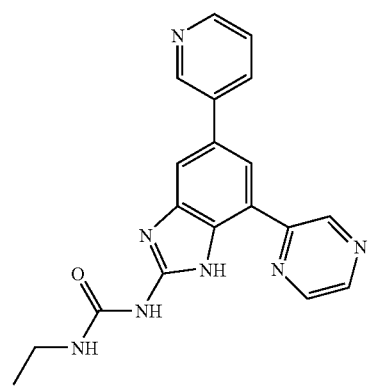
I-110
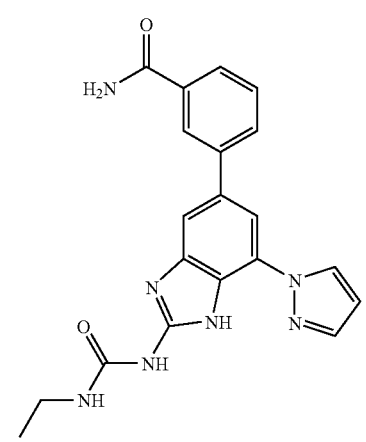
I-111
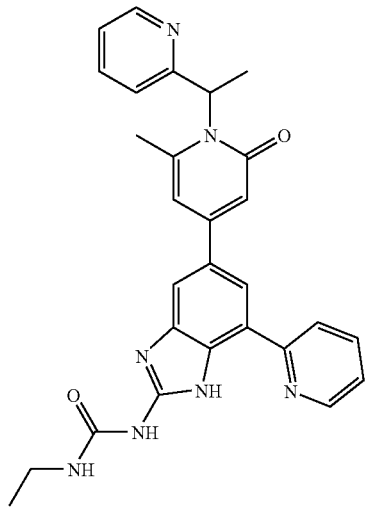
I-112
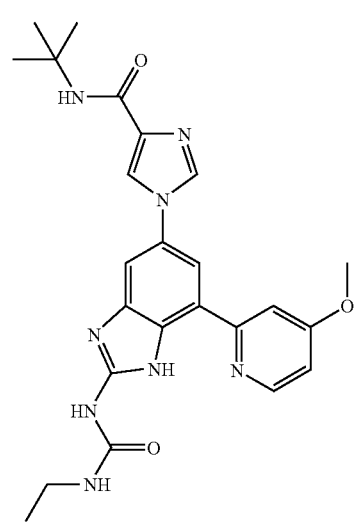
I-113
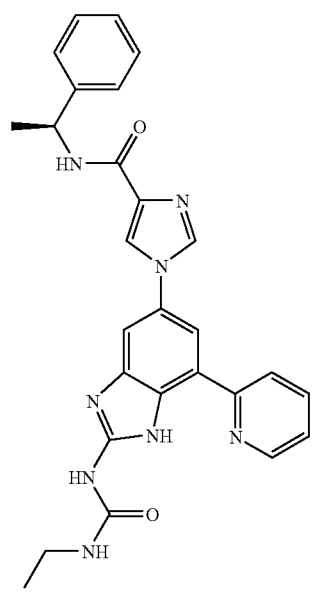

213 214
-continued -continued
I-114
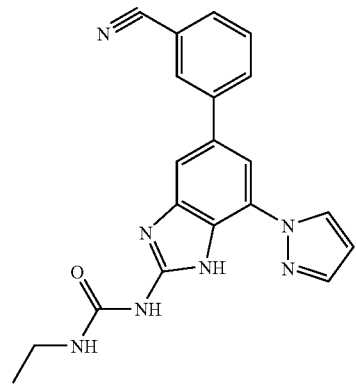
I-117
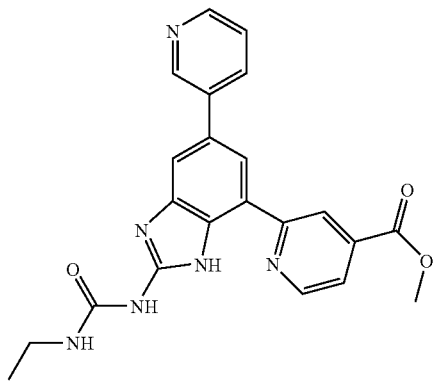
I-115
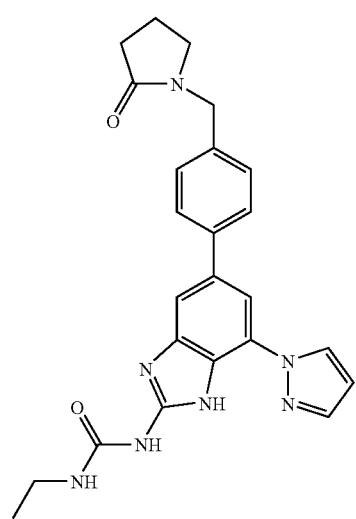
I-118
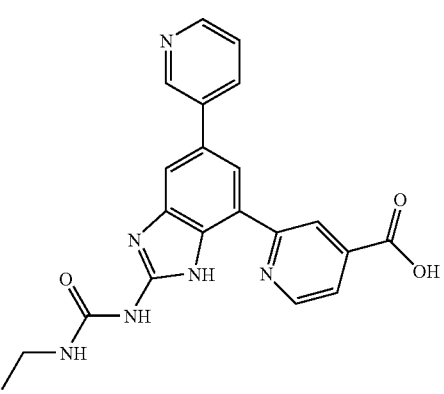
I-119
I-116
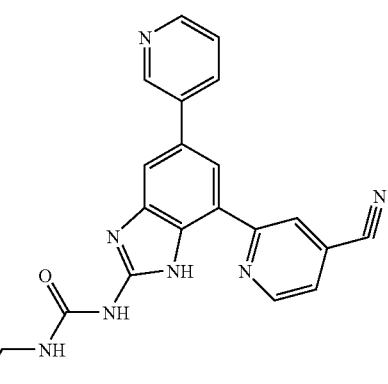
I-120
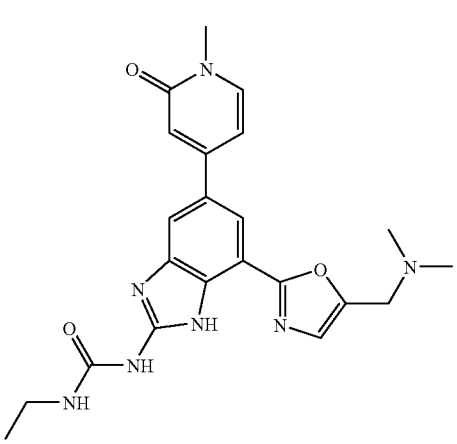

-continued
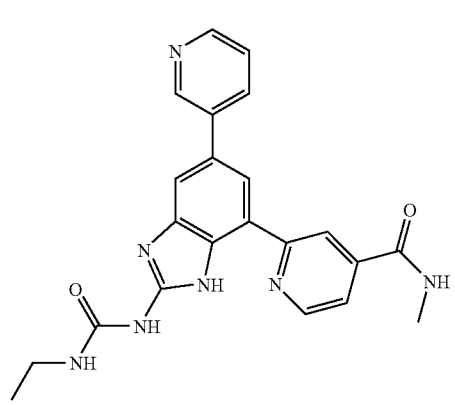
I-121
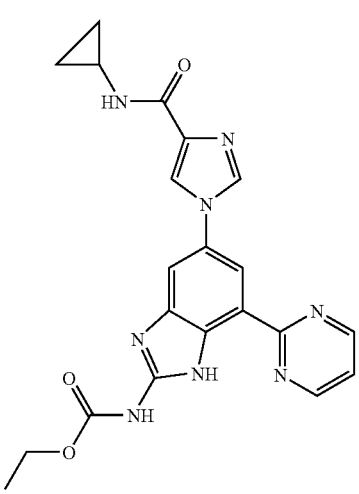
I-124
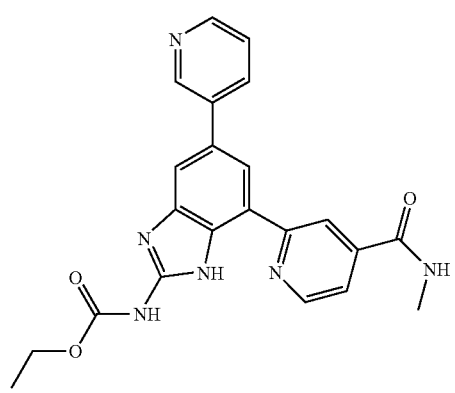
I-122
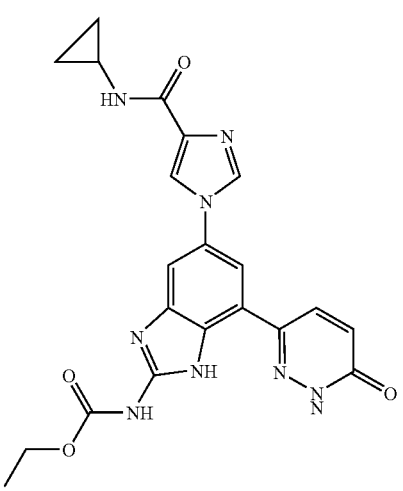
I-125
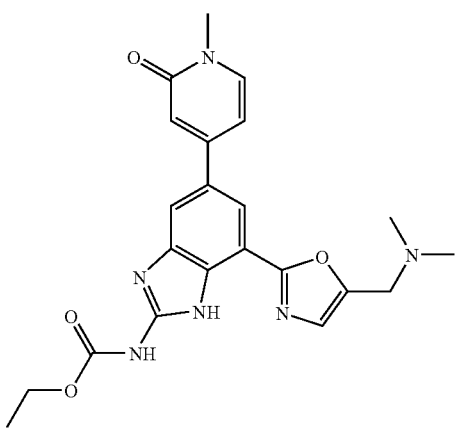
I-123
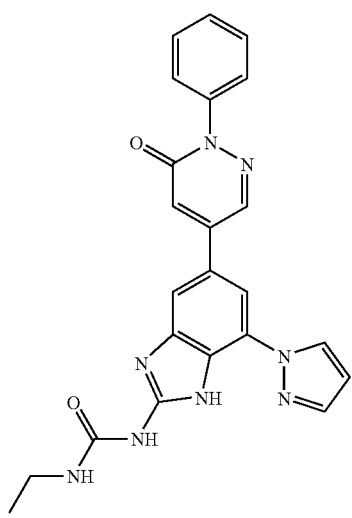
I-126

-continued
I-127
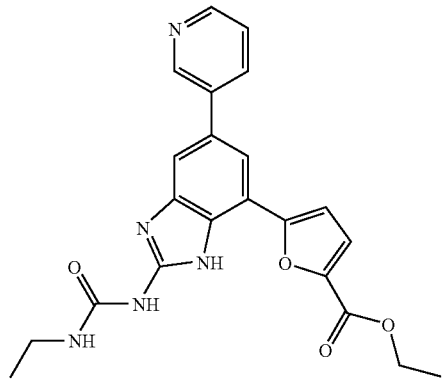
I-128
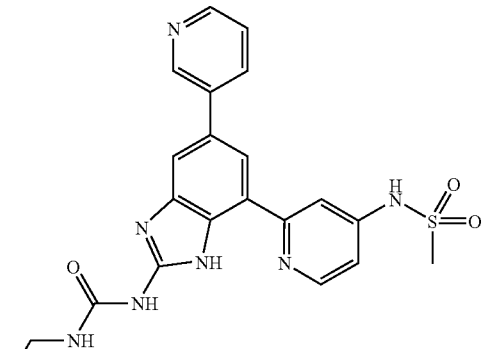
I-129
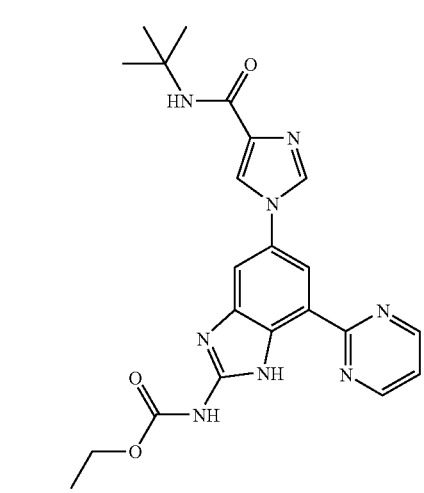
-continued
I-130
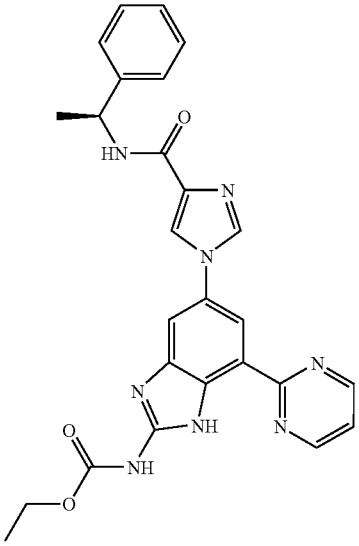
I-131
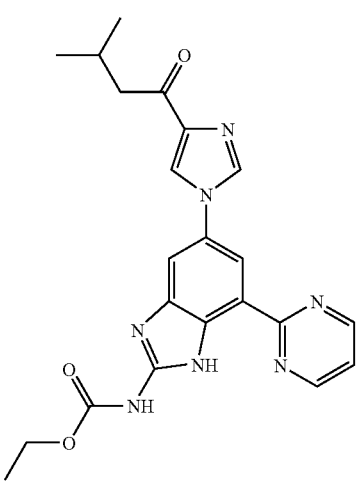
I-132
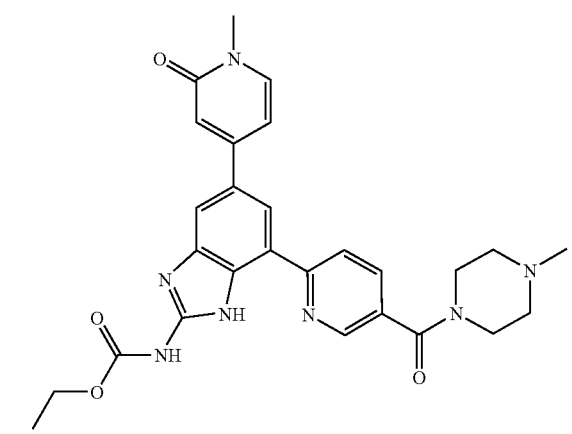

-continued

I-133

I-134

I-135

-continued

I-136

I-137

I-138

-continued
I-139
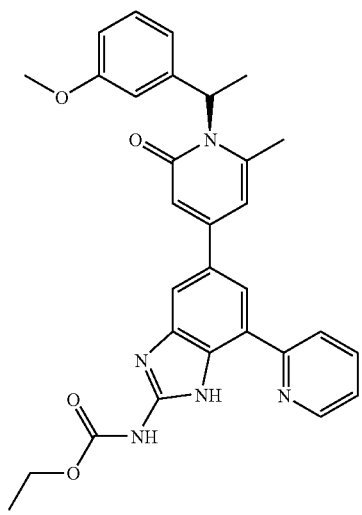
I-142
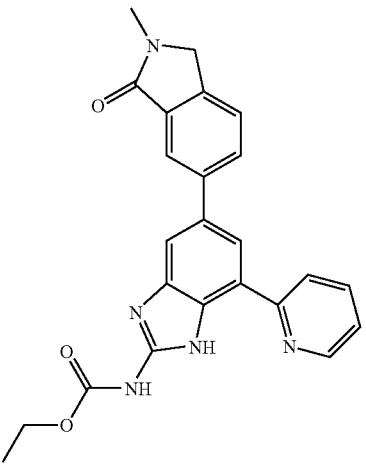
I-140
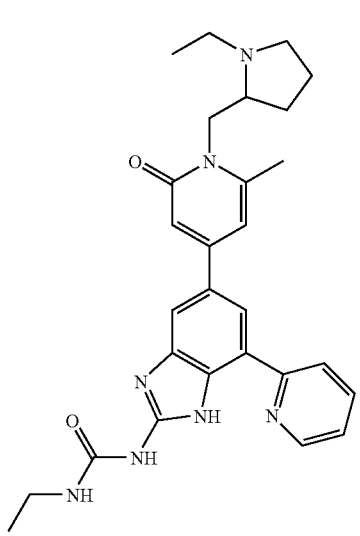
I-143
I-141
I-144
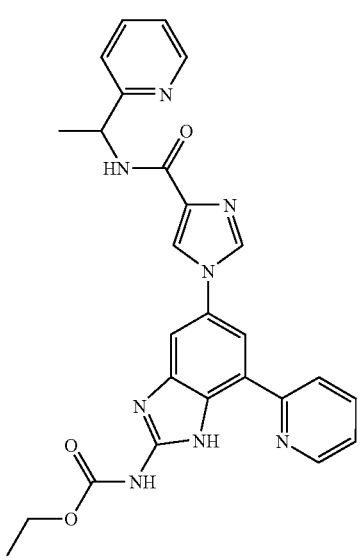

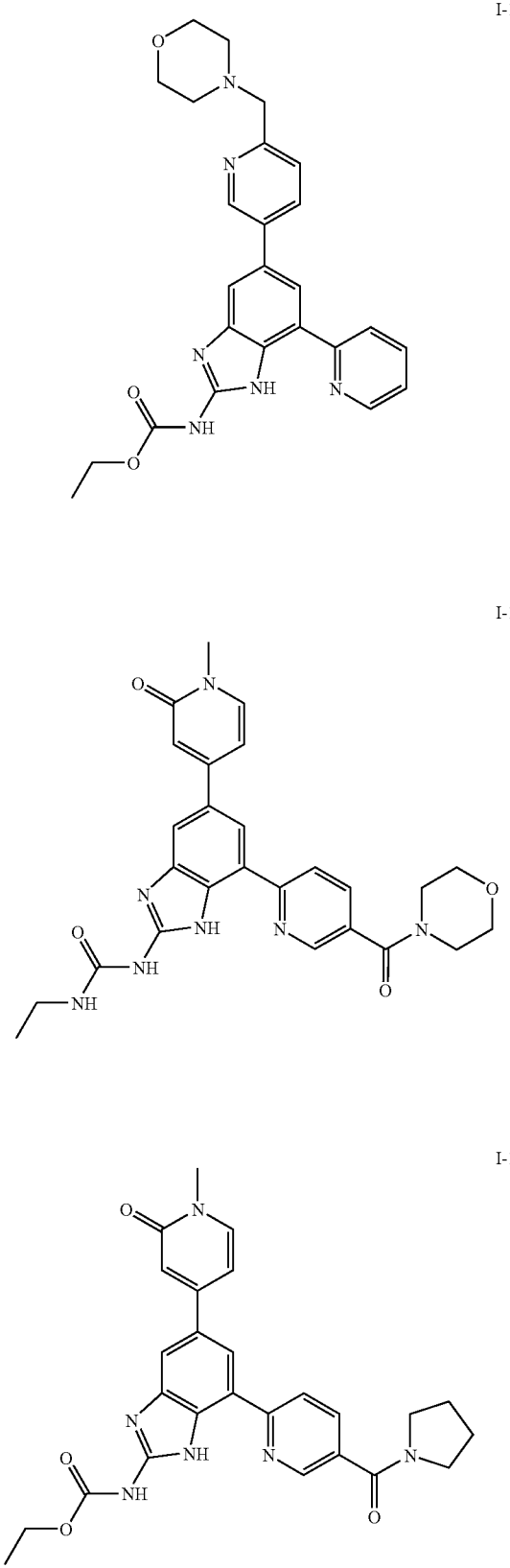
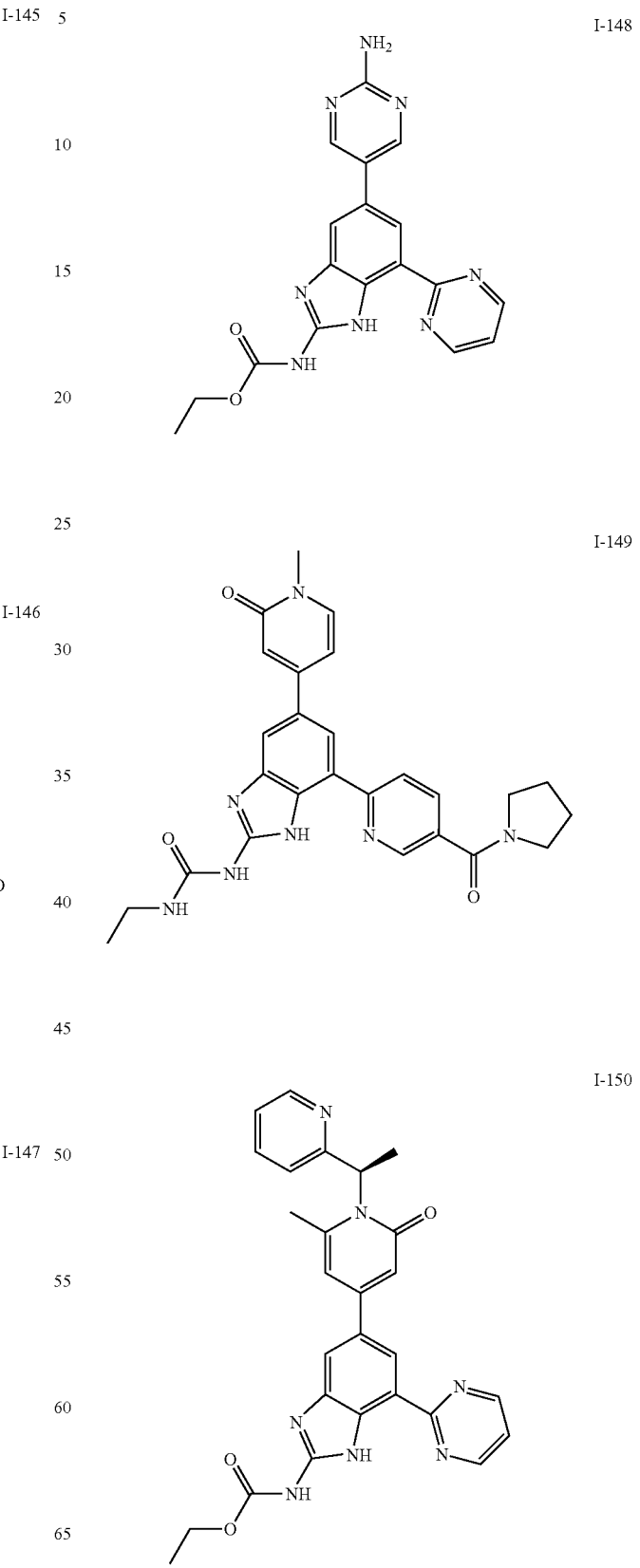

225
-continued
I-152
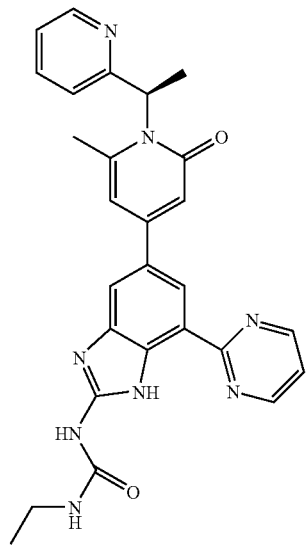
226
-continued
I-151
I-153
I-154
I-155
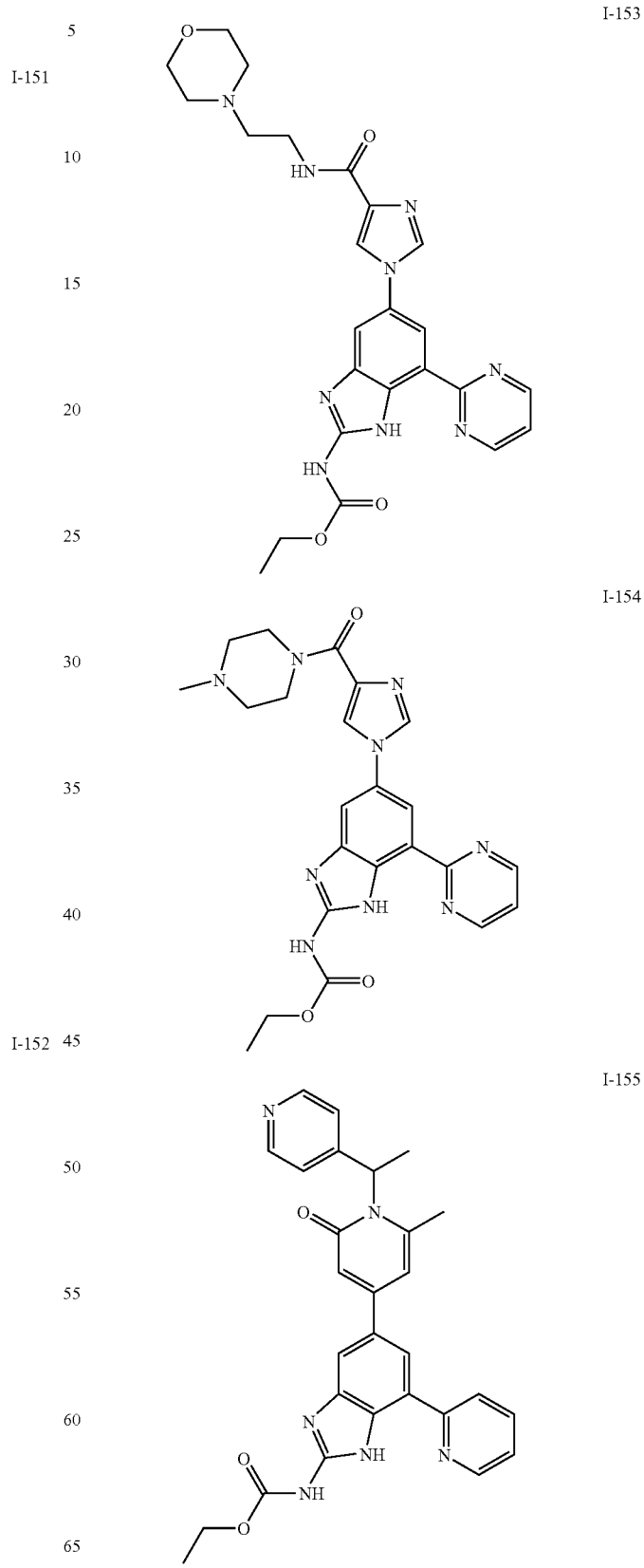

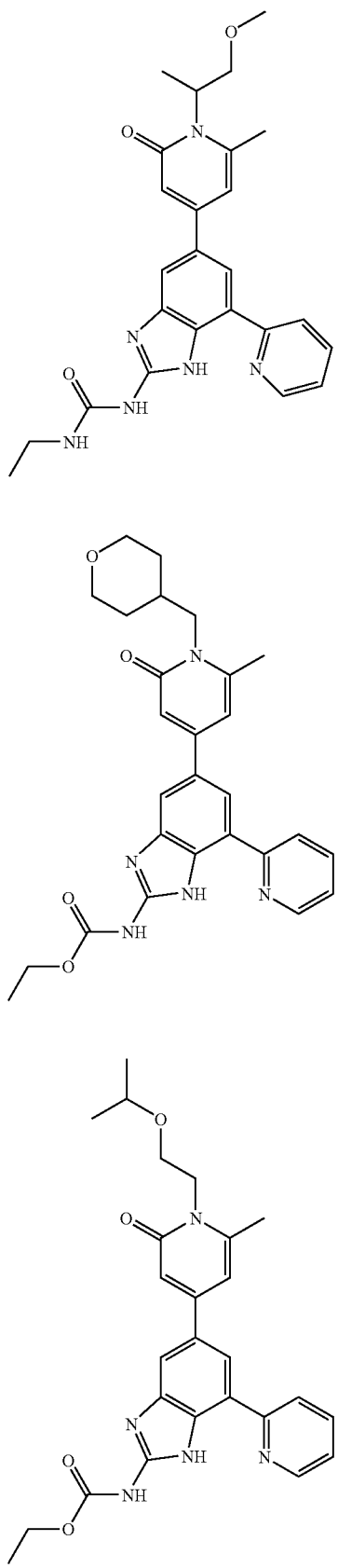
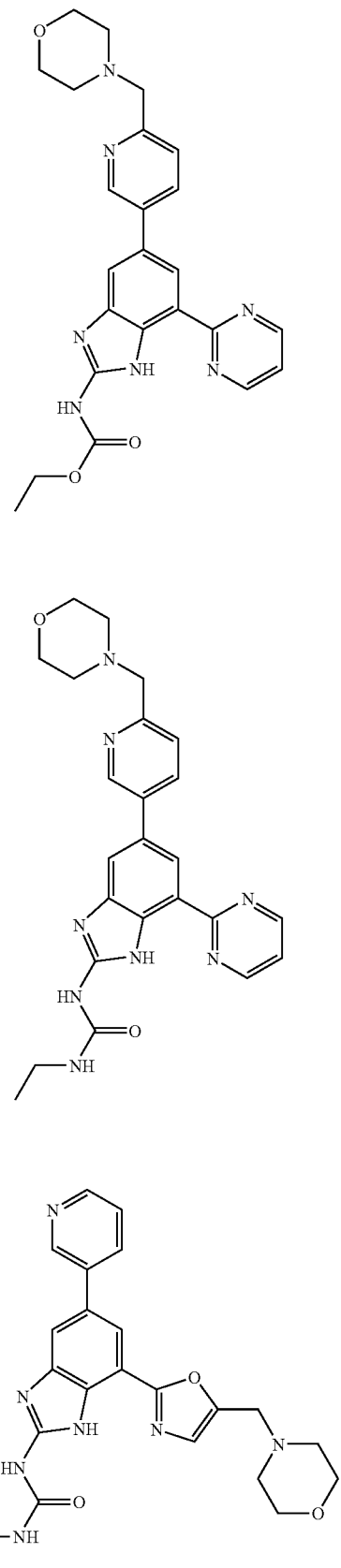

I-162
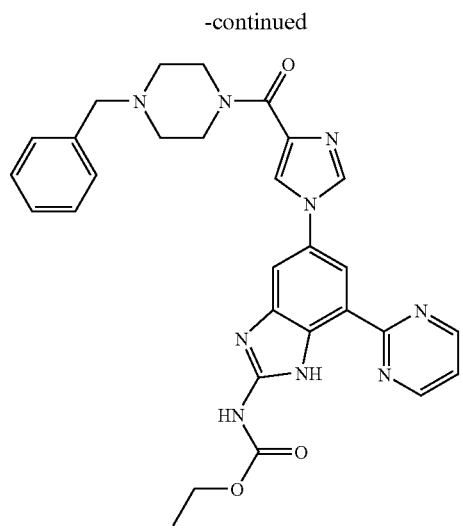
I-165
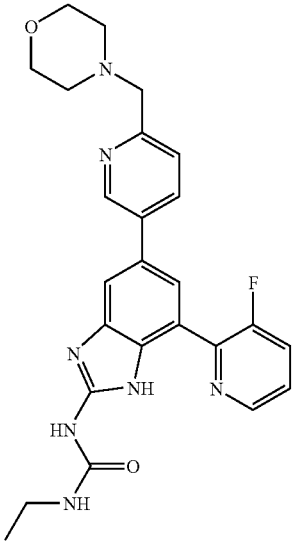
I-163
I-166
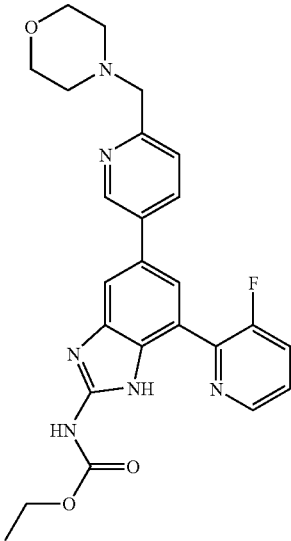
I-164
I-167
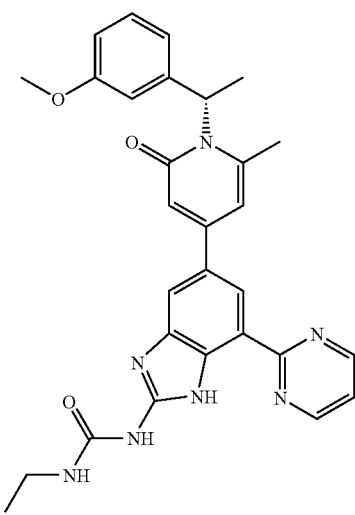

I-168
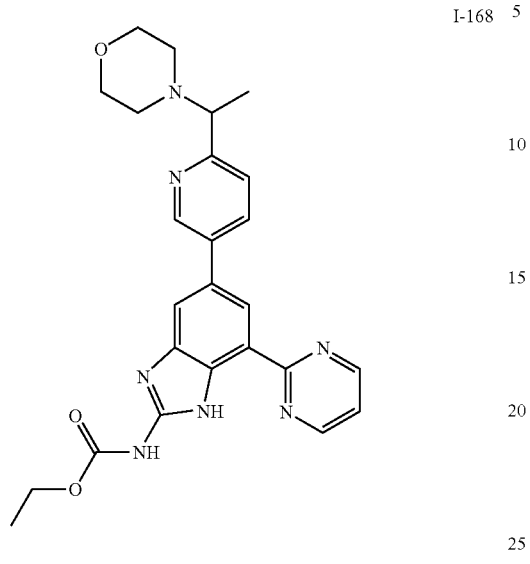
I-169
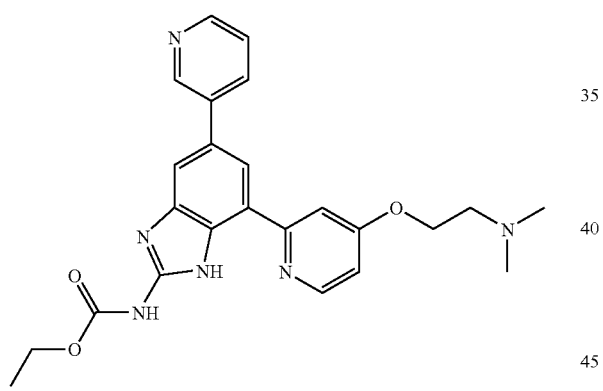
I-170
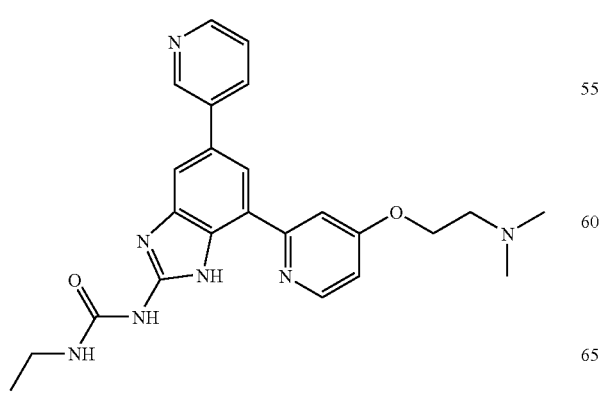
I-171
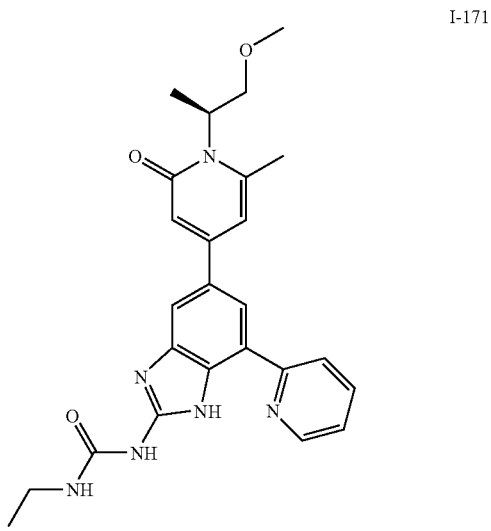
I-172
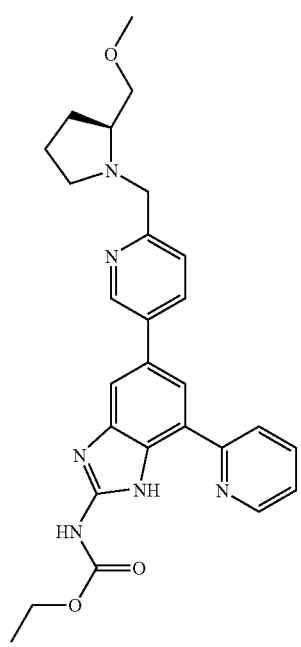

-continued
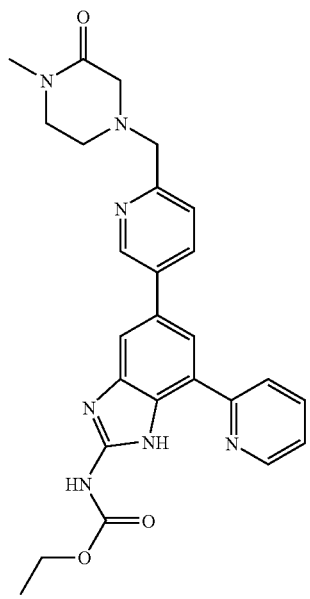
I-173
-continued
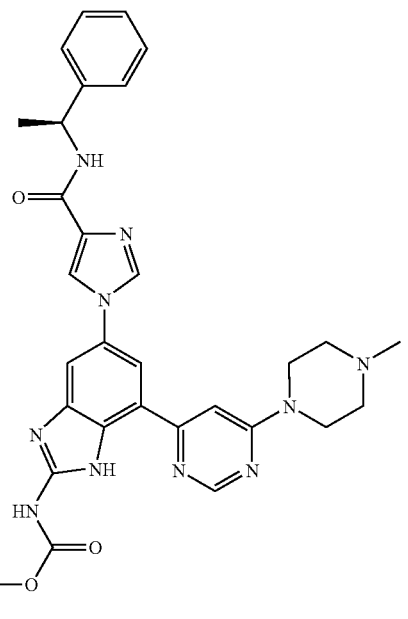
I-175
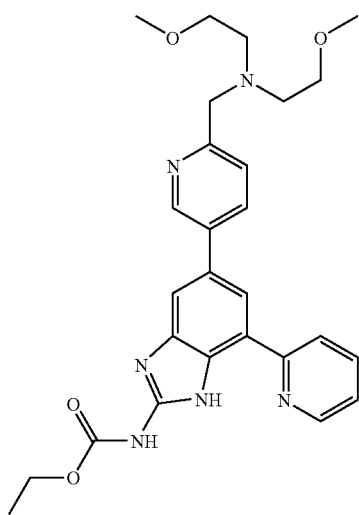
I-174
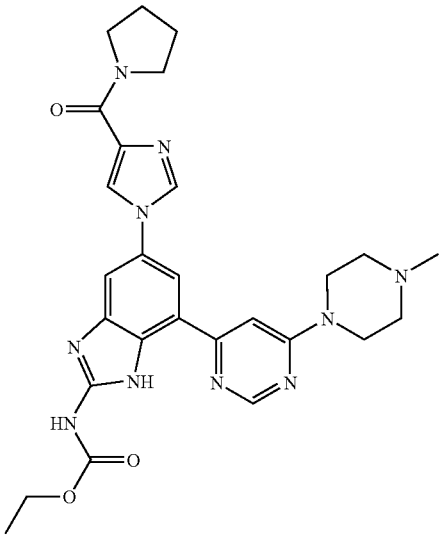
I-176

I-177 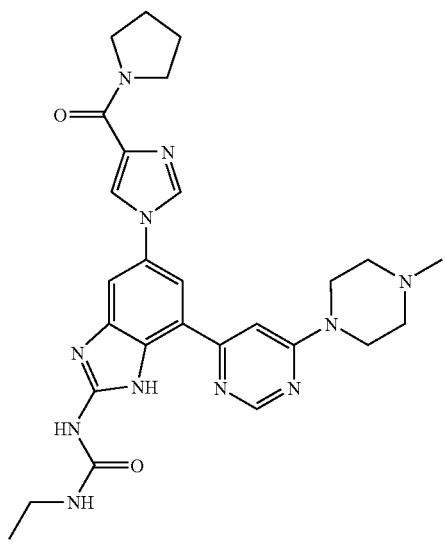
I-180 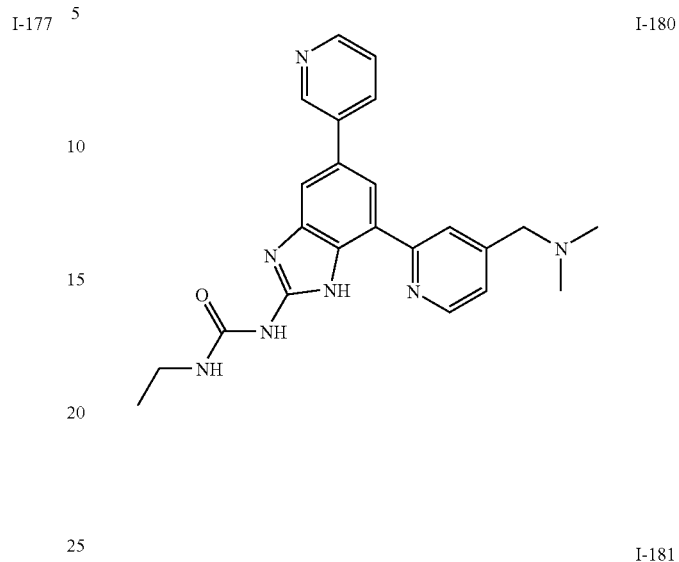
I-178 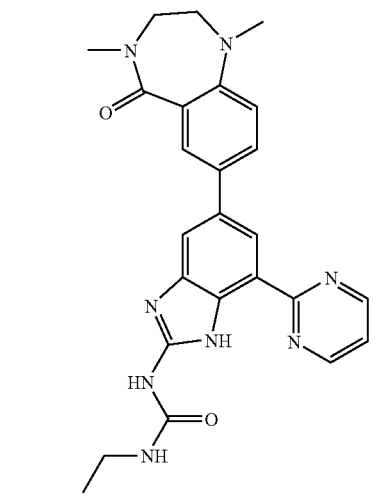
I-181 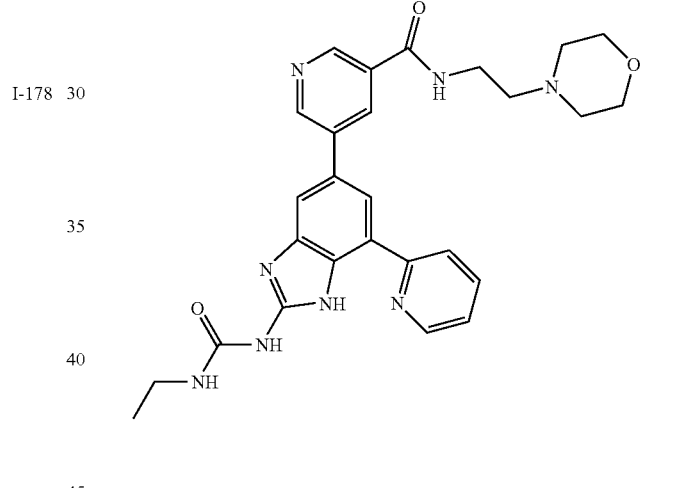
I-179 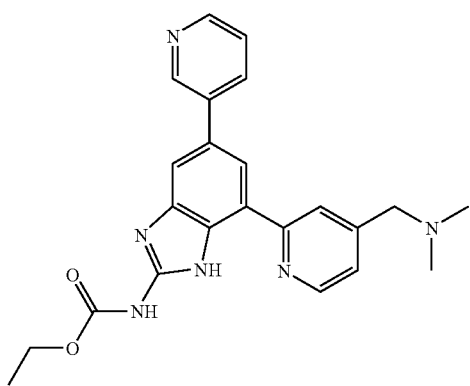
I-182 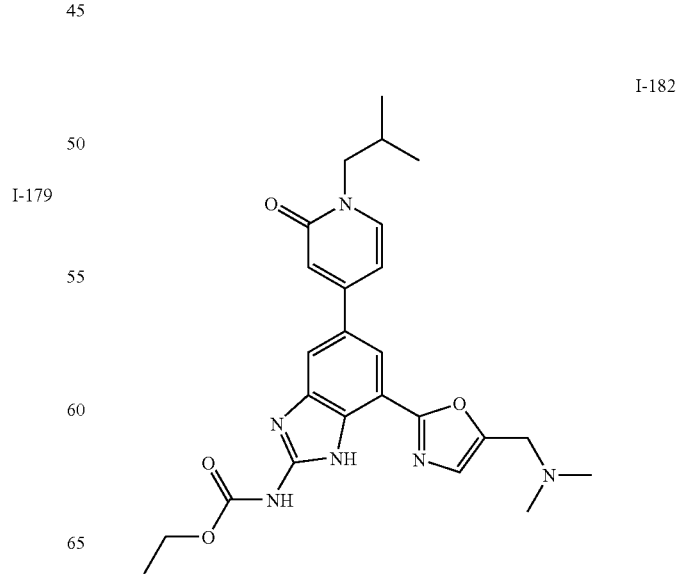

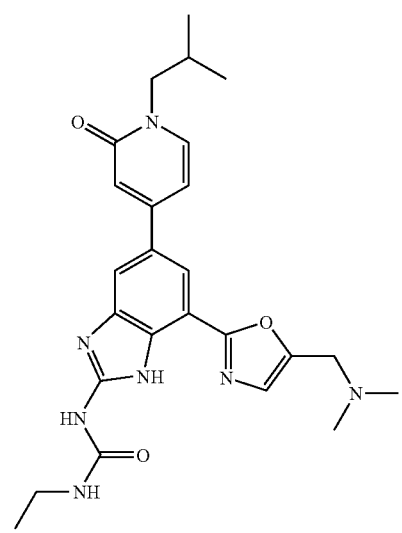
I-183
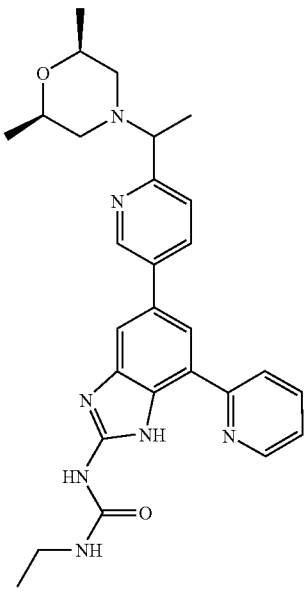
I-186
I-185
I-187

-continued
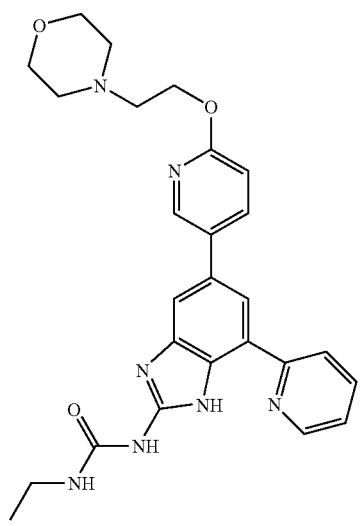
I-188
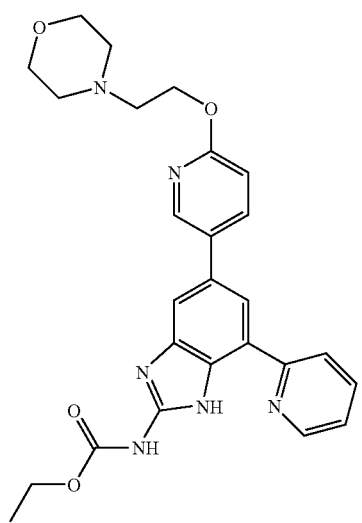
I-189
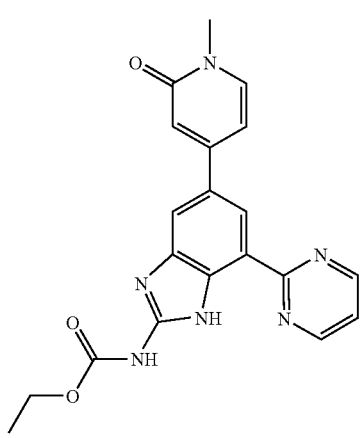
I-190
-continued
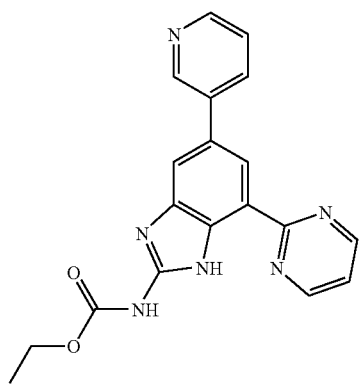
I-191
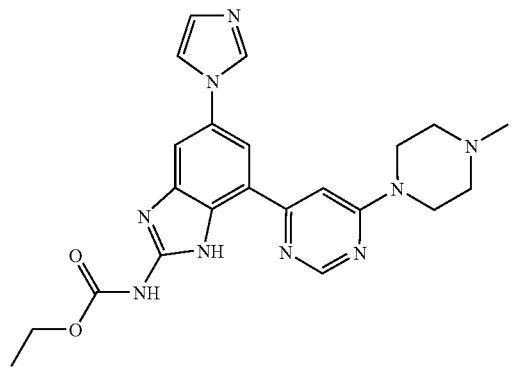
I-192
I-193

-continued
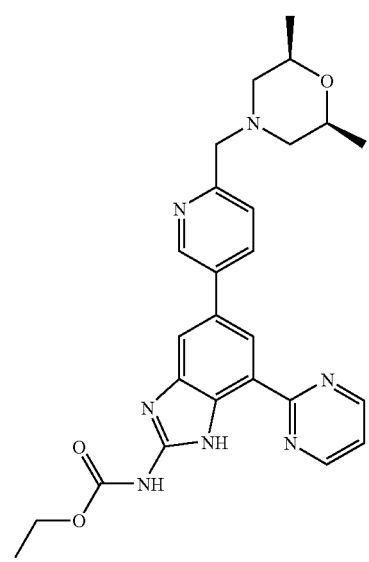
I-194
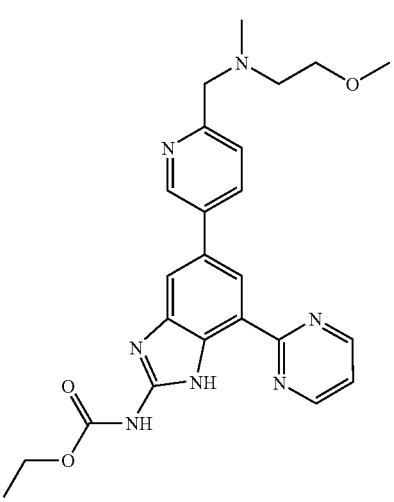
I-197
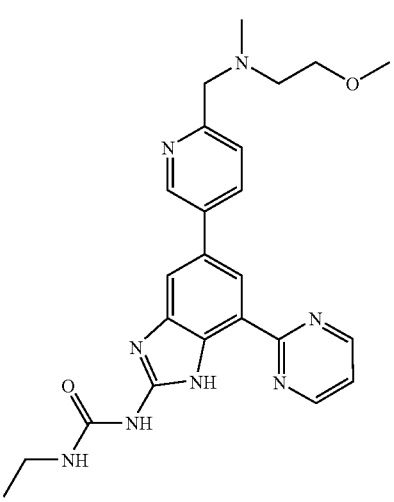
I-198
I-195
I-196
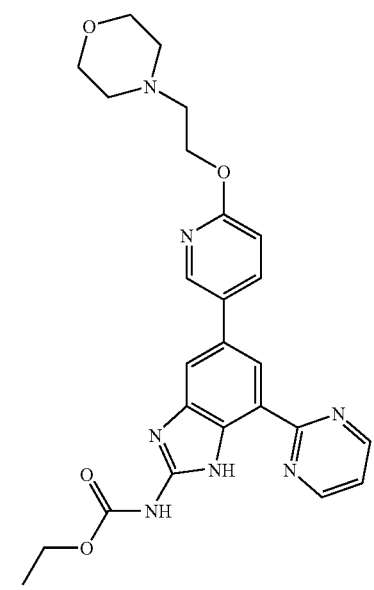
I-199

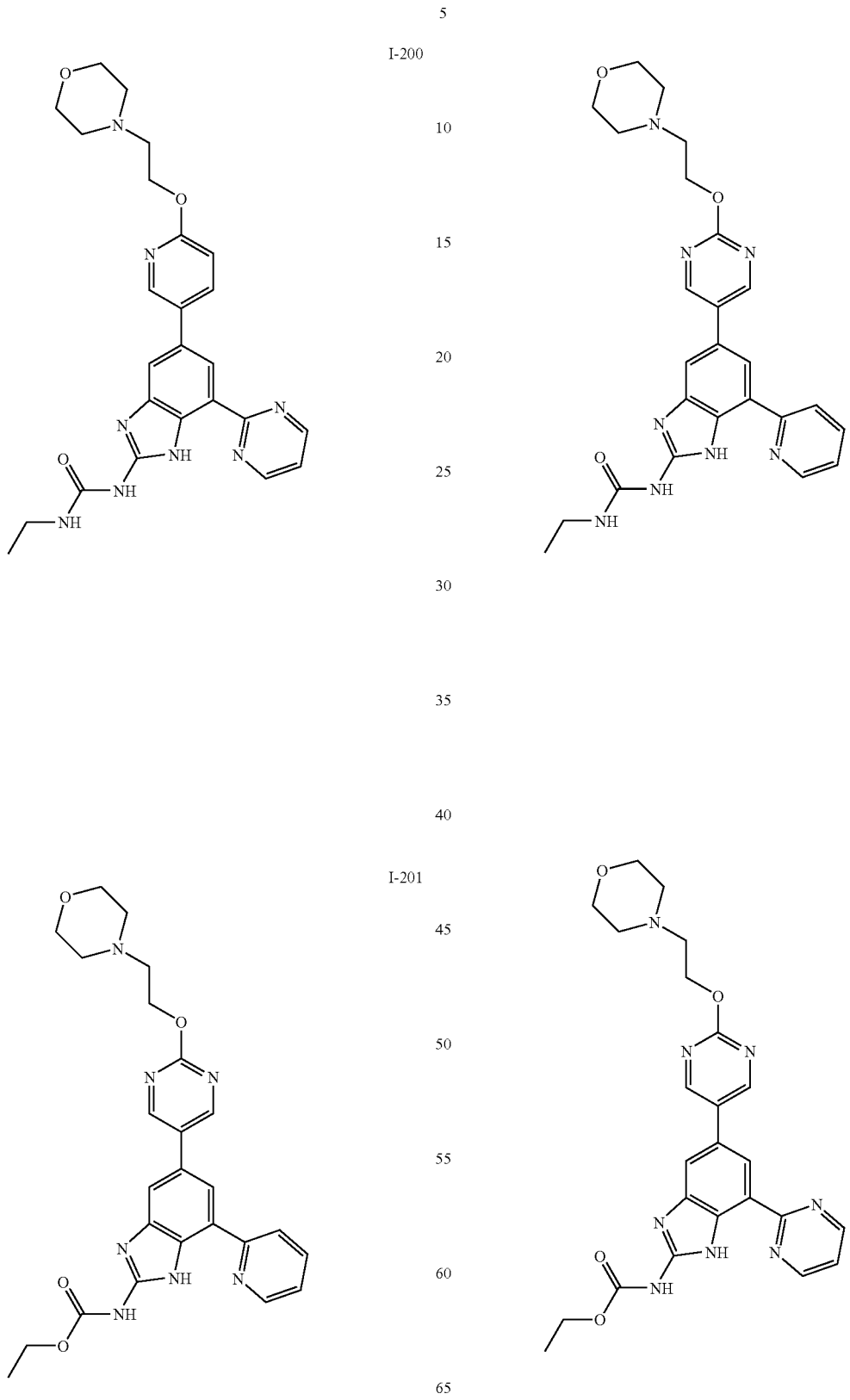

-continued
I-204
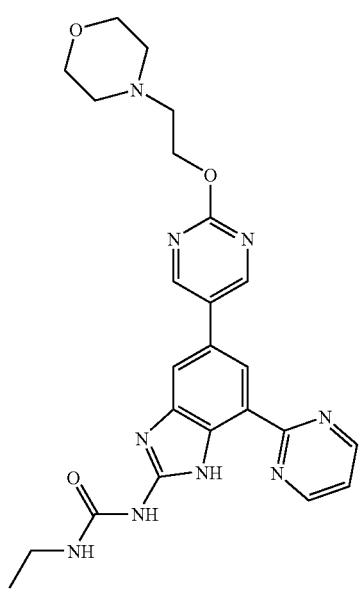
I-205
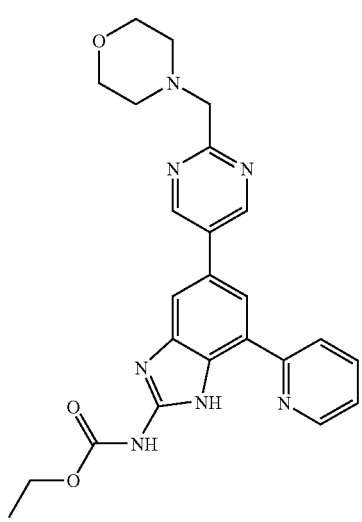
I-206
I-207
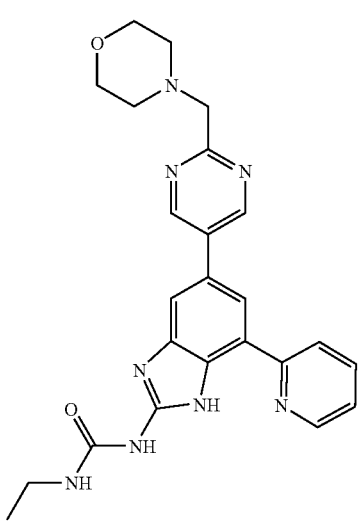
I-208
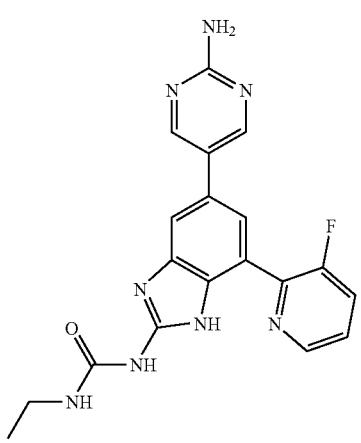
I-209
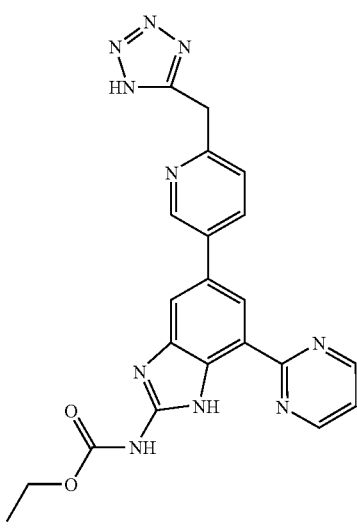

-continued
I-210
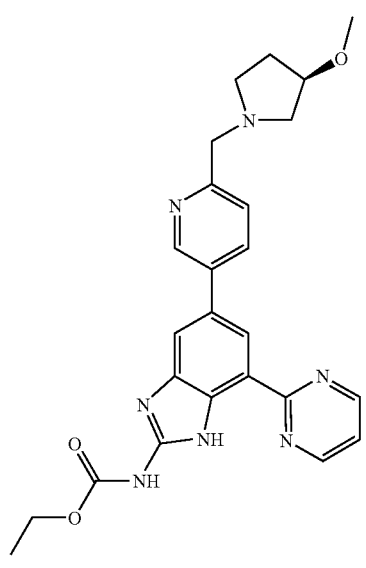
I-211
I-212
-continued
I-213
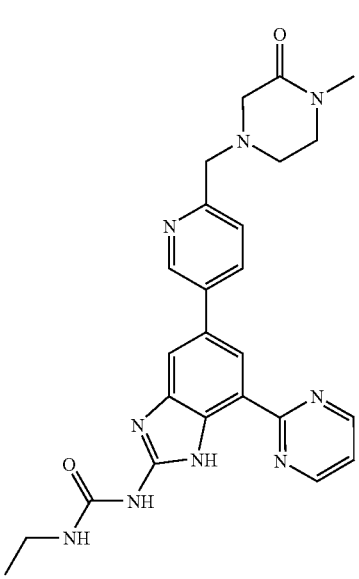
I-214
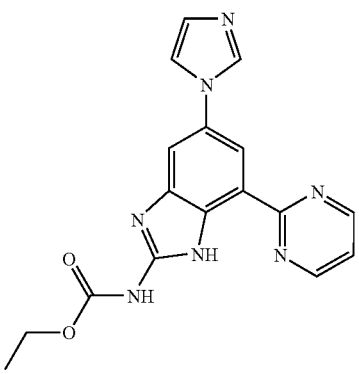
I-215
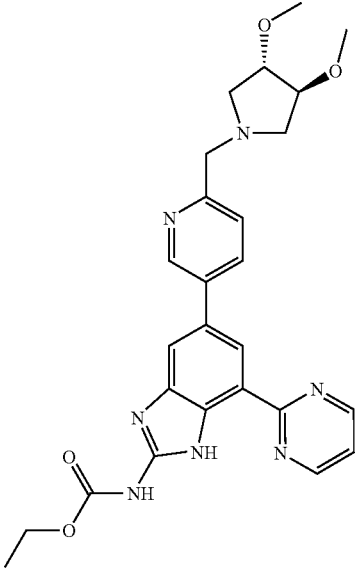

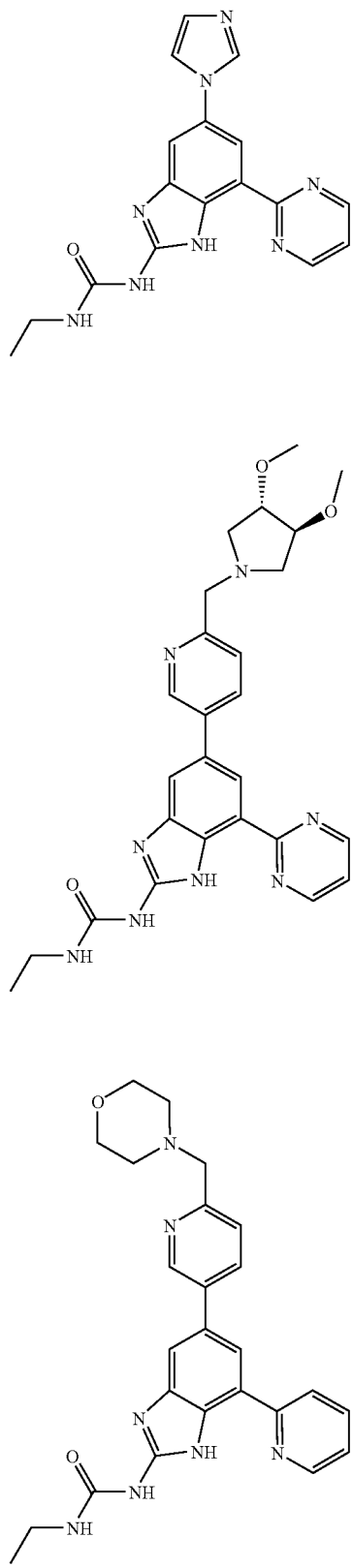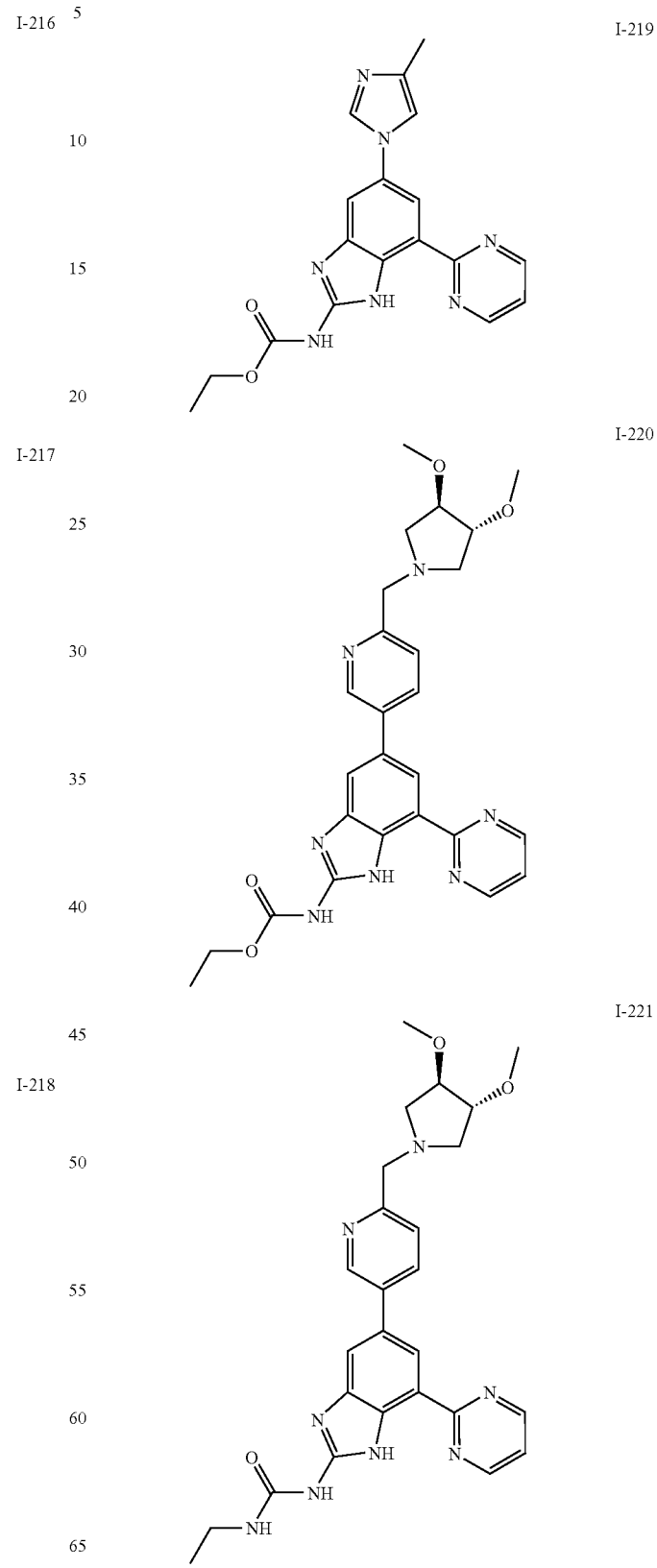

-continued
I-222
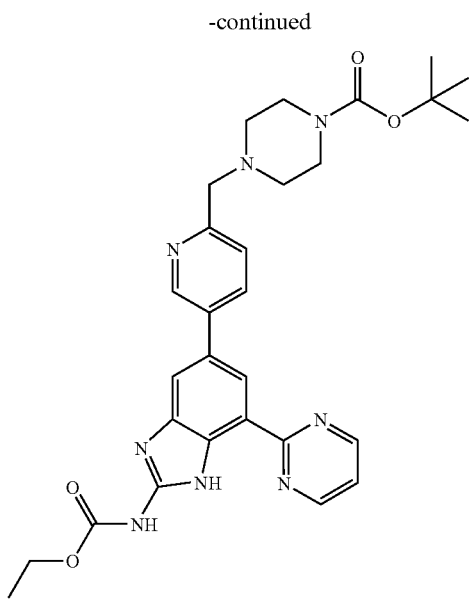
I-223
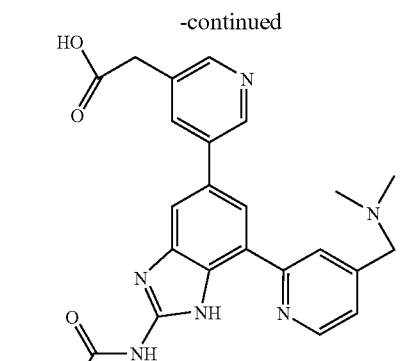
I-224
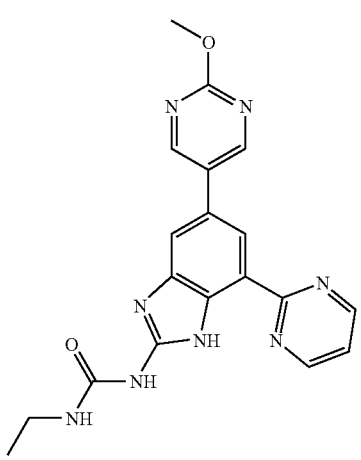
-continued
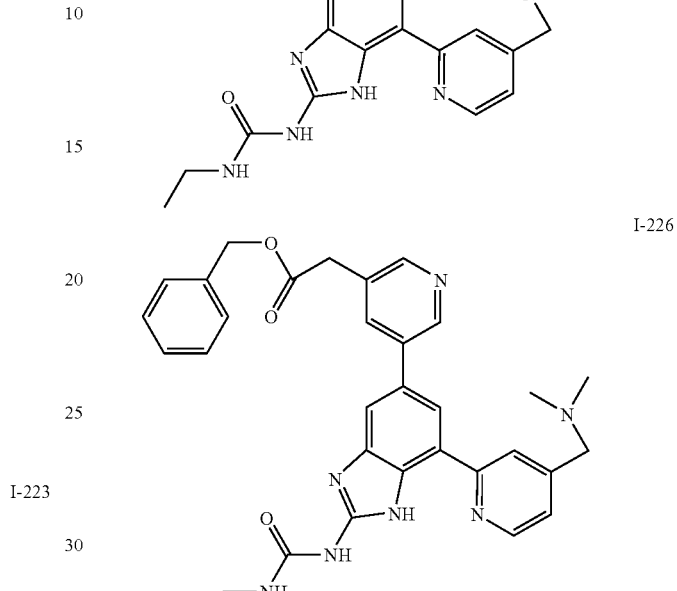
I-226
I-227
I-228
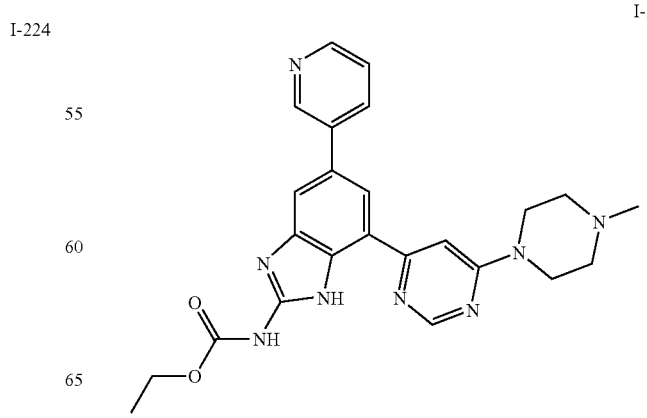

253
-continued
I-229
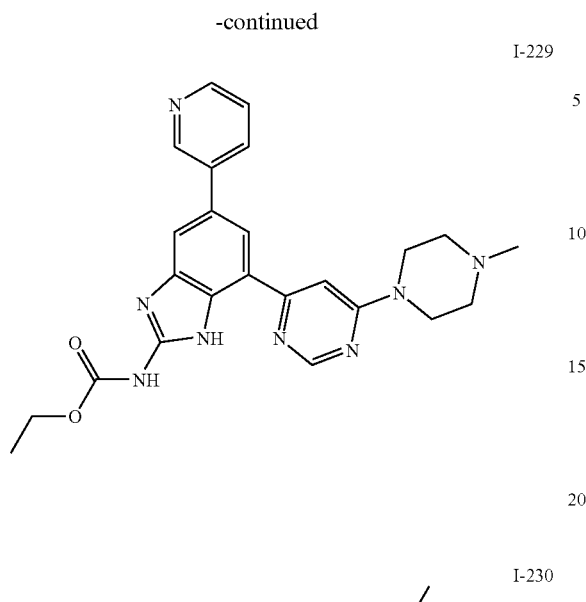
I-230
I-231
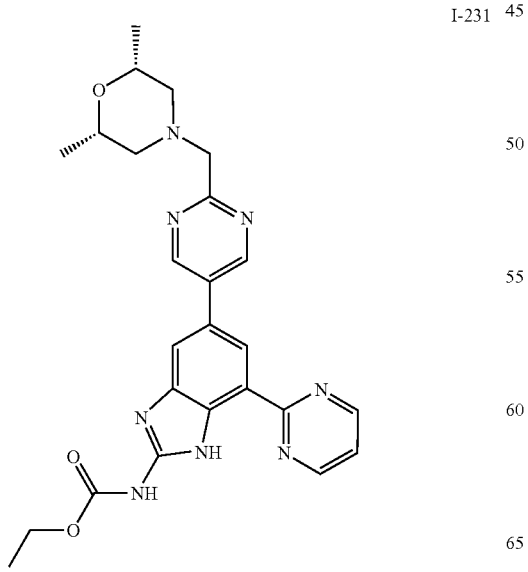
254
-continued
I-232
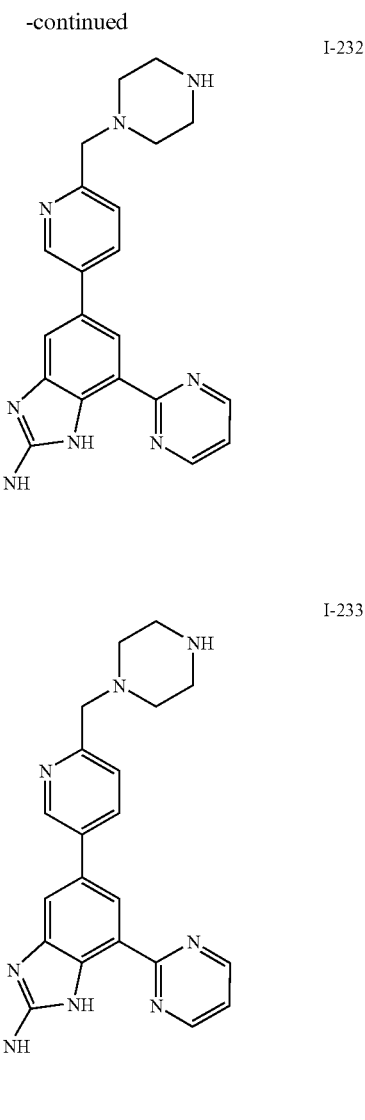
I-233
I-234
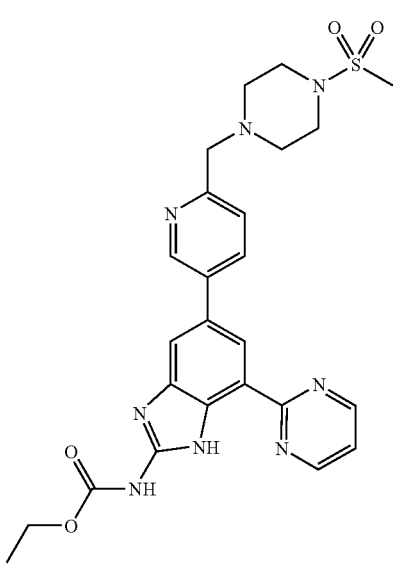

-continued
I-235
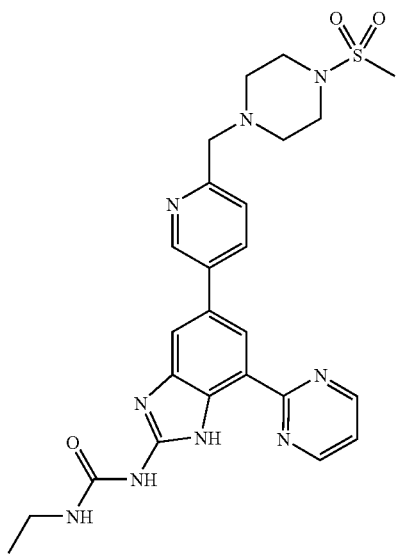
I-236
I-237
I-238
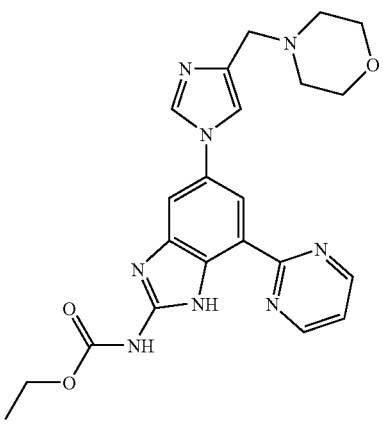
I-239
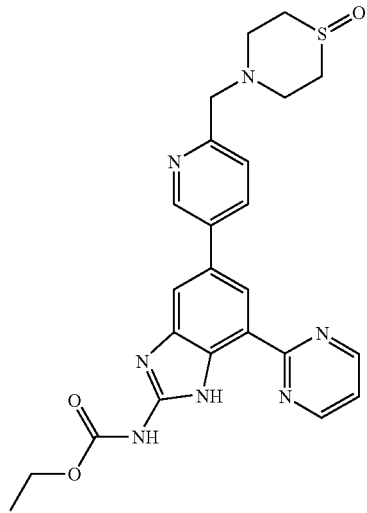
I-240
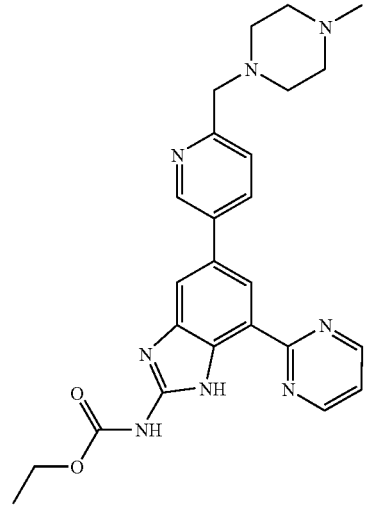

I-241 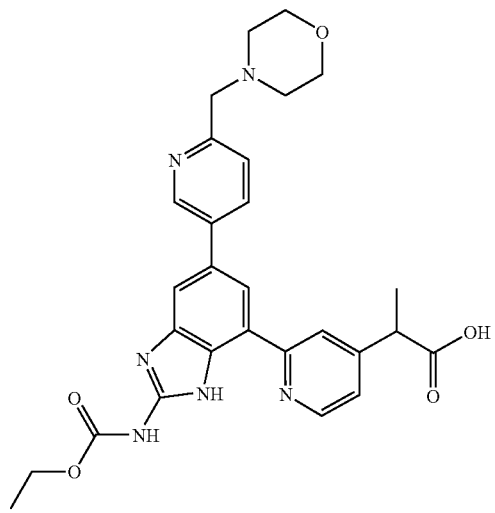
I-244 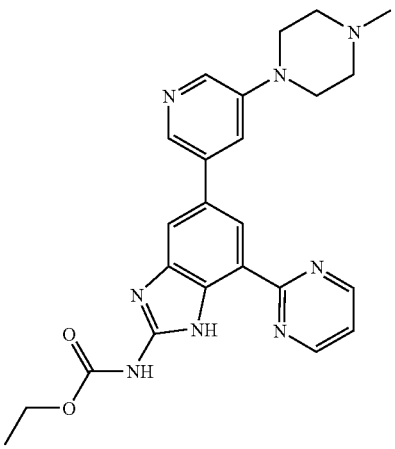
I-242 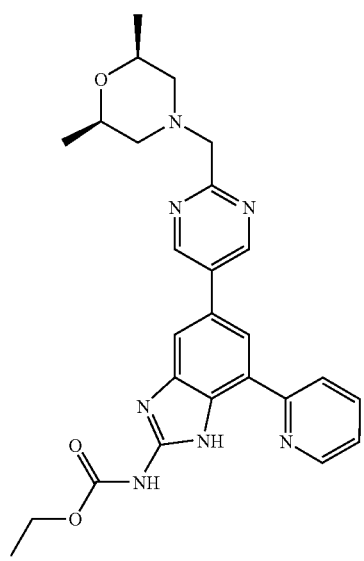
I-245 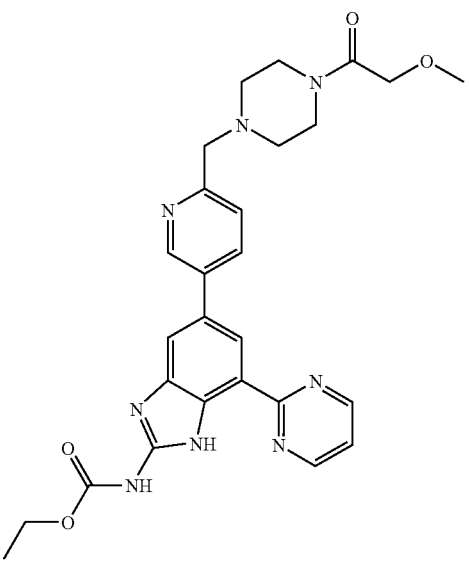
I-243
I-246 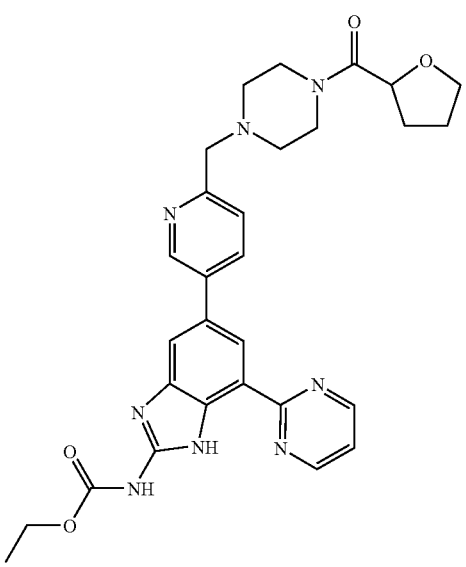

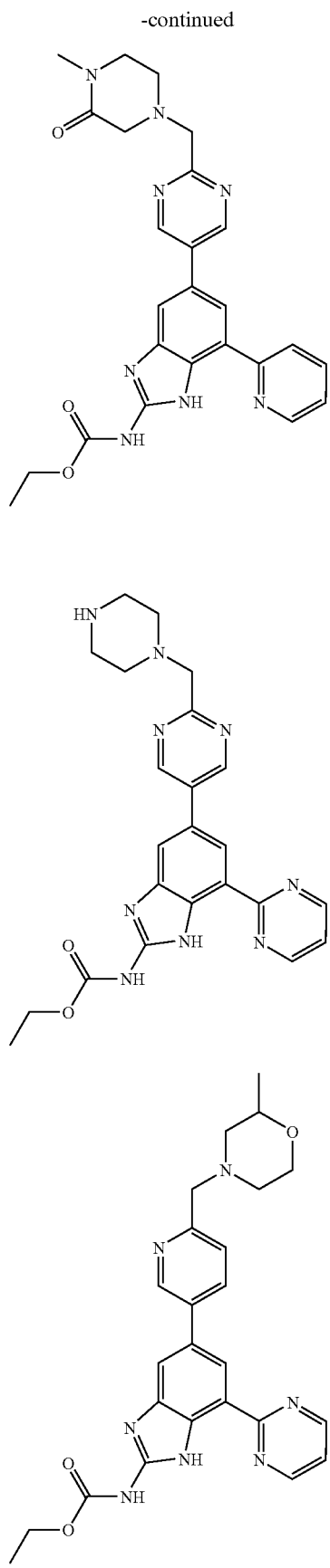

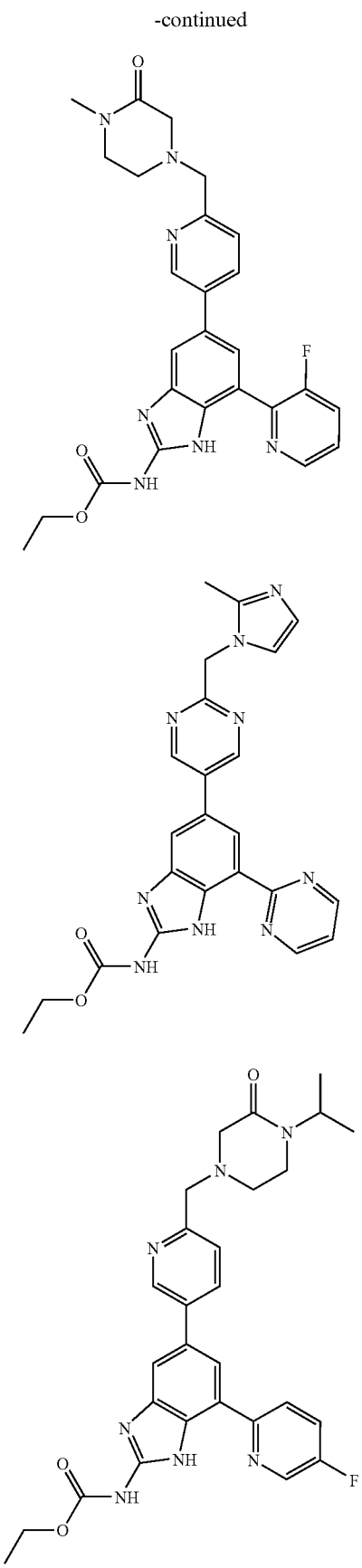
I-253
I-254
I-255
I-256
I-257

263 264
I-258
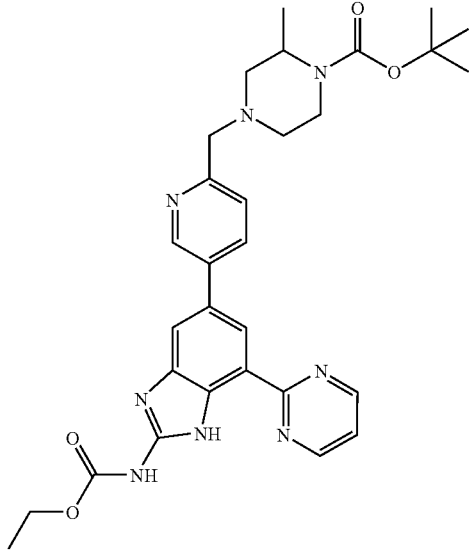
I-260
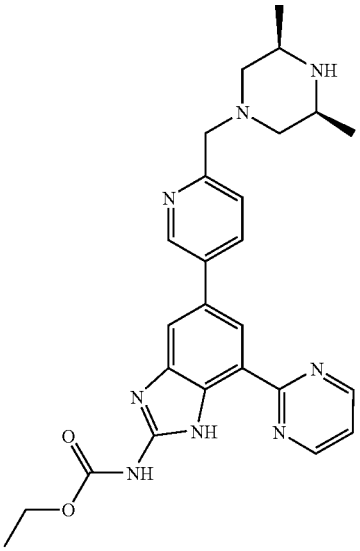
I-261
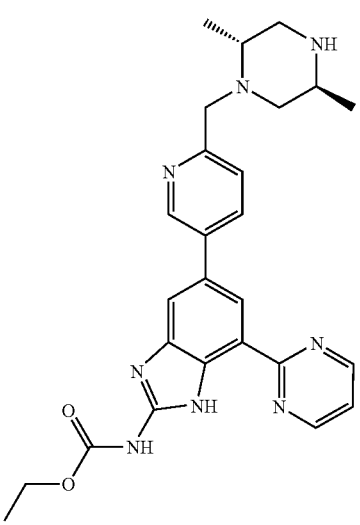
I-259
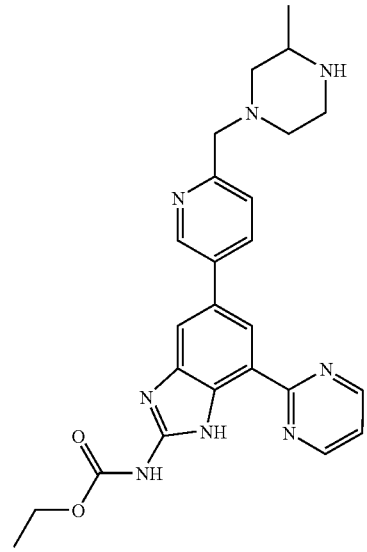
I-262
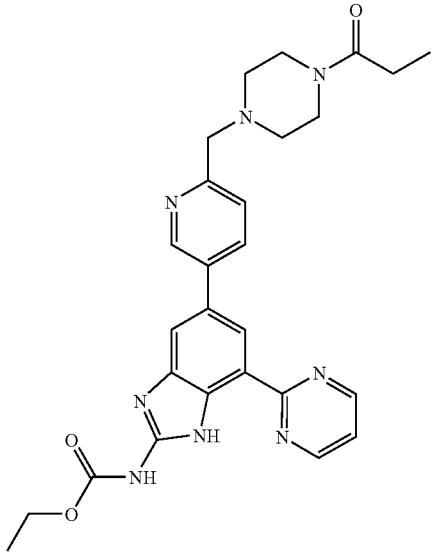

-continued
I-263
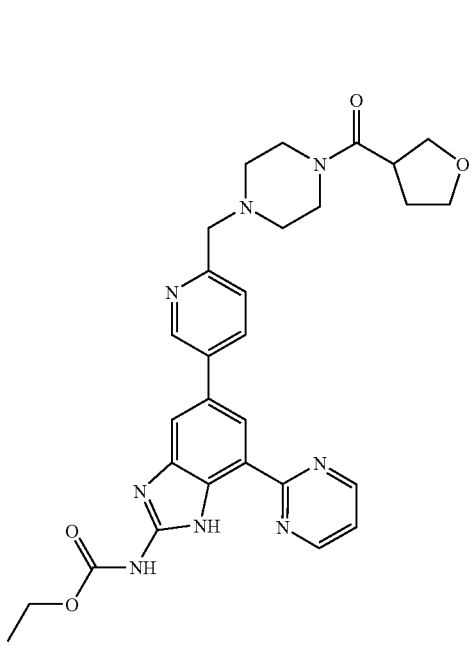
I-264
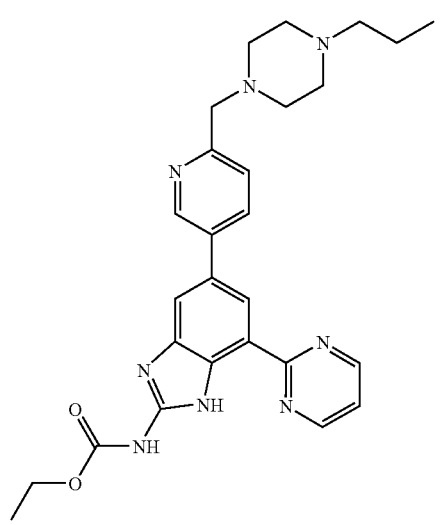
-continued
I-265
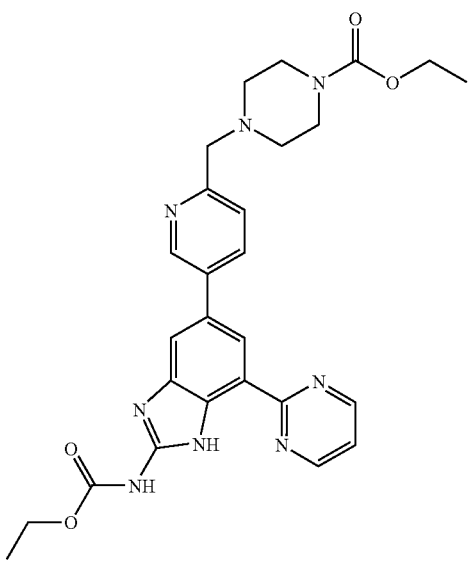
I-266
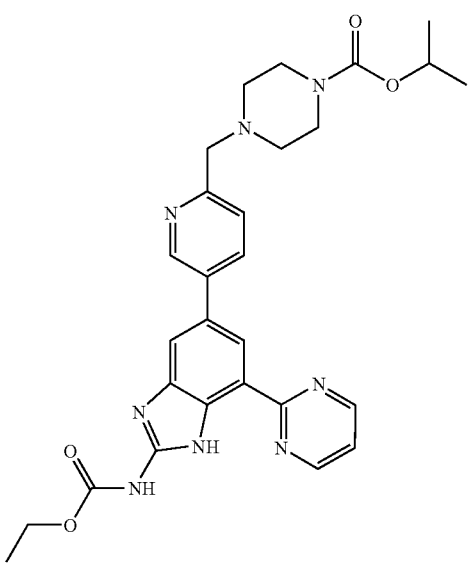

I-267
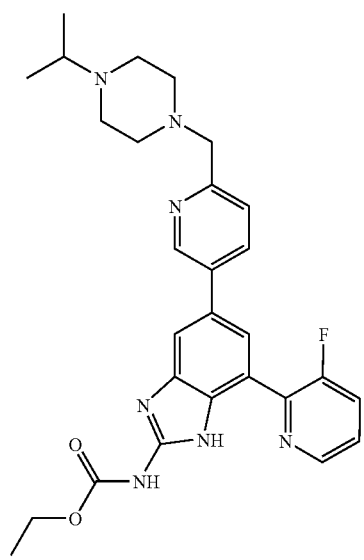
I-269
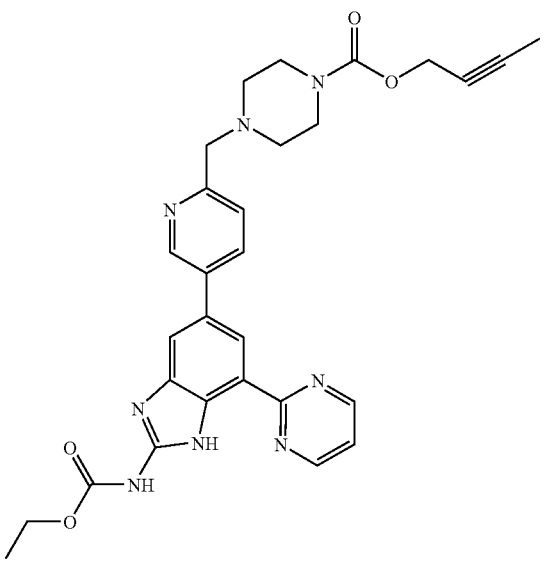
I-268
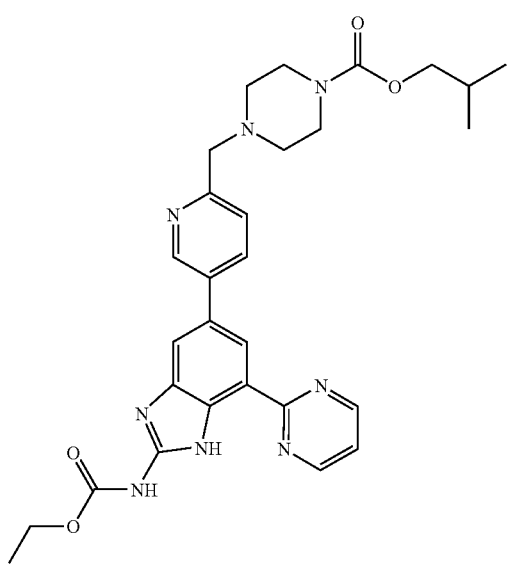
I-270
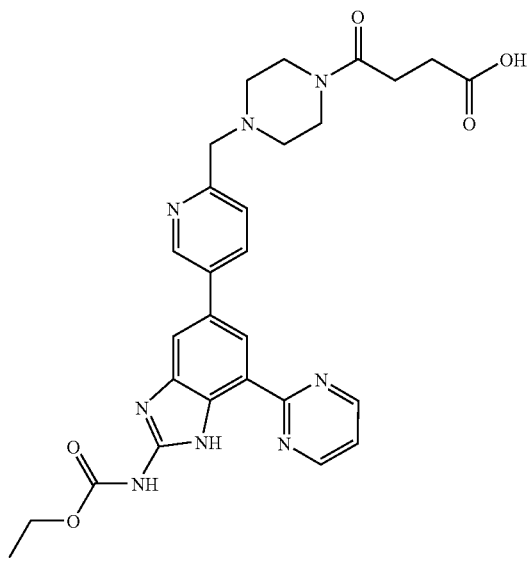

I-271
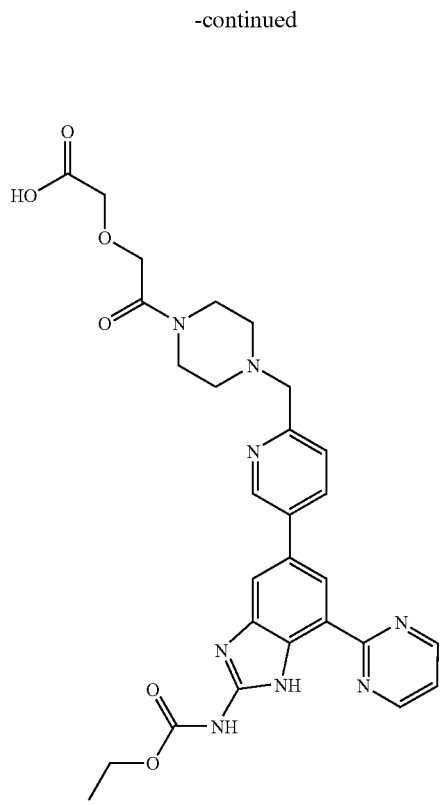
I-272
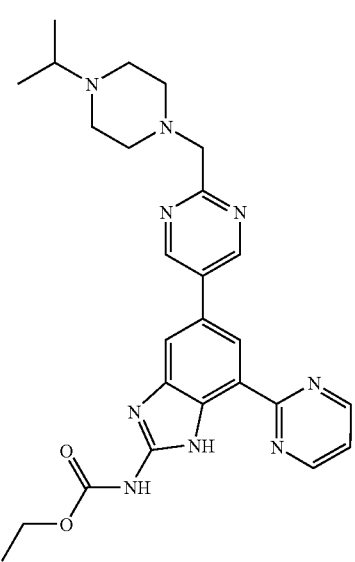
I-273
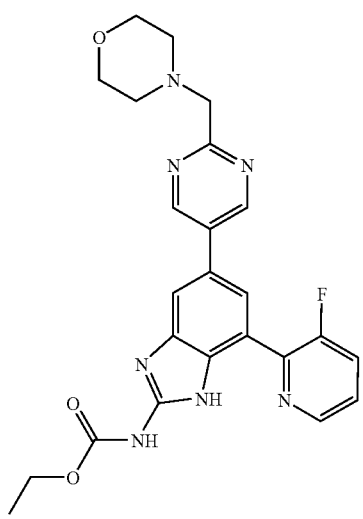
I-274
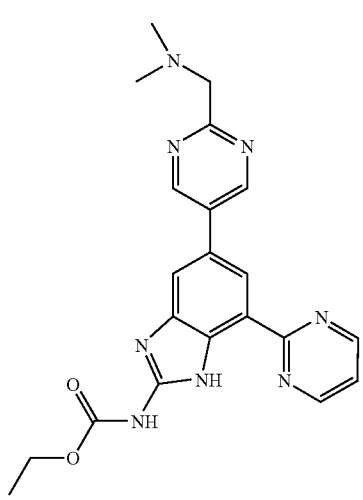
I-275
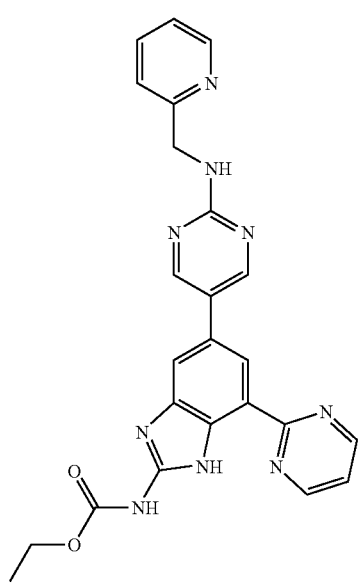

-continued
I-276
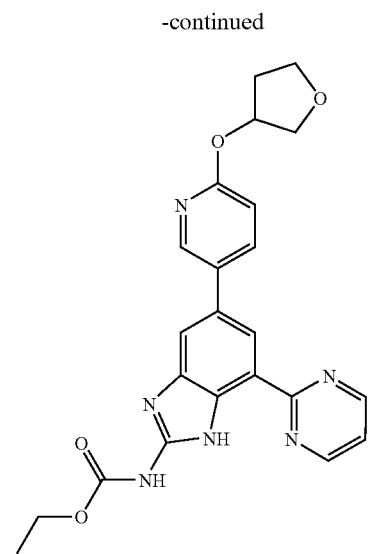
I-277
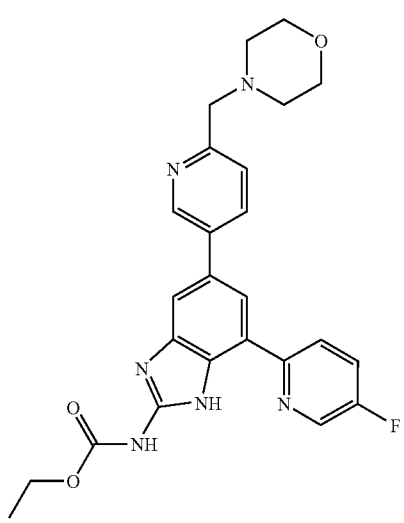
I-278
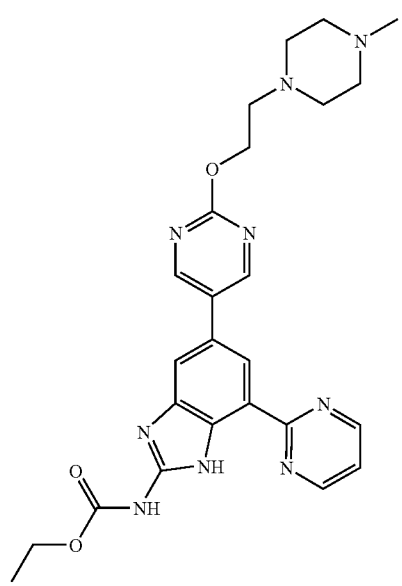
-continued
I-279
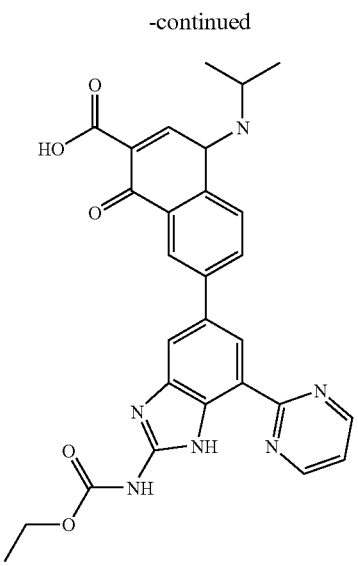
I-280
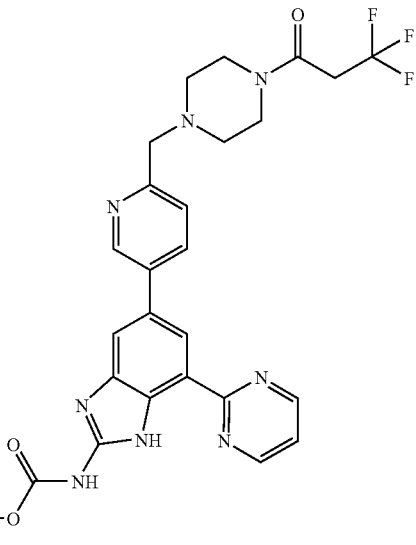
I-281
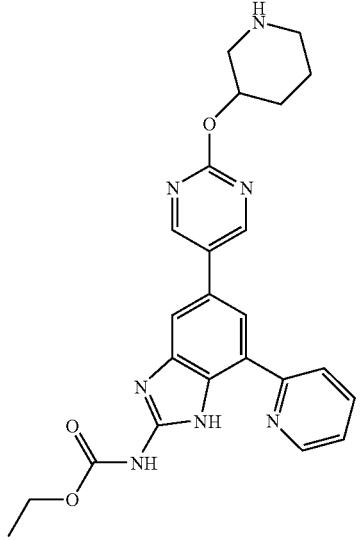

-continued
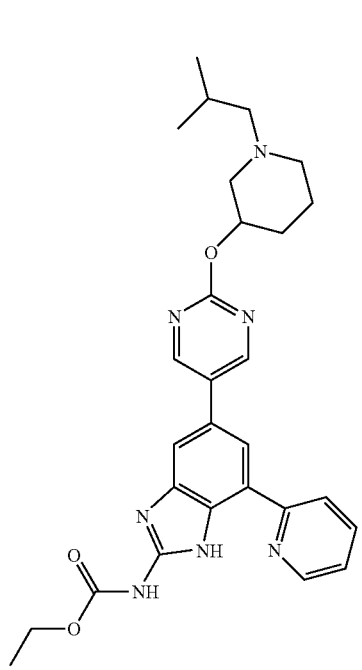
I-282
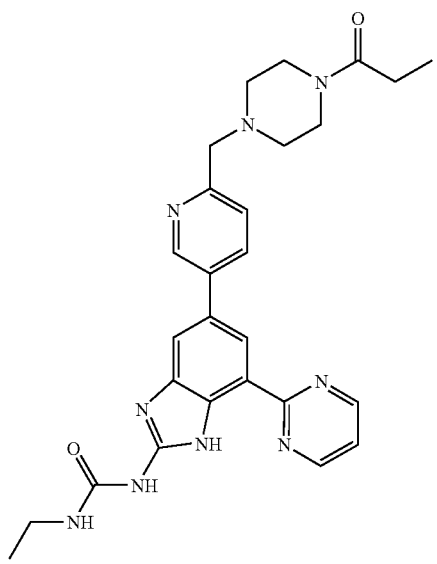
I-284
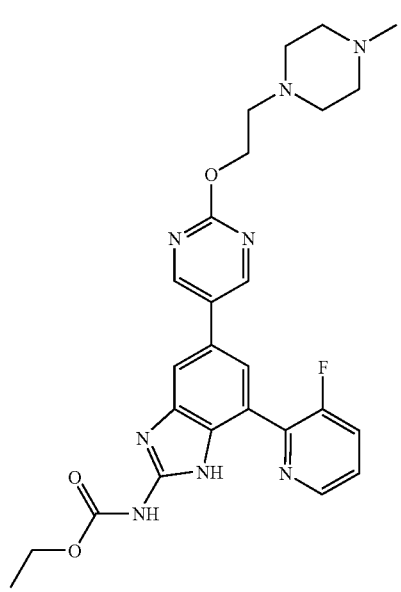
I-283
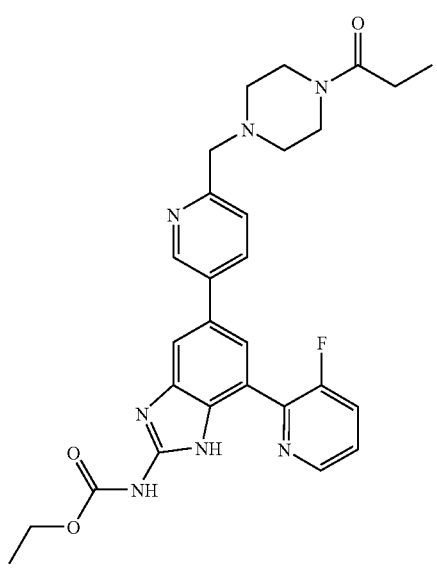
I-285

-continued
I-286
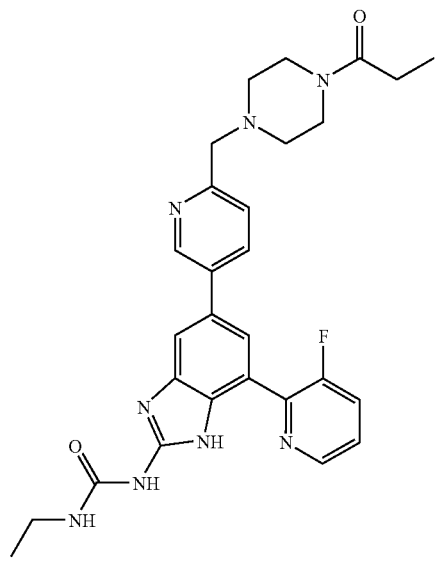
I-287
I-288
-continued
I-289
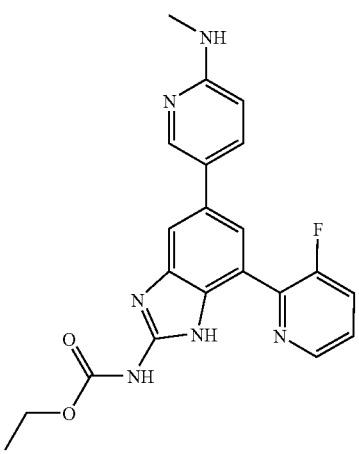
I-290
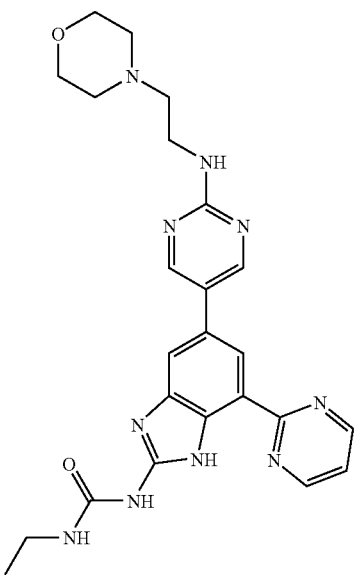
I-291
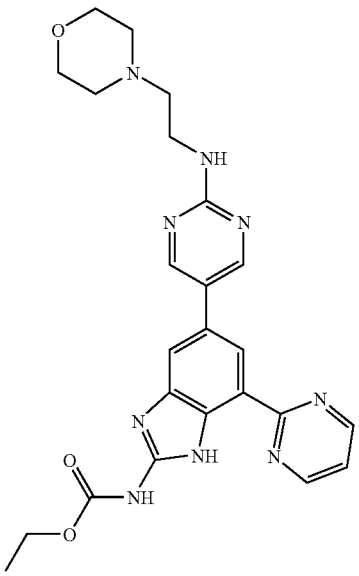

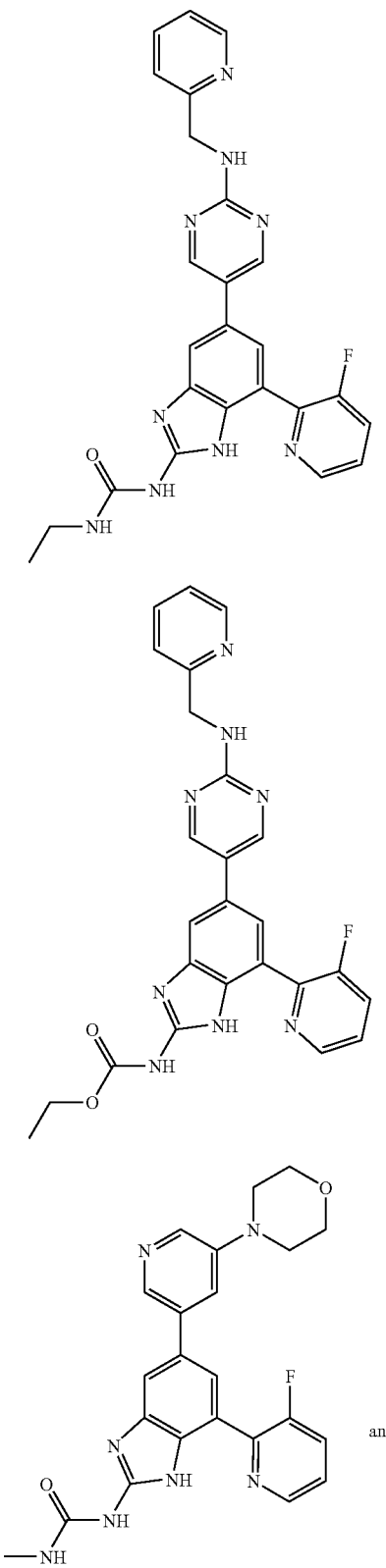

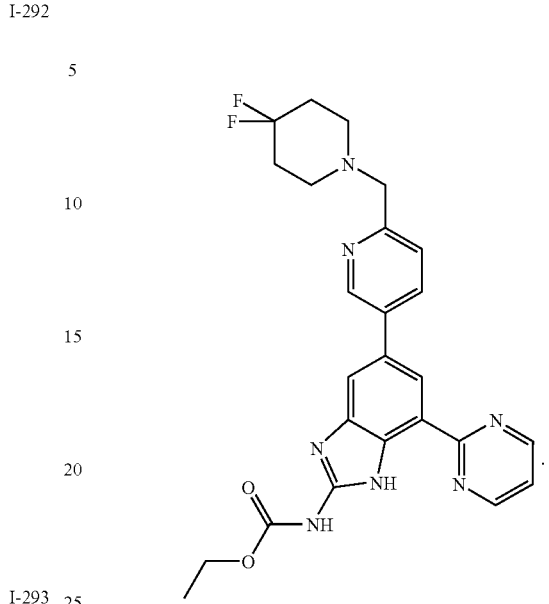

21. A composition comprising an antimicrobially effective amount of a compound according to claim 1 or claim 20, and a pharmaceutically acceptable carrier, adjuvant, or vehicle.

22. A method of controlling, treating or reducing the advancement, severity or effects of a nosocomial or a non-nosocomial *Staphylococcus aureus, Enterococcus faecalis*, or *Streptococcus pneumoniae* bacterial infection in a patient, comprising the step of administering to said patient a composition according to claim 21.

23. A method of controlling, treating or reducing the advancement, severity or effects of a nosocomial or a non-nosocomial *Staphylococcus aureus, Enterococcus faecalis*, or *Streptococcus pneumoniae* bacterial infection in a patient, comprising the step of administering to said patient a compound according to claim 1.

24. The method according to claim 22 or 23, wherein the bacterial infection to be treated is selected from one or more of the following: a urinary tract infection, a respiratory infection, pneumonia, prostatitis, a skin or soft tissue infection, an intra-abdominal infection, a blood stream infection, or an infection of febrile neutropenic patients.

* * * * *